United States Patent
Berasi et al.

(10) Patent No.: US 11,365,253 B2
(45) Date of Patent: Jun. 21, 2022

(54) ANTI-ROBO2 ANTIBODIES, COMPOSITIONS, METHODS AND USES THEREOF

(71) Applicants: Pfizer Inc., New York, NY (US); Boston Medical Center Corporation, Boston, MA (US)

(72) Inventors: Stephen Berasi, Arlington, MA (US); Janet Elizabeth Buhlmann, Brookline, MA (US); Eric M. Bennett, Arlington, MA (US); Nathan Higginson-Scott, Boston, MA (US); Huilan Gao, West Roxbury, MA (US); Zong Sean Juo, Cambridge, MA (US); Stefano V. Gulla, Boston, MA (US); Christine Huard, Somerville, MA (US); Sreekumar R. Kodangattil, Lexington, MA (US); Jian Li, Chestnut Hill, MA (US); Weining Lu, Boston, MA (US); Xueping Fan, Boston, MA (US); David J. Salant, Boston, MA (US)

(73) Assignees: Pfizer Inc., New York, NY (US); Boston Medical Center Corporation, Boston, MA (US)

( * ) Notice: Subject to any disclaimer, the term of this patent is extended or adjusted under 35 U.S.C. 154(b) by 20 days.

(21) Appl. No.: 16/614,701

(22) PCT Filed: Jun. 8, 2018

(86) PCT No.: PCT/US2018/036629
§ 371 (c)(1),
(2) Date: Nov. 18, 2019

(87) PCT Pub. No.: WO2018/227063
PCT Pub. Date: Dec. 13, 2018

(65) Prior Publication Data
US 2020/0157212 A1    May 21, 2020

Related U.S. Application Data

(60) Provisional application No. 62/517,233, filed on Jun. 9, 2017.

(51) Int. Cl.
| | | |
|---|---|---|
| C07H 21/04 | (2006.01) |
| C12P 21/06 | (2006.01) |
| C12N 15/87 | (2006.01) |
| C12N 1/20 | (2006.01) |
| C12N 15/74 | (2006.01) |
| A61K 39/00 | (2006.01) |
| A61K 39/395 | (2006.01) |
| C07K 16/00 | (2006.01) |
| C07K 16/28 | (2006.01) |
| A61P 13/12 | (2006.01) |
| C12N 15/85 | (2006.01) |

(52) U.S. Cl.
CPC .......... *C07K 16/2803* (2013.01); *A61P 13/12* (2018.01); *C12N 15/85* (2013.01); *C07K 2317/21* (2013.01); *C07K 2317/33* (2013.01); *C07K 2317/34* (2013.01); *C07K 2317/565* (2013.01); *C07K 2317/622* (2013.01); *C07K 2317/76* (2013.01); *C07K 2317/92* (2013.01); *C12N 2015/8518* (2013.01)

(58) Field of Classification Search
None
See application file for complete search history.

(56) References Cited

U.S. PATENT DOCUMENTS

2003/0152921 A1* 8/2003 Dumas Milne Edwards .............. C12N 9/00 435/6.16

FOREIGN PATENT DOCUMENTS

WO    WO2013103811    7/2013

OTHER PUBLICATIONS

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*
Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*
Goel et al., Plasticity within the antigen-combining site may manifest as molecular mimicry in the humoral immune response. J Immunol. Dec. 15, 2004; 173(12):7358-67. (Year: 2004).*
Kanyavuz et al., Breaking the law: unconventional strategies for antibody diversification. Nat Rev Immunol. Jun. 2019; 19(6):355-368. (Year: 2019).*
Howitt et al. Binding site for Robo receptors revealed by dissection of the leucine-rich repeat region of Slit. EMBO J (2004)23:4406-44121. (Year: 2004).*
Evans et al. Robo2 acts in trans to inhibit Slit-Robo1 repulsion in pre-crossing commissural axons. Evans et al. eLife 2015;4: e08407 . (Year: 2015).*
Anonymous, "Anti-Robo2 antibody ab85278," (https://www.abcam.com/Robo2-antibody-ab85278.pdf) (retrieved Jul. 26, 2018) (3 pages).

(Continued)

*Primary Examiner* — Maher M Haddad
(74) *Attorney, Agent, or Firm* — Norton Rose Fulbright US LLP

(57) ABSTRACT

The invention provides antibodies, and antigen-binding fragments thereof, that specifically bind to ROBO2, as well as uses, and methods thereof.

22 Claims, 14 Drawing Sheets
Specification includes a Sequence Listing.

(56) References Cited

OTHER PUBLICATIONS

Anonymous, "Human ROBO2 Antibody, MAB3147," Feb. 7, 2018 (https://www.resources.rndsystems.com/pdfs/datasheets/mab3147.pdf) (retrieved Jul. 26, 2018).
De Wit, et al., "Specification of synaptic connectivity by cell surface interactions," Nature Reviews. *Neuroscience*, 17(1):22-35 (2016).
Fan et al., "SLIT2/ROBO2 signaling pathway inhibits nonmuscle myosin IIA activity and destabilizes kidney podocyte adhesion," *JCI Insight*, 1(19):e86934 (2016).
Gershoni, et al., "Epitope mapping: the first step in developing epitope-based vaccines," Biodmgs, ADIS International Ltd., 21(3):145-156 (2007).
Mather, "The Chick Embryo; A new drug delivery model for neuroblastoma," Thesis, University of Liverpool, Aug. 1, 2014 (138 pages).
Sundaresan, et al., "Dynamic expression patterns of Robo (Robo1 and Robo2) in the developing murine central nervous system," *Journal of Comparative Neurology*, 468(4):467-481 (2004).
Xu et al., "Whole-exome and targeted sequencing identify ROBO1 and ROBO2 mutations as progression-related drivers in myelodysplastic syndromes," *Nature Communications*, 6(8806) (2015).

* cited by examiner

```
ROBO2    PRIVEHPSDVIVSKGEPTTLNCKAEGRPTPTIEWYKDGERVETDKDDPRSHRMLLPSGSL    60

******** ******  ******************* ************************

ROBO1    PRIVEHPSDLIVSKGEPATLNCKAEGRPTPTIEWYKGGERVETDKDDPRSHRMLLPSGSL

ROBO2    FFLRIVHGRRSKPDEGSYVCVARNYLGEAVSRNASLEVALLRDDFRQNPTDVVVAAGEPA   120

********* * **** ************** ******* ********* ** ** ****

ROBO1    FFLRIVHGRKSRPDEGVYVCVARNYLGEAVSHNASLEVAILRDDFRQNPSDVMVAVGEPA

ROBO2    ILECQPPRGHPEPTIYWKKDKVRIDDKEERISIRGGKLMISNTRKSDAGMYTCVGTNMVG   180

************** ****       *** *** ********  ******* * *******

ROBO1    VMECQPPRGHPEPTISWKKDGSPLDDKDERITIRGGKLMITYTRKSDAGKYVCVGTNMVG

ROBO2    ERDSDPAELT    190
         ** *  ****
ROBO1    ERESEVAELT
```

FIG. 9

```
ROBO2   31   PRIVEHPSDVIVSKGEPTTLNCKAEGRPTPTIEWYKDGERVETDKDDPRSHRM    83
ROBO1   68   PRIVEHPSDLIVSKGEPATLNCKAEGRPTPTIEWYKGGERVETDKDDPRSHRM   120
ROBO2   84   LLPSGSLFFLRIVHGRRsKPDEGSYVCVARNYLGEAVSRNASLE   127
ROBO1  121   LLPSGSLFFLRIVHGRKsRPDEGVYVCVARNYLGEAVSHDASLE   164
```

FIG. 10

ANTI-ROBO2 ANTIBODIES, COMPOSITIONS, METHODS AND USES THEREOF

CROSS-REFERENCE TO RELATED APPLICATION

This application is a United States National Phase Application filed under 35 U.S.C. § 371 from International Patent Application No. PCT/US2018/036629, filed on Jun. 8, 2018, which claims the benefit of U.S. Provisional Application No. 62/517,233, filed Jun. 9, 2017, which are whereby incorporated by reference here in their entireties.

SEQUENCE LISTING

The instant application contains a Sequence Listing which has been submitted electronically in ASCII format and is hereby incorporated by reference in its entirety. Said ASCII copy, created on Nov. 18, 2019, is named PCFC-0042-301-SL.txt and is 357,963 bytes in size.

PARTIES TO A JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are BOSTON MEDICAL CENTER CORP. and PFIZER INC.

BACKGROUND

Chronic kidney disease (CKD) is a worldwide public health problem, which often leads to end-stage renal failure. CKD affects an estimated 13% of the population or ~27 million in the United States and over 500 million people worldwide. The prevalence of CKD is predicted to continue to increase because of the ongoing epidemic of diabetes and obesity within the general population. About half a million CKD patients in the US (~7 million worldwide) will progress to end-stage renal disease (ESRD) and need dialysis or kidney transplantation for survival. The morbidity and mortality of ESRD are high and cost Americans at least $40 billion each year.

Proteinuria (i.e., the presence of an excess of serum proteins in the urine which is commonly defined as a urine albumin level >30 mg/day) is an early biomarker, risk factor and surrogate outcome of CKD in patients with and without diabetes. Treatment to reduce the level of proteinuria during early stages of CKD can slow progression to ESRD. However, there is no treatment currently available for CKD patients with proteinuria.

Podocytes are specialized epithelial cells that extend primary and secondary processes to cover the outer surface of the glomerular basement membrane. The actin-rich interdigitating secondary processes (i.e., foot processes) from neighboring podocytes create filtration slits bridged by a semi-porous slit-diaphragm that forms the final barrier to protein permeation. Proteinuria is the clinical signature of podocyte injury in diabetic and non-diabetic kidney disease. There is a growing number of published studies showing that hereditary, congenital, or acquired abnormalities in the molecular component of podocytes leads to proteinuria. Whereas genetic mutations of podocyte slit-diaphragm proteins such as nephrin and podocin are associated with hereditary forms of proteinuric kidney disease, it has become increasingly evident that the proteins that make up and associate with the slit-diaphragm are more than a simple passive structural barrier. Rather, substantial evidence suggests that these proteins form a balanced signaling network that may influence podocyte foot process structure and function through interaction with the actin cytoskeleton.

Roundabout Receptor 2 (ROBO2, also referred to as Roundabout Guidance Receptor 2 or Roundabout homolog 2) is a receptor for SLIT ligands, and SLIT-ROBO2 signaling was first characterized as a chemorepulsive guidance cue to control axon pathfinding during nervous system development. Recent data have shown that ROBO2 is also a podocyte protein expressed at the basal surface of glomerular podocytes in the kidney. ROBO2 forms a complex with nephrin in the glomerular filtration barrier and acts as a negative regulator to inhibit nephrin-induced actin dynamics. The loss of ROBO2 both alters the actin/myosin dynamics of the podocyte as well as increases adhesion to the glomerular basement membrane.

Patients suffering from many glomerular diseases (including Focal Segmental Glomerular Sclerosis) currently have no therapies available to preserve renal function. Further, there is no treatment currently available for CKD patients with proteinuria. Accordingly, there is a long-felt need for a therapeutic that modulates ROBO2-SLIT signaling, thereby preserving or modulating podocyte function and potentially decreasing proteinuria.

SUMMARY OF THE INVENTION

The invention provides antibodies (and antigen-binding fragments thereof) that specifically bind to ROBO2, as well as uses, and associated methods thereof. Those skilled in the art will recognize, or be able to ascertain using no more than routine experimentation, many equivalents to the specific embodiments of the invention described herein. Such equivalents are intended to be encompassed by the following embodiments (E).

E1. An isolated antibody or antigen-binding fragment thereof, that binds to an epitope in Ig Domain 1, or Ig Domains 1 and 2, of Roundabout Receptor 2 (ROBO2), wherein said epitope comprises residue R100, according to the numbering of SEQ ID NO:1.

E2. The antibody or antigen-binding fragment thereof of E1, wherein said epitope further comprises one or more residues selected from the group consisting of: V96, G98, R99, and S101, according to the numbering of SEQ ID NO:1.

E3. The antibody or antigen-binding fragment thereof of E1 or E2, wherein said epitope further comprises residues V96, G98, R99, and S101, according to the numbering of SEQ ID NO:1.

E4. The antibody or antigen-binding fragment thereof of any one of E1-E3, wherein said epitope comprises one or more residues selected from the group consisting of: E69, E72, R79, H81, R82, R94, and P103, according to the numbering of SEQ ID NO:1.

E5. The antibody or antigen-binding fragment thereof of any one of E1-E4, wherein said epitope comprises one or more residues selected from the group consisting of: E69, E72, R79, H81, R82, R94, and P103, according to the numbering of SEQ ID NO:1.

E6. The antibody or antigen-binding fragment thereof of any one of E1-E5, wherein said antibody, or antigen-binding fragment thereof, does not substantially bind to an epitope wherein R100 is replaced with K.

E7. The antibody, or antigen-binding fragment thereof, of any one of E1-E6, wherein said antibody, or antigen-binding fragment thereof, does not substantially bind a mutated epitope wherein the amino acid residue R100 is replaced with K, and wherein the amino acid residue K102 is replaced with R (ROBO2-KSR), according to the numbering of SEQ ID NO:1.

E8. The antibody, or antigen-binding fragment thereof, of any one of E1-E6, wherein said antibody, or antigen-binding fragment thereof, binds said epitope with a binding affinity ($K_D$) value that is at least 100-fold less, at least 200-fold less, at least 300-fold less, at least 400-fold less, at least 500-fold less, at least 600-fold less, at least 700-fold less, at least 800-fold less, at least 900-fold less, or at least 1000-fold less, than its $K_D$ value for an epitope wherein R100 is replaced with K.

E9. The antibody, or antigen-binding fragment thereof, of any one of E1-E8, wherein said antibody, or antigen-binding fragment thereof, does not substantially bind ROBO1.

E10. The antibody, or antigen-binding fragment thereof, of any one of E1-E8, wherein said antibody, or antigen-binding fragment thereof, specifically binds a mutant ROBO1 wherein amino acid residue K137 of ROBO1 is replaced with R, and amino acid residue R139 of ROBO1 is replaced with K (ROBO1-RSK), according to the numbering of SEQ ID NO:9.

E11. The antibody, or antigen-binding fragment thereof, of any one of E1-E8, wherein said antibody, or antigen-binding fragment thereof, binds ROBO2 with a binding affinity ($K_D$) value that is at least 100-fold less, at least 200-fold less, at least 300-fold less, at least 400-fold less, at least 500-fold less, at least 600-fold less, at least 700-fold less, at least 800-fold less, at least 900-fold less, or at least 1000-fold less, than its $K_D$ value for ROBO1.

E12. The antibody, or antigen-binding fragment thereof, of E8 or E11, wherein said $K_D$ value is measured by surface plasmon resonance (SPR), optionally using a Biacore T200 instrument.

E13. The antibody, or antigen-binding fragment thereof, of E8 or E11, wherein said $K_D$ value is measured by bio-layer interferometry (BLI), optionally using a ForteBio Octet instrument.

E14. The antibody, or antigen-binding fragment thereof, of any one of E9-E13, wherein said ROBO1 is a human ROBO1.

E15. The antibody, or antigen-binding fragment thereof, of E14, wherein said ROBO1 comprises SEQ ID NO:13.

E16. The antibody, or antigen-binding fragment thereof, of any one of E1-E15, wherein said ROBO2 is a human ROBO2.

E17. The antibody, or antigen-binding fragment thereof, of E16, wherein said ROBO2 comprises SEQ ID NO:5.

E18. The antibody, or antigen-binding fragment thereof, of any one of E1-E17, comprising a heavy chain variable region (VH) that comprises:
  (a) a VH complementarity determining region one (CDR-H1) comprising the amino acid sequence of SEQ ID NO:24,
  (b) a VH complementarity determining region two (CDR-H2) comprising the amino acid sequence of SEQ ID NO:25; and
  (c) a VH complementarity determining region three (CDR-H3) comprising the amino acid sequence of SEQ ID NO:26.

E19. The antibody, or antigen-binding fragment thereof, of any one of E1-E18, comprising the CDR-H1, CDR-H2, and CDR-H3 sequences of SEQ ID NO:32.

E20. An isolated antibody, or antigen-binding fragment thereof, that specifically binds ROBO2, comprising a VH that comprises:
  (a) a CDR-H1 comprising the amino acid sequence of SEQ ID NO:24,
  (b) a CDR-H2 comprising the amino acid sequence of SEQ ID NO:25; and
  (c) a CDR-H3 comprising the amino acid sequence of SEQ ID NO:26.

E21. The antibody, or antigen-binding fragment thereof, of any one of E1-E20, comprising a VH framework derived from a human germline VH3 framework sequence.

E22. The antibody, or antigen-binding fragment thereof, of any one of E 1-E20, comprising a VH framework derived from a human germline VH1 framework sequence.

E23. The antibody, or antigen-binding fragment thereof, of any one of E1-E20, comprising a VH framework derived from a human germline VH5 framework sequence.

E24. The antibody, or antigen-binding fragment thereof, of any one of E1-E20, comprising a human VH germline consensus framework sequence.

E25. The antibody, or antigen-binding fragment thereof, of any one of E1-E24, comprising a VH framework sequence derived from a human germline VH sequence selected from the group consisting of: DP54, DP47, DP50, DP31, DP46, DP71, DP75, DP10, DP7, DP49, DP51, DP38, DP79, DP78, DP73, VH1 consensus, VH2 consensus, VH3 consensus, VH4 consensus, and VH5 consensus.

E26. The antibody, or antigen-binding fragment thereof, of any one of E1-E25, comprising a framework VH sequence derived from a human germline VH sequence selected from the group consisting of DP54, DP47, DP50, DP31, DP46, DP49, and DP51.

E27. The antibody, or antigen-binding fragment thereof, of any one of E1-E26, comprising a framework VH sequence derived from a human germline VH sequence selected from the group consisting of DP54, DP47, DP50, and DP31.

E28. The antibody, or antigen-binding fragment thereof, of any one of E1-E27, comprising a VH framework sequence derived from a human germline DP54 sequence.

E29. The antibody, or antigen-binding fragment thereof, of any one of E1-E28, comprising a light chain variable region (VL) that comprises:
  (a) a VL complementarity determining region one (CDR-L1) comprising the amino acid sequence of SEQ ID NO:29,
  (b) a VL complementarity determining region two (CDR-L2) comprising the amino acid sequence of SEQ ID NO:30; and
  (c) a VL complementarity determining region three (CDR-L3) comprising the amino acid sequence of SEQ ID NO:31.

E30. The antibody, or antigen-binding fragment thereof, of any one of E1-E29, comprising the CDR-L1, CDR-L2, and CDR-L3 sequences of SEQ ID NO:39.

E31. An isolated antibody, or antigen-binding fragment thereof, that specifically binds ROBO2, comprising the CDR-H1, CDR-H2, and CDR-H3 sequences of SEQ ID NO:32, and the CDR-L1, CDR-L2, and CDR-L3 sequences of SEQ ID NO:39.

E32. An isolated antibody, or antigen-binding fragment thereof, that specially binds ROBO2 comprising:
(i) a VH that comprises:
(a) a CDR-H1 comprising the amino acid sequence of SEQ ID NO:24,
(b) a CDR-H2 comprising the amino acid sequence of SEQ ID NO:25; and
(c) a CDR-H3 comprising the amino acid sequence of SEQ ID NO:26;
and (ii) a VL that comprises:
(a) a CDR-L1 comprising the amino acid sequence of SEQ ID NO:29,
(b) a CDR-L2 comprising the amino acid sequence of SEQ ID NO:30; and
(c) a CDR-L3 comprising the amino acid sequence of SEQ ID NO:31.

E33. The antibody, or antigen-binding fragment thereof, of any one of E1-E32, comprising a VL framework derived from a human germline $V_K$ framework sequence.

E34. The antibody, or antigen-binding fragment thereof, of any one of E1-E32, comprising a VL framework derived from a human germline $V_\lambda$ framework sequence.

E35. The antibody, or antigen-binding fragment thereof, of any one of E1-E32, comprising a human VL germline consensus framework sequence.

E36. The antibody, or antigen-binding fragment thereof, of any one of E1-E35, comprising a VL framework sequence derived from a human germline VL sequence selected from the group consisting of DPK9, DPK12, DPK18, DPK24, HK102_V1, DPK1, DPK8, DPK3, DPK21, Vg_38 K, DPK22, DPK15, DPL16, DPL8, V1-22, Vλ consensus, Vλ1 consensus, Vλ3 consensus, $V_K$ consensus, $V_K$1 consensus, $V_K$2 consensus, and $V_K$3 consensus.

E37. The antibody, or antigen-binding fragment thereof, of any one of E1-E33, E35, and E36, comprising a VL framework sequence derived from a human germline $V_K$1 sequence.

E38. The antibody, or antigen-binding fragment thereof, of any one of E1-E36, comprising a VL framework sequence derived from a human germline VL sequence selected from the group consisting of DPK9, HK102_V1, DPK1, and DPK8.

E39. The antibody, or antigen-binding fragment thereof, of any one of E1-E36, comprising a VL framework sequence derived from a human germline DPK9 sequence.

E40. The antibody, or antigen-binding fragment thereof, of any one of E1-E39, comprising a VL framework sequence and a VH framework sequence, and wherein one or both of the VL framework sequence or VH framework sequence is at least 90% identical to the human germline framework sequence from which it is derived.

E41. The antibody, or antigen-binding fragment thereof, of any one of E1-E40, comprising a VL framework sequence and a VH framework sequence, and wherein one or both of the VL framework sequence or VH framework sequence is at least 90%, at least 91%, at least 92%, at least 93%, at least 94%, at least 95%, at least 96%, at least 97%, at least 98%, at least 99%, or 100% identical to the human germline framework sequence from which it is derived.

E42. The antibody, or antigen-binding fragment thereof, of any one of E1-E41, comprising a VL framework sequence and a VH framework sequence, and wherein one or both of the VL framework sequence or VH framework sequence is identical to the human germline framework sequence from which it is derived.

E43. The antibody, or antigen-binding fragment thereof, of any one of embodiments E1-E42, comprising a VH comprising an amino acid sequence at least 90% identical to any one of SEQ ID NOs: 32, 43, 49, 55, 70, 73, 76, 79, 82, 85, 88, 115, 119, 126, 127, 128, 129, 130, 131, and 132.

E44. The antibody, or antigen-binding fragment thereof, of any one of E1-E43, comprising a VH comprising an amino acid sequence at least 90%, at least 91%, at least 92%, at least 93%, at least 94%, at least 95%, at least 96%, at least 97%, at least 98%, at least 99%, or 100% identical to any one of SEQ ID NOs: 32 and 126-132.

E45. The antibody, or antigen-binding fragment thereof, of any one of E1-E44, comprising a VH comprising the amino acid sequence of any one of SEQ ID NOs: 32 and 126-132.

E46. The antibody, or antigen-binding fragment thereof, of any one of E1-E45, comprising a VL comprising an amino acid sequence at least 90% identical to SEQ ID NO:39, 46, 52, 58, 61, 64, 67, 91, 94, 97, 99, 101, 103, 105, 107, 109, 111, 113, and 133.

E47. The antibody, or antigen-binding fragment thereof, of any one of E1-E46, comprising a VH comprising an amino acid sequence at least 90%, at least 91%, at least 92%, at least 93%, at least 94%, at least 95%, at least 96%, at least 97%, at least 98%, at least 99%, or 100% identical to SEQ ID NO:39 or 133.

E48. The antibody, or antigen-binding fragment thereof, of any one of E1-E47, comprising a VL comprising the amino acid sequence of SEQ ID NO:39 or 133.

E49. The antibody, or antigen-binding fragment thereof, of any one of E1-E48, comprising an Fc domain.

E50. The antibody, or antigen-binding fragment thereof, of E49, wherein the Fc domain is the Fc domain of an IgA (for example $IgA_1$ or $IgA_2$), IgD, IgE, IgM, or IgG (for example $IgG_1$, $IgG_2$, $IgG_3$, or $IgG_4$).

E51. The antibody, or antigen-binding fragment thereof, of E50 wherein the Fc domain is the Fc domain of an IgG.

E52. The antibody, or antigen-binding fragment thereof, of E51, wherein the IgG is selected from the group consisting of $IgG_1$, $IgG_2$, $IgG_3$, or $IgG_4$.

E53. The antibody, or antigen-binding fragment thereof, of E52, wherein the IgG is $IgG_1$.

E54. The antibody, or antigen-binding fragment thereof, of any one of E1-E53, comprising a heavy chain comprising an amino acid sequence at least 90% identical to any one of SEQ ID NOs: 38, 45, 51, 57, 72, 75, 78, 81, 84, 87, 90, 118, 121, 134, 135, 136, 137, 138, 139, and 140.

E55. The antibody, or antigen-binding fragment thereof, of any one of E1-E54, comprising a heavy chain comprising an amino acid at least 90%, at least 91%, at least 92%, at least 93%, at least 94%, at least 95%, at least 96%, at least 97%, at least 98%, at least 99%, or 100% identical to any one of SEQ ID NOs: 38, 134, 135, 136, 137, 138, 139, and 140.

E56. The antibody, or antigen-binding fragment thereof, of any one of E1-E55, comprising a heavy chain comprising the amino acid sequence of any one of SEQ ID NOs: 38, 134, 135, 136, 137, 138, 139, and 140.

E57. The antibody, or antigen-binding fragment thereof, of any one of E1-E56, comprising a light chain comprising an amino acid sequence at least 90% identical to any one of SEQ ID NOs. 42, 48, 54, 60, 63, 66, 69, 93, 96, 98, 100, 102, 104, 106, 108, 110, 112, 114, and 141.

E58. The antibody, or antigen-binding fragment thereof, of any one of E1-E57, comprising a LC comprising an amino acid sequence at least 90%, at least 91%, at least 92%, at least 93%, at least 94%, at least 95%, at least 96%, at least 97%, at least 98%, at least 99%, or 100% identical to SEQ ID NO:42 or 141.

E59. The antibody, or antigen-binding fragment thereof, of any one of E1-E58, comprising a light chain comprising the amino acid sequence of SEQ ID NO:42 or 141.

E60. The antibody, or antigen-binding fragment thereof, of any one of E1-E59, comprising the VH sequence encoded by the plasmid deposited at the ATCC and having ATCC Accession No. PTA-123265 or PTA-123700.

E61. The antibody, or antigen-binding fragment thereof, of any one of E1-E60, comprising the VL sequence encoded by the plasmid deposited at the ATCC and having ATCC Accession No. PTA-123266 or PTA-123701.

E62. An antibody, or antigen binding fragment thereof, comprising a VH encoded by the plasmid deposited at the ATCC and having ATCC Accession No. PTA-123265 or PTA-123700.

E63. An antibody, or antigen binding fragment thereof, comprising a VL encoded by the plasmid deposited at the ATCC and having ATCC Accession No. PTA-123266 or PTA-123701.

E64. An antibody, or antigen binding fragment thereof, comprising a VH encoded by the plasmid deposited at the ATCC and having ATCC Accession No. PTA-123265 and a VL encoded by the plasmid deposited at the ATCC and having ATCC Acc. No. PTA-123266.

E65. An antibody, or antigen binding fragment thereof, comprising a VH encoded by the plasmid deposited at the ATCC and having ATCC Accession No. PTA-123700 and a VL encoded by the plasmid deposited at the ATCC and having ATCC Acc. No. PTA-123701.

E66. An antibody, or antigen binding fragment thereof, comprising a VH encoded by the plasmid deposited at the ATCC and having ATCC Accession No. PTA-123700 and a VL encoded by the plasmid deposited at the ATCC and having ATCC Acc. No. PTA-123266.

E67. An antibody, or antigen binding fragment thereof, comprising a VH encoded by the plasmid deposited at the ATCC and having ATCC Accession No. PTA-123265 and a VL encoded by the plasmid deposited at the ATCC and having ATCC Acc. No. PTA-123701.

E68. An antibody, or antigen-binding fragment thereof, that competes for binding to ROBO2 with an antibody or antigen-binding fragment thereof of any one of E1-E67.

E69. An antibody, or antigen-binding fragment thereof, that competes for binding to ROBO2 with an antibody selected from the group consisting of: Abcs35, 93H2, Ab1, Ab3, Ab9, Ab13, Ab17, Ab21, Ab22, Ab25, Ab29, Ab32, Ab40, Ab45, Ab46, Ab58, Ab83, Ab96, Ab112, Ab123, Abcs1, Abcs2, Abcs4, Abcs5, Abcs12, Abcs20, Abcs25, Abcs40, Abcs50, Abcs55, CTIR2-1, CTIR2-2, CTIR2-3, CTIR2-4, CTIR2-5, CTIR2-6, CTIR2-7, CTIR2-8, CTIR2-9, CTIR2-10, CTIR2-11, CTIR2-12, CTIR2-13, CTIR2-14, CTIR2-15, CTIR2-16, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O.

E70. An antibody, or antigen-binding fragment thereof, that competes for binding to ROBO2 with an antibody selected from the group consisting of: Abcs35, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O.

E71. An antibody, or antigen-binding fragment thereof, that specifically binds ROBO2, wherein said antibody, or antigen-binding fragment thereof, binds substantially the same epitope as an antibody or antigen-binding fragment thereof of any one of E1-E67.

E72. An antibody, or antigen-binding fragment thereof, that specifically binds ROBO2, wherein said antibody, or antigen-binding fragment thereof, binds substantially the same epitope as an antibody selected from the group consisting of: Abcs35, 93H2, Ab1, Ab3, Ab9, Ab13, Ab17, Ab21, Ab22, Ab25, Ab29, Ab32, Ab40, Ab45, Ab46, Ab58, Ab83, Ab96, Ab112, Ab123, Abcs1, Abcs2, Abcs4, Abcs5, Abcs12, Abcs20, Abcs25, Abcs40, Abcs50, Abcs55, CTIR2-1, CTIR2-2, CTIR2-3, CTIR2-4, CTIR2-5, CTIR2-6, CTIR2-7, CTIR2-8, CTIR2-9, CTIR2-10, CTIR2-11, CTIR2-12, CTIR2-13, CTIR2-14, CTIR2-15, CTIR2-16, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O.

E73. An antibody, or antigen-binding fragment thereof, that specifically binds ROBO2, wherein said antibody, or antigen-binding fragment thereof, binds substantially the same epitope as an antibody selected from the group consisting of: Abcs35, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O.

E74. An antibody, or antigen-binding fragment thereof, that specifically binds ROBO2, wherein said antibody, or antigen-binding fragment thereof, binds the same epitope as an antibody selected from the group consisting of: Abcs35, 93H2, Ab1, Ab3, Ab9, Ab13, Ab17, Ab21, Ab22, Ab25, Ab29, Ab32, Ab40, Ab45, Ab46, Ab58, Ab83, Ab96, Ab112, Ab123, Abcs1, Abcs2, Abcs4, Abcs5, Abcs12, Abcs20, Abcs25, Abcs40, Abcs50, Abcs55, CTIR2-1, CTIR2-2, CTIR2-3, CTIR2-4, CTIR2-5, CTIR2-6, CTIR2-7, CTIR2-8, CTIR2-9, CTIR2-10, CTIR2-11, CTIR2-12, CTIR2-13, CTIR2-14, CTIR2-15, CTIR2-16, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O.

E75. An antibody, or antigen-binding fragment thereof, that specifically binds ROBO2, wherein said antibody, or antigen-binding fragment thereof:
(i) binds substantially the same epitope as an antibody selected from Abcs35 and 93H2, and
(ii) does not bind ROBO1, but binds a ROBO1-RSK mutant wherein amino acid residue K137 is replaced with R, and wherein amino acid residue R139 is replaced with K, according to the numbering of SEQ ID NO:9.

E76. The antibody, or antigen-binding fragment thereof, of any one of E1-E75, wherein the antibody or antigen-binding fragment is an Fc fusion protein, a monobody, a maxibody, a bifunctional antibody, an scFab, an scFv, or a peptibody.

E77. The antibody, or antigen-binding fragment thereof, of E1-76, wherein the antibody, or antigen binding fragment thereof, binds ROBO2 with a $K_D$ value of or less than: about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM.

E78. The antibody, or antigen-binding fragment thereof, of E1-77, wherein the antibody, or antigen binding fragment thereof, wherein said antibody or antigen-binding fragment (a) inhibits binding of SLIT and ROBO2; (b) reduces the binding of srGAP1 and ROBO2; or the binding of Nck and ROBO2; and/or (c) inhibits ROBO2-dependent SLIT-N activity.

E79. An isolated nucleic acid molecule, comprising one or more nucleotide sequences encoding the antibody, or antigen-binding fragment thereof, of any one of E1-E78.

E80. An isolated nucleic acid comprising the nucleotide sequence of SEQ ID NO:143

E81. An isolated nucleic acid comprising the nucleotide sequence of SEQ ID NO:144.

E82. An isolated nucleic acid comprising the nucleotide sequence of SEQ ID NO:145.

E83. An isolated nucleic acid comprising the nucleotide sequence of SEQ ID NO:146.

E84. An isolated nucleic acid comprising the nucleotide sequence of the insert of the plasmid deposited at the ATCC and having Accession Number PTA-123265.

E85. An isolated nucleic acid comprising the nucleotide sequence of the insert of the plasmid deposited at the ATCC and having Accession Number PTA-123266.

E86. An isolated nucleic acid comprising the nucleotide sequence of the insert of the plasmid deposited at the ATCC and having Accession Number PTA-123700.

E87. An isolated nucleic acid comprising the nucleotide sequence of the insert of the plasmid deposited at the ATCC and having Accession Number PTA-123701.

E88. A vector comprising the nucleic acid of any one of E79-E87.

E89. A host cell comprising the nucleic acid of any one of E79-E87.

E90. A host cell comprising the vector of E89.

E91. The host cell of E90, wherein said cell is a mammalian cell.

E92. The host cell of E91, wherein said host cell is a CHO cell, a HEK-293 cell, or an Sp2.0 cell.

E93. A method of making an antibody, or antigen-binding fragment thereof, comprising culturing the host cell of any one of E89-E92 under a condition wherein said antibody or antigen-binding fragment is expressed by said host cell.

E94. The method of E93, further comprising isolating said antibody or antigen-binding fragment thereof.

E95. A pharmaceutical composition comprising an antibody or antigen-binding fragment thereof of any one of E1-E78, and a pharmaceutically acceptable carrier or excipient.

E96. A method of reducing the activity of ROBO2, comprising administering to a subject in need thereof a therapeutically effective amount of the antibody, or antigen-binding fragment thereof, of any one of embodiments E1-E78, or the pharmaceutical composition of E95.

E97. A method of treating a renal disease, comprising administering to a subject in need thereof a therapeutically effective amount of the antibody, or antigen-binding fragment thereof, of any one of E1-E78, or the pharmaceutical composition of E95.

E98. A method of preserving or modulating podocyte function, comprising administering to a subject in need thereof a therapeutically effective amount of the antibody, or antigen-binding fragment thereof, of any one of E1-E78, or the pharmaceutical composition of E95.

E99. A method of treating a glomerular disease, comprising administering to a subject in need thereof a therapeutically effective amount of the antibody, or antigen-binding fragment thereof, of any one of any one of E1-E78, or the pharmaceutical composition of E95.

E100. A method of treating Focal Segmental Glomerular Sclerosis (FSGS), comprising administering to a subject in need thereof a therapeutically effective amount of the antibody, or antigen-binding fragment thereof, of any one of E1-E78, or the pharmaceutical composition of E95.

E101. A method of treating nephropathy, comprising administering to a subject in need thereof a therapeutically effective amount of the antibody, or antigen-binding fragment thereof, of any one of E1-E78, or the pharmaceutical composition of E95.

E102. The method of E101, wherein said nephropathy is IgA nephropathy.

E103. The method of any one of E96-E102, wherein said subject is a human.

E104. The method of any one of E96-E103, comprising administering said antibody or antigen-binding fragment thereof, or pharmaceutical composition, intravenously.

E105. The method of any one of E96-E103, comprising administering said antibody or antigen-binding fragment thereof, or pharmaceutical composition, subcutaneously.

E106. The method of any one of E96-E105, wherein said antibody or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, or once every four months.

E107. The antibody, or antigen-binding fragment thereof, of any one of E1-E78, or the pharmaceutical composition of E95, for use as a medicament.

E108. The antibody, or antigen-binding fragment thereof, of any one of E1-E78, or the pharmaceutical composition of E95, for use in reducing the activity of ROBO2 in a subject.

E109. The antibody, or antigen-binding fragment thereof, of any one of E1-E78, or the pharmaceutical composition of E95, for use in preserving or modulating podocyte function in a subject.

E110. The antibody, or antigen-binding fragment thereof, of any one of E1-E78, or the pharmaceutical composition of E95, for use in treating a glomerular disease (such as FSGS) in a subject.

E111. The antibody, or antigen-binding fragment thereof, of any one of E1-E78, or the pharmaceutical composition of E95, for use in treating nephropathy (such as IgA nephropathy) in a subject.

BRIEF DESCRIPTION OF THE DRAWINGS

FIG. 9 shows the alignment of the Ig1 and 2 domains of human ROBO2 and ROBO1. These sequences are from residue 31 to 220 in ROBO2, according to the numbering of SEQ ID NO:1, and 68 to 257 of ROBO1, according to the numbering of SEQ ID NO:9. The RSK motif of ROBO2 from 100 to 102 and KSR motif of ROBO1 from 137-139 are underlined. TOP: residues 31-220 of SEQ ID NO:1; bottom: residues 68 to 257 of SEQ ID NO:9.

FIG. 10 shows the alignment of the Ig1 domains of human ROBO2 from residues 31 to 127 (numbering according to SEQ ID NO:1), aligned with ROBO1 from residues 68-164 (numbering according to SEQ ID NO:9). The amino acid residues that differ between ROBO2 and ROBO1 which could potentially confer the specific recognition of ROBO2, but not ROBO1 by 93H2 antibody are highlighted.

DETAILED DESCRIPTION OF THE INVENTION

1. Overview

Figure 1:
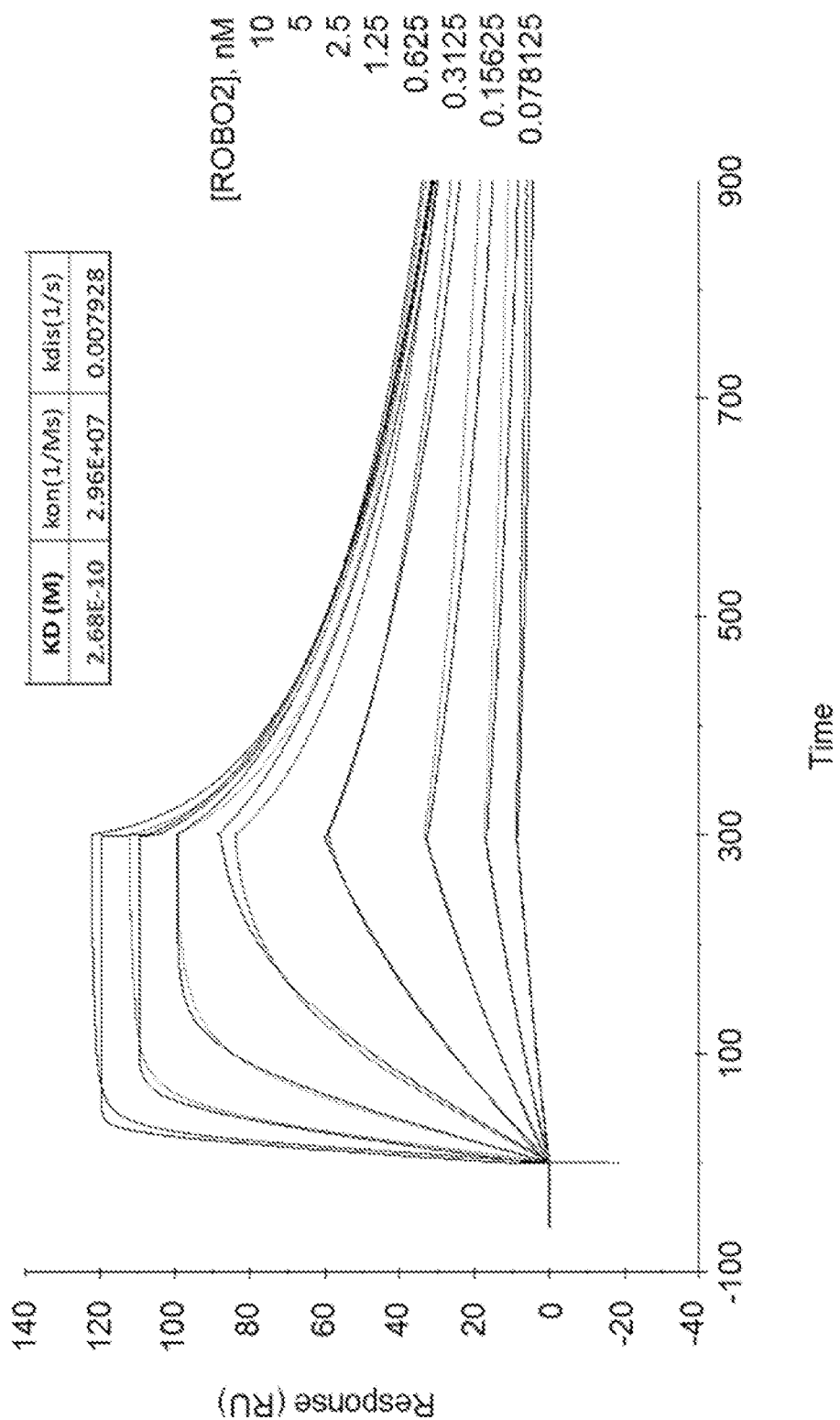
FIG. 1 demonstrates that Abcs35 binds to human ROBO2 with high affinity. Using surface plasmon resonance (SPR), the KD of Abcs35 was determined to be 0.268 nM. First, an 8-point, 2-fold dilution series of Abcs35 was immobilized to 300RU on a CM5 chip; sensors were then exposed to ROBO2 Ig1,Ig2-His. Association and dissociation were followed over time.

Previous studies have shown that, SLIT2/ROBO2 is a negative signal in kidney podocytes which inhibits and counterbalances nephrin induced actin polymerization. Podocyte specific knockout of ROBO2 significantly reduces glomerular defects in proteinuric animal models, protects podocyte foot process structure, and protects mice from nephrotoxic serum (NTS) induced severe proteinuria. Loss of ROBO2 also preserves podocyte adhesion to the Glioblastoma (GBM) in a high salt (DOCA) model of hypertensive nephropathy due to regulation of myosin dynamics. These data, along with the observation that a patient with ROBO2 chromosomal translocation lacks proteinuria, led the inventors to believe that blocking of SLIT2-ROBO2 signaling pathway could increase nephrin-induced actin polymerization to reduce proteinuria. Blocking of ROBO2 signaling may also restore glomerular filtration barrier in proteinuric disease by up-regulation of nephrin induced actin polymerization. As such, a neutralizing antibody that inhibits binding of SLIT ligands to ROBO2 could lead to a renoprotection effect.

One particular difficulty in obtaining a ROBO2-specific antibody is that ROBO2 and ROBO1 share a high degree of sequence similarity, in particular in their ligand-binding domains Ig1 and Ig2 (see sequence alignment in FIGS. 9 and 10). 93% of the residues in the SLIT-binding domain (Ig1 and Ig2) of ROBO1 and ROBO2 are either identical or similar. Surprisingly, as disclosed and exemplified herein, the inventors have identified a unique epitope in ROBO2 and produced monoclonal antibodies that specifically bind to ROBO2 but not ROBO1. In particular, this unique epitope comprises a key residue that determines the specificity of the antibody: residue R100 (according to the numbering of human ROBO2 shown in SEQ ID NO:1). As shown in Example 5, mutating residues 100-102 of ROBO2 (RSK) to corresponding residues of ROBO1 (KSR) abolishes the binding of ROBO2-specific antibodies; while mutating corresponding residues of ROBO1 (KSR) to ROBO2 (RSK) causes ROBO2-specific antibodies to bind to the mutated ROBO1. Since S101 is conserved/identical between ROBO2 and ROBO1, and the crystal structure shows that the side chain of K102 is pointing away from the antibody-antigen interface (which means that K102 is not directly involved in ROBO2-antibody interaction), our data clearly support that R100 is solely driving the binding specificity of ROBO2-specific antibodies.

The discovery of this ROBO2-specific epitope is very surprising. Not only is R100 solely responsible for ROBO2-specificity, but also, in most cases, R to K substitution is considered "conservative" substitution (both have positively-charged side chains) and does not substantially affect binding. This is not the case here. Mutating R to K abolishes antigen-antibody binding, illustrating the importance of R residue at this position.

2. Definitions

Specific amino acid residue positions in ROBO2 are numbered according to SEQ ID NO:1 (human ROBO2). However, the present invention is not limited to SEQ ID NO:1. Corresponding residues from other ROBO2 homologs, isoforms, variants, or fragments can be identified according to sequence alignment or structural alignment that is known in the art. For example, alignments can be done by hand or by using well-known sequence alignment programs such as ClustalW2, or "BLAST 2 Sequences" using default parameters.

Antibodies

An "antigen-binding fragment" of an antibody refers to a fragment of a full-length antibody that retains the ability to specifically bind to an antigen (preferably with substantially the same binding affinity). Examples of an antigen-binding fragment includes (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., 1989 Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al., 1988, Proc. Natl. Acad. Sci. USA 85:5879-5883. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al, 1993, Proc. Natl. Acad. Sci. USA 90:6444-6448; Poljak et al., 1994, Structure 2:1121-1123).

An antibody "variable domain" refers to the variable region of the antibody light chain (VL) or the variable region of the antibody heavy chain (VH), either alone or in combination. As known in the art, the variable regions of the heavy and light chains each consist of four framework regions (FR) connected by three complementarity determining regions (CDRs), and contribute to the formation of the antigen-binding site of antibodies.

"Complementarity Determining Regions" (CDRs) can be identified according to the definitions of the Kabat, Chothia, the accumulation of both Kabat and Chothia, AbM, contact, North, and/or conformational definitions or any method of CDR determination well known in the art. See, e.g., Kabat et al., 1991, Sequences of Proteins of Immunological Interest, 5th ed. (hypervariable regions); Chothia et al., 1989, Nature 342:877-883 (structural loop structures). The identity of the amino acid residues in a particular antibody that make up a CDR can be determined using methods well known in the art. AbM definition of CDRs is a compromise between Kabat and Chothia and uses Oxford Molecular's AbM antibody modeling software (Accelrys®). The "contact" definition of CDRs is based on observed antigen contacts, set forth in MacCallum et al., 1996, J. Mol. Biol., 262:732-745. The "conformational" definition of CDRs is based on residues that make enthalpic contributions to antigen binding (see, e.g., Makabe et al., 2008, J. Biol. Chem., 283: 1156-1166). North has identified canonical CDR conformations using a different preferred set of CDR definitions (North et al., 2011, J. Mol. Biol. 406: 228-256). In another approach, referred to herein as the "conformational definition" of CDRs, the positions of the CDRs may be identified as the residues that make enthalpic contributions to antigen binding (Makabe et al., 2008, J Biol. Chem. 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, North, extended, AbM, contact, and/or conformational definitions.

Residues in a variable domain are numbered according Kabat, which is a numbering system used for heavy chain variable domains or light chain variable domains of the compilation of antibodies. See, Kabat et al., 1991, Sequences of Proteins of Immunological Interest, 5th Ed. Public Health Service, National Institutes of Health, Bethesda, Md. Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the version 2.3.3 release of Abysis (www.abysis.org) is used herein to assign Kabat numbering to variable regions CDR-L1, CDR-L2, CDR-L3, CDR-H2, and CDR-H3. AbM definition is used for CDR-H1.

Specific amino acid residue positions in an antibody may also be numbered according to Kabat.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3 CDR3-FR4.

An "epitope" refers to the area or region of an antigen to which an antibody specifically binds, e.g., an area or region comprising residues that interacts with the antibody. Epitopes can be linear or conformational.

The term "paratope" is derived from the above definition of "epitope" by reversing the perspective, and refers to the area or region of an antibody molecule which is involved in binding of an antigen, e.g., an area or region comprising residues that interacts with the antigen. A paratope may be linear or conformational (such as discontinuous residues in CDRs).

The epitope/paratope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, Hydrogen/deuterium exchange Mass Spectrometry (HX-MS) and various competition binding methods. As each method relies on a unique principle, the description of an epitope is intimately linked to the method by which it has been determined. Thus, the epitope/paratope for a given antibody/antigen pair will be defined differently depending on the mapping method employed.

At its most detailed level, the epitope/paratope for the interaction between an antibody (Ab) and antigen (Ag) can be defined by the spatial coordinates defining the atomic contacts present in the Ag-Ab interaction, as well as information about their relative contributions to the binding thermodynamics. At one level, an epitope/paratope residue can be characterized by the spatial coordinates defining the atomic contacts between the Ag and Ab. In one aspect, the epitope/paratope residue can be defined by a specific criterion, e.g., distance between atoms in the Ab and the Ag (e.g., a distance of equal to or less than about 4 Å (such as 3.8 Å used in the Examples here) from a heavy atom of the cognate antibody and a heavy atom of the antigen. In another aspect, an epitope/paratope residue can be characterized as participating in a hydrogen bond interaction with the cognate antibody/antigen, or with a water molecule that is also hydrogen bonded to the cognate antibody/antigen (water-mediated hydrogen bonding). In another aspect, an epitope/paratope residue can be characterized as forming a salt bridge with a residue of the cognate antibody/antigen. In yet another aspect, an epitope/paratope residue can be characterized as a residue having a non-zero change in buried surface area (BSA) due to interaction with the cognate antibody/antigen. At a less detailed level, epitope/paratope can be characterized through function, e.g., by competition binding with other Abs. The epitope/paratope can also be defined more generically as comprising amino acid residues for which substitution by another amino acid will alter the characteristics of the interaction between the Ab and Ag (e.g., alanine scanning).

In the context of an X-ray derived crystal structure defined by spatial coordinates of a complex between an antibody, e.g., a Fab fragment or two Fab fragments, and its antigen, unless otherwise specified, an epitope residue refers to a ROBO2 residue (i) having a heavy atom (i.e., a non-hydrogen atom) that is within a distance of about 4 Å (e.g., 3.8 Å) from a heavy atom of the cognate antibody; (ii) participating in a hydrogen bond with a residue of the cognate antibody, or with a water molecule that is also hydrogen bonded to the cognate antibody (water-mediated hydrogen bonding), (iii) participating in a salt bridge to a residue of the cognate antibody, and/or (iv) having a non-zero change in buried surface area (BSA) due to interaction with the cognate antibody. In general, a cutoff is imposed for BSA to avoid inclusion of residues that have minimal interactions. Therefore, unless otherwise specified, epitope residues under category (iv) are selected if it has a BSA of 20 $Å^2$ or greater, or is involved in electrostatic interactions when the antibody binds to ROBO2. Similarly, in the context of an X-ray derived crystal structure, unless otherwise specified or contradicted by context, a paratope residue, refers to an antibody residue (i) having a heavy atom (i.e., a non-hydrogen atom) that is within a distance of about 4 Å from a heavy atom of ROBO2, (ii) participating in a hydrogen bond with a ROBO2 residue, or with a water molecule that is also hydrogen bonded to ROBO2 (water-mediated hydrogen bonding), (iii) participating in a salt bridge to a residue of ROBO2, and/or (iv) having a non-zero change in buried surface area due to interaction with ROBO2. Again, unless otherwise specified, paratope residues under category (iv) are selected if it has a BSA of 20 $Å^2$ or greater, or is involved in electrostatic interactions when antibody binds to ROBO2. Residues identified by (i) distance or (iv) BSA are often referred to as "contact" residues.

From the fact that descriptions and definitions of epitopes, dependent on the epitope mapping method used, and obtained at different levels of detail, it follows that comparison of epitopes for different Abs on the same Ag can similarly be conducted at different levels of detail. For example, epitopes described on the amino acid level, e.g., determined from an X-ray structure, are said to be identical if they contain the same set of amino acid residues. Epitopes characterized by competition binding are said to be overlapping if the binding of the corresponding antibodies are mutually exclusive, i.e., binding of one antibody excludes simultaneous or consecutive binding of the other antibody; and epitopes are said to be separate (unique) if the antigen is able to accommodate binding of both corresponding antibodies simultaneously.

The epitope and paratope for a given antibody/antigen pair may be identified by routine methods. For example, the general location of an epitope may be determined by assessing the ability of an antibody to bind to different fragments or variant ROBO2 polypeptides as more fully described previously elsewhere herein. Specific residues within ROBO2 that make contact with specific residues within an antibody may also be determined using routine methods, such as those described in the examples. For example, antibody/antigen complex may be crystallized. The crystal structure may be determined and used to identify specific sites of interaction between the antibody and antigen.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a ROBO2 epitope is an antibody that binds this epitope with greater affinity, avidity, more readily, and/or with greater duration than it binds to other ROBO2 epitopes or non-ROBO2 epitopes. It is also understood by reading this definition that, for example, an antibody (or moiety or epitope) which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody which recognizes and binds to its cognate antigen in a sample, but does not substantially recognize or bind other molecules in the sample, specifically binds to that cognate antigen. Thus, under designated assay conditions, the specified binding moiety (e.g., an antibody or an antigen-binding portion thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, BIAcore™ (GE Healthcare, Piscataway, N.J.), fluorescence-activated cell sorting (FACS), Octet™ (FortéBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice background signal or noise and more typically more than 10 times background, even more specifically, an antibody is said to "specifically bind" an antigen when the equilibrium dissociation constant ($K_D$) value is 1 µM, such as ≤100 nM, ≤10 nM, ≤100 pM, ≤10 pM, or ≤1 pM.

The term "compete", as used herein with regard to an antibody, means that binding of a first antibody, or an antigen-binding portion thereof, to an antigen reduces the subsequent binding of the same antigen by a second antibody or an antigen-binding portion thereof. In general, the binding a first antibody creates steric hindrance, conformational change, or binding to a common epitope (or portion thereof), such that the binding of the second antibody to the same antigen is reduced. Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE® system). For example, SPR can be used in an in vitro competitive binding inhibition assay to determine the ability of one antibody to inhibit the binding of a second antibody. Another assay for measuring antibody competition uses an ELISA-based approach.

Furthermore, a high throughput process for "binning" antibodies based upon their competition is described in International Patent Application No. WO2003/48731. Competition is present if one antibody (or fragment) reduces the binding of another antibody (or fragment) to ROBO2. For example, a sequential binding competition assay may be used, with different antibodies being added sequentially. The first antibody may be added to reach binding that is close to saturation. Then, the second antibody is added. If the binding of second antibody to ROBO2 is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other. An exemplary antibody competition assay (and overlapping epitope analysis) by SPR is provided in the Examples.

The term "treatment" includes prophylactic and/or therapeutic treatments. If it is administered prior to clinical manifestation of a condition, the treatment is considered prophylactic. Therapeutic treatment includes, e.g., ameliorating or reducing the severity of a disease, or shortening the length of the disease.

"About" or "approximately," when used in connection with a measurable numerical variable, refers to the indicated value of the variable and to all values of the variable that are within the experimental error of the indicated value (e.g. within the 95% confidence interval for the mean) or ±10% of the indicated value, whichever is greater. Numeric ranges are inclusive of the numbers defining the range.

Binding Affinity

The binding affinity of an antibody can be expressed as $K_D$ value, which refers to the dissociation rate of a particular antigen-antibody interaction. $K_D$ is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M), and the smaller the $K_D$, the stronger the affinity of binding. $K_D$ values for antibodies can be determined using methods well established in the art. One exemplary method for measuring Kd is surface plasmon resonance (SPR), typically using a biosensor system such as a BIACORE® system. BIAcore kinetic analysis comprises analyzing the binding and dissociation of an antigen from chips with immobilized molecules (e.g. molecules comprising epitope binding domains), on their surface. Another method for determining the Kd of an antibody is by using Bio-Layer Interferometry, typically using OCTET® technology (Octet QKe system, ForteBio). Alternatively, or in addition, a KinExA® (Kinetic Exclusion Assay) assay, available from Sapidyne Instruments (Boise, Id.) can also be used.

In some aspects, the $K_D$ value is measured by surface plasmon resonance (SPR). ROBO2 may be immobilized, e.g., on a solid surface. ROBO2 may be immobilized to a chip, for example by covalent coupling (such as amine coupling). The chip may be a CM5 sensor chip.

As the analyte binds to the ligand the accumulation of protein on the sensor surface causes an increase in refractive index. This refractive index change is measured in real time (sampling in a kinetic analysis experiment is taken every 0.1 s), and the result plotted as response units (RU) versus time (termed a sensorgram). Importantly, a response (background response) will also be generated if there is a difference in the refractive indices of the running and sample buffers. This background response must be subtracted from the sensorgram to obtain the actual binding response. The background response is recorded by injecting the analyte through a control or reference flow cell, which has no ligand or an irrelevant ligand immobilized to the sensor surface. The real-time measurement of association and dissociation of a binding interaction allows for the calculation of association and dissociation rate constants and the corresponding affinity constants. One RU represents the binding of 1 pg of protein per square mm. More than 50 pg per square mm of analyte binding is generally needed in practice to generate good reproducible responses. Between 85 and 370 RU of ROBO2 may be immobilized. Between 85 and 225 RU of ROBO2 may be immobilized.

Dissociation of the antibody from the ROBO2 may be monitored for about 3600 seconds. The SPR analysis may be conducted, and the data collected at between about 15° C. and about 37° C. The SPR analysis may be conducted, and the data collected at between about 25° C. and 37° C. The SPR analysis may be conducted, and the data collected at about 37° C. The SPR analysis may be conducted, and the data collected at 37° C. The $K_D$ value may be measured by SPR using a BIAcore T200 instrument. The SPR rates and affinities may be determined by fitting resulting sensorgram data to a 1:1 model in BIAcore T200 Evaluation software version 1.0. The collection rate may be about 1 Hz.

Another method for determining the $K_D$ of an antibody is by using Bio-Layer Interferometry (BLI), typically using OCTET® technology (Octet QKe system, ForteBio). In some embodiments, biosensor analysis is used. Typically, one interactant is immobilized on the surface of the biosensor ("ligand," such as an antibody) and the other remains in solution ("analyte", such as an antigen). The assay begins with an initial baseline or equilibration step using assay buffer. Next, a ligand (such as an antibody) is immobilized on the surface of the biosensor (loading), either by direct immobilization or capture-based method. After ligand immobilization, biosensors are dipped into buffer solution for a baseline step to assess assay drift and determine loading level of ligand. After the baseline step, biosensors are dipped into a solution containing the ligand's binding partner, the analyte (association). In this step, the binding interaction of the analyte to the immobilized ligand is measured. Following analyte association, the biosensor is dipped into buffer solution without analyte, and the bound analyte is allowed to come off the ligand (dissociation). The series of assay steps is then repeated on new or regenerated biosensors for each analyte being tested. Each binding response is measured and reported in real time on a sensorgram trace. The instrument may be Octet QKe system, Octet RED96 system, Octet QK384 system, or RED384 system.

3. Roundabout (ROBO) Receptors

The secreted SLIT glycoproteins and their Roundabout (ROBO) receptors were originally identified as important axon guidance molecules. They function as a repulsive cue with an evolutionarily conserved role in preventing axons from migrating to inappropriate locations during the assembly of the nervous system. In addition, the SLIT-ROBO interaction is involved in the regulation of cell migration, cell death and angiogenesis and, as such, has a pivotal role during the development of other tissues such as the lung, kidney, liver and breast.

Figure 14:
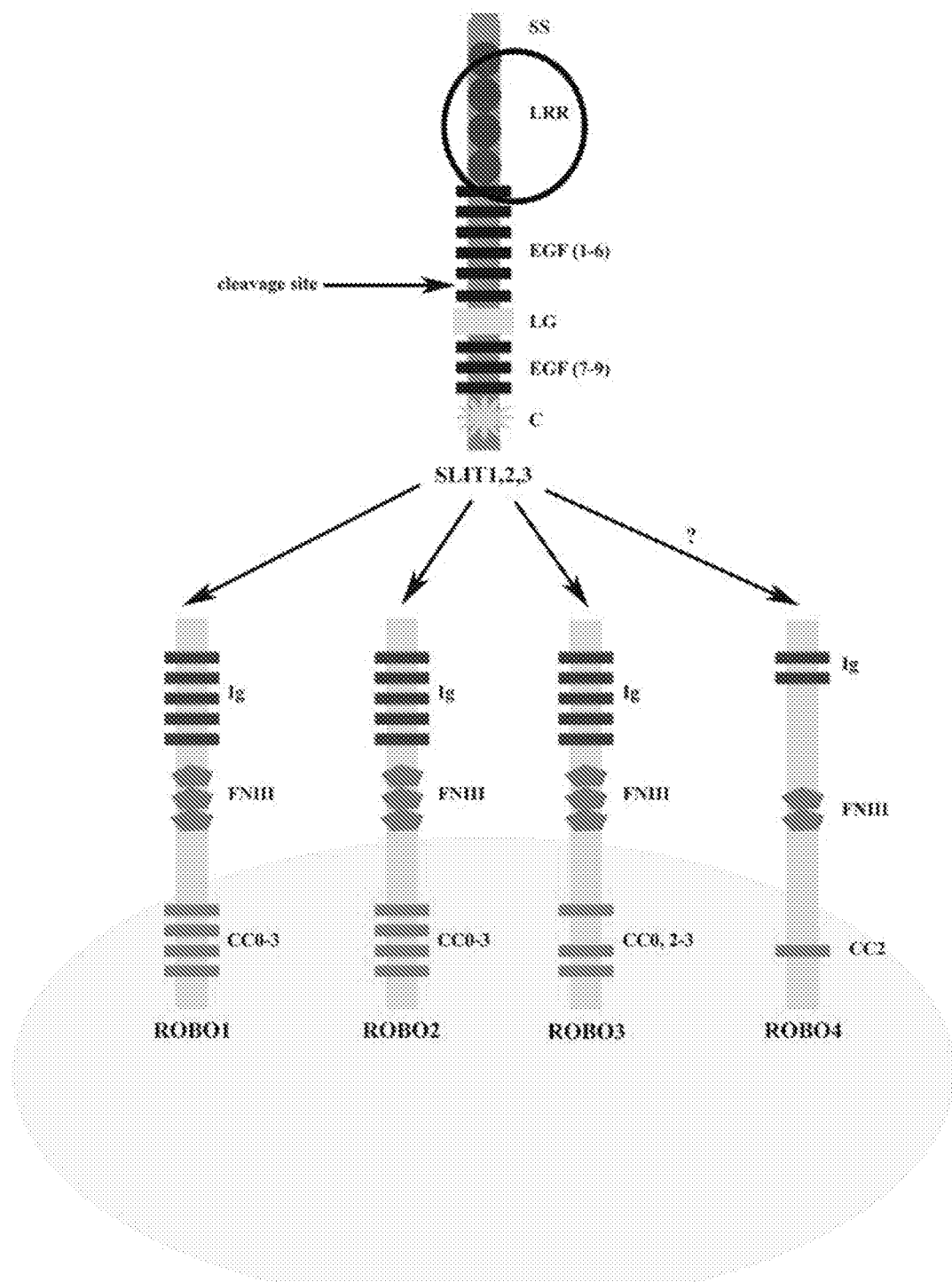
FIG. 14 is a graphic presentation showing the domains of SLIT and ROBO proteins.

While invertebrates have a single SLIT protein; vertebrates have three homologous SLITs named SLIT1, SLIT2 and SLIT3. SLITs are secreted proteins associated with the extracellular matrix. The protein sequence of all SLITs shows a high degree of conservation and have the same structure: an N-terminus signal peptide; four tandem leucine-rich repeat domains (LRR) termed D1-D4; six epidermal growth factor (EGF)-like domains; a laminin G-like domain; a further one (invertebrates) or three (vertebrates) EGF-like domains and a C terminal cysteine knot domain (FIG. 14). SLITS can be cleaved to yield a short C-terminus fragment of unknown function (SLIT-C product) and a long N-terminus fragment (SLIT-N product) that is active and mediates binding to ROBOs. SLIT ligands, as well as cleavage products (e.g., SLIT-N) described herein can be used to assess ROBO2 activity, as well as neutralizing effect of a ROBO2-antibody.

Four ROBO receptors have been characterized in vertebrates: ROBO1/Dutt1; ROBO2; ROBO3/Rig-1 and ROBO4/Magic Roundabout. ROBO1, ROBO2 and ROBO3 share a common extracellular domain structure that is reminiscent of cell adhesion molecules. This region contains five immunoglobulin-like (Ig) domains followed by three fibronectin type 3 (FN3) repeats (FIG. 14). The D2 LRR domain of the SLITs and Ig1 and Ig2 domains of the ROBOs are evolutionary conserved and are involved in binding. Ig1 and Ig2 domains of ROBO together are also referred to as SLIT-binding domain.

Exemplary ROBO sequences are provided in Table 11. The sequence of full-length human ROBO2 precursor is shown as SEQ ID NO:1. A signal peptide (residues 1-21 of SEQ ID NO:1) of the precursor is cleaved to produce mature ROBO2. Residues 22-859 form extracellular domain, residues 860-880 form transmembrane domain, and residue 881-1378 form cytoplasmic domain.

Functional domains of other ROBO proteins are known or can be determined by sequence alignment against human ROBO2 described herein.

Upon ROBO-SLIT binding, Rho GTPases and their regulators (GAPs and GEFs) are involved in downstream signaling pathway. In the presence of SLIT, SLIT-ROBO Rho GTPase activating protein 1 (srGAP1) binds to the CC3 domain of ROBO and inactivates RhoA and Cdc42. These effector proteins are able to mediate, among other outcomes, repulsion, control of cytoskeletal dynamics and cell polarity. In the presence of SLIT, Vilse/CrossGAP can also bind to the CC2 domain of ROBO and inhibit Rac1 and Cdc42. Rac1 is also activated by the recruitment of the GEF protein Son of sevenless (Sos) via the adaptor protein Dreadlocks (Dock), which binds to the CC2-3 domain of ROBO. This activates the downstream target of Rac1 and p21-activated kinase (Pak), which also binds to ROBO CC2-3 domains. These downstream signaling partners of ROBO control repulsion and cytoskeletal dynamics. The tyrosine kinase Abelson (Abl) can also bind ROBO CC3 domain and antagonizes ROBO signaling through phosphorylation of the CC1 domain and mediates cell adhesion. Enabled (Ena), a substrate of Abl, also binds ROBO CC1 and CC2 domains. All these downstream ROBO-SLIT molecules may be used to assess ROBO2 activity, as well as neutralizing effect of a ROBO2-antibody.

In the kidney, ROBO2 forms a complex with nephrin through adaptor protein Nck. In contrast to the role of nephrin that promotes actin polymerization, SLIT-ROBO2 signaling inhibits nephrin-induced actin polymerization. Thus, the binding of ROBO2 intracellular domain and Nck may be used to assess ROBO2 activity, as well as neutralizing effect of a ROBO2-antibody.

In some aspects, the ROBO2 is human ROBO2. In some aspects, the sequence of wild type ROBO2 is SEQ ID NO:1. In some aspects, the ROBO2 is rat ROBO2. In some aspects, the ROBO2 is mouse ROBO2. In some aspects, the ROBO2 is primate ROBO2. In some aspects, the ROBO2 is ape ROBO2. In some aspects, the ROBO2 is monkey ROBO2. In some aspects, the ROBO2 is cynomologus monkey ROBO2.

Exemplary human SLIT2 sequence is provided in Table 11 (SEQ ID NO:142). A signal peptide (residues 1-30 of SEQ ID NO:142) of the precursor is cleaved to produce mature SLIT2. Residues 31-1131 form SLIT-N product, and residues 1122-1529 form SLIT-C product. Functional domains of other SLIT proteins are known or can be determined by sequence alignment against human SLIT2 described herein.

4. Antibodies to ROBO2

In some aspects, the invention provides ROBO2 antibodies. In some embodiments, the antibody specifically binds ROBO2, but does not substantially bind its close family member ROBO1. Sequences of exemplary antibodies of the invention are shown in Table 11. As shown in the Examples, in certain embodiments, the antibody of the invention inhibits the binding of SLIT to ROBO2, and is hence referred to as a "neutralizing" or "blocking" antibody. A neutralizing or blocking antibody, means that an antibody whose binding to ROBO2: inhibits the interaction between ROBO2 or an ROBO2 fragment and its ligand SLIT; and/or (ii) results in inhibition of at least one biological function of ROBO2. Assays to determine the neutralization by an antibody of the invention are described elsewhere herein and/or known in the art.

In certain embodiments, the antibody, or antigen-binding fragment thereof, bind to ROBO2 with a binding affinity ($K_D$) value that is at least 100-fold less, than its $K_D$ value for a ROBO1 under substantially the same assay conditions. For example, the ratio of $K_D$ for ROBO2 versus $K_D$ for ROBO1 can be 1:100 or less, 1:250 or less, 1:500 or less, 1:1000 or less, 1:2500 or less, 1:5000 or less, or 1:10,000 or less.

Figure 12:
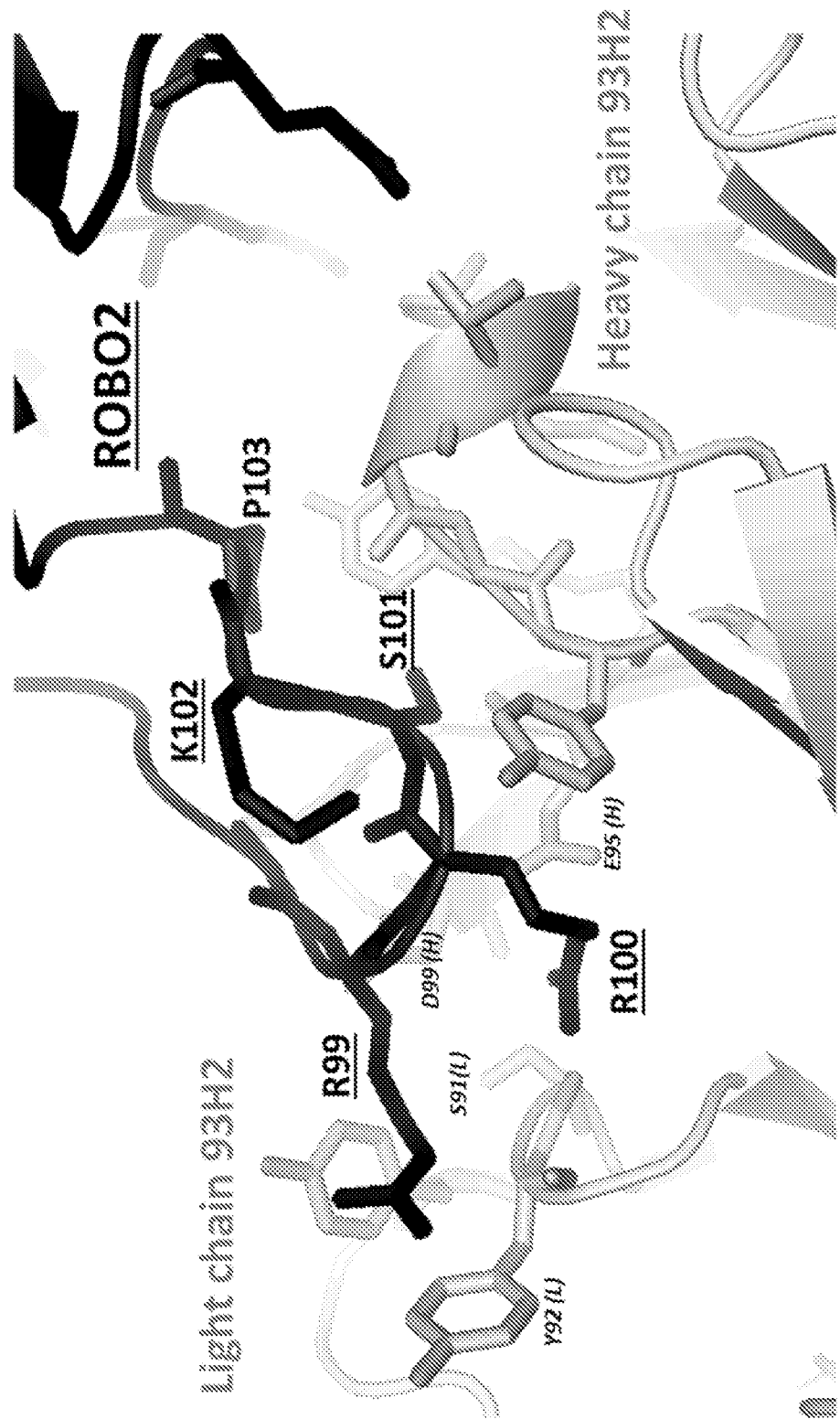
FIG. 12 depicts the specific amino acid residue interactions between 93H2 and ROBO2 Ig1, in particular near "RSK" sequence (residues 100-102) of ROBO2.

As shown in the Examples, the principal binding epitope in human ROBO2 targeted by the ROBO2-specific antibody is a flexible loop (residues H97-P103 of SEQ ID NO:1) in the Ig1 domain (FIG. 12). Additional minor epitope residues that also contribute to binding is via a separate loop (E72-H81) of ROBO2 (SEQ ID NO:1). However, the binding to the latter epitope is optional.

Crystal structure studies also show that the stability of principal interface between antibody and ROB2 is largely contributed by R99 and R100 of ROBO2 (FIG. 12). Since R99 is conserved between ROBO1 and ROBO2, R100 appears to be the sole residue that determines binding specificity of an exemplary antibody of the invention—antibody 93H2. That is, when R100 is replaced with corresponding ROBO1 residue K137, the mutation abolishes the binding of ROBO2-specific antibodies. In contrast, mutating the corresponding residue of ROBO1 K137 to R (corresponding to R100 of SEQ ID NO:1) causes ROBO2-specific antibodies to bind to the mutated ROBO1 (referred to herein as "ROBO1-RSK", see Table 14). Accordingly, in one aspect, the invention provides an antibody or antigen-binding fragment thereof, that binds to an epitope in Ig Domain 1, or Ig Domains 1 and 2 of ROBO2, wherein the epitope comprises residue R100; in certain embodiments, the antibody or antigen-binding fragment does not bind a mutated epitope comprises K100, according to the numbering of SEQ ID NO:1.

The antibodies of the invention demonstrate exquisite sensitivity for the RSK motif at amino acid residues 100-102 of ROBO2, according to the numbering of SEQ ID NO:1. More specifically, when the RSK motif at amino acid residues 100-102 of ROBO2, according to the numbering of SEQ ID NO:1, are replaced with the corresponding ROBO1-KSR motif, i.e., amino acid residues K137, S138 and R139, according to the numbering of SEQ ID NO:9, the mutation abolishes the binding of ROBO2-specific antibodies of the invention. Additionally, mutating corresponding residues of ROBO1 (K137 and R139, according to the numbering of SEQ ID NO:9) to ROBO2 residues R100 and K102, according to the numbering of SEQ ID NO:1) causes ROBO2-specific antibodies of the invention to bind to the mutated ROBO1, referred to herein as ROBO1-RSK. Accordingly, in one aspect, the invention provides an antibody or antigen-binding fragment thereof, that binds to an epitope in Ig Domain 1, or Ig Domains 1 and 2 of ROBO2, wherein said epitope comprises residues R100, S101, and optionally K102 (K102 is optional, see Table 10A), but does not bind a mutated ROBO2 epitope wherein R100 is replaced with K, K102 is replaced with R, and S101 remains unchanged, according to the numbering of SEQ ID NO:1 (the mutated ROBO2 is referred to herein as "ROBO2-KSR"). Further, the antibody of the invention binds to a ROBO1 mutant wherein the amino acid residues K137 and R139 are replaced with R137 and K139, respectively, according to the amino acid sequence of SEQ ID NO:9 (the mutated ROBO1 is referred to herein as "ROBO1-RSK"). Thus, surprisingly, the antibody of the invention binds wild type ROBO2, does not bind wild type ROBO1, does not bind ROBO2-KSR mutant but binds ROBO1-RSK mutant. The invention therefore encompasses an antibody that binds wild type ROBO2, does not bind ROBO1, but binds ROBO1-RSK mutant.

TABLE 16

| wild type ROBO2 | R100 | S101 | K102 |
| wild type ROBO1 | K137 | S138 | R139 |
| ROBO2-KSR | K100 | S101 | R102 |
| ROBO1-RSK | R137 | S138 | K139 |

In certain embodiments, the antibody, or antigen-binding fragment thereof, binds to a ROBO2 epitope comprising R100 with a binding affinity ($K_D$) value that is at least 100-fold less under substantially the same assay conditions, than its $K_D$ value for a ROBO2 epitope wherein R100 is replaced with K. For example, the ratio of $K_D$ for a ROBO2 epitope comprising R100 versus $K_D$ for a ROBO2 epitope wherein R100 is replaced by K can be 1:100 or less, 1:250 or less, 1:500 or less, 1:1000 or less, 1:2500 or less, 1:5000 or less, or 1:10,000 or less.

In certain embodiments, the epitope may further comprise one or more of the following residues in addition to R100: V96, G98, R99, and S101. See Table 10A ("primary" residues). In certain embodiments, the epitope may further comprise one or more residues that are believed to be contributing to antibody-antigen interaction: E69, E72, R79, H81, R82, R94, and P103. See Table 10A ("contributing" residues). In certain embodiments, the epitope may further comprise one or more residues that are believed to be "optional" for antibody-antigen interaction: K66, D67, R70, V71, T73, D74, D77, P78, H97, and K102. See Table 10A ("optional" residues).

The antibody, or an antigen binding fragment thereof, may be selected from the group consisting of: Abcs35, 93H2, Ab1, Ab3, Ab9, Ab13, Ab17, Ab21, Ab22, Ab25, Ab29, Ab32, Ab40, Ab45, Ab46, Ab58, Ab83, Ab96, Ab112, Ab123, Abcs1, Abcs2, Abcs4, Abcs5, Abcs12, Abcs20, Abcs25, Abcs40, Abcs50, Abcs55, CTIR2-1, CTIR2-2, CTIR2-3, CTIR2-4, CTIR2-5, CTIR2-6, CTIR2-7, CTIR2-8, CTIR2-9, CTIR2-10, CTIR2-11, CTIR2-12, CTIR2-13, CTIR2-14, CTIR2-15, CTIR2-16, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O, antigen binding fragments thereof, and mutants, variants, derivatives and substantially similar versions thereof.

In certain embodiments, the antibody, or antigen binding fragment thereof, comprises one or more of the following paratope residues: (i) heavy chain T30, G31, Y32, Y33, E95, G97, and D99, and (ii) light chain Y32 and Y92. See Table 10B ("primary" residues). In certain embodiments, the paratope may further comprise one or more residues that are believed to be contributing to antibody-antigen interaction: (i) heavy chain G26, T28, W50, K53, D98, D101, and I102, and (ii) light chain S91, G93, and T96. See Table 10B ("contributing" residues). In certain embodiments, the paratope may further comprise one or more residues that are believed to be "optional" for antibody-antigen interaction: (i) heavy chain E1, V2, Y27, H35, T73, R94, and S96; and (ii) light chain Y49, Q55, and S56. See Table 10B ("optional" residues).

In certain embodiments, the antibody, or antigen binding fragment thereof, comprises one or more of the following paratope residues (based on BSA, with 20 Å$^2$ cutoff, Kabat numbering): (i) heavy chain Gly31, Tyr32, Tyr33, Trp50, Glu95, Gly97, Asp98, and Asp99; (ii) light chain Tyr32, Tyr49, Ser91, Tyr92, and Ser93.

In certain embodiments, the antibody, or antigen binding fragment thereof, comprises one or more of the following paratope residues (based on BSA, no cutoff, Kabat numbering): (i) heavy chain Gly31, Tyr32, Tyr33, His35, Trp50, Glu95, Ser96, Gly97, Asp98, and Asp99; (ii) light chain Tyr32, Tyr49, Ser91, Tyr92, Ser93, and Thr96.

In certain embodiments, the antibody, or antigen binding fragment thereof, comprises one or more the following paratope residues (based on H-bond, Kabat numbering): (i) heavy chain Glu95, Gly97, Asp98, and Asp99; (ii) light chain Ser91 and Tyr92.

In certain embodiments, the antibody, or antigen binding fragment thereof, comprises one or more the following paratope residues (based on salt bridge, Kabat numbering): heavy chain Glu95 and Asp98.

In certain embodiments, the antibody, or antigen binding fragment thereof, comprises one or more the following paratope residues (based on distance <3.8 Å, Kabat numbering): (i) heavy chain Gly31, Tyr32, Tyr33, Trp50, Glu95, Ser96, Gly97, Asp98, and Asp99; (ii) light chain Tyr32, Ser91, and Tyr92.

In certain embodiments, the antibody, or antigen binding fragment thereof, (a) comprises at least one paratope residue (numbering according to Kabat) that is within 3.8 Å of at least one epitope residue on ROBO2 (numbering according to SEQ ID NO:1), as follows: epitope residue Arg94 is within 3.8 Å of paratope residue H/Asp98; epitope residue Gly98 is within 3.8 Å of paratope residues H/Gly97 and H/Asp99; epitope residue Arg99 is within 3.8 Å of paratope residues H/Asp99, L/Tyr32 and L/Tyr92; epitope residue Arg100 within 3.8 Å of paratope residues H/Tyr33, H/Trp50, H/Glu95, L/Ser91, and L/Tyr92; epitope residue Ser101 is within 3.8 Å of paratope residues H/Tyr32, H/Tyr33, H/Glu95, H/Ser96, and H/Gly97; epitope residue Lys 102 is within 3.8 Å of paratope residues H/Gly31; and epitope residue Pro103 is within 3.8 Å of paratope residues H/Gly31 and H/Tyr32;

(b) comprises at least one paratope residue (numbering according to Kabat) which can form a hydrogen bond with an epitope residue of ROBO2 (numbering according to SEQ ID NO:1) as follows: epitope residue Arg94 can form a hydrogen bond with paratope residue H/Asp98; epitope residue Arg99 can form a hydrogen bond with paratope residue H/Aso99 and L/Tyr92; epitope residue Arg100 can form a hydrogen bond with paratope residue H/Glu95, L/Ser91, and L/Tyr 92; and epitope residue Ser101 can form a hydrogen bond with paratope residue H/Glu95 and H/Gly97;

(c) comprises at least one paratope residue (numbering according to Kabat) which can form a salt bridge with an epitope residue of ROBO2 (numbering according to SEQ ID NO:1) as follows: epitope residue Arg94 can form a salt bridge with paratope residue H/Asp98; and epitope residue Arg100 can form a salt bridge with paratope residue H/Glu95; or (d) comprises at least one paratope residue (numbering according to Kabat) which comprises a non-zero change in BSA due to interaction with an epitope residue (numbering according to SEQ ID NO:1) as follows: epitope residue Arg94 interacts with paratope residue H/Asp98 and L/Tyr49; epitope residue Val96 interacts with paratope residue H/Gly97; epitope residue His97 interacts with paratope residue H/Gly97; epitope residue Gly98 interacts with paratope residues H/Gly97; epitope residue Arg99 interacts with paratope residues H/Asp99, L/Tyr32, and L/Tyr92; epitope residue Arg100 interacts with paratope residues H/Tyr33, H/Trp50, H/Glu95, L/Ser91, L/Tyr92, and L/Ser93; epitope residue Ser101 interacts with paratope residues H/Tyr32, H/Tyr33, H/Glu95, H/Ser96, and H/Gly97; epitope residue Lys 102 interacts with paratope residues H/Gly31; and epitope residue Pro103 interacts with paratope residues H/Gly31 and H/Tyr32.

In certain embodiments, the antibody or antigen-binding fragment thereof comprises the following heavy chain CDR sequences: (i) CDR-H1 comprising SEQ ID NO:24, CDR-H2 comprising SEQ ID NO:25, and CDR-H3 comprising SEQ ID NO:26; and/or (ii) the following light chain CDR sequences: CDR-L1 comprising SEQ ID NO:29, CDR-L2 comprising SEQ ID NO:30, and CDR-L3 comprising SEQ ID NO:31.

In certain embodiments, the antibody or antigen-binding fragment thereof comprises the following heavy chain CDR sequences: (i) CDR-H1 comprising SEQ ID NO:24, CDR-H2 comprising SEQ ID NO:44, and CDR-H3 comprising SEQ ID NO:26; and/or (ii) the following light chain CDR sequences: CDR-L1 comprising SEQ ID NO:29, CDR-L2 comprising SEQ ID NO:30, and CDR-L3 comprising SEQ ID NO:47.

In certain embodiments, the antibody, or antigen-binding fragment thereof, described herein comprises the following heavy chain CDR sequences: (i) a CDR-H1 sharing at least 90%, at least 91%, at least 92%, at least 93%, at least 94%, or at least 95% identical to SEQ ID NO:24, a CDR-H2 sharing at least 90%, at least 91%, at least 92%, at least 93%, at least 94%, or at least 95% identity with SEQ ID NO:25 or SEQ ID NO:44, and a CDR-H3 sharing at least 90%, at least 91%, at least 92%, at least 93%, at least 94%, or at least 95% identity with SEQ ID NO:26; and/or (ii) the following light chain CDR sequences: a CDR-L1 sharing at least 90%, at least 91%, at least 92%, at least 93%, at least 94%, or at least 95% identity with SEQ ID NO:29, a CDR-L2 sharing at least 90%, at least 91%, at least 92%, at least 93%, at least 94%, or at least 95% identity with SEQ ID NO:30, and a CDR-L3 sharing at least 90%, at least 91%, at least 92%, at least 93%, at least 94%, or at least 95% identity with SEQ ID NO:31 or SEQ ID NO:47.

In certain embodiments, no more than one 10, no more than 9, no more than 8, no more than 7, no more than 6, no more than 5, no more than 4, no more than 3, no more than 2, or no more than 1 substitution is made in CDR-L1, relative to SEQ ID NO:29. In certain embodiments, no more than 6, no more than 5, no more than 4, no more than 3, no more than 3, no more than 2, or no more than one substitution is made in CDR-L2, relative to SEQ ID NO:30. In certain embodiments, no more than 6, no more than 5, no more than 4, no more than 3, no more than 3, no more than 2, or no more than one substitution is made in CDR-L3, relative to SEQ ID NO:31 or SEQ ID NO:47. In some embodiments, no more than 9, no more than 8, no more than 7, no more than 6, no more than 5, no more than 4, no more than 3, no more than 2, or no more than 1 substitution is made in CDR-H1, relative to SEQ ID NO:24. In some embodiments, no more than 18, no more than 17, no more than 16, no more than 15, no more than 14, no more than 13, no more than 12, no more than 11, or no more than one 10, no more than 9, no more than 8, no more than 7, no more than 6, no more than 5, no more than 4, no more than 3, no more than 2, or no more than 1 substitution is made in CDR-H2, relative to SEQ ID NO:25 or SEQ ID NO:44. In some embodiments, no more than 9, no more than 8, no more than 7, no more than 6, no more than 5, no more than 4, no more than 3, no more than 2, or no more than 1 substitution is made in CDR-H3, relative to SEQ ID NO:26. In certain embodiments, the substitution(s) do not change binding affinity ($K_D$) value by more than 1000-fold, more than 100-fold, or 10-fold. In certain embodiments, the substitution is a conservative substitution according to Table 1. In certain embodiments, the substitution is not one of the primary or contributing paratope residues as shown in Table 10B. In certain embodiments, the substitution is not one of the primary, contributing, or optional paratope residues as shown in Table 10B.

TABLE 1

Amino Acid Substitutions

| Original Residue | Conservative Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr(Y) | Phe | Trp; Phe; Thr; Ser |
| Val (V) | Leu | Ile; Leu; Met; Phe; Ala; Norleucine |

The antibody, or antigen-binding fragment thereof, may comprise a VH framework comprising a human germline VH framework sequence. The VH framework sequence can be derived from a human VH3 germline, a VH1 germline, a VH5 germline, or a VH4 germline. Preferred human germline heavy chain frameworks are frameworks derived from VH1, VH3, or VH5 germlines. For example, VH frameworks from the following germlines may be used: IGHV3-23, IGHV3-7, or IGHV1-69 (germline names are based on IMGT germline definition). Preferred human germline light chain frameworks are frameworks derived from VK or Vλ germlines. For example, VL frameworks from the following germlines may be used: IGKV1-39 or IGKV3-20 (germline names are based on IMGT germline definition). Alternatively, or in addition, the framework sequence may be a human germline consensus framework sequence, such as the framework of human Vλ1 consensus sequence, VK1 consensus sequence, VK2 consensus sequence, VK3 consensus sequence, VH3 germline consensus sequence, VH1 germline consensus sequence, VH5 germline consensus sequence, or VH4 germline consensus sequence. Sequences of human germline frameworks are available from various public databases, such as V-base, IMGT, NCBI, or Abysis.

The antibody, or antigen-binding fragment thereof, may comprise a VL framework comprising a human germline VL framework sequence. The VL framework may comprise one or more amino acid substitutions, additions, or deletions, while still retaining functional and structural similarity with the germline from which it was derived. In some aspects, the VL framework is at least 90%, at least 91%, at least 92%, at least 93%, at least 94%, at least 95%, at least 96%, at least 97%, at least 98%, at least 99%, or 100% identical to a human germline VL framework sequence. In some aspects, the antibody, or antigen binding fragment thereof, comprises a VL framework comprising 1, 2, 3, 4, 5, 6, 7, 8, 9, 10 amino acid substitutions, additions or deletions relative to the human germline VL framework sequence.

The human germline VL framework may be the framework of DPK9 (IMGT name: IGKV1-39). The human germline VL framework may be the framework of DPK12 (IMGT name: IGKV2D-29). The human germline VL framework may be the framework of DPK18 (IMGT name: IGKV2-30). The human germline VL framework may be the framework of DPK24 (IMGT name: IGKV4-1). The human germline VL framework may be the framework of HK102_V1 (IMGT name: IGKV1-5). The human germline VL framework may be the framework of DPK1 (IMGT name: IGKV1-33). The human germline VL framework may be the framework of DPK8 (IMGT name: IGKV1-9). The human germline VL framework may be the framework of DPK3 (IMGT name: IGKV1-6). The human germline VL framework may be the framework of DPK21 (IMGT name: IGKV3-15). The human germline VL framework may be the framework of Vg_38 K (IMGT name: IGKV3-11). The human germline VL framework may be the framework of DPK22 (IMGT name: IGKV3-20). The human germline VL framework may be the framework of DPK15 (IMGT name: IGKV2-28). The human germline VL framework may be the framework of DPL16 (IMGT name: IGLV3-19). The human germline VL framework may be the framework of DPL8 (IMGT name: IGLV1-40). The human germline VL framework may be the framework of V1-22 (IMGT name: IGLV6-57). The human germline VL framework may be the framework of human Vλ consensus sequence. The human germline VL framework may be the framework of human Vλ1 consensus sequence. The human germline VL framework may be the framework of human Vλ3 consensus sequence. The human germline VL framework may be the framework of human VK consensus sequence. The human germline VL framework may be the framework of human VK1 consensus sequence. The human germline VL framework may be the framework of human VK2 consensus sequence. The human germline VL framework may be the framework of human VK3 consensus sequence.

The antibody, or antigen-binding fragment thereof, may comprise a VH framework comprising a human germline VH framework sequence. The VH framework may comprise one or more amino acid substitutions, additions, or deletions, while still retaining functional and structural similarity with the germline from which it was derived. In some aspects, the VH framework is at least 90%, at least 91%, at least 92%, at least 93%, at least 94%, at least 95%, at least 96%, at least 97%, at least 98%, at least 99%, or 100% identical to a human germline VH framework sequence. In some aspects, the antibody, or antigen binding fragment thereof, comprises a VH framework comprising 1, 2, 3, 4, 5, 6, 7, 8, 9, 10 amino acid substitutions, additions or deletions relative to the human germline VH framework sequence.

The human germline VH framework may be the framework of DP54 or IGHV3-7. The human germline VH framework may be the framework of DP47 or IGHV3-23. The human germline VH framework may be the framework of DP71 or IGHV4-59. The human germline VH framework may be the framework of DP75 or IGHV1-2_02. The human germline VH framework may be the framework of DP10 or IGHV1-69. The human germline VH framework may be the framework of DP7 or IGHV1-46. The human germline VH framework may be the framework of DP49 or IGHV3-30. The human germline VH framework may be the framework of DP51 or IGHV3-48. The human germline VH framework may be the framework of DP38 or IGHV3-15. The human germline VH framework may be the framework of DP79 or IGHV4-39. The human germline VH framework may be the framework of DP78 or IGHV4-30-4. The human germline VH framework may be the framework of DP73 or IGHV5-51. The human germline VH framework may be the framework of DP50 or IGHV3-33. The human germline VH framework may be the framework of DP46 or IGHV3-30-3. The human germline VH framework may be the framework of DP31 or IGHV3-9. The human germline VH framework may be the framework of human VH germline consensus sequence. The human germline VH framework may be the framework of human VH3 germline consensus sequence. The human germline VH framework may be the framework of human VH5 germline consensus sequence. The human germline VH framework may be the framework of human VH1 germline consensus sequence. The human germline VH framework may be the framework of human VH4 germline consensus sequence.

In certain embodiments, the antibody, or antigen-binding fragment thereof, described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:32, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:39. Any combination of these VL and VH sequences is also encompassed by the invention.

In certain embodiments, the antibody, or antigen-binding fragment thereof, described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to one of the group consisting of SEQ ID NOs: 126, 127, 128, 129, 130, 131, and 132; and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:133. Any combination of these VH and VL sequences is also encompassed by the invention.

In some embodiments, the antibody, or antigen-binding fragment thereof, described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to one of the group consisting of SEQ ID NOs: 43, 49, 55, 70, 73, 76, 79, 82, 85, 88, 115, and 119; and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to any of SEQ ID NOs: 46, 52, 58, 61, 64, 67, 91, 94, 97, 99, 101, 103, 105, 107, 109, 111, and 113. Any combination of these VL and VH sequences is also encompassed by the invention.

In certain embodiments, the antibody or antigen-binding fragment thereof described herein comprises (i) a CDR-H1 comprising SEQ ID NO:24, a CDR-H2 comprising SEQ ID NO:25, a CDR-H3 comprising SEQ ID NO:26, a CDR-L1 comprising SEQ ID NO:29; a CDR-L2 comprising SEQ ID NO:30, and a CDR-L3 comprising SEQ ID NO:31; and (ii)

a VL framework comprising a sequence that is at least 66%, at least 74%, at least 76%, at least 80%, at least 96%, at least 97%, or at least 99% identical to the framework sequence of human germline DPK9, and a VH framework comprising a sequence that is at least 73%, at least 75%, at least 79%, at least 90%, at least 93%, at least 94%, or at least 99% identical to the framework sequence of human germline DP-75. In certain embodiments, the VH framework is DP-75. Other similar framework regions are also predicted to deliver advantageous antibodies or antibody fragments of the invention comprising CDRs of SEQ ID NOs: 24, 25, and 26 include: DP-8, DP-15, DP-14, DP-7, DP-25, DP-10, DP-88, IGHV7-4-1*02, DP-73, IGHV5-10-1*01 and IGHV5-10-1*04, which share 99%, 94%, 94%, 94%, 93%, 90%, 90%, 79%, 75%, 73%, and 73% sequence identity, respectively, with the FW region of DP-75, and comprise four or fewer amino acid differences in the common structural features: (A) residues directly underneath CDR (Vernier Zone): H2, H47, H48, H49, H67, H69, H71, H73, H93, H94; (B) VH/VL Chain packing Residues: H37, H39, H45, H47, H91, H93; and (C) canonical CDR Structural support residues: H24, H71, H94 (all Kabat numbering). Particularly preferred are framework regions of DP-8, DP-15, DP-14, DP-7 and DP-25 sharing 99%, 94%, 94%, 94%, and 93% identity with DP-75, respectively, and one or fewer amino acid differences in these common structural features.

In certain embodiments, the VL framework is DPK9. Other similar framework regions are also predicted to deliver advantageous antibodies of the invention comprising CDRs of SEQ ID NOs: 29, 30, and 31 include: DPK5, DPK4, DPK1, IGKV1-5*01, DPK24, DPK21, DPK15, IGKV1-13*02, IGKV1-17*01, DPK8, IGKV3-11*01, and DPK22, which share 99%, 97%, 97%, 96%, 80%, 76%, 66%, 97%, 97%, 96%, 76%, and 74% sequence identity, respectively, with the FW region of DPK-9, and comprise one or fewer amino acid difference in common structural features: (A) residues directly underneath CDR (Vernier Zone), L2, L4, L35, L36, L46, L47, L48, L49, L64, L66, L68, L69, L71; (B) VH/VL Chain packing Residues: L36, L38, L44, L46, L87; and (C) canonical CDR Structural support residues L2, L48, L64, L71 (all Kabat Numbering). Particularly preferred are framework regions of DPK5, DPK4, DPK1, IGKV1-5*01, DPK24, DPK21, and DPK15, which share 99%, 97%, 97%, 96%, 80%, 76%, and 66% sequence identity with DPK9, respectively, and have no amino acid difference in these common structural features.

In certain embodiments, the antibody, or antigen-binding fragment thereof, described herein comprises an Fc domain. The Fc domain can be derived from IgA (e.g., IgA$_1$ or IgA$_2$), IgG, IgE, or IgG (e.g., IgG$_1$, IgG$_2$, IgG$_3$, or IgG$_4$). In some embodiments, the Fc domain comprises wild type sequence of an Fc domain. In some embodiments, the Fc domain comprises one or more mutations resulting in altered biological activity. For example, mutations may be introduced into the Fc domain to reduce the effector activity (e.g., WO 2005/063815), and/or to increase the homogeneity during the production of the recombinant protein. In some embodiments, the Fc domain is the Fc domain of human IgG1 and comprises one or more of the following effector-null mutations: L234A, L235A, and G237A (numbering according to the EU index). In some embodiments, the lysine located in the C-terminal position of the Fc domain is deleted to increase the homogeneity during the production of the recombinant protein. In some embodiments, the lysine located in the C-terminal position of the Fc domain is present.

In certain embodiments, the antibody, or antigen-binding fragment thereof, described herein comprises: (i) a heavy chain CH1 domain that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to any of SEQ ID NO:34; (ii) a heavy chain CH2 domain that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to any of SEQ ID NO:36; (iii) a heavy chain CH3 domain that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to any of SEQ ID NO:37; and/or (iv) a light chain CL domain that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:41. Any combination of these CH1, CH2, CH3, and CL sequences is also encompassed by the invention.

In certain embodiments, the antibody, or antigen-binding fragment thereof, described herein comprises (i) a HC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:38; and/or (ii) a LC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:42. Any combination of these HC and LC sequences is also encompassed by the invention.

In certain embodiments, The antibody, or antigen-binding fragment thereof, described herein comprises (i) a HC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:45; and/or (ii) a LC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, 01100% identical to SEQ ID NO:48. Any combination of these HC and LC sequences is also encompassed by the invention.

In certain embodiments, The antibody, or antigen-binding fragment thereof, described herein comprises (i) a HC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to any one of SEQ ID NOs: 38, 134, 135, 136, 137, 138, 139, and 140; and/or (ii) a LC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:42 or 141. Any combination of these HC and LC sequences is also encompassed by the invention.

Also provided by the invention is an antibody, or antigen-binding fragment thereof, that competes for binding to human ROBO2 with any of the antibody, or antigen-binding fragment thereof, described herein, such as any one of the antibodies provided herein (or antigen-binding fragment thereof). For example, if the binding of an antibody, or an antigen-binding portion thereof, to human ROBO2 hinders the subsequent binding to human ROBO2 by Abcs35, the antibody or an antigen-binding portion thereof competes with Abcs35 for human ROBO2 binding.

Also provided by the invention is an antibody, or antigen-binding fragment thereof, that binds to the same human ROBO2 epitope as any of the antibody, or antigen-binding fragment thereof, described herein, such as any one of the antibodies provided herein or antigen-binding fragment thereof. For example, antibody competition assay (and overlapping epitope analysis) can be assessed by SPR or BLI, as described in detail herein.

The antibodies and antigen-binding fragments provided by the invention include monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion, domain antibodies (dAbs), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies and antigen-binding fragments may be murine, rat, human, or any other origin (including chimeric or humanized antibodies). In some embodiments, the antibody is a monoclonal antibody. In some embodiments, the antibody is a chimeric, humanized or human antibody. In certain embodiments, the antibody is a human antibody. In certain embodiments, the antibody is a humanized antibody.

The binding affinity of an antibody can be expressed as a $K_D$ value, which refers to the dissociation rate of a particular antigen-antibody interaction. $K_D$ is the ratio of the rate of dissociation, also called the "off-rate ($k_{off}$)", to the association rate, or "on-rate ($k_{on}$)". Thus, $K_D$ equals $k_{off}/k_{on}$ (dissociation/association) and is expressed as a molar concentration (M), and the smaller the $K_D$, the stronger the affinity of binding. $K_D$ values for antibodies can be determined using methods well established in the art. Unless otherwise specified, "binding affinity" refers to monovalent interactions (intrinsic activity; e.g., binding of an antibody to an antigen through a monovalent interaction).

In certain embodiments, the antibody, or antigen-binding fragment thereof, of the invention has an affinity ($K_D$) value of not more than about $1 \times 10^{-6}$ M, such as not more than about $1 \times 10^{-7}$ M, not more than about $9 \times 10^{-3}$ M, not more than about $8 \times 10^{-3}$ M, not more than about $7 \times 10^{-8}$ M, not more than about $6 \times 10^{-8}$ M, not more than about $5 \times 10^{-8}$ M, not more than about $4 \times 10^{-8}$ M, not more than about $3 \times 10^{-8}$ M, not more than about $2 \times 10^{-8}$ M, not more than about $1 \times 10^{-3}$ M, not more than about $9 \times 10^{-9}$ M, not more than about $8 \times 10^{-9}$ M, not more than about $7 \times 10^{-9}$ M, not more than about $6 \times 10^{-9}$ M, not more than about $5 \times 10^{-9}$ M, not more than about $4 \times 10^{-9}$ M, not more than about $3 \times 10^{-9}$ M, not more than about $2 \times 10^{-9}$ M, not more than about $1 \times 10^{-9}$ M, not more than about $9 \times 10^{-10}$ M, not more than about $8 \times 10^{-10}$ M, not more than about $7 \times 10^{-10}$ M, not more than about $6 \times 10^{-10}$ M, not more than about $5 \times 10^{-10}$ M, not more than about $4 \times 10^{-10}$ M, not more than about $3 \times 10^{-10}$ M, not more than about $2 \times 10^{-10}$ M, not more than about $1 \times 10^{-10}$ M, not more than about $9 \times 10^{-11}$ M, not more than about $8 \times 10^{-11}$ M, not more than about $7 \times 10^{-11}$ M, not more than about $6 \times 10^{-11}$ M, not more than about $5 \times 10^{-11}$ M, not more than about $4 \times 10^{-11}$ M, not more than about $3 \times 10^{-11}$ M, not more than about $2 \times 10^{-11}$ M, not more than about $1 \times 10^{-11}$ M, not more than about $9 \times 10^{-12}$ M, not more than about $8 \times 10^{-12}$ M, not more than about $7 \times 10^{-12}$ M, not more than about $6 \times 10^{-12}$ M, not more than about $5 \times 10^{-12}$ M, not more than about $4 \times 10^{-12}$ M, not more than about $3 \times 10^{-12}$ M, not more than about $2 \times 10^{-12}$ M, not more than about $1 \times 10^{-12}$ M, not more than about $9 \times 10^{-13}$ M, not more than about $8 \times 10^{-13}$ M, not more than about $7 \times 10^{-13}$ M, not more than about $6 \times 10^{-13}$ M, not more than about $5 \times 10^{-13}$ M, not more than about $4 \times 10^{-13}$ M, not more than about $3 \times 10^{-13}$ M, not more than about $2 \times 10^{-13}$ M, not more than about $1 \times 10^{-13}$ M, from about $1 \times 10^{-7}$ M to about $1 \times 10^{-14}$ M, from about $9 \times 10^{-8}$ M to about $1 \times 10^{-14}$ M, from about $8 \times 10^{-8}$ M to about $1 \times 10^{-14}$ M, from about $7 \times 10^{-8}$ M to about $1 \times 10^{-14}$ M, from about $6 \times 10^{-8}$ M to about $1 \times 10^{-14}$ M, from about $5 \times 10^{-8}$ M to about $1 \times 10^{-14}$ M, from about $4 \times 10^{-8}$ M to about $1 \times 10^{-14}$ M, from about $3 \times 10^{-8}$ M to about $1 \times 10^{-14}$ M, from about $2 \times 10^{-8}$ M to about $1 \times 10^{-14}$ M, from about $1 \times 10^{-8}$ M to about $1 \times 10^{-14}$ M, from about $9 \times 10^{-8}$ M to about $1 \times 10^{-14}$ M, from about $8 \times 10^{-8}$ M to about $1 \times 10^{-14}$ M, from about $7 \times 10^{-8}$ M to about $1 \times 10^{-14}$ M, from about $6 \times 10^{-8}$ M to about $1 \times 10^{-14}$ M, from about $5 \times 10^{-8}$ M to about $1 \times 10^{-14}$ M, from about $4 \times 10^{-8}$ M to about $1 \times 10^{-14}$ M, from about $3 \times 10^{-8}$ M to about $1 \times 10^{-14}$ M, from about $2 \times 10^{-8}$ M to about $1 \times 10^{-14}$ M, from about $1 \times 10^{-9}$ M to about $1 \times 10^{-14}$ M, from about $1 \times 10^{-7}$ M to about $1 \times 10^{-13}$ M, from about $9 \times 10^{-8}$ M to about $1 \times 10^{-13}$ M, from about $8 \times 10^{-8}$ M to about $1 \times 10^{-13}$ M, from about $7 \times 10^{-8}$ M to about $1 \times 10^{-13}$ M, from about $6 \times 10^{-8}$ M to about $1 \times 10^{-13}$ M, from about $5 \times 10^{-8}$ M to about $1 \times 10^{-13}$ M, from about $4 \times 10^{-8}$ M to about $1 \times 10^{-13}$ M, from about $3 \times 10^{-8}$ M to about $1 \times 10^{-13}$ M, from about $2 \times 10^{-8}$ M to about $1 \times 10^{-13}$ M, from about $1 \times 10^{-8}$ M to about $1 \times 10^{-13}$ M, from about $9 \times 10^{-8}$ M to about $1 \times 10^{-13}$ M, from about $8 \times 10^{-8}$ M to about $1 \times 10^{-13}$ M, from about $7 \times 10^{-8}$ M to about $1 \times 10^{-13}$ M, from about $6 \times 10^{-8}$ M to about $1 \times 10^{-13}$ M, from about $5 \times 10^{-8}$ M to about $1 \times 10^{-13}$ M, from about $4 \times 10^{-8}$ M to about $1 \times 10^{-13}$ M, from about $3 \times 10^{-8}$ M to about $1 \times 10^{-13}$ M, from about $2 \times 10^{-8}$ M to about $1 \times 10^{-13}$ M, or from about $1 \times 10^{-9}$ M to about $1 \times 10^{-13}$ M.

The value of $K_D$ can be determined directly by well-known methods, and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein.

One exemplary method for measuring binding affinity ($K_D$) value is surface plasmon resonance (SPR), typically using a biosensor system such as a BIACORE® system. SPR refers to an optical phenomenon that allows for the analysis of real-time biospecific interactions by detection of alterations in protein concentrations within a biosensor matrix, for example using the BIACORE® system. BIAcore kinetic analysis comprises analyzing the binding and dissociation of an antigen from a chip with an immobilized molecule (e.g., a molecule comprising an antigen-binding domain), on their surface; or the dissociation of an antibody, or antigen-binding fragment thereof, from a chip with an immobilized antigen.

In certain embodiments, the SPR measurement is conducted using a BIACORE® T100 or T200 instrument. For example, a standard assay condition for surface plasmon resonance can be based on antibody immobilization of approximately 100-500 Response Units (RU) of IgG on the SPR chip. Purified target proteins are diluted in buffer to a range of final concentrations and injected at a requisite flow rate (e.g. 10-100 µl/min) to allow the calculation of Ka. Dissociation is allowed to proceed to establish off-rate, followed by 3 M $MgCl_2$ (or 20 mM NaOH) for regeneration of the chip surface. Sensorgrams are then analyzed using a kinetics evaluation software package. In an exemplary embodiment, the SPR assay is according to the conditions as set forth in the Examples.

In certain embodiments, the binding affinity ($K_D$) value is measured using solution-based kinetic exclusion assay (KinExA™). In a particular embodiment, the KinExA measurement is conducted using a KinExA™ 3200 instrument (Sapidyne). The Kinetic Exclusion Assay (KinExA™) is a general-purpose immunoassay platform (basically a flow spectrofluorimeter) that is capable of measuring equilibrium dissociation constants, and association and dissociation rate constants for antigen/antibody interactions. Since KinExA™ is performed after equilibrium has been obtained it is an advantageous technique to use for measuring the $K_D$ of high affinity interactions where the off-rate of the interaction may be very slow. The KinExA™ methodology can be conducted generally as described in Drake et al (2004) Analytical Biochem. 328, 35-43.

Another method for determining the $K_D$ of an antibody is by using Bio-Layer Interferometry (BLI), typically using OCTET® technology (e.g., Octet QKe system) from ForteBio. In an exemplary embodiment, the Octet assay is according to the conditions as set forth in the Examples. In certain embodiments, the BLI measurement is conducted according to the following: sensor tips coated with a proprietary anti-human antibody (ForteBio) undergo BLI signal stabilization by dipping in running buffer (such as 10 mM Hepes Buffered Saline (HBS) containing 0.05% tween-20) for 120s. The antibody is then captured by dipping the sensors into a running buffer solution (buffer may contain 1-10 ug/mL of the antibody) for 300s. The signal is then stabilized by dipping the sensor tips back into running buffer for 120s. The tips are then transferred into solution containing the cognate antigen. The binding of antibody-antigen is measured over 180s prior to the sensor tips being transferred to running buffer in order to monitor receptor dissociation over 180s. In case of ROBO, typically a 7-point dose response of the antigen (may range from 1-2 nM in doubling dilutions) is measured. Additionally, sensor tips with no antibody captured are exposed to the antigen in order to monitor non-specific binding of the receptors to the sensor tips. A $2^{nd}$ reference type also includes a tip with antibody captured upon on it but with subsequent exposure to running buffer only with no antigen. This allows for double-referencing to eliminate both non-specific binding as well as system noise and the underlying baseline drift attributed to the antibody dissociating from the anti-human Fc sensor tip. The raw under goes double reference subtraction and is then fit to a 1:1 Langmuir type binding model to determine affinity and kinetic parameters.

In general, an anti-ROBO2 antibody should bind to ROBO2 with high affinity, in order to effectively block the activities of ROBO2. It is desirable that the anti-ROBO2 antibody have binding affinities ($K_D$) in low nanomolar and picomolar range, such as about $1\times10^{-8}$ M or lower.

Activity Assays

In certain embodiments, the antibody, or antigen-binding fragment thereof, of the invention is a neutralizing antibody that reduces at least one activity of ROBO2-SLIT signaling. Such activity includes, but it not limited to, binding between ROBO2 and SLIT ligand, binding of intracellular signaling molecules (such as srGAP1 or Nck) to the intracellular domainROBO2, and/or downstream activities of ROBO2-SLIT signaling (such as actin polymerization, podocyte adhesion, and/or SLIT2-N mediated inhibition of neuronal cell migration), among other ROBO2-SLIT activities known in the art. Whether an antibody, or antigen-binding fragment thereof, reduces an activity of ROBO2 can be assessed by a number of assays. For example, assays can be used to determine whether the antibody, or antigen-binding fragment thereof: (a) inhibits the binding of SLIT to ROBO2; (b) reduces the binding of srGAP1 and ROBO2; or the binding of Nck and ROBO2; and/or (c) inhibits ROBO2-dependent SLIT2-N activity.

In certain embodiments, the antibody, or antigen-binding fragment thereof, inhibits the binding of SLIT ligand to ROBO2 (e.g., can be assessed by competitive binding between the antibody and SLIT to ROBO2). For example, an assay may compare (i) the binding of ROBO2 and SLIT in the presence of the antibody, or antigen-binding fragment thereof, with (ii) the binding of ROBO2 and SLIT in the absence of the antibody, or antigen-binding fragment thereof. The reduction in binding of ROBO2 and SLIT can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%, in the presence of the anti-ROBO2 antibody, or antigen-binding fragment thereof. The expected binding of SLIT to ROBO2 in the absence of the antibody, or antigen-binding fragment thereof, can be set as 100%.

In certain embodiments, the antibody, or antigen-binding fragment thereof, inhibits the binding of SLIT to ROBO2, with a half maximal inhibitory concentration ($IC_{50}$) of not more than about $1\times10^{-7}$ M, not more than about $1\times10^{-8}$ M, not more than about $1\times10^{-9}$ M, not more than about $1\times10^{-10}$ M, not more than about $1\times10^{-11}$ M, not more than about $1\times10^{-12}$ M, not more than about $1\times10^{-13}$ M, not more than about $1\times10^{-14}$ M, not more than about $1\times10^{-15}$ M, from about $1\times10^{-7}$ M to about $5\times10^{-14}$ M, from about $1\times10^{-7}$ M to about $1\times10^{-14}$ M, from about $1\times10^{-7}$ M to about $5\times10^{-13}$ M, from about $1\times10^{-7}$ M to about $1\times10^{-13}$ M, from about $1\times10^{-7}$ M to about $5\times10^{-12}$ M, or from about $1\times10^{-7}$ M to about $1\times10^{-12}$ M. The $IC_{50}$ may be assessing using a fragment of SLIT or ROBO2, such as SLIT-N, and Ig domain 1 of ROBO2, or Ig domains 1 & 2 of ROBO2.

The inhibitory activity of an antibody, or antigen-binding fragment thereof, can also be assessed by measuring the level of ROBO2-dependent SLIT-N activity, such as actin polymerization, podocyte adhesion, and/or SLIT2-N mediated inhibition of neuronal cell migration. For example, the assay can compare (i) neuronal cell migration in the presence of ROBO2, SLIT, and the antibody, or antigen-binding fragment thereof, with (ii) neuronal cell migration in the presence of ROBO2, SLIT, but in the absence of the antibody, or antigen-binding fragment thereof. The reduction in neuronal cell migration can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%, in the presence of the anti-ROBO2 antibody, or antigen-binding fragment thereof. The baseline neuronal cell migration in the absence of the antibody, or antigen-binding fragment thereof, can be set as 100%.

In certain embodiments, the antibody, or antigen-binding fragment thereof, inhibits ROBO2-dependent SLIT-N activity, such as actin polymerization, podocyte adhesion, and/or SLIT2-N mediated inhibition of neuronal cell migration), with a half maximal inhibitory concentration ($IC_{50}$) of not more than about $1\times10^{-7}$ M, not more than about $1\times10^{-8}$ M, not more than about $1\times10^{-9}$ M, not more than about $1\times10^{-10}$ M, not more than about $1\times10^{-11}$ M, not more than about $1\times10^{-12}$ M, not more than about $1\times10^{-13}$ M, not more than about $1\times10^{-14}$ M, not more than about $1\times10^{-15}$ M, from about $1\times10^{-7}$ M to about $5\times10^{-14}$ M, from about $1\times10^{-7}$ M to about $1\times10^{-14}$ M, from about $1\times10^{-7}$ M to about $5\times10^{-13}$ M, from about $1\times10^{-7}$ M to about $1\times10^{-13}$ M, from about $1\times10^{-7}$ M to about $5\times10^{-12}$ M, or from about $1\times10^{-7}$ M to about $1\times10^{-12}$ M. In certain embodiments, $IC_{50}$ of from about $1\times10^{-10}$ M to about $1\times10^{-13}$ M is preferred. In certain embodiments, $IC_{50}$ of from about $5\times10^{-11}$ M to about $5\times10^{-12}$ M is preferred.

In certain embodiments, the characteristics of the antibody, or antigen-binding fragment thereof, of the invention is further assessed using other biological activity assays, e.g., in order to evaluate its potency, pharmacological activity, and potential efficacy as a therapeutic agent. Such assays are known in the art and depend on the intended use for the antibody. Examples include e.g., toxicity assays, immunogenicity assays, stability assays, and/or PK/PD profiling.

Nucleic Acids and Methods of Producing Anti-ROBO2 Antibodies

The invention also provides polynucleotides encoding any of the antibodies, including antibody portions and modified antibodies, of the invention as described herein. The invention also provides a method of making any of the polynucleotides described herein. Polynucleotides can be made and expressed by procedures known in the art.

In one aspect, the invention provides polynucleotides or compositions, comprising polynucleotides encoding any of the following ROBO2 antibodies and antigen-binding portions thereof: Abcs35, 93H2, Ab1, Ab3, Ab9, Ab13, Ab17, Ab21, Ab22, Ab25, Ab29, Ab32, Ab40, Ab45, Ab46, Ab58, Ab83, Ab96, Ab112, Ab123, Abcs1, Abcs2, Abcs4, Abcs5, Abcs12, Abcs20, Abcs25, Abcs40, Abcs50, Abcs55, CTIR2-1, CTIR2-2, CTIR2-3, CTIR2-4, CTIR2-5, CTIR2-6, CTIR2-7, CTIR2-8, CTIR2-9, CTIR2-10, CTIR2-11, CTIR2-12, CTIR2-13, CTIR2-14, CTIR2-15, CTIR2-16, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O.

The invention also provides polynucleotides or compositions, comprising polynucleotides encoding an antibody, or antigen-binding fragment thereof, that binds substantially the same epitope as an antibody selected from the group consisting of: Abcs35, 93H2, Ab1, Ab3, Ab9, Ab13, Ab17, Ab21, Ab22, Ab25, Ab29, Ab32, Ab40, Ab45, Ab46, Ab58, Ab83, Ab96, Ab112, Ab123, Abcs1, Abcs2, Abcs4, Abcs5, Abcs12, Abcs20, Abcs25, Abcs40, Abcs50, Abcs55, CTIR2-1, CTIR2-2, CTIR2-3, CTIR2-4, CTIR2-5, CTIR2-6, CTIR2-7, CTIR2-8, CTIR2-9, CTIR2-10, CTIR2-11, CTIR2-12, CTIR2-13, CTIR2-14, CTIR2-15, CTIR2-16, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O.

The invention also provides polynucleotides or compositions, comprising polynucleotides encoding an antibody, or antigen-binding fragment thereof, that competes for binding to ROBO2 with an antibody selected from the group consisting of: Abcs35, 93H2, Ab1, Ab3, Ab9, Ab13, Ab17, Ab21, Ab22, Ab25, Ab29, Ab32, Ab40, Ab45, Ab46, Ab58, Ab83, Ab96, Ab112, Ab123, Abcs1, Abcs2, Abcs4, Abcs5, Abcs12, Abcs20, Abcs25, Abcs40, Abcs50, Abcs55, CTIR2-1, CTIR2-2, CTIR2-3, CTIR2-4, CTIR2-5, CTIR2-6, CTIR2-7, CTIR2-8, CTIR2-9, CTIR2-10, CTIR2-11, CTIR2-12, CTIR2-13, CTIR2-14, CTIR2-15, CTIR2-16, Abcs35-A, Abcs35-B, Abcs35-C, Abcs35-D, Abcs35-E, Abcs35-F, Abcs35-G, Abcs35-H, Abcs35-I, Abcs35-J, Abcs35-K, Abcs35-L, Abcs35-M, Abcs35-N, and Abcs35-O.

The invention also provides polynucleotides or compositions, comprising a sequence encoding a protein comprising the amino acid sequence selected from the group consisting of: (i) SEQ ID NOs: 32, 43, 126-132, (ii) SEQ ID NOs: 39, 46, 133, and (iii) any combination thereof.

The invention also provides polynucleotides or compositions, comprising a nucleic acid sequence selected from any of SEQ ID NOs: 143, 144, 145, 146, and any combination thereof.

The invention also provides polynucleotides or compositions comprising the same, wherein the polynucleotide comprises the sequence of the DNA insert of the plasmid deposited with the ATCC having ATCC Accession No. PTA-123265, No. PTA-123266, No. PTA-123700 and No. PTA-123701.

In another aspect, the invention provides polynucleotides and variants thereof encoding an anti-ROBO2 antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any nucleic acid disclosed herein such as, but not limited to, a nucleic acid comprising the nucleic acid of SEQ ID NOs: 143, 144, 145, and 146.

In another aspect, the invention includes polynucleotides wherein the nucleic acid sequence is set forth in any one of SEQ ID NOs: 143-146.

In one embodiment, the VH and VL domains, or antigen-binding portion thereof, or full-length HC or LC, are encoded by separate polynucleotides. Alternatively, both VH and VL, or antigen-binding portion thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a native antibody or a portion thereof. These amounts are not meant to be limiting, and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Exemplary host cells include an *E. coli* cell, a yeast cell, an insect cell, a simian COS cell, a Chinese hamster ovary (CHO) cell, or a myeloma cell where the cell does not otherwise produce an immunoglobulin protein. Preferred host cells include a CHO cell, a Human embryonic kidney (HEK) 293 cell, or an Sp2.0 cell, among many cells well-known in the art.

An antibody fragment can also be produced by proteolytic or other degradation of a full-length antibody, by recombinant methods, or by chemical synthesis. A polypeptide fragment of an antibody, especially shorter polypeptides up to about 50 amino acids, can be conveniently made by chemical synthesis. Methods of chemical synthesis for proteins and peptides are known in the art and are commercially available.

The antibody, or antigen-binding fragment thereof, of the invention may be affinity matured. For example, an affinity matured antibody can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and WO2004/058184).

5. Formulations and Uses

The antibody, or antigen-binding fragment thereof, of the invention can be formulated as a pharmaceutical composition. The pharmaceutical composition may further comprise a pharmaceutically acceptable carrier, excipient, and/or stabilizer (Remington: The Science and practice of Pharmacy 20th Ed., 2000, Lippincott Williams and Wilkins, Ed. K. E. Hoover), in the form of lyophilized formulation or aqueous solution. As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy, 20th Ed., Mack Publishing, 2000).

Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

Diagnostic Uses

The antibody, or antigen-binding fragment thereof, of the invention can be used for various therapeutic or diagnostic purposes. For example, the antibody, or antigen-binding fragment thereof, of the invention may be used as an affinity purification agent (e.g., for in vitro purification of ROBO2), as a diagnostic agent (e.g., for detecting expression of ROBO2 in specific cells, tissues, or serum). Exemplary diagnostic assays for ROBO2 may comprise, e.g., contacting a sample, obtained from a patient, with an anti-ROBO2 antibody of the invention, wherein the anti-ROBO2 antibody is labeled with a detectable label or reporter molecule.

The invention encompasses use of the antibodies disclosed herein as diagnostic imaging methods for the visualization of ROBO2 in a sample, cell, tissue or patient. For instance, the antibody can be conjugated to an imaging agent such that the presence of the antibody can be detected thereby detecting the presence of ROBO2.

Therapeutic Uses

Exemplary therapeutic uses of the antibody, or antigen-binding fragment thereof, of the invention include treating a renal disease, such as a glomerular disease, FSGS. The antibody, or antigen-binding fragment thereof, of the invention may also be used in prophylactic treatment (e.g., administering to a subject who has not exhibited a disease symptom but is susceptible to a renal disease such as a glomerular disease, FSGS).

In another aspect, the invention includes treatment of any disorder, disease or condition mediated by or associated with an increased level of protein in the urine compared with the level of protein in urine in the absence of the disease, disorder or condition. Such disease, disorder or condition includes, but is not limited to, lupus nephritis, IgA nephropathy, membranous nephropathy (MN), minimal change disease (MCD), fibrosis (such as liver fibrosis), nonalcoholic steatohepatitis (NASH), proteinuria, albuminuria, glomerulonephritis, diabetic nephropathy, nephrotic syndrome, focal glomerulosclerosis, acute renal failure, acute tubulointerstitial nephritis, pyelonephritis, renal graft rejection, and reflux nephropathy.

For therapeutic applications, the antibody, or antigen-binding fragment thereof, of the invention can be administered to a mammal, especially a human by conventional techniques, such as intravenously (as a bolus or by continuous infusion over a period of time), intramuscularly, intraperitoneally, intra-cerebrospinally, subcutaneously, intra-articularly, intrasynovially, intrathecally, orally, topically, or by inhalation. The antibody, or antigen-binding fragment thereof, of the invention also is suitably administered by intra-tumoral, peri-tumoral, intra-lesional, or peri-lesional routes.

Accordingly, in one aspect, the invention provides a method of reducing the activity of ROBO2, comprising administering to a subject (e.g., a human) in need thereof a therapeutically effective amount of the antibody, or antigen-binding fragment thereof, of the invention.

In another aspect, the invention provides a method of preserving or modulating podocyte function, comprising administering to a subject (e.g., a human) in need thereof a therapeutically effective amount of the antibody, or antigen-binding fragment thereof, of the invention.

In certain embodiments, the subject suffers from or is susceptible to a renal disease. In certain embodiments, the renal disease is a glomerular disease. In certain embodiments, the renal disease is FSGS.

In certain embodiments, the subject suffers from or is susceptible to nephropathy.

Dosing and Administration

In certain embodiments, the antibody, or antigen-binding fragment thereof, of the invention is administered subcutaneously. In certain embodiments, the antibody, or antigen-binding fragment thereof, of the invention is administered intravenously.

The pharmaceutical compositions may be administered to a subject in need thereof at a frequency that may vary with the severity of the renal disease. In the case of prophylactic therapy, the frequency may vary depending on the subject's susceptibility or predisposition to a renal disease.

The compositions may be administered to patients in need as a bolus or by continuous infusion. For example, a bolus administration of an antibody present as a Fab fragment may be in an amount of from 0.0025 to 100 mg/kg body weight, 0.025 to 0.25 mg/kg, 0.010 to 0.10 mg/kg or 0.10-0.50 mg/kg. For continuous infusion, an antibody present as an Fab fragment may be administered at 0.001 to 100 mg/kg body weight/minute, 0.0125 to 1.25 mg/kg/min, 0.010 to 0.75 mg/kg/min, 0.010 to 1.0 mg/kg/min. or 0.10-0.50 mg/kg/min for a period of 1-24 hours, 1-12 hours, 2-12 hours, 6-12 hours, 2-8 hours, or 1-2 hours.

For administration of an antibody present as a full-length antibody (with full constant regions), dosage amounts may be from about 1 mg/kg to about 10 mg/kg, from about 2 mg/kg to about 10 mg/kg, from about 3 mg/kg to about 10 mg/kg, from about 4 mg/kg to about 10 mg/kg, from about 5 mg/kg to about 10 mg/kg, from about 1 mg/kg to about 20 mg/kg, from about 2 mg/kg to about 20 mg/kg, from about 3 mg/kg to about 20 mg/kg, from about 4 mg/kg to about 20 mg/kg, from about 5 mg/kg to about 20 mg/kg, about 1 mg/kg or more, about 2 mg/kg or more, about 3 mg/kg or more, about 4 mg/kg or more, about 5 mg/kg or more, about 6 mg/kg or more, about 7 mg/kg or more, about 8 mg/kg or more, about 9 mg/kg or more, about 10 mg/kg or more, about 11 mg/kg or more, about 12 mg/kg or more, about 13 mg/kg or more, about 14 mg/kg or more, about 15 mg/kg or more, about 16 mg/kg or more, about 17 mg/kg or more, about 19 mg/kg or more, or about 20 mg/kg or more. The frequency of the administration would depend upon the severity of the condition. Frequency could range from three times per week to once every two or three weeks.

Additionally, the compositions may be administered to patients via subcutaneous injection. For example, a dose of 1 to 100 mg anti-ROBO2 antibody can be administered to patients via subcutaneous or intravenous injection administered twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, or once every three months. For example, antibody Abcs35 has an estimated half-life of about 19 days with approximately 60% bioavailability following subcutaneous (SC) administration. This half-life supports subcutaneous or intravenous injection at every week, or every 2-6 weeks, such as once every 2 weeks or once every 4 weeks.

In certain embodiments, the half-life of the anti-ROBO2 antibody in human is about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, from about 5 days to about 40 days, from about 5 days to about 35 days, from about 5 days to about 30 days, from about 5 days to about 25 days, from about 10 days to about 40 days, from about 10 days to about 35 days, from about 10 days to about 30 days, from about 10 days to about 25 days, from about 15 days to about 40 days, from about 15 days to about 35 days, from about 15 days to about 30 days, or from about 15 days to about 25 days, In certain embodiments, the pharmaceutical composition is administered subcutaneously or intravenously at every 2-6 weeks, with a dose from about 0.1 mg/kg to about 10 mg/kg, from about 0.5 mg/kg to about 10 mg/kg, from about 1 mg/kg to about 10 mg/kg, from about 1.5 mg/kg to about 10 mg/kg, from about 2 mg/kg to about 10 mg/kg, from about 0.1 mg/kg to about 8 mg/kg, from about 0.5 mg/kg to about 8 mg/kg, from about 1 mg/kg to about 8 mg/kg, from about 1.5 mg/kg to about 8 mg/kg, from about 2 mg/kg to about 8 mg/kg, from about 0.1 mg/kg to about 5 mg/kg, from about 0.5 mg/kg to about 5 mg/kg, from about 1 mg/kg to about 5 mg/kg, from about 1.5 mg/kg to about 5 mg/kg, from about 2 mg/kg to about 5 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 9.5 mg/kg, or about 10.0 mg/kg.

In certain embodiments, the pharmaceutical composition is administered subcutaneously or intravenously at every 2-6 weeks, with a dose of about 3.0 mg/kg. In certain embodiments, the pharmaceutical composition is administered subcutaneous or intravenously every 2-6 weeks, with a dose of from about 2.0 mg/kg to about 10.0 mg/kg.

In one exemplary embodiment, pharmaceutical composition is administered subcutaneously every 2 weeks.

In certain embodiments, the pharmaceutical composition is administered intravenously or intravenously at every 2-6 weeks, with a dose of about 10.0 mg/kg. In certain embodiments, the pharmaceutical composition is administered subcutaneous or intravenously every 2-6 weeks, with a dose of from about 1.0 mg/kg to about 10.0 mg/kg.

In one exemplary embodiment, pharmaceutical composition is administered intravenously every month.

The antibody, or antigen-binding fragment thereof, of the invention can be used as monotherapy or in combination with other therapies to treat, e.g., a renal disease. Other therapies for treating real disease are well-known in the art and are not listed herein.

6. Kits

The invention also provides kits or an article of manufacture comprising an antibody, or antigen binding fragment thereof, of the invention, and instructions for use. Accordingly, in some embodiments, provided is a kit or an article of manufacture, comprising a container, a composition within the container comprising an anti-ROBO2 antagonist antibody, and a package insert containing instructions to administer a therapeutically effective amount of the anti-ROBO2 antagonist antibody for treatment of a patient in need thereof.

In certain embodiments, the kit can contain both a first container having a dried protein and a second container having an aqueous formulation. In certain embodiments, kits containing single and multi-chambered pre-filled syringes (e.g., liquid syringes and lyosyringes) are included.

The instructions relating to the use of antibodies, or antigen binding fragments thereof, of the invention generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). The container may further comprise a second pharmaceutically active agent.

Kits may optionally provide additional components such as buffers and interpretive information. Normally, the kit comprises a container and a label or package insert(s) on or associated with the container.

7. Biological Deposit

Representative materials of the present invention were deposited in the American Type Culture Collection, 10801 University Boulevard, Manassas, Va. 20110-2209, USA, on Jun. 23, 2016. Vector Abcs35-VH having ATCC Accession No. PTA-123265 comprises a DNA insert encoding the heavy chain variable region of antibody Abcs35, vector Abcs35-VL having ATCC Accession No. PTA-123266 comprises a DNA insert encoding the light chain variable region of antibody Abcs35. Further, additional representative materials of the present invention were deposited at the ATCC on Dec. 20, 2016. Vector Abcs35-J-VH having ATCC Accession No. PTA-123700 comprises a DNA insert encoding the heavy chain variable region of antibody Abcs35-J, vector Abcs35-J-VL having ATCC Accession No. PTA-123701 comprises a DNA insert encoding the light chain variable region of antibody Abcs35-J. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

Pfizer Inc., an assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

Exemplary methods and materials are described herein, although methods and materials similar or equivalent to those described herein can also be used in the practice or testing of the present invention. The materials, methods, and examples are illustrative only and not intended to be limiting.

Example 1. Generation of Anti-ROBO2 Antibodies

Abcs35 is a fully human IgG1 antibody against the ROBO2 protein that neutralizes SLIT2 ligand binding. A single ROBO2-specific antibody clone, 93H2, was isolated and multiple rounds of affinity maturation were used to increase the affinity from approximately 37 nM to 0.268 nM as described below.
Selection of Anti-ROBO2 Antibodies by Phage Display Anti-ROBO2 scfvs were selected from an antibody phage display library by screening with the extracellular domain (ECD) of human ROBO2. The human ROBO2 ECD was biotinylated with Sulfo-NHS-LC-Biotin (Pierce) according to the manufacturer's protocol. This biotinylated ROBO2 ECD was used to select binders from an scfv antibody phage display library then captured on streptavidin-coated magnetic Dynabeads M-280 (Invitrogen) using standard methods. Three rounds of selection were performed with decreasing concentrations of the target (ROBO2 ECD) as follows: 200 nM ($1^{st}$ round), 100 nM ($2^{nd}$ round), and 50 nM ($3^{rd}$ round). To obtain antibodies specific to ROBO2, which did not substantially bind the related ROBO1 protein, all selections were performed in the presence of increasing concentrations of human ROBO1 ECD as follows, 50 nM ($1^{st}$ round), 100 nM ($2^{nd}$ round), and 200 nM ($3^{rd}$ round). From this screen, 110 scfv hits were identified as binding to the ROBO2 ECD, which were converted to IgGs using standard methods.
ELISA to Measure Binding of Human IgGs to ROBO2 and ROBO1 ECD.

ELISA plates were coated with either 1 pg of ROBO2 ECD or 1 pg of ROBO1 ECD and a standard ELISA protocol was followed. Antibodies were detected with an anti-human IgG HRP secondary (Southern Biotech); the ELISA was developed using 3,3',5,5'-Tetramethylbenzidine and absorbance read at 450 nm on an Envision plate reader (Perkin Elmer). After reformatting from scfv to IgG1, antibody clone 93H2 was the only one that exhibited binding to specific binding to ROBO2 with minimal binding to ROBO1.
Affinity Maturation of 93H2 mAb.

To increase the affinity and potency, two approaches were applied. First, 93H2 focused phage display libraries were generated by splice overlap extension PCR. 93H2 focused phage display libraries consisted of five mutagenesis libraries that were built using NNK codon containing mutagenic primers that aimed to mutate VH-CDR1, VH-CDR2, VL-CDR1, VL-CDR2 and VL-CDR3, respectively. The resulting libraries with a total combined diversity of $1.1 \times 10^9$ were displayed on phage and selected for ROBO2 Ig1-Ig2 binding. After rescuing the 5 libraries, 2 rounds of selection were performed. In the $1^{st}$ round, 200 pM of human ROBO2 Ig1-Ig2 was used in solution to bind phage for 30 minutes at room temperature followed by streptavidin magnetic bead capture. To obtain antibodies specific to ROBO2 selections were performed in the presence of 200 nM of human ROBO1. To obtain ROBO2 specific scfvs with slow off rate, the washed beads were incubated with non-biotinylated ROBO2 Ig1-Ig2 overnight. In the $2^{nd}$ round, 2 nM biotinylated ROBO2 Ig1-Ig2 was incubated with the output phage from the 1st round in solution for 30 minutes followed by streptavidin magnetic bead capture.

A total of 3800 clones from the output phage pools were screened in bacterial periplasm format by human ROBO2 Ig1-Ig2 protein binding ELISA using standard protocols. Over 110 variants specifically binding ROBO2 were identified and reformatted into full-length human IgG.

The second approach was designed based on the resolved crystal structure of 93H2 complexed to ROBO2 Ig1 (FIG. 12). The same library screening paradigm was followed as described for the first approach. A total of 27 IgG variants were generated for screening using the assays described above.

From all the clones screened, the top 20 affinity optimized clones were identified consisting of 15 clones from the heavy chain libraries, 3 clones from the light chain libraries, and 2 clones from the structure-based libraries, each with a single unique mutation in the light chain.

Using Octet technology, Ab96 and Ab123 were shown to bind ROBO2 Ig1-Ig2 with relative Kd values of 1.2 nM and 1.4 nM respectively, exhibiting a 25-30-fold improvement on the Kd of 93H2 (37 nM). Ab96 and Ab123 along with another 18 clones having favorable affinity enhancements, underwent additional heavy and light chain shuffling.

The lead affinity matured clone (Abcs35) arose from this process and is comprised of the heavy chain variable domain from clone Ab96 and the light chain variable domain from Ab123. Abcs35 antibody binds to ROBO2 Ig1-2 with Kd=279 pM using both Octet method and SPR method, indicating a ~300-fold affinity improvement.

Example 2. Identification and Characterization of ROBO2 Specific Neutralizing Antibodies Antibodies generated as a result of the affinity maturation campaign were screened by numerous assays for neutralization of SLIT2-N binding, selective binding to ROBO2 over ROBO1, and inhibition of SLIT2-N functional activity (see Table 2). A ROBO2-SLIT2-N homogenous time resolved fluorescence (HTRF) assay was used to identify antibodies that were capable of blocking SLIT2-N binding to ROBO2. In this assay, terbium (Tb) labeled-SNAP tagged ROBO2 expressing HEK293 cells were incubated with 5 nM d2-labeled SLIT-2N in the presence of 1 nM anti-ROBO2 antibodies for 1 hour. After incubation, fluorescence at 665 nm and 620 nm was measured on an Envision multilabel plate reader. The HTRF Ratio was calculated as follows: fluorescence at 665 nm/fluorescence at 620 nm×10,000. Maximal signal was defined as the HTRF ratio of Tb-labeled ROBO2 cells with d2-labeled SLIT2-N in the absence of antibody, the minimum signal was defined as the HTRF ratio of Tb-labeled ROBO2 expressing HEK293 cells only. One nanomolar (nM) parental antibody, 93H2, was unable to block the HTRF assay, therefore this concentration was selected to identify clones with a higher affinity than 93H2 (Table 2, HTRF Ratio column). Antibodies that demonstrated single point neutralization of SLIT2-N binding were then evaluated for dose-dependent neutralization of the HTRF assay to identify clones with a lower inhibitory concentration 50 ($IC_{50}$, the concentration at which half-maximal signal inhibition is observed). 93H2 and parental affinity matured antibodies (Ab series) were evaluated in 7-point, 10-fold dilution series with a top concentration of 1000 nM. Antibodies derived from chain (Abcs series) or CDR shuffling (CTIR-2 series) were evaluated in 11-point, 5-fold dilution series with a top concentration of 1500 nM (Table 2 HTRF $IC_{50}$).

The parental 93H2 antibody was highly ROBO2 specific, therefore affinity matured antibodies with single point neutralizing activity were screened by flow cytometry to ensure ROBO2 selectivity had been maintained. To evaluate ROBO2 selectivity, human embryonic kidney 293 (HEK293) cells overexpressing either human ROBO1 or ROBO2 were incubated with selected antibodies at a single concentration for 30 minutes at 4° C. 93H2 and parental affinity matured antibodies (Ab series) were stained with 0.1 µg/ml of the indicated antibody and antibodies derived from chain (Abcs series) or CDR shuffling (CTIR-2 series) were stained with 2.5 µg/ml of the indicated antibody. Binding of the antibodies was detected using a secondary fluorochrome conjugated anti-human IgG F(ab')$_2$ antibody and samples were analyzed on a Fortessa cytometer (BD Biosciences). The fold ROBO2 selectivity was calculated as the geometric mean fluorescence intensity (Geo MFI) with ROBO2 cells/ Geo MFI with ROBO1 cells. A fold change higher than 3 was considered to be ROBO2 specific (Table 2, Fold Selectivity). Some affinity matured clones had increased ROBO1 reactivity, for example Abcs 55, CTI-R2-10 and CTIR2-13.

Table 2 is a summary of assays used to screen antibodies against ROBO1 and/or ROBO2 to identify an antibody that specifically recognized ROBO2 but not ROBO1 with high affinity. The assays performed included a single point neutralization Homogenous Time Resolved Fluorescence (HTRF) assay to identify clones that were able to neutralize the assay under conditions where the parental antibody did not neutralize. Full dose curves were performed in the same assay for select antibodies. Recognition of native, surface expressed protein and ROBO2 selectivity was evaluated by flow cytometry. Antibodies were tested at a single concentration for binding to human embryonic kidney 293 (HEK293) cells overexpressing either human ROBO1 or ROBO2. When antibodies demonstrated binding to surface expressed protein, the fold selectivity was determined by dividing the geometric mean fluorescence intensity (Geo MFI) on ROBO2 cells by the Geo MFI on ROBO1 cells. Anything with a value of greater than 3 was deemed to be selective for ROBO2. Outcomes of the various screening assays conducted for each antibody are highlighted in the final column.

Figure 6:
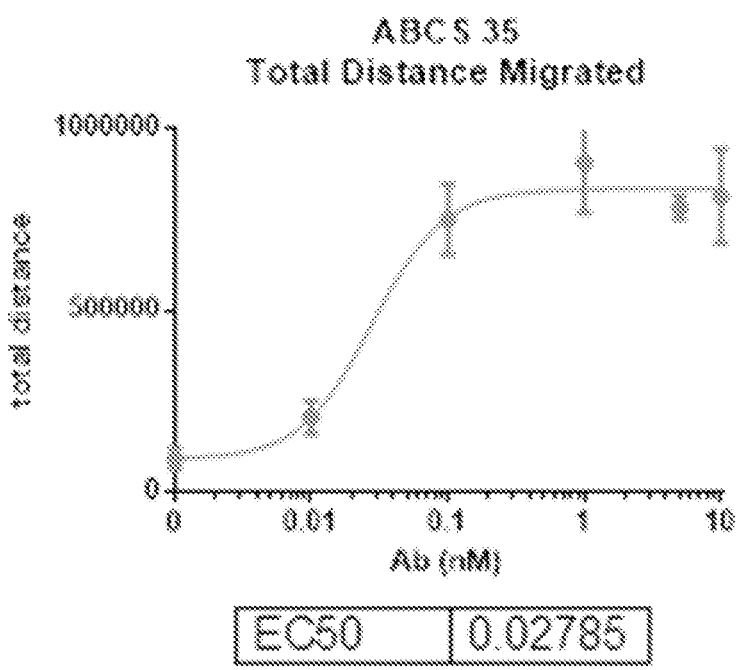
FIG. 6 depicts the dose-dependent inhibition of SLIT2-N mediated inhibition of neuronal cell migration. As described in Table 5, SVZ neuronal tissue cell explants were cultured overnight in the presence of 1 nM SLIT2-N and titrated amounts of Abcs35. Abcs35 was able to restore neuronal cell migration in a dose-dependent manner, essentially reversing ROBO2-dependent SLIT2-N-mediated Inhibition of neuronal cell migration.

The final selection screen was functional neutralization of ROBO2-dependent SLIT2-N activity. SLIT2-ROBO2 interactions are key regulators of axonal migration during development. It is known that SLIT2 is chemo-repulsive for subventricular zone neurons and that this activity is ROBO2 dependent. Neuronal tissue explants from the subventricular zone (SVZ) of rats were isolated and embedded in a collagen matrix. In the presence of SLIT2-N, neuronal cell migration is inhibited (SVZa assay); antibodies were evaluated for the dose-dependent ability to restore neuronal cell migration in the SVZa assay. Tissue explants were incubated in the presence of 1 nM SLIT2-N with or without titrated amounts of select ROBO2-specific antibodies. After incubation, cells were fixed with 4% paraformaldehyde and stained with Hoechst 33342. Wide-field fluorescence images were acquired on the Operetta High Content Imager (Perkin Elmer) with a 10× high NA objective. Nine fields per well with 5% overlap were taken to capture the entire center area of the well. A Z-stack for each field was acquired consisting of 6 planes with 1 µm distance between each plane to capture the full depth of the tissue explant. Analysis was performed in Volocity software (Perkin Elmer). All fields in each well were stitched together. Area of the tissue explant in the center and each nucleus outside of the tissue explant were detected by Hoechst 33342 staining. Individual nuclei were counted and the distance of the center of each nucleus to the closest edge of the tissue explant was measured in µm. The mean migration distance of nuclei in the well was multiplied by the nuclei count to obtain the total migration distance for each well. All selected affinity matured antibodies had lower $IC_{50}$s relative to the parental 93H2 antibody in the SVZa assay (Table 5) with Abcs35 having the lowest $IC_{50}$ of 0.027 nM (FIG. 6).

TABLE 2

Characterization of ROBO1/ROBO2 Antibodies

| | Evaluation Assays | | | | |
|---|---|---|---|---|---|
| Antibody Clone | HTRF* Ratio[a] Average ± s.d | HTRF $IC_{50}$ (nM)[b] | Fold Selectivity for ROBO2/ ROBO1[c] | Fold Selectivity for RSK/KSR[d] | Overall outcomes from all assays |
| Abcs35 | 3942 ± 194 | 0.041 | 4.8 | 6.6 | Neutralizer, I.A., selective, selective |
| 93H2 | 13821 ± 606 | 4.216 | >100 | >100 | Parental, selective, selective |
| Ab1 | 13977 ± 306 | N.T. | N.B.** | N.T. | non-neutralizer, non-binder, did not pursue |
| Ab3 | 6612 ± 509 | 0.133 | 92.0 | N.T. | Neutralizer, I.A., selective |
| Ab9 | 13611 ± 244 | N.T. | N.B. | N.T. | non-neutralizer, non-binder, did not pursue |
| Ab13 | 13751 ± 1132 | N.T. | N.B. | N.T. | non-neutralizer, non-binder, did not pursue |
| Ab17 | 13477 ± 1960 | N.T. | N.B. | N.T. | non-neutralizer, non-binder, did not pursue |

TABLE 2-continued

Characterization of ROBO1/ROBO2 Antibodies

| Antibody Clone | Evaluation Assays | | | | |
|---|---|---|---|---|---|
| | HTRF* Ratio$^a$ Average ± s.d | HTRF IC$_{50}$ (nM)$^b$ | Fold Selectivity for ROBO2/ROBO1$^c$ | Fold Selectivity for RSK/KSR$^d$ | Overall outcomes from all assays |
| Ab21 | 13120 ± 883 | N.T. | N.B. | N.T. | non-neutralizer, non-binder, did not pursue |
| Ab22 | 5729 ± 1534 | 0.229 | 67.4 | N.T. | neutralizer, I.A., selective |
| Ab25 | 12662 ± 3202 | N.T. | N.B. | N.T. | non-neutralizer, non-binder, did not pursue |
| Ab29 | 7726 ± 889 | 0.097 | >100 | N.T. | neutralizer, I.A., selective |
| Ab32 | 6002 ± 399 | 0.234 | 90.3 | N.T. | neutralizer, I.A., selective |
| Ab40 | 7432 ± 273 | 0.728 | >100 | N.T. | neutralizer, I.A., selective |
| Ab45 | 8313 ± 1686 | N.T. | N.B. | N.T. | non-neutralizer, non-binder, did not pursue |
| Ab46 | 5714 ± 1787 | 0.109 | >100 | N.T. | neutralizer, I.A., selective |
| Ab58 | 5571 ± 505 | 0.282 | 21.8 | N.T. | neutralizer, I.A., selective |
| Ab83 | 4769 ± 627 | 0.437 | 40.6 | N.T. | neutralizer, I.A., selective |
| Ab96 | 3675 ± 1702 | 0.166 | 35.0 | N.T. | neutralizer, I.A., selective |
| Ab112 | 7297 ± 1178 | 0.174 | 39.2 | N.T. | neutralizer, I.A., selective |
| Ab123 | 7706 ± 1000 | 0.260 | 80.5 | N.T. | neutralizer, I.A., selective |
| Abcs1 | 14532 ± 1495 | N.T. | N.T. | N.T. | Non-neutralizer, did not test for binding |
| Abcs2 | 14658 ± 832 | N.T. | N.T. | N.T. | Non-neutralizer, did not test for binding |
| Abcs4 | 13392 ± 1481 | N.T. | N.T. | N.T. | Non-neutralizer, did not test for binding |
| Abcs5 | 3538 ± 382 | 0.036 | 5.1 | 6.7 | neutralizer, I.A., selective, selective |
| Abcs12 | 2910 ± 1188 | 0.032 | 15.7 | >100 | neutralizer, I.A., selective, selective |
| Abcs20 | 3973 ± 3 | 0.04 | 5.2 | 7.0 | neutralizer, I.A., selective, selective |
| Abcs25 | 3876 ± 372 | 0.042 | 3.3 | 8.1 | neutralizer, I.A., selective (borderline), selective |
| Abcs40 | 3391 ± 192 | 0.048 | 4.8 | 9.3 | neutralizer, I.A., selective, selective |
| Abcs50 | 2713 ± 1596 | 0.051 | 3.9 | 1.3 | neutralizer, I.A. selective (borderline), cross-reactive |
| Abcs55 | 3046 ± 325 | 0.057 | 1.5 | 1.5 | neutralizer, I.A., cross-reactive, cross-reactive |
| CTIR2-1 | 4541 ± 135 | 0.1593 | N.T. | N.T. | neutralizer, I.A. |
| CTIR2-2 | 4331 ± 430 | 0.1087 | N.T. | N.T. | neutralizer, I.A. |
| CTIR2-3 | 4054 ± 60 | 0.1543 | N.T. | N.T. | neutralizer, I.A. |
| CTIR2-4 | 6167 ± 187 | 0.3803 | N.T. | N.T. | neutralizer, I.A. |
| CTIR2-5 | 5177 ± 783 | 0.1652 | N.T. | N.T. | neutralizer, I.A. |
| CTIR2-6 | 4159 ± 609 | 0.067 | 35.0 | >100 | neutralizer, I.A., selective, selective |
| CTIR2-7 | 3668 ± 795 | 0.136 | N.T. | N.T. | neutralizer, I.A. |
| CTIR2-8 | 3859 ± 116 | 0.108 | N.T. | N.T. | neutralizer, I.A. |
| CTIR2-9 | 3537 ± 238 | 0.064 | 14.8 | >100 | neutralizer, I.A., selective |
| CTIR2-10 | 3924 ± 379 | 0.04 | 2.3 | 1.4 | neutralizer, I.A., cross-reactive, cross-reactive |
| CTIR2-11 | 4784 ± 148 | 0.182 | N.T. | N.T. | neutralizer, I.A. |
| CTIR2-12 | 4585 ± 518 | 0.076 | N.T. | N.T. | neutralizer, I.A. |
| CTIR2-13 | 3529 ± 87 | 0.055 | 2.3 | 2.5 | neutralizer, I.A. |

TABLE 2-continued

Characterization of ROBO1/ROBO2 Antibodies

| Antibody Clone | Evaluation Assays | | | | |
|---|---|---|---|---|---|
| | HTRF* Ratio$^a$ Average ± s.d | HTRF $IC_{50}$ (nM)$^b$ | Fold Selectivity for ROBO2/ ROBO1$^c$ | Fold Selectivity for RSK/KSR$^d$ | Overall outcomes from all assays |
| CTIR2-14 | 3714 ± 71 | 0.037 | 23.9 | >100 | neutralizer, I.A., selective, selective |
| CTIR2-15 | 3746 ± 167 | 0.05 | 12.1 | >100 | neutralizer, I.A., selective, selective |
| CTIR2-16 | 3732 ± 85 | 0.056 | 6.2 | 66.5 | neutralizer, I.A., selective, selective |
| No antibody | 11919 ± 1625 | | | | |
| Cells alone | 3174 ± 487 | | | | |
| 46A4** | | | 1.3 | 2.3 | Cross-reactive |

*HTRF = Homogenous Time Resolved Fluorescence.
$^a$The HTRF Ratio is calculated as 665 nm/620 nm × 10,000. HTRF assays were run with 5 nM d2-labeled SLIT2-N and antibodies were added at 1 nM. The parental 93H2 was not able to inhibit this assay at 1 nM; any antibody that showed inhibition at this single concentration was deemed to be of higher affinity/interest;
$^b IC_{50}$ = inhibitory concentration 50, the concentration at which half-maximal signal inhibition is observed; 93H2 and parental affinity matured antibodies (Ab series) were evaluated in 7-point, 10-fold dilution series with a top concentration of 1000 nM. Antibodies derived from chain (Abcs series) or CDR shuffling (CTIR-2 series) were evaluated in 11-point, 5-fold dilution series with a top concentration of 1500 nM, N.T. = not tested;
$^c$Fold selectivity was calculated as Geometric Mean Fluorescent Intensity (Geo MFI) of ROBO2/Geo MFI of ROBO1 binding. Anything with a fold selectivity <3 was considered to not be highly selective for ROBO2; N.B. = No binding to ROBO2, therefore fold binding could not be determined, N.T. = not tested; 93H2 and parental affinity matured antibodies (Ab series) were stained with 0.1 µg/ml of the indicated antibody and antibodies derived from chain (Abcs series) or CDR shuffling (CTIR-2 series) were stained with 2.5 µg/ml of the indicated antibody.
**46A4 is a positive control antibody that reacts both ROBO1 and ROBO2 in fold binding assays;
$^d$Fold selectivity was calculated as Geometric Mean Fluorescent Intensity (Geo MFI) of ROBO1-RSK/Geo MFI of ROBO2-KSR binding. Anything with a fold selectivity <3 was considered to not be highly selective for ROBO2, assay conditions were the same as described for
$^e$ROBO2/ROBO1 selectivity.
Outcomes: results are listed in order of assays listed in the table (left to right), I.A. = Improved Affinity

Example 3. In Vitro Pharmacology of Abcs35 and Abcs25

Based upon several criteria, Abcs25 and Abcs35 were selected for further characterization. Using flow cytometry, improvement in the binding $EC_{50}$ to human ROBO2 relative to the parental 93H2 was evaluated. Starting at 6.7 nM, 11-point, 3-fold dilution series were made for each antibody and used to stain HEK293 overexpressing human ROBO2 as described above for the ROBO2 fold selectivity (Example 2). Both Abcs 25 and Abcs35 demonstrated higher affinity binding to human ROBO2 with lower $EC_{50}$s (Table 3). In addition to measuring improved binding to human ROBO2, it was important to ensure that high affinity binding to both cynomolgus monkey ROBO2 and rat ROBO2 was maintained. Using HEK293 cells overexpressing either cynomolgus monkey ROBO2 or rat ROBO2, the relative dose-dependent binding of 93H2, Abcs25 and Abcs35 was evaluated as described above. High affinity binding to both cynomolgus monkey and rat ROBO2 was maintained in Abcs25 and Abcs35 (Table 4). The KD of Abcs35 was determined to be 0.268 nM by surface plasmon resonance (SPR) using a Biacore T200. Briefly, Abcs35 was immobilized to 300 resonance units (RU) on a CM5 chip. Association of ROBO2 Ig1-Ig2-His (ROBO2) was measured over 5 minutes and dissociation was followed for a period of 10 minutes. An 8-point, 2-fold dilution series of ROBO2 was used to determine the KD (FIG. 1).

Table 3 is a summary of the Effective Concentration 50 ($EC_{50}$) values, concentration at which the half-maximal signal of antibody binding to cells is observed, of the parental ROBO2 specific antibody, 93H2, and two selected affinity matured clones, Abcs35 and Abcs25. The $EC_{50}$ was determined by evaluating the dose-dependent binding to either cells overexpressing human ROBO2 or a mutant form of ROBO1 containing the RSK epitope from ROBO2.

TABLE 3

Dose-dependent Binding ($EC_{50}$ Determination) of ROBO2 Specific Antibodies

| Antibody Clone | ROBO2 cells $EC_{50}$ (nM) | ROBO1-RSK cells $EC_{50}$ (nM) |
|---|---|---|
| Abcs35 | 0.055 | 0.074 |
| 93H2 | 0.133 | 0.370 |
| Abcs25 | 0.056 | 0.061 |

The top 2 lead antibodies were compared to the original selective ROBO2 parental antibody, 93H2, an 11-point, 3-fold dilution series with a top concentration of 6.7 nM (1 µg/ml). $EC_{50}$ = Effective Concentration 50, the concentration at which the half-maximal signal is observed. $EC_{50}$s were not determined for the other antibody clones listed.

Table 4 is a summary of the $EC_{50}$ values of the parental ROBO2 specific antibody, 93H2, and two selected affinity matured clones, Abcs35 and Abcs25, to either human, cynomolgus monkey or rat ROBO2 orthologs. The $EC_{50}$ was determined by evaluating the dose-dependent binding to HEK293 cells either overexpressing human ROBO2, cynomolgus monkey ROBO2 or rat ROBO2.

TABLE 4

Antibody Binding to ROBO2 Orthologs

| Antibody Clone | $EC_{50}$ Human (nM) | $EC_{50}$ Cynomolgus Monkey (nM) | $EC_{50}$ Rat (nM) |
|---|---|---|---|
| Abcs35 | 0.082 ± 0.038 | 0.145 ± 0.053 | 0.048 ± 0.013 |
| 93H2 | 0.133 ± 0.078 | 0.316 ± 0.102 | 1.204 ± 1.503 |
| Abcs25 | 0.068 ± 0.036 | 0.128 ± 0.039 | 0.062 ± 0.038 |

The top 2 lead antibodies were compared to the original selective ROBO2 parental antibody, 93H2, an 11-point, 3-fold dilution series with a top concentration of 6.7 nM (1 µg/ml). $EC_{50}$ = Effective Concentration 50, the concentration at which the half-maximal signal is observed. $EC_{50}$s were not determined for the other antibody clones listed. $EC_{50}$ are represented as the average value + standard deviation. Number of replicate experiments per ROBO ortholog: Human n = 5, Cynomolgus monkey n = 3 and Rat n = 3.

Table 5 is a summary of the Inhibitory Concentration 50 ($IC_{50}$) values, the concentration at which half-maximal signal inhibition is observed, for neutralization of SLIT2-N mediated inhibition of neuronal cell migration (SVZa assay) by selected ROBO2 specific antibodies. The SVZa assay involves the isolation of neuronal tissue explants from the subventricular zone (SVZ) of rats. When embedded in a collagen matrix, neuronal cells migrate out of the explant; in the presence of SLIT2-N, neuronal cell migration is inhibited and this is ROBO2 dependent. In the presence of neutralizing anti-ROBO2 antibodies, neuronal cell migration is restored. Tissue explants were incubated in the presence of 1 nM SLIT2-N in the presence or absence of titrated amounts of selected ROBO2-specific antibodies and reversal of SLIT2-N mediated inhibition of migration was evaluated. Dose-dependent inhibition of SLIT2-N activity was seen with all the antibodies tested over a range of $IC_{50}s$. Values for Abcs35, Abcs25 and CTIR2-15 represent the average of two independent experiments, whereas others represent a single experiment.

TABLE 5

Inhibition of ROBO2-dependent Neuronal Cell Migration (SVZa assay)

| Antibody Clone | $IC_{50}$ (nM) |
| --- | --- |
| Abcs35 | 0.039 ± 0.003 |
| 93H2 | 1.69 |
| Abcs20 | 0.47 |
| Abcs25 | 0.31 ± 0.13 |
| Abcs40 | 0.11 |
| Abcs55 | 0.98 |
| CTIR2-14 | 0.11 |
| CTIR2-15 | 0.020 ± 0.001 |
| CTIR2-16 | 0.41 |

Example 4. In Vivo Pharmacology

Figure 7:
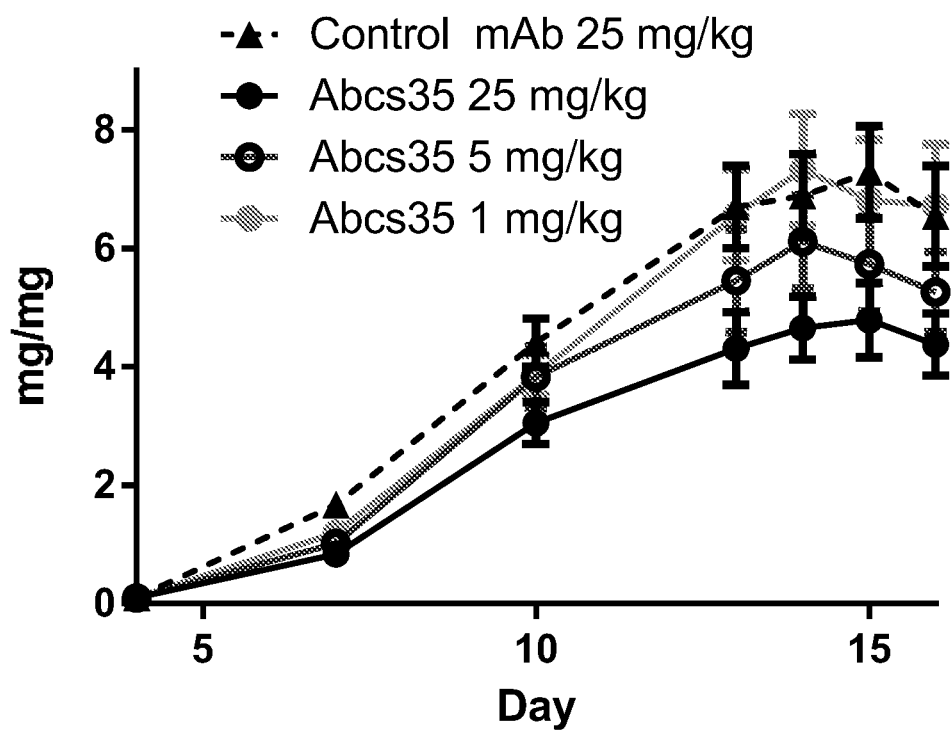
FIG. 7 demonstrates the in vivo efficacy of Abcs35 (inhibition of proteinuria with treatment of Abcs35) in the rat Passive Heymann Nephritis model. Twelve animals in each of the indicated groups were treated subcutaneously with the indicated dose of Abcs35 or an irrelevant control monoclonal antibody every three days starting the day before the induction of the model on day 0. The Y axis indicates the ratio of urine albumin to creatinine (mg/mg) as a measure of leakage of protein into the urine, indicative of podocyte damage. Lewis rats were injected with sheep anti-sera raised against rat kidney brush border (anti Fx1a, basement membrane and podocytes). The rats develop an immune response to the sheep sera which has bound the rat podocytes. As podocytes are damaged and efface, proteinuria increases. Treatment with the highest dose of Abcs35 reduced proteinuria 39% maximally with a p value less than 0.001 by repeated measure ANOVA statistical analyses compared to the control antibody treatment. The dose effect was also statistically significant with a p value less than 0.001.
Figure 8:
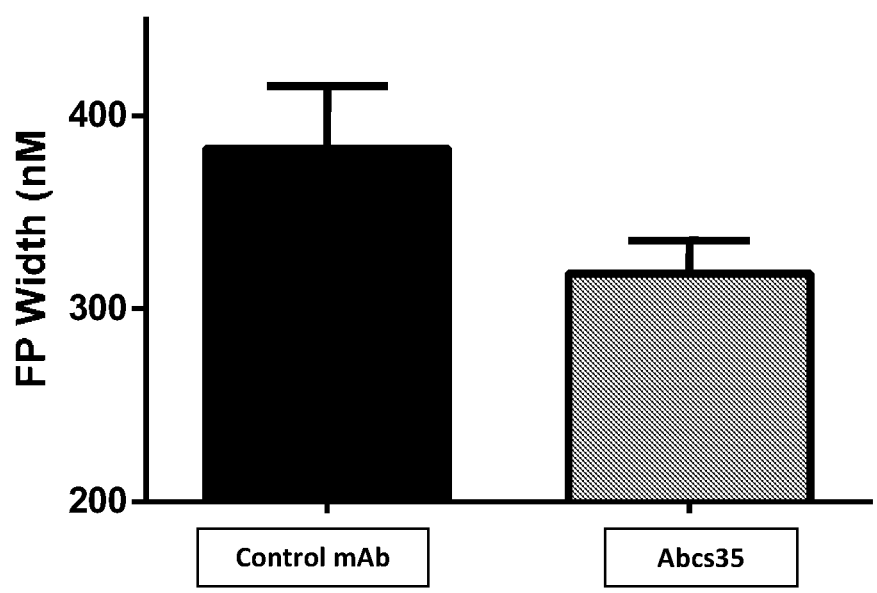
FIG. 8 demonstrates that treatment with Abcs35 reduces damage to podocyte substructure in the Passive Heymann Nephritis Model. Twelve animals in each of the indicated groups were treated subcutaneously with the indicated dose of Abcs35 or an irrelevant control monoclonal antibody every three days at 25 mg/kg to achieve 100% target coverage starting the day before the induction of the model on day 0 as shown in FIG. 7. Following animal sacrifice at day 16 selected kidney samples were digitally imaged using a transmission electron microscope. Without repetition, three capillary loops of the first three glomeruli found at 200× magnification, were imaged at 5000× and 10,000× magnification. ImageJ software (version 1.47v; National Institutes of Health, Bethesda, Md.) was used to manually trace and measure the width of foot processes (FP) adjacent to per unit length of the glomerular basement membrane (GBM) on high magnification transmission electron microscopy images. The podocyte foot processes of the Abcs35 treated animal were significantly shorter (p value less than 0.01 by two tailed T test) than the control antibody treated animals, indicating that they are less effaced and are protected from the glomerular insult.

Treatment of rats with Abcs35 reduces proteinuria and protects podocyte foot process architecture. As shown in FIGS. 7 and 8, treatment of rats in the Passive Heymann Nephritis model, a model of podocyte-driven glomerular chronic kidney disease, reduced the amount of proteinuria in a dose-dependent manner. In short, Lewis rats are injected with sheep anti-sera raised against rat kidney brush border (anti-Fx1a (Probetex Inc), basement membrane and podocytes). The rats develop an immune response to the sheep sera which has bound the rat podocytes. Complement activation then leads to podocyte effacement and an increase in proteinuria between day 3 and 12 followed by a plateau. This mechanism closely resembles that found in Membranous Nephropathy where autoantibodies against the podocyte protein PLA2R (in 70% of cases) cause podocyte effacement and nephrotic range proteinuria following complement engagement. Rats were pretreated 24 hours before the model start with a dose range to cover approximately 80, 90 and 99% (1, 5, and 25 mg/kg) of glomerular ROBO2 and every 72 hours thereafter. The maximal reduction in proteinuria was 39% and a repeated measures ANOVA statistical analysis confirmed the dose response with a p value of 0.0003. There was no reduction in immune complex deposition in the kidney as determined by complement IHC scoring, indicating the response was due to a podocyte protective effect. To further provide confidence in the modulation of podocyte function and structure, quantitative analysis of electron micrographs of podocyte substructure was performed (as described below). The distance between slit diaphragms of interdigitating foot processes was calculated across multiple capillary loops, determining the average foot process width. The foot process width of an effaced podocyte will be larger than that of a normal uneffaced podocyte. As shown in FIG. 8, the foot process width of the Abcs35 treated animals at the 25 mg/kg dose was significantly shorter (19% reduction) that the control antibody treated animals. This data supported the hypothesis that the reduction of proteinuria was due to an alteration in podocyte substructure.

Collection, Sampling, and Sectioning:

Full face sample kidneys (one kidney per animal) fixed by immersion (4% formaldehyde/1% glutaraldehyde) were received, trimmed to include just the cortex, and five samples of each kidney were embedded in epoxy resin. The first embedded sample of each kidney was sectioned. If it contained three glomeruli this sample was thin sectioned and imaged. If this first sample did not contain glomeruli, the other embedded samples from that kidney were sequentially sectioned and similarly evaluated to find a sample with three glomeruli.

Viewing and Imaging:

Selected kidney samples were digitally imaged using a transmission electron microscope (Hitachi H-7100) and a digital CCD camera system (Advanced Microscopy Techniques, Danvers, Mass.). Without repetition, three capillary loops of the first three glomeruli found at 200× magnification, were imaged at 5000× and 10,000× magnification. This resulted in 18 digital images per kidney (i.e. three glomeruli per kidney sample×three areas per glomerulus×2 magnifications). To allow evaluation in a blinded fashion, each image was identified only with study number, animal number, sample number, and magnification.

Podocyte Foot Process Width and Slit-Diaphragm Density Measurement.

ImageJ software (version 1.47v; National Institutes of Health, Bethesda, Md., USA) was used to manually trace and measure the width of foot processes adjacent to per unit length of the glomerular basement membrane (GBM) on high magnification transmission electron microscopy images.

Example 5. Identification of ROBO2 Specific Epitope

Material Preparation, Crystallization, Data Collection, and Structure Determination:

Purification of ROBO2 Ig1 domain. The Ig1 domain of ROBO2 with 6×histidine tag at C-terminus, was transiently expressed in mammalian cells and purified through Ni Excel column with imidazole gradient elution. The protein was further purified to homogeneity via size exclusion chromatography using HiLoad 26/200 Superdex 200 (GE Healthcare).

Generation of 93H2 Fab. Anti-ROBO2 mAb 93H2 was digested with immobilized Papain for 12 hours per manufacturer protocol (Thermo/Pierce). Protein A50 (Poros) was used to separate the Fab from digested pool. The Fab was then further purified to homogeneity via size exclusion chromatography using HiLoad 26/200 Superdex 200 (GE Healthcare).

Complex Generation. The 93H2 Fab and the Ig1 domain of ROBO2 were mixed at 1:1.1 ratio for complex formation. Final size exclusion step using a HiLoad 26/200 Superdex 200 column (GE Healthcare) was performed to separate the excess of ROBO2. The purified complex was concentrated to 10.6 mg/ml for crystallization setup.

Crystallization. Crystals of the 93H2 Fab in complex with the Ig1 domain of ROBO2 were obtained in the following condition: 100 mM Sodium Citrate pH5.6, 100 mM Lithium Sulfate, 12% PEG6000. This condition yielded plate-shaped crystals that diffracted to 2.9 Å.

Data collection. Crystals were transiently cryo-protected and synchrotron data collection was performed remotely at the 17 ID beamline of Advanced Photon Source (APS). Image frames were processed using software AutoPROC (Global Phasing Ltd). The data belongs to space group P21, with unit cells as follows: a=76.46 Å, b=221.85 Å, c=129.31 Å, b=95.86°, with six complexes per asymmetric unit.

Structure determination and refinement. The molecular replacement search models are composed of homology models of the variable and constant domains of 93H2 Fab, as well as the Ig1 domain of ROBO1 publicly available via Protein Database Bank (access id: 2V9Q). After multiple runs of search, molecular replacement solutions of all 6 copies of the complex were placed into crystal lattice with high degree of confidence. After model rebuilding, refinement was performed using software autoBUSTER (Global Phasing Ltd), with the final refinement R/Rfree factors at 2.94 Å are 0.1646 and 0.2251, respectively. Structures are in good geometry with RMSD of bond 0.010 Å, RMSD of angles 1.23°.

Antibody-Antigen Interface and Mutagenesis Studies

FIG. 10 depicts the Ig1 domain of ROBO2 and ROBO1, which is the principal recognition site for SLIT1/SLIT2, exhibits 96.2% sequence similarity (102/106) and 92.5% sequence identity (98/106). Facing two virtually identical frameworks, any lead antibody capable of binding exclusively to ROBO2 but not ROBO1 has to be able to differentiate at least one of the following 8 residues on ROBO2 (corresponding residues in ROBO1 are listed in parenthesis): V40 (L), T48 (A), D67 (G), R100 (K), K102 (R), S107 (V), R122 (H), and N123 (D).

The crystal structure of the Ig1 domain of ROBO2 in complex with Fab of 93H2 mAb was determined at 2.94 angstrom with 6 copies of the complex per asymmetric unit. Due to differences in crystal packing environment, the 6 copies of complex can be grouped into 2 distinct conformations and provide additional insights into the conformational variability of binding interfaces between ROBO2 and 93H2.

Figure 11:
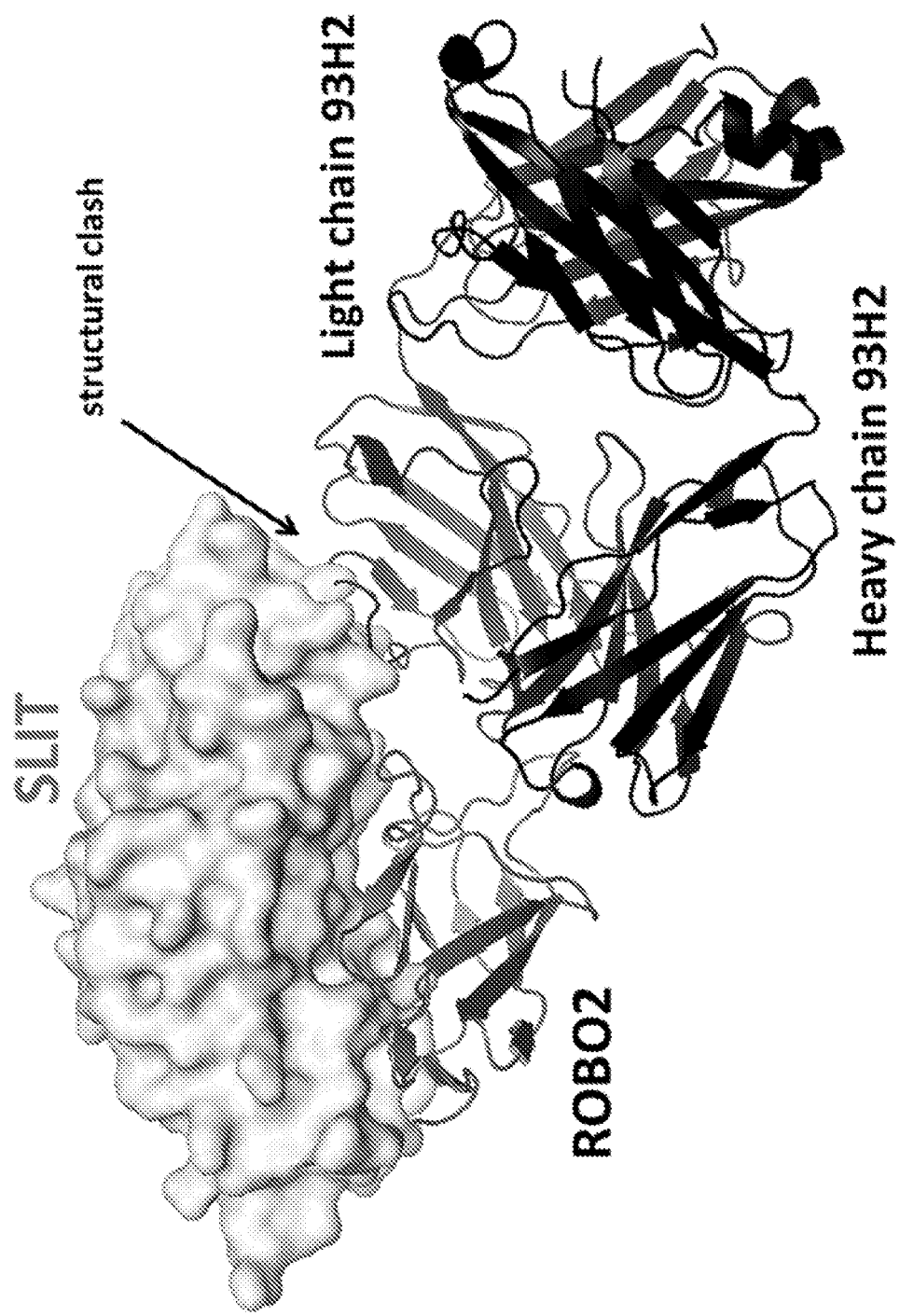
FIG. 11 depicts the aligned crystal structures of ROBO2-SLIT2 and ROBO2-93H2, revealing that the light chain of 93H2, only sparsely interacts with ROBO2, providing the necessary structural hindrance to inhibit the interaction between ROBO2 and SLIT2.

Aligning the crystal structures of ROBO2-SLIT2 and ROBO2-93H2 reveals that the light chain of 93H2, only sparsely interacting with ROBO2, provides the necessary structural hindrance to prevent the interaction between ROBO2 and SLIT2 (FIG. 11). When the binding affinity of ROBO2 with 93H2 is higher than that with SLIT2, 93H2 will provide sufficient steric blockage to prevent ROBO2-SLIT2 interaction and its downstream signaling.

The principal binding epitope on the Ig1 domain of ROBO2 targeted by 93H2 is a flexible loop (residues H97-P103) of ROBO2 (FIG. 12). An additional minor epitope contributed to 93H2 binding is via a separate loop (E72-H81) of ROBO2. However, the binding to the latter epitope is optional, as revealed in the complexes in different conformations; it is not a determining factor to dictate 93H2's specificity toward ROBO2.

The stability of principal interface between 93H2 and ROB2 is largely contributed by R99 and R100 of ROBO2 (FIG. 12). R100 forms extensive hydrogen bonding with E95 of heavy chain as well as the carbonyl group from S91 and Y92 of light chain of 93H2 to solidify the recognition. R99 of ROBO2 also contacts D99 of heavy chain and Y92 of light chain to further stabilize the interaction. Since R99 is conserved between ROBO1 and ROBO2, R100 is the sole residue that determines binding specificity of 93H2 towards ROBO2.

Mutagenesis studies further confirm the structural observation and prediction: mutating residues 100-102 of ROBO2 from RSK to KSR abolishes mutant ROBO2's ability to interact with 93H2; while mutating residues 100-102 of ROBO1 from KSR to RSK enables this mutant ROBO1 to interact with 93H2, which is ROBO2-specific (studies described below). Since S101 is conserved between ROBO2 and ROBO1, and the side chain of K102 does not involve ROBO2 interaction (pointing away from interface), it becomes evident that R100 is solely driving the binding specificity of 93H2 toward ROBO2.

Figure 2:
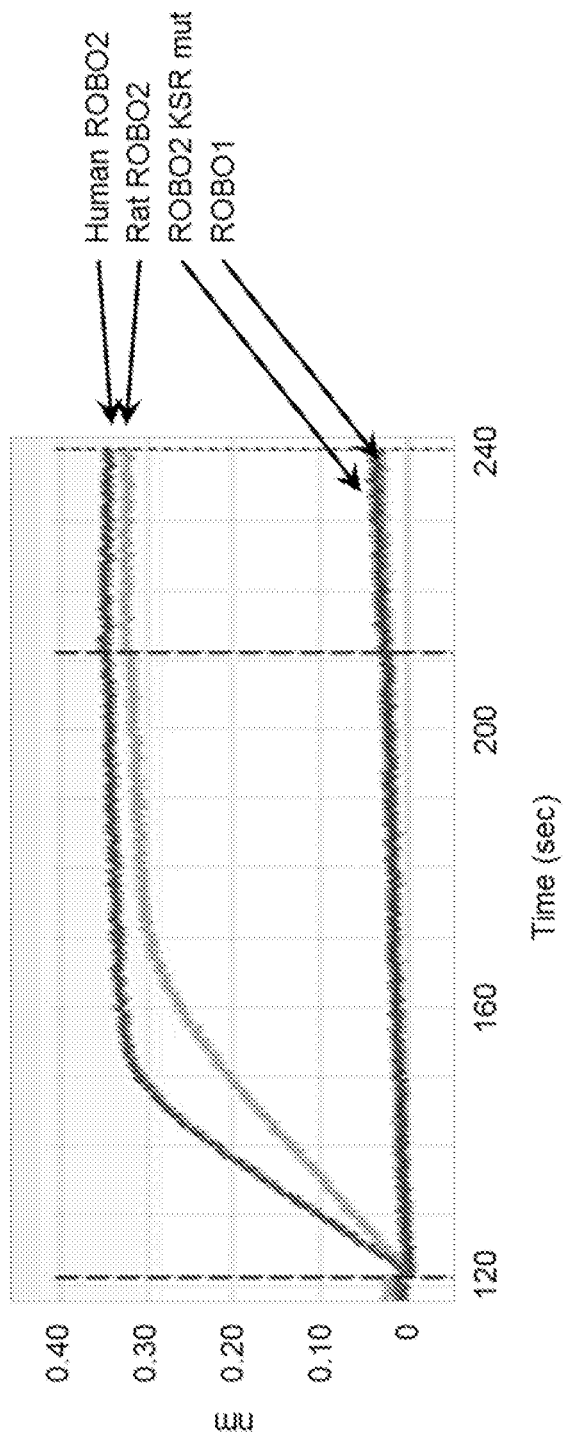
FIG. 2 demonstrates the specificity of the binding of Abcs35 to the RSK epitope of ROBO2 utilizing recombinant protein. Octet Red AHC (Anti-Human IgG FC) Sensors were loaded with Abcs35. The loaded sensors were then exposed to Human ROBO2 Ig1-2, Rat ROBO2 Ig 1-2, Human ROBO2 Ig1-2 with the RSK mutated to KSR as in ROBO1, or ROBO1 Ig1-2 then the sensors were moved to PBS only, lacking any ROBO1 or 2 proteins. The arrows indicate curves for each of the ROBO proteins tested. The human and rat ROBO2 proteins bound Abcs35, whereas ROBO1 and ROBO2-KSR proteins did not bind.

Based upon the crystal structure described above, the following experiments were done to confirm the epitope specificity of 93H2 and/or affinity matured clones Abcs35. Using Octet Red, epitope specificity was confirmed biochemically. Abcs35, at 10 µg/ml, was captured on AHC sensors for 60 seconds. Recombinant human ROBO2 Ig1-Ig2, rat ROBO1 Ig1-Ig2, human ROBO2 containing the ROBO1 KSR sequence (ROBO2-KSR mutant), and human ROBO1 Ig1-Ig2, prepared at 100 nM, were used to interact with captured Abcs35. Association time was 100 seconds then dissociation was followed for 20 seconds. Abcs35 specifically bound human and rat ROBO2 but not human ROBO1 or the ROBO2-KSR mutant protein (FIG. 2).

Figure 3:
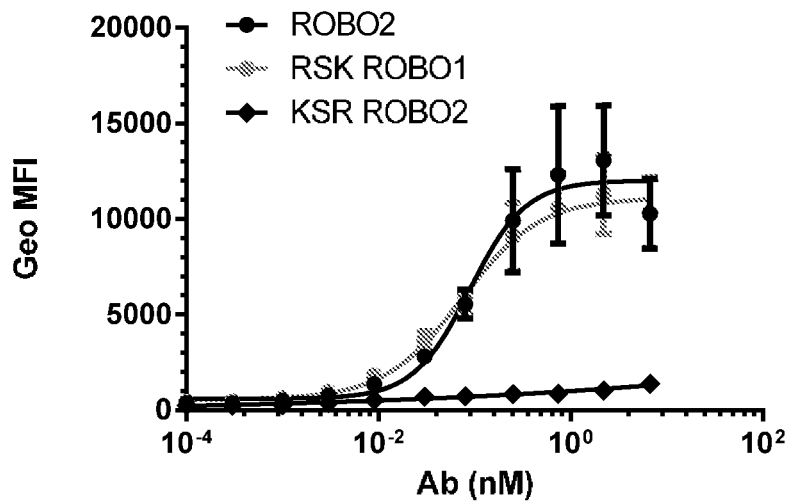
FIG. 3 depicts the dose-dependent binding of Abcs35 to human ROBO2 and the specific recognition of the RSK epitope in ROBO2. An 11 point, 3-fold dilution series was made with Abcs35 and binding to HEK293 cells overexpressing either human ROBO2 (positive control, black circles), human ROBO1 mutated to contain the RSK motif from ROBO2 (grey circles) or ROBO2 mutated to contain the KSR motif from ROBO1 (black diamonds) was evaluated. Dose-dependent binding is seen only with native ROBO2 or ROBO1-RSK, but not ROBO2-KSR, indicating that Abcs35 binds ROBO2 and specifically the RSK motif within ROBO2.
Figure 4:
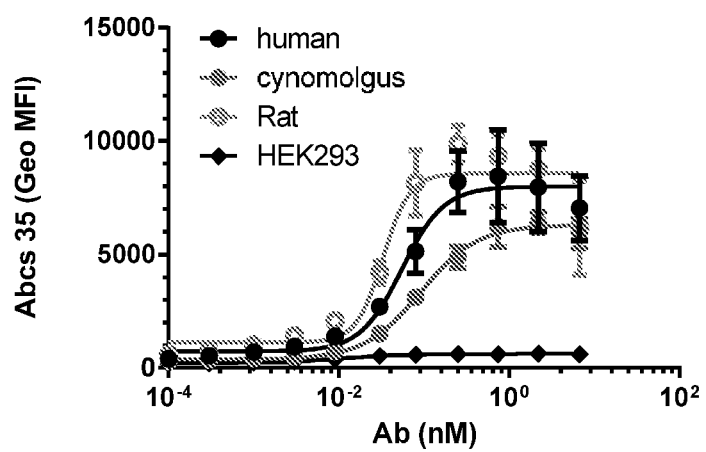
FIG. 4 demonstrates that Abcs35 cross-reacts with both cynomolgus monkey and rat ROBO2 orthologs. An 11 point, 3-fold dilution series was made with Abcs35 and used to evaluate binding to either control HEK293 cells (black diamonds) or HEK293 cells overexpressing human ROBO2 (closed black circles), cynomolgus monkey ROBO2 (closed grey circles), or rat ROBO2 (open grey circles). Dose-dependent binding is seen on cells expressing human, cynomolgus monkey or rat ROBO2 but not control HEK293 cells, indicating Abcs35 recognizes both orthologs.
Figure 5:
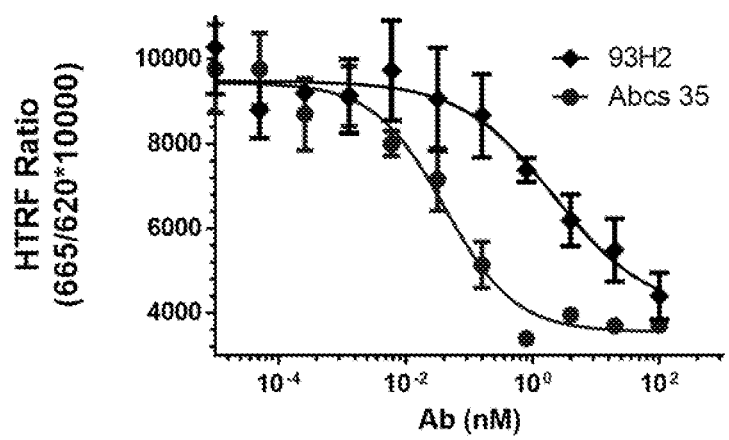
FIG. 5 demonstrates the dose-dependent inhibition of SLIT2-N binding to ROBO2 as assessed by Homogenous Time Resolved Fluorescence (HTRF). Both the parental 93H2 and affinity matured Abcs35 neutralize SLIT2-N binding.

RSK specificity for Abcs35, along with 93H2 and Abcs25, also was confirmed in a cell-based binding assay using flow cytometry. HEK293 cells overexpressing ROBO2 containing the KSR sequence from ROBO1 (ROBO2-KSR) or ROBO1 containing the RSK sequence from ROBO2 (ROBO1-RSK) were generated. As described above in Example 3, dose-dependent binding was evaluated. Abcs35 demonstrated specific binding to cells expressing human ROBO2 and ROBO1-RSK cells but no binding was observed to cells expressing the mutant ROBO2-KSR protein (FIG. 3). Along with Abcs35, 93H2 and Abcs25 demonstrated dose-dependent and specific binding to cells expressing the mutant ROBO1-RSK protein, with Abcs25 and Abcs35 having higher affinities than the parental 93H2 (Table 3).

Epitope and Paratope Analysis

Figure 13:
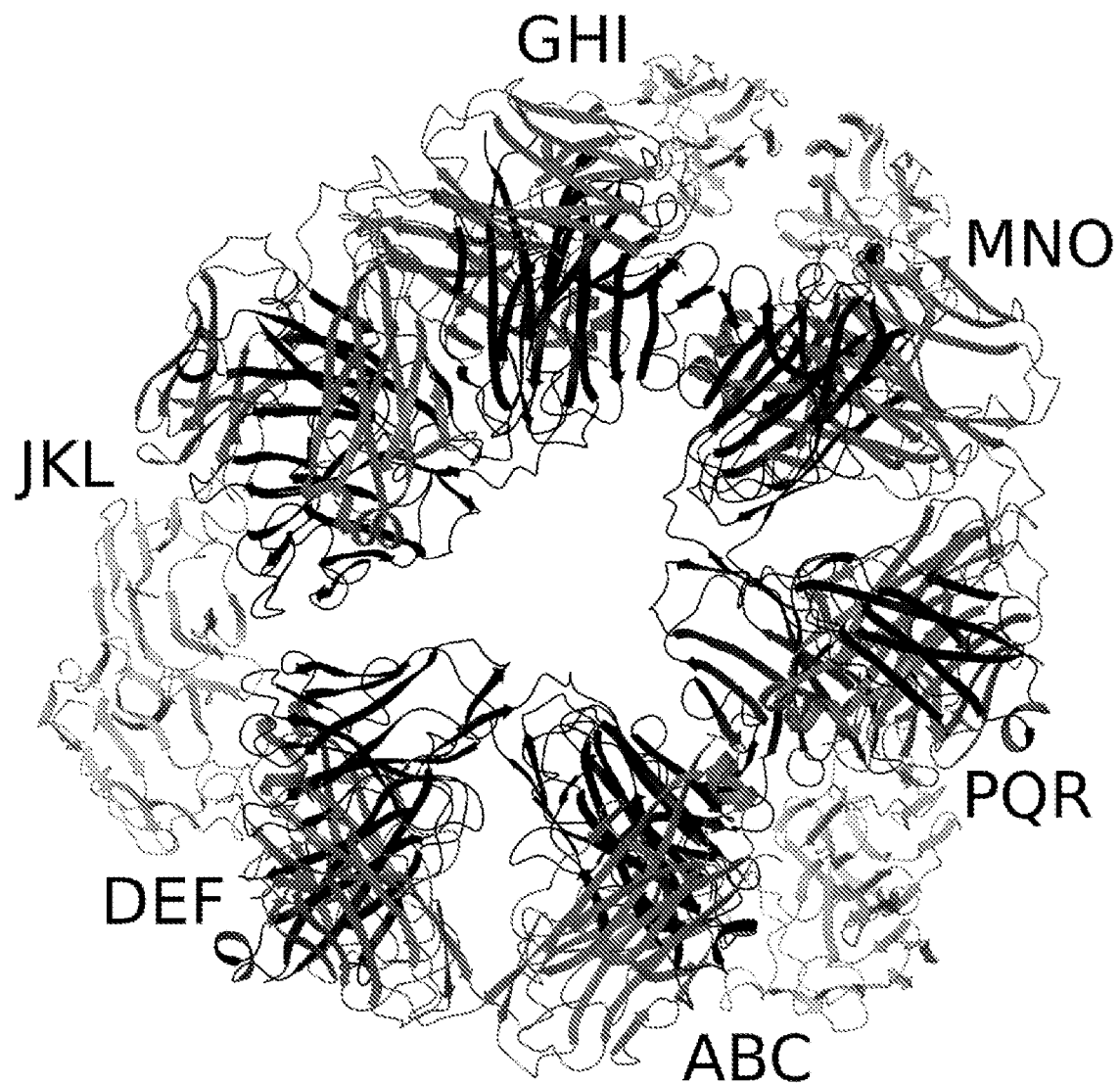
FIG. 13 shows the crystal structure of the Ig1 domain of ROBO2 in complex with the Fab of 93H2. The structure is composed of 6 copies of the ROBO2-93H2 complex, arranged in a ring-like configuration in each asymmetric unit of the crystal lattice.

The overall crystal structure of the Ig1 domain of ROBO2 in complex with the Fab of 93H2 is shown in FIG. 13. The asymmetric unit contains 6 copies of the ROBO2-93H2 complex, arranged in a ring-like configuration in the crystal lattice. This arrangement allows visualizing the same complex in 6 slightly different local environments. Some additional differences between the crystal structure and solution behavior may occur due to differences in solution conditions (such as pH) in the two environments. In the structure, chains A, D, G, J, M and P are instances of the antibody heavy chain; chains B, E, H, K, N, and Q are instances of the antibody light chain; chains C, F, I, L, O, and R are instances of the ROBO2 Ig1 domain. Primary Fab/antigen interactions occur among the following six chain groups: (A, B, C), (D, E, F), (G, H, I), (J, K, L), (M, N, O), and (P, Q, R). The antigen residues from position 71 to 81 show considerable flexibility among the six independent copies of the structure. Although the PQR copy has the lowest B factors for both antibody chains, the antigen Ig1 domain in the ABC version of the complex has the lowest RMSd (~0.6 Å) relative to the previously published ROBO2 structure (PDB entry 2V9R; Morlot et. al, *Proc. Natl. Acad. Sci. USA* 2007, 103, 14923-8). All six copies of the complex may contain relevant snapshots of flexible behavior that occurs in solution, but interactions that occur in more of the six copies may be more energetically favorable and therefore more important.

The structure was visualized in Maestro 10 (Schrodinger, LLC, New York, N.Y.) using the Contacts panel to locate interactions where the inter-atomic contact distances between ROBO2 and Fab were <=1.3 times the sum of the Van Der Waals radii of the two atoms. Table 6 shows the ROBO2 residues which make contact with the antibody, how many of the 6 copies of the complex show the residue interacting with the antibody, and which Fab chains are involved (note that crystal packing interactions between different complexes, such as interactions between [A,B,C] and [D,E,F] are not included). The amino acids in ROBO2 positions 69-82 and 131-140 contain multiple residues making contact with the antibody in at least half of the complexes in the asymmetric unit, largely defining the epitope for 93H2 binding.

Table 7 shows the 93H2 residues which make contact with ROBO2, whether they are in the CDRs, and which of the six ROBO2 copies in the structure show an interaction. All three heavy chain CDRs make contact in all six copies, while only the CDR-1 and CDR-3 of the light chain make contact in all six copies. There are also framework contacts with H1, H2, H73, and L49 contacting ROBO2 in at least some copies of the complex. Table 7 further indicates whether the contacts involve 93H2 side chains in a least one of the complexes. In two cases (H96 and L93) the contacts with ROBO2 are exclusively made by the residue backbone and not the side chain.

It is possible to further characterize the importance of the epitope and paratope residues identified in Tables 6 and 7. For example, when contacts are primarily with the backbone, or when the contacts are energetically neutral, the residue may tolerate a wide range of mutations. Significant contacts of an entire side chain with the other binding partner, or high conservation in a computational evolution simulation, are evidence that a particular residue may have increased importance relative to other residues. For the 93H2 crystal structure, we examined the contacts of the side chains for residues involved in antibody/antigen contacts. We also used the crystal structure of 93H2 to construct homology models of the variable domains for Abcs35-J (SEQ IDs 127 and 133), using the MODELLER software package (Webb & Sali, *Current Protocols in Bioinformatics*, John Wiley & Sons, Inc., 5.6.1-5.6.32, 2014). As noted above, the PQR copy of the 93H2/ROBO2 complex had the lowest B factors, but the ABC copy more closely resembled a previously published version of the ROBO2 domain. Therefore, we constructed two homology models, one using the ABC complex as the template, and one using the PQR complex as the template. As an alternative approach for identifying the most important residues in the interface, we subjected key regions of these homology models to a genetic algorithm for sequence optimization in the Rosetta software package, as described by Smith & Kortemme (*PLOS One*, 2011, http://dx.doi.org/10.1371/journal.pone.0020451 and *J. Mol. Bio.* 402, 2(17), 460-74 (2010)), disabling environment-dependent hydrogen bond scoring, and using a Boltzmann weight of 0.228. A total of 50 or 100 backbone variants were simulated for each cluster of residues (each containing 8 or fewer residues), for 5 generations of the genetic algorithm, with 5,000 or 20,000 sequences per backbone variant per generation (the smaller numbers were used for clusters of up to 8 residues, while the larger numbers were used to increase sampling for the single cluster that had 9 residues). The output of the protocol includes statistics on which amino acids occur most frequently at each sampled position. If amino acids were distributed randomly, then since there are 20 amino acids, each would be present with a frequency of approximately 5%. Generally, however, one or a few residues are present at frequencies significantly higher than 5%, indicating a structural or binding preference for specific amino acids. Table 8 lists ROBO2 residues where the wild type residue had a frequency>10%, indicating that the existing residue is one of those preferred for the antibody/antigen interaction. Some residues were chosen as part of multiple residue clusters for the simulations, and were therefore simulated multiple times; in such cases Table 8 shows a representative result. Some residues involved in the simulations were second-layer residues not directly involved in the antibody-antigen interface and were included only to allow higher variation for neighboring residues that did make direct contacts. But only residues which were observed to make direct contacts (i.e., those in Table 6) were considered for inclusion in Table 8. Some residues (such as Asp77) had high frequency when simulating one homology model (based on the ABC complex) but not the other (based on the PQR complex), due to the differences in the ROBO2 conformation.

The analogous analysis for the Abcs35-J antibody residues appears in Table 9, which lists antibody residues where the existing antibody residue had a frequency of >10%, indicating that the existing residue is one of those preferred for the antibody/antigen interaction. Only residues noted to have contacts with the antigen (i.e., those in Table 7) appear in Table 9.

An overall qualitative ranking of importance for residues in the antibody/antigen interface was established based on the following criteria, each of which indicates higher importance: (A) consistent interactions seen in the six independently refined complexes in the crystal structure asymmetric unit, as shown in Tables 6 and 7, (B) involvement of the side chain in antibody/antigen binding as shown for the antibody in Table 7, particularly cases involving the terminal side chain atoms or hydrogen bonding of the side chain, (C) high sequence conservation in a computational genetic algorithm sequence optimization, as shown in Tables 8 and 9, and (D) mutagenesis studies as described above. A residue meeting two or more of these criteria may be defined has playing a "primary" role, while other residues of lower importance may be defined as having a "contributing" role (moderate importance) or "optional" role (lower importance). An amino acid which meets criteria (A) and (C) but contributes only backbone interactions to the interface may still be judged to have a less than "primary" role if it is routinely present in many antibodies with broad specificity, and is conserved in the simulations primarily because it supports a canonical CDR conformation. An example of such a residue is Tyr(H27), in which case the side chain only rarely makes incidental contacts with ROBO2 and only via the Cβ side chain atom. The rankings for the ROBO2 residues are shown in Table 10A, while rankings for the antibody are shown in Table 10B. The comments column in each table indicates any key features not already captured in Tables 6-9.

TABLE 6

Summary of ROBO2 epitope residues interacting with the 93H2 Fab

| Robo2 residue # | # complexes with Fab interaction | Fab chains interacting |
|---|---|---|
| K66 (103) | 2/6 | GJ |
| D67 (104) | 1/6 | J |
| E69 (106) | 6/6 | ADGJMP |

TABLE 6-continued

Summary of ROBO2 epitope residues interacting with the 93H2 Fab

| Robo2 residue # | # complexes with Fab interaction | Fab chains interacting |
|---|---|---|
| R70 (107) | 3/6 | JMP |
| V71 (108) | 3/6 | GMP |
| E72 (109) | 5/6 | AGJMP |
| T73 (110) | 2/6 | MP |
| D74† (111) | 2/6 | MP |
| D77† (114) | 3/6 | AMP |
| P78 (115) | 2/6 | NQ |
| R79 (116) | 3/6 | AMP; NQ |
| S80 (117) | 2/6 | MP |
| H81 (118) | 5/6 | AGMP |
| R82 (119) | 4/6 | DGMP |
| R94 (131) | 3/6 | GMP; NQ |
| V96 (133) | 6/6 | ADGJMP |
| H97 (134) | 4/6 | DJMP |
| G98 (135) | 6/6 | ADGJMP |
| R99 (136) | 6/6 | ADGJMP; BEHKNQ |
| R100 (137) | 6/6 | ADGJMP; BEHKNQ |
| S101 (138) | 6/6 | ADGJMP |
| K102 (139) | 6/6 | ADGJMP |
| P103 (140) | 6/6 | ADGJMP |

Notes:
Heavy chains are A, D, G, J, M, P, and light chains are B, E, H, K, N, Q. ROBO2 residue numbers are as in SEQ ID NO. 1, with numbering from the structure in parentheses.
†This residue is disordered in ROBO2 chain I.

TABLE 7

Summary of 93H2 paratope residues interacting with ROBO2

| 93H2 Residue # | # complexes w/ROBO2 interaction | ROBO chains interacting | Side chain contact with ROBO2? |
|---|---|---|---|
| E(H1) | 3/6 | COR | Y |
| V(H2) | 3/6 | COR | Y |
| G(H26) | 3/6 | COR | NA |
| Y(H27) | 5/6 | CILOR | Y |
| T(H28) | 6/6 | CFILOR | Y |
| T(H30) | 6/6 | CFILOR | Y |
| G(H31) | 6/6 | CFILOR | NA |
| Y(H32) | 6/6 | CFILOR | Y |
| Y(H33) | 6/6 | CFILOR | Y |
| H(H35) | 6/6 | CFILOR | Y |
| W(H50) | 6/6 | CFILOR | Y |
| N(H53) | 2/6 | IL | Y |
| T(H73) | 5/6 | CILOR | Y |
| R(H94) | 1/6 | O | Y |
| E(H95) | 6/6 | CFILOR | Y |
| S(H96) | 6/6 | CFILOR | N |
| G(H97) | 6/6 | CFILOR | NA |
| D(H98) | 3/6 | IOR | Y |
| D(H99) | 6/6 | CFILOR | Y |
| D(H101) | 2/6 | OR | Y |
| I(H102) | 2/6 | OR | Y |
| Y(L32) | 6/6 | CFILOR | Y |
| Y(L49) | 2/6 | OR | Y |
| Q(L55) | 2/6 | OR | Y |
| S(L56) | 2/6 | OR | Y |
| S(L91) | 6/6 | CFILOR | Y |
| Y(L92) | 6/6 | CFILOR | Y |
| S(L93)†‡ | 5/6 | CFIOR | N |
| T(L96)† | 6/6 | CFILOR | Y |

Notes:
Bold underlined residue identifiers indicate CDRs.
†These residues are adjacent; due to the short L3 loop, Kabat positions L94 and L95 are empty.
‡Disordered in chain L.

TABLE 8

ROBO2 Residues with High Frequency in Genetic Algorithm

| Robo2 residue # | High frequency residues (% frequency) |
|---|---|
| K66 | Q (>70%), K (>10%) |
| R70 | R (>90%) |
| V71 | V (>90%) |
| E72 | E (>80%) |
| D74 | D (>20%), R (>20%), K (>10%) |
| D77 | D (>80%) |
| R79 | R (>90%) |
| S80 | D (>70%), S (>10%) |
| R82 | R (>50%), A (>20%) |
| R94 | R (>90%) |
| G98 | G (>90%) |
| R100 | R (>90%) |
| S101 | S (>90%) |
| K102 | R (>20%), N (>20%), K (>10%), S (>10%) |

TABLE 9

Abcs35-J Residues with High Frequency in Genetic Algorithm

| Kabat residue # | High frequency residues (% frequency) |
|---|---|
| G(H26) | G (>90%) |
| T(H30) | T (>80%), R (>10%) |
| G(H31) | G (>90%) |
| Y(H32) | F (>50%), Y (>40%) |
| K(H53) | K (>90%) |
| E(H95) | E (>90%) |
| G(H97) | G (>90%) |
| S(L91) | S (>90%) |
| G(L93) | G (>90%) |

TABLE 10A

Ranking of ROBO2 Residue Importance in the Binding Interface

| ROBO2 residue # | Importance | Notes |
|---|---|---|
| K66 (103) | Optional | Water-mediated contacts with antibody |
| D67 (104) | Optional | Interaction with N(H53) only in complex JKL |
| E69 (106) | Contributing | Interaction with T(H30) |
| R70 (107) | Optional | Side chain sometimes makes intra-chain salt bridge |
| V71 (108) | Optional | Side chain involved in intra-chain packing |
| E72 (109) | Contributing | Interacts with G(H26). May be protonated in crystal. |
| T73 (110) | Optional | Side chain mostly involved in intra-chain packing |
| D74† (111) | Optional | Salt bridge with E(H1) in subset of crystal complexes |
| D77† (114) | Optional | H-bond with V(H2) in subset of crystal complexes |
| P78 (115) | Optional | Van Der Walls contact in subset of crystal complexes |
| R79 (116) | Contributing | H-bond, VDW contacts in subset of crystal complexes |
| H81 (118) | Contributing | Interaction with Y(H32) |
| R82 (119) | Contributing | Interaction with T(H28) |
| R94 (131) | Contributing | Interaction with D(H98) |
| V96 (133) | Primary | Packing against CDR-H3 and CDR-H1 |
| H97 (134) | Optional | Backbone-driven contacts |
| G98 (135) | Primary | Addition of a side chain likely to disrupt binding |
| R99 (136) | Primary | VDW, Cation/Pi contacts with Y(L32) and Y(L92) |

TABLE 10A-continued

Ranking of ROBO2 Residue Importance in the Binding Interface

| ROBO2 residue # | Importance | Notes |
|---|---|---|
| R100 (137) | Primary | H-bonding to CDR-H3, CDR-L3; mutagenesis data. |
| S101 (138) | Primary | H-bonding with CDR-H3 |
| K102 (139) | Optional | Backbone-driven contacts |
| P103 (140) | Contributing | Packs against CDR-H1 |

Note:
the relative order of importance is Primary > Contributing > Optional

TABLE 10B

Ranking of Antibody Residue Importance in the Binding Interface

| Kabat residue # | Importance | Notes |
|---|---|---|
| E(H1) | Optional | Different contacts in different versions of the complex. |
| V(H2) | Optional | Different contacts in different versions of the complex. |
| G(H26) | Contributing | Adding side chain would disrupt intrachain packing |
| Y(H27) | Optional | Side chain mostly involved in intrachain packing |
| T(H28) | Contributing | Interacts with R82 |
| T(H30) | Primary | Interacts with E69 |
| G(H31) | Primary | Interacts with K102; side chain may not be tolerated |
| Y(H32) | Primary | Interacts with His81 |
| Y(H33) | Primary | Significant packing with primary residue R100 |
| H(H35) | Optional | Mostly important for intrachain loop stability. |
| W(H50) | Contributing | Minor but consistent packing w/primary residue R100 |
| K(H53) | Contributing | 93H2 has N; Abcs35-J has K, may interact with D67 |
| T(H73) | Optional | Minor packing contacts with E69 |
| R(H94) | Optional | Mostly important for internal antibody loop stability |
| E(H95) | Primary | Consistently forms salt bridge w/primary residue R100 |
| S(H96) | Optional | Backbone-driven contacts |
| G(H97) | Primary | Side chain would likely disrupt binding |
| D(H98) | Contributing | Salt bridge to R94 in a subset of x-ray complexes |
| D(H99) | Primary | Backbone H-bonding with R99 |
| D(H101) | Contributing | Contact in a subset of x-ray complexes |
| I(H102) | Contributing | Contact in a subset of x-ray complexes |
| Y(L32) | Primary | Consistently packs with primary residue R100 |
| Y(L49) | Optional | Minor contact with R94 in a subset of x-ray complexes |
| Q(L55) | Optional | Contact with P115 in subset of x-ray complexes |
| S(L56) | Optional | Contact with P115 in subset of x-ray complexes |
| S(L91) | Contributing | Backbone H-bonding with primary residue R100 |
| Y(L92) | Primary | Consistently packs with primary residue R100 |
| G(L93) | Contributing | Abcs35-J has G, 93H2 has S. Backbone-mediated. |
| T(L96) | Contributing | Minor packing with R100; intrachain loop stability. |

Notes:
the relative order of importance is Primary > Contributing > Optional.
CDR residues are bold and underlined.

In addition, commonly used criteria for epitope/paratope residues include residues: (i) having a heavy atom (i.e., a non-hydrogen atom) that is within a distance of about 4 Å from a heavy atom of the cognate antibody; (ii) participating in a hydrogen bond with a residue of the cognate antibody, or with a water molecule that is also hydrogen bonded to the cognate antibody (water-mediated hydrogen bonding), (iii) participating in a salt bridge to a residue of the cognate antibody; or (iv) BSA of 20 Å$^2$ or greater, or is involved in electrostatic interactions when antibody binds to antigen. These interactions are summarized as follows:

TABLE 10C

ROBO2 epitope residues and corresponding 93H2 paratope residues (consensus from 6 copies)

| Epitope Residue# | Consensus 93H2/VH | Contact by distance <3.8 Å 93H2/VL |
|---|---|---|
| Arg94 | Asp98 | |
| Val96 | | |
| His97 | | |
| Gly98 | Gly97, Asp99 | |
| Arg99 | Asp99 | Tyr32, Tyr92 |
| Arg100 | Tyr33, Trp50, Glu95 | Ser91, Tyr92 |
| Ser101 | Tyr32, Tyr33, Glu95, Ser96, Gly97 | |
| Lys102 | Gly31 | |
| Pro103 | Gly31, Tyr32 | |

TABLE 10D

List of ROBO2 residues that involve hydrogen bonding, as well as their cognate interacting residues on 93H2. (consensus from 6 copies)

| ROBO2 Residue# | Consensus 93H2/VH | Hydrogen bonds 93H2/VL |
|---|---|---|
| Arg94 | Asp98/H | |
| Val96 | | |
| His97 | | |
| Gly98 | | |
| Arg99 | Asp99/H | Tyr92 |
| Arg100 | Glu95/H | Ser91, Tyr92 |
| Ser101 | Glu95/H, Gly97/H | |
| Lys102 | | |
| Pro103 | | |

TABLE 10E

List of ROBO2 residues that involve salt bridge interactions, as well as their cognate interacting residues on 93H2. (consensus from 6 copies)

| ROBO2 Residue# | Consensus 93H2/VH | Salt bridge 93H2/VL |
|---|---|---|
| Arg94 | Asp98 | |
| Val96 | | |
| His97 | | |
| Gly98 | | |
| Arg99 | | |
| Arg100 | Glu95 | |
| Ser101 | | |
| Lys102 | | |
| Pro103 | | |

TABLE 10F

Interactions defined by BSA, subject to 20 Å² cut off.
(consensus from 6 copies)

| ROBO2 Residue # | Consensus 93H2/VH | Contact by BSA 93H2/VL |
|---|---|---|
| Arg94 | Asp98 | Tyr49 |
| Val96 | Gly97 | |
| His97 | Gly97 | |
| Gly98 | Gly97 | |
| Arg99 | Asp99 | Tyr32, Tyr92 |
| Arg100 | Tyr33, Trp50, Glu95 | Ser91, Tyr92, Ser93 |
| Ser101 | Tyr32, Tyr33, Glu95, Gly97 | |
| Lys102 | Gly31 | |
| Pro103 | Gly31, Tyr32 | |

TABLE 10G

Interactions defined by BSA, no cut off.
(consensus from 6 copies)

| ROBO2 Residue # | Consensus 93H2/VH | Contact by BSA 93H2/VL |
|---|---|---|
| Arg94 | Asp98 | Tyr49 |
| Val96 | Tyr32, Ser96, Gly97 | |
| His97 | Gly97 | |
| Gly98 | Gly97, Asp99 | |
| Arg99 | Asp99 | Tyr32, Ser91, Tyr92 |
| Arg100 | Tyr33, His35, Trp50, Glu95, Asp99 | Ser91, Tyr92, Ser93, Thr96 |
| Ser101 | Gly31, Tyr32, Tyr33, Glu95, Ser96, Gly97 | |
| Lys102 | Gly31 | |
| Pro103 | Gly31, Tyr32 | |

Example 6. Characterization of Germline Antibodies

Additional germlined antibodies based on Abcs35, named Abcs-A through Abcs-O (Table 12) were generated. These germlined antibodies replaced certain non-germline residues in Abcs35 (3 residues in heavy chain and 1 residue in light chain) with corresponding human germline residues.

Antibodies with mutations to introduce germline sequences within the framework regions were assessed in a number of in vitro assays: 1) SPR, 2) neutralization of SLIT2-N:ROBO2 interactions, 3) binding to ROBO2 orthologs, ROBO1 homolog and the specific RSK motif from ROBO2, and 4) the restoration of neuronal cell migration in the presence of SLIT2-N.

Affinity was measured by standard SPR methods as described in Example 3. Briefly, antibodies were immobilized to a specific measure of resonance units (RU) on a CM5 chip. Association of ROBO2 Ig1-Ig2-His (ROBO2) and dissociation will be followed for a period of time. Antibodies were used at 10 nM, 1 nM and 0.1 nM concentrations to determine the KD. Table 13 shows the changes in KD imparted by the germline mutations introduced.

TABLE 13

$K_D$ of each germlined antibody

| Antibody | $K_D$ (pM) |
|---|---|
| Abcs35 | 85.66 |
| Abcs35-A | 99.01 |
| Abcs35-B | 123.20 |
| Abcs35-C | 82.14 |
| Abcs35-D | 124.98 |
| Abcs35-eE | 128.32 |
| Abcs35-F | 194.02 |
| Abcs35-G | 130.92 |
| Abcs35-H | 194.13 |
| Abcs35-I | 144.55 |
| Abcs35-J | 93.90 |
| Abcs35-K | 141.66 |
| Abcs35-L | 148.64 |
| Abcs35-M | 216.84 |
| Abcs35-N | 145.83 |
| Abcs35-O | 217.46 |

Figure 15:
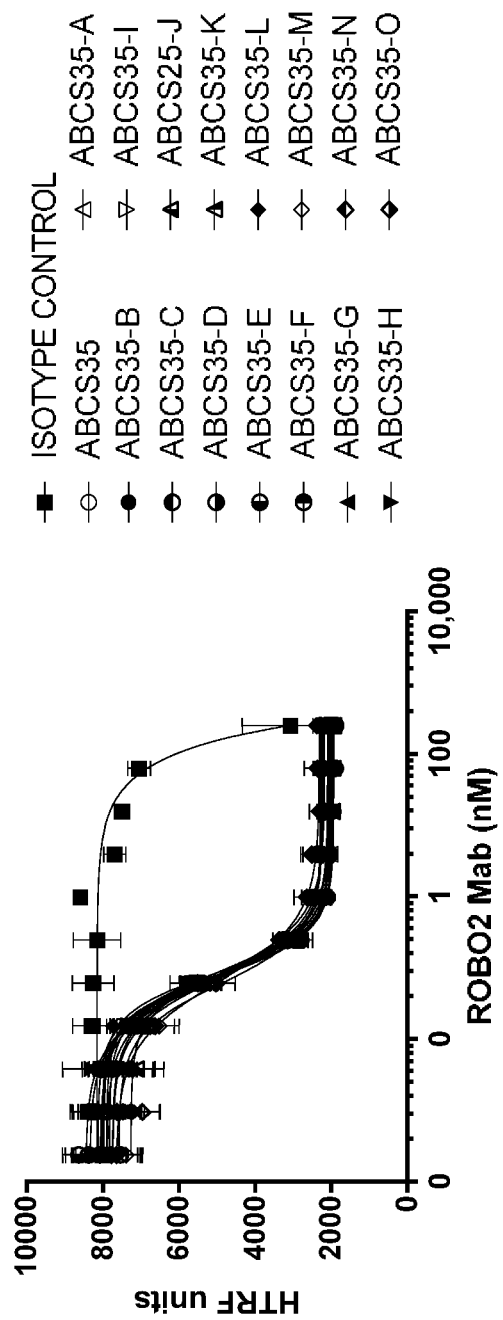
FIG. 15 depicts the dose-dependent inhibition of SLIT2N binding to ROBO2 expressing cells in the HTRF assay. Introduction of germline mutations had no significant impact on the ability of the antibody to neutralize SLIT2 binding.
Figure 16A:
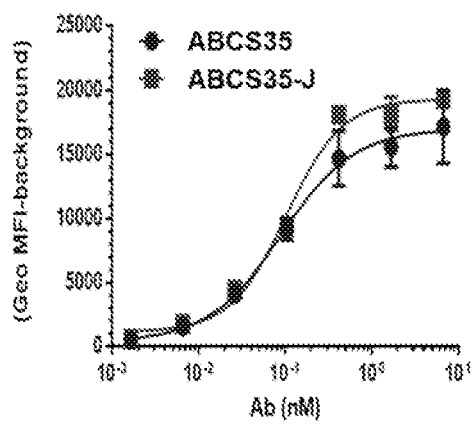
FIGS. 16A-16F demonstrate that Abcs35 (black circles) and Abcs35-J (grey squares) have nearly identical binding profiles. Human ROBO2 (FIG. 16A), cynomolgus monkey ROBO2 (FIG. 16B), rat ROBO2 (FIG. 16C), human ROBO1 (FIG. 16D), ROBO1 containing the ROBO2 RSK epitope (FIG. 16E), or ROBO2 containing the ROBO1 KSR epitope (FIG. 16F) are shown.
Figure 16B:
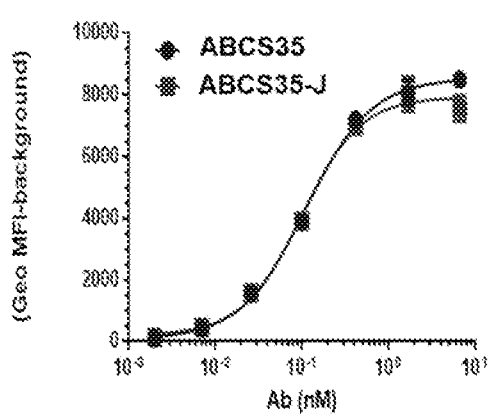
Figure 16C:
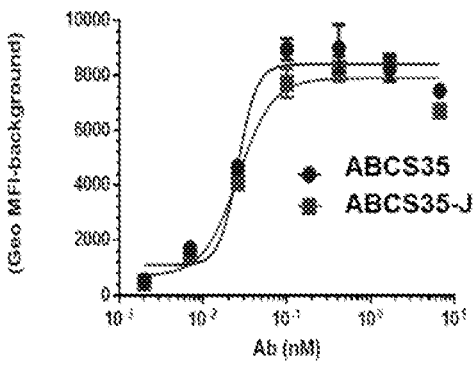
Figure 16D:
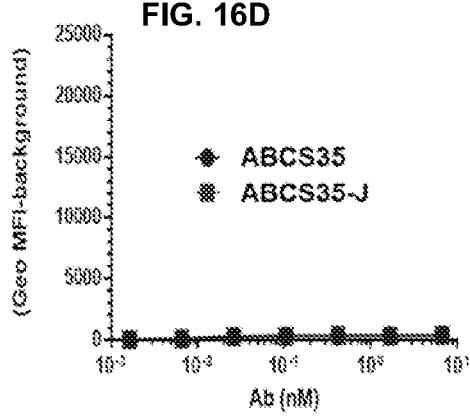
Figure 16E:
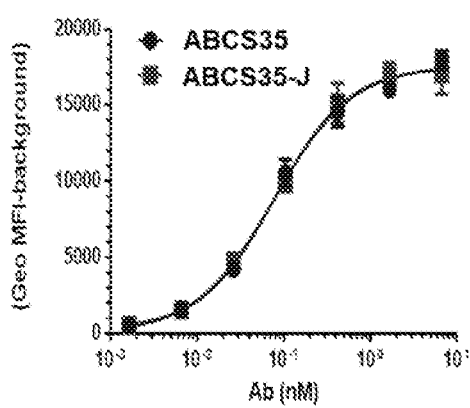
Figure 16F:
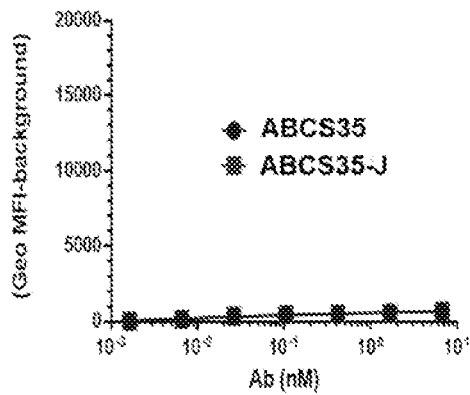

Neutralization of SLIT2-N binding to ROBO2 was assessed ROBO2:SLIT2-N homogenous time resolved fluorescence (HTRF) assay as described in Example 2. Briefly the HTRF assay was performed as follows: terbium (Tb) labeled-SNAP tagged ROBO2 expressing HEK293 cells were incubated with d2-labeled SLIT-2N in the presence of anti-ROBO2 antibodies for 1 hour. After incubation, fluorescence at 665 nm and 620 nm was measured on an Envision multi-label plate reader. The HTRF Ratio was calculated as follows: fluorescence at 665 nm/fluorescence at 620 nm×10,000. Maximal signal was defined as the HTRF ratio of Tb-labeled ROBO2 cells with d2-labeled SLIT2-N in the absence of antibody, the minimum signal was defined as the HTRF ratio of Tb-labeled ROBO2 expressing HEK293 cells only. FIG. 15 shows nearly indistinguishable dose-dependent inhibition of the HTRF signal by all the germline antibodies and Table 14 is a table containing the $IC_{50}$ value determined for each germline antibody. These data show that introduction of germline mutations had no significant impact on the ability of the antibody to neutralize SLIT2 binding.

TABLE 14

$IC_{50}$ values for each germline antibody.

| Antibody | $IC_{50}$ (nM) |
|---|---|
| Control Ab | ~125 |
| Abcs35 | 0.07605 |
| Abcs35-A | 0.07282 |
| Abcs35-B | 0.07646 |
| Abcs35-C | 0.07396 |
| Abcs35-D | 0.06386 |
| Abcs35-E | 0.06514 |
| Abcs35-F | 0.07659 |
| Abcs35-G | 0.07538 |
| Abcs35-H | 0.08287 |
| Abcs35-I | 0.07451 |
| Abcs35-J | 0.07443 |
| Abcs35-K | 0.07519 |
| Abcs35-L | 0.07959 |
| Abcs35-M | 0.05908 |
| Abcs35-N | 0.09031 |
| Abcs35-O | 0.06241 |

The binding profile of Abcs35-J compared to Abcs35 was determined for human ROBO2, orthologs from cynomolgus monkey and rat, human ROBO1 and specificity for the RSK epitope from ROBO2 but not KSR from ROBO1. Binding was assessed by flow cytometry as described in Examples 2 (homolog specificity), Example 3 (ortholog reactivity) and Example 5 (RSK vs KSR epitope specificity). Briefly, human embryonic kidney 293 (HEK293) cells overexpressing 1 of 6 ROBO molecules: 1) human ROBO1, 2) human ROBO2, 3) cynomolgus monkey ROBO2, 4) rat ROBO2, 5) mutant ROBO2 containing the ROBO1 KSR motif or 6) mutant ROBO1 containing the RSK motif from ROBO2 were incubated with titrated amounts of selected antibodies. Binding of the antibodies was detected using a secondary fluorochrome conjugated anti-human IgG F(ab')$_2$ antibody and samples analyzed on a Fortessa cytometer (BD Biosciences). Table 15 demonstrates that there was no significant difference in the binding affinity of Abcs35-J compared to Abcs35 for ROBO2 from human, cynomolgus monkey, rat or the ROBO2 RSK epitope. FIGS. 16A-16F depicts binding profiles of Abcs35 (black circles) or Abcs35-J (grey squares) to human ROBO2 (FIG. 16A), cynomolgus monkey ROBO2 (FIG. 16B), rat ROBO2 (FIG. 16C), human ROBO1 (FIG. 16D), ROBO1 containing the ROBO2 RSK epitope (FIG. 16E) or ROBO2 containing the ROBO1 KSR epitope (FIG. 16 F).

TABLE 15

$EC_{50}$ values for Abcs35 and ABCS-J against human ROBO2, cynomolgus monkey ROBO2, rat ROBO2 or HEK293 cells expressing ROBO1 containing the RSK epitope from ROBO2

| mAb | $EC_{50}$ (nM) | | | |
| --- | --- | --- | --- | --- |
| | Human ROBO2 | Cynomolgus monkey ROBO2 | Rat ROBO2 | ROBO1-RSK |
| Abcs35 | .089 | .111 | .026 | .077 |
| Abcs35-J | .102 | .099 | .026 | .079 |

Figure 17:
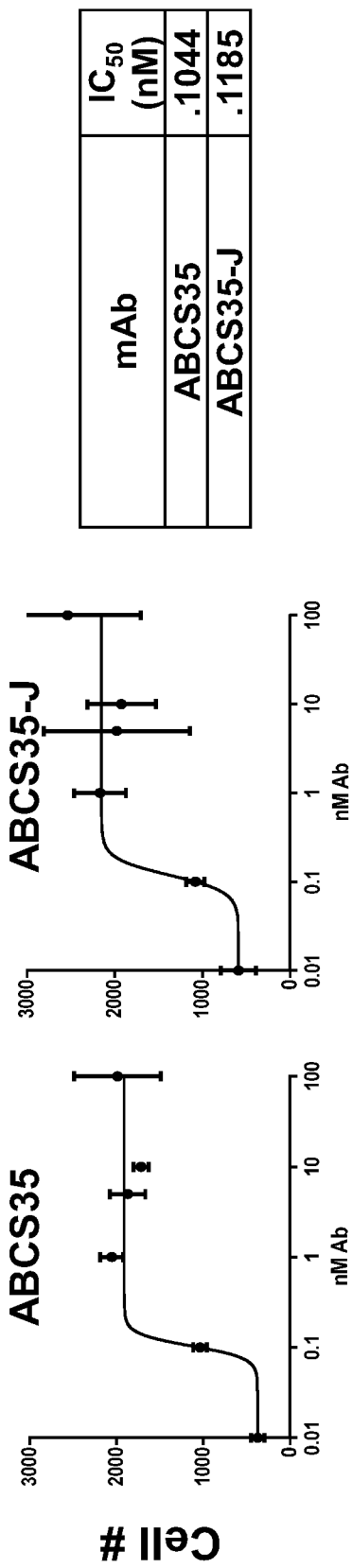
FIG. 17 shows the dose-dependent inhibition of neuronal cell migration in the presence of either Abcs35 or Abcs35-J. The $IC_{50}$ values indicate there is no significant difference in the potency of the antibodies.

Functional neutralization of SLIT2 activity for Abcs35-J as compared to Abcs35 was assessed in the SVZ assay. As described in Example 2, tissue explants will be incubated in the presence of 1 nM SLIT2-N with or without titrated amounts of select ROBO2-specific antibodies. After incubation, cells were fixed with 4% paraformaldehyde and stained with Hoechst 33342. Data acquisition was performed on an Operetta High Content Imager (Perkin Elmer) and analysis using Volocity software (Perkin Elmer) was used to determine the number of cells that had migrated. As can be seen in FIG. 17, there was no difference in the potency of Abcs35-J as compared to Abcs35 to inhibit cell migration in the SVZa assay.

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description and/or sequence listings and/or drawings.

In so far as specific examples found herein do not fall within the scope of an invention, said specific example may be explicitly disclaimed.

The use of the term "or" in the claims is used to mean "and/or" unless explicitly indicated to refer to alternatives only or the alternatives are mutually exclusive, although the disclosure supports a definition that refers to only alternatives and "and/or." As used herein the specification, "a" or "an" may mean one or more, unless clearly indicated otherwise. As used herein in the claim(s), when used in conjunction with the word "comprising", the words "a" or "an" may mean one or more than one. As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The words "comprises/comprising" and the words "having/including" when used herein with reference to the present invention are used to specify the presence of stated features, integers, steps or components but does not preclude the presence or addition of one or more other features, integers, steps, components or groups thereof.

Although the disclosed teachings have been described with reference to various applications, methods, and compositions, it will be appreciated that various changes and modifications can be made without departing from the teachings herein and the claimed invention below. The examples are provided to better illustrate the disclosed teachings and are not intended to limit the scope of the teachings presented herein. While the present teachings have been described in terms of these exemplary embodiments, numerous variations and modifications of these exemplary embodiments are possible without undue experimentation. All such variations and modifications are within the scope of the current teachings.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The description and examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

TABLE 11

| SEQUENCES | | |
|---|---|---|
| SEQ | DESCRIPTION | SEQUENCE |
| 1 | Human ROBO2 (Signal peptide underlined) | <u>MSLLMFTQLLLCGFLYVRVDG</u><br>SRLRQEDFPPRIVEHPSDVIVSKGEPTTLNCKAEGRPTPTIEWYKDGERVETDKDDPRSHRM<br>LLPSGSLFFLRIVHGRRSKPDEGSYVCVARNYLGEAVSRNASLEVALLRDDFRQNPTDVVVA<br>AGEPAILECQPPRGHPEPTIYWKKDKVRIDDKEERISIRGGKLMISNTRKSDAGMYTCVGTN<br>MVGERDSDPAELTVFERPTFLRRPINQVVLEEEAVEFRCQVQGDPQPTVRWKKDDADLPRGR<br>YDIKDDYTLRIKKTMSTDEGTYMCIAENRVGKMEASATLTVRAPPQFVVRPRDQIVAQGRTV<br>TFPCETKGNPQPAVFWQKEGSQNLLFPNQPQQPNSRCSVSPTGDLTITNIQRSDAGYYICQA<br>LTVAGSILAKAQLEVTDVLTDRPPPIILQGPANQTLAVDGTALLKCKATGDPLPVISWLKEG<br>FTFPGRDPRATIQEQGTLQIKNLRISDTGTYTCVATSSSGETSWSAVLDVTESGATISKNYD<br>LSDLPGPPSKPQVTDVTKNSVTLSWQPGTPGTLPASAYIIEAFSQSVSNSWQTVANHVKTTL<br>YTVRGLRPNTIYLFMVRAINPQGLSDPSPMSDPVRTQDISPPAQGVDHRQVQKELGDVLVRL<br>HNPVVLTPTTVQVTWTVDRQPQFIQGYRVMYRQTSGLQATSSWQNLDAKVPTERSAVLVNLK<br>KGVTYEIKVRPYFNEFQGMDSESKTVRTTEEAPSAPPQSVTVLTVGSYNSTSISVSWDPPPP<br>DHQNGIIQEYKIWCLGNETRFHINKTVDAAIRSVIIGGLFPGIQYRVEVAASTSAGVGVKSE<br>PQPIIIGRRNEVVITENNNSITEQITDVVKQPAFIAGIGGACWVILMGFSIWLYWRRKKRKG<br>LSNYAVTFQRGDGGLMSNGSRPGLLNAGDPSYPWLADSWPATSLPVNNSNSGPNEIGNFGRG<br>DVLPPVPGQGDKTATMLSDGAIYSSIDFTTKTSYNSSSQITQATPYATTQILHSNSIHELAV<br>DLPDPQWKSSIQQKTDLMGFGYSLPDQNKGNNGGKGGKKKKNKNSSKPQKNNGSTWANVPLP<br>PPPVQPLPGTELEHYAVEQQENGYDSDSWCPPLPVQTYLHQGLEDELEEDDDRVPTPPVRGV<br>ASSPAISFGQQSTATLTPSPREEMQPMLQAHLDELTRAYQFDIAKQTWHIQSNNQPPQPPVP<br>PLGYVSGALISDLETDVADDDADDEEEALEIPRPLRALDQTPGSSMDNLDSSVTGKAFTSSQ<br>RPRPTSPFSTDSNTSAALSQSQRPRPTKKHKGGRMDQQPALPHRREGMTDEEALVPYSKPSF<br>PSPGGHSSSGTASSKGSTGPRKTEVLRAGHQRNASDLLDIGYMGSNSQGQFTGEL |
| 2 | Cynomolgus ROBO2 (Signal peptide underlined) | <u>MSLLMFTQLMLCGFLYVRVDG</u><br>SRLRQEDFPPRIVEHPSDVIVSKGEPTTLNCKAEGRPTPTIEWYKDGERVETDKDDPRSHRM<br>LLPSGSLFFLRIVHGRRSKPDEGSYVCVARNYLGEAVSRNASLEVALLRDDFRQNPTDVVVA<br>AGEPAILECQPPRGHPEPTIYWKKDKVRIDDKEERISIRGGKLMISNTRKSDAGMYTCVGTN<br>MVGERDSDPAELTVFERPTFLRRPINQVVLEEEAVEFRCQVQGDPQPTVRWKKDDADLPRGR<br>YDIKDDYTLRIKKTMSTDEGTYMCIAENRVGKMEASATLTVRAPPQFVVRPRDQIVAQGRTV<br>TFPCETKGNPQPAVFWQKEGSQNLLFPNQPQQPNSRCSVSPTGDLTITNIQRSDAGYYICQA<br>LTVAGSILAKAQLEVTDVLTDRPPPIILQGPANQTLAVDGTALLKCKATGDPLPVISWLKEG<br>FTFLSRDPRATIQEQGTLQIKNLRISDTGTYTCVATSSSGETSWSAVLDVTESGATISKNYD<br>LNDLPGPPSKPQVTDVTKNSVTLSWQPGTPGTLPASAYIIEAFSQSVSNSWQTVANHVKTTL<br>YTVRGLRPNTIYLFMVRAINPQGLSDPSPMSDPVRTQDISPPAQGVDHRQVQKELGDVLVRL<br>HNPVVLTPTTVQVTWTVDRQPQFIQGYRVMYRQTSGLQATSSWQNLDAKVPNERSAVLVNLK<br>KGVTYEIKVRPYFNEFQGMDSESKTVRTTEEAPSAPPQSVTVLTVGSYNSTSISVSWDPPPP<br>DHQNGILQEYKIWCLGNETRFHINKTVDAAIRSVIIGGLFPGIQYRVEVAASTSAGVGVKSE<br>PQPIIIGRRNEVVITENNNSITEQITDVVKQPAFIAGIGGACWVILMGFSIWLYWRRKKRKG<br>LSNYAVTFQRGDGGLMTNGSRPGLLNAGDPSYPWLADSWPATSLPVNNSNSGPNDIGNFGRG<br>DVLPPVPGQGDKTATMLSDGAIYSSIDFTTKTTYNSSSQITQATPYATTQILHSNSIHELAV<br>DLPDPQWKSSIQQKTDLMGFGYSLPDQNKGNNGGKGGKKKKNKNSSKPQKNNGSTWANVPLP<br>PPPVQPLPGTELEHYAAEQQENGYDSDSWCPPLPVQTYLHQGLEDELEEDDDRVPTPPVRGV<br>ASSPAISFGQQSTATLTPSPREEMQPMLQAHLDELTRAYQFDIAKQTWHIQSNNQPPQPPVP<br>PLGYVSGALISDLETDVPDDDADDEEEALEIPRPLRALDQTPGSSMDNLDSSVTGKAFTSSQ<br>RPRPTSPFSTDSNTSAAVSQSQRPRPTKKHKGGRMDQQPALPHRREGMTDEEALVPYSKPSF<br>PSPGGHSSSGTASSKGSTGPRKAEVLRAGHQRNASDLLDIGYMGSNSQGQFTGEL |
| 3 | Rat ROBO2 (Signal peptide underlined) | <u>MTPLMFTLLLLFGFLCIRTDG</u><br>SRLRQEDFPPRIVEHPSDVIVSKGEPTTLNCKAEGRPTPTIEWYKDGERVETDKDDPRSHRM<br>LLPSGSLFFLRIVHGRRSKPDEGTYVCVARNYLGEAVSRNASLEVALLRDDFRQNPTDVVVA<br>AGEPAILECQPPRGHPEPTIYWKKDKVRIDEKEERISIRGGKLMISNTRKSDAGMYTCVGTN<br>MVGERDSDPAELTVFERPTFLRRPINQVVLEDEPAEFRCQVQGDPQPTVRWKKDDADLPRGR<br>YDIKDDYTLRIKKAISADEGTYVCIAENRVGKVEASATLTVRAPPQFVVRPRDQIVAQGRTV<br>TFPCETKGNPQPAVFWQKEGSQNLLFPNQPQQPNSRCSVSPTGDLTITNIQRSDAGYYICQA<br>LTVAGSILAKAQLEVTDVLTDRPPPIILQGPINQTLAVDGTALLKCKATGEPLPVISWLKEG<br>FTFLGRDPRATIQDQGTLQIKNLRISDTGTYTCVATSSSGETSWSAVLDVTESGATISKNYD<br>TNDLPGPPSKPQVTDVTKNSVTLSWQPGTPGVLPASAYIIEAFSQSVSNSWQTVANHVKTTL<br>YTVRGLRPNTIYLFMVRAINPQGLSDPSPMSDPVRTQDISPPAQGVDHRQVQKELGDVTVRL<br>HNPVVLTPTTVQVTWTVDRQPQFIQGYRVMYRQTSGLQASTVWQNLDAKVPTERSAVLVNLK<br>KGVTYEIKVRPYFNEFQGMDSESKTIRTTEEAPSAPPQSVTVLTVGSHNSTSISVSWDPPPA<br>DHQNGIIQEYKIWCLGNETRFHINKTVDATIRSVVIGGLFPGIQYRVEVAASTSAGVGVKSE<br>PQPIIIGGRNEVVITENNNSITEQITDVVKQPAFIAGIGGACWVILMGFSIWLYWRRKKRKG<br>LSNYAVTFQRGDGGLMSNGSRPGLLNTGDPSYPWLADSWPATSLPVNNSNSGPNEIGNFGRG<br>DVLPPVPGQGDKTATMLSDGAIYSSIDFTTKTTYNSSSQITQATPYATTQILHSNSIHELAV<br>DLPDPQWKSSVQQKSDLMGFAYSLPDQNKGNNGGKGGKKKKTKNSSKAQKNNGSTWANVPLP<br>PPPVQPLPGTELGHYPAEQENGYDSDSWCPPLPVQTYLHQGMEDELEEDEDRVPTPPVRGVA<br>SSPAISFGQQSTATLTPSPREEMQPMLQAHLDELTRAYQFDIAKQTWHIQSNTPPPQPPVPP<br>LGYASGALISDLETDVPDEDADDEEEPLEIPRPLRALDQTPGSSMDNLDSSVTGKAFTSSQR<br>QRPTSPFSTDSNTSAAQNQSQRPRPTKKHKGGRMDPQPVLPHRREGMPDEESLVPYSKPSFS<br>PGGHSSSGTASSKGSTGPRKAEILRGSHQRNANDLLDIGYVGSNSQGQFTGEL |

TABLE 11-continued

SEQUENCES

| SEQ | DESCRIPTION | SEQUENCE |
|---|---|---|
| 4 | Mouse ROBO2 (Signal peptide underlined) | MNPLMFTLLLLFGFLCIQIDG<br><br>SRLRQEDFPPPRIVEHPSDVIVSKGEPTTLNCKAEGRPTPTIEWYKDGERVETDKDDPRSHRM<br>LLPSGSLFFLRIVHGRRSKPDEGSYVCVARNYLGEAVSRNASLEVALLRDDFRQNPTDVVVA<br>AGEPAILECQPPRGHPEPTIYWKKDKVRIDDKEERISIRGGKLMISNTRKSDAGMYTCVGTN<br>MVGERDSDPAELTVFERPTFLRRPINQVVLEEEAVEFRCQVQGDPQPTVRWKKDDADLPRGR<br>YDIKDDYTLRIKKAMSTDEGTYVCIAENRVGKVEASATLTVRAPPQFVVRPRDQIVAQGRTV<br>TFPCETKGNPQPAVFWQKEGSQNLLFPNQPQQPNSRCSVSPTGDLTITNIQRSDAGYYICQA<br>LTVAGSILAKAQLEVTDVLTDRPPPIILQGPINQTLAVDGTALLKCKATGEPLPVISWLKEG<br>FTFLGRDPRATIQDQGTLQIKNLRISDTGTYTCVATSSSGETSWSAVLDVTESGATISKNYD<br>MNDLPGPPSKPQVTDVSKNSVTLSWQPGTPGVLPASAYIIEAFSQSVSNSWQTVANHVKTTL<br>YTVRGLRPNTIYLFMVRAINPQGLSDPSPMSDPVRTQDISPPAQGVDHRQVQKELGDVVVRL<br>HNPVVLTPTTVQVTWTVDRQPQFIQGYRVMYRQTSGLQASTVWQNLDAKVPTERSAVLVNLK<br>KGVTYEIKVRPYFNEFQGMDSESKTVRTTEEAPSAPPQSVTVLTVGSHNSTSISVSWDPPPA<br>DHQNGIIQEYKIWCLGNETRFHINKTVDAAIRSVVIGGLFPGIQYRVEVAASTSAGVGVKSE<br>PQPIIIGGRNEVVITENNNSITEQITDVVKQPAFIAGIGGACWVILMGFSIWLYWRRKKRKG<br>LSNYAVTFQRGDGGLMSNGSRPGLLNAGDPNYPWLADSWPATSLPVNNSNSGPNEIGNFGRG<br>DVLPPVPGQGDKTATMLSDGAIYSSIDFTTKTTYNSSSQITQATPYATTQILHSNSIHELAV<br>DLPDPQWKSSVQQKTDLMGFGYSLPDQNKGNNALLYIPDYRLAEGLSNRMPHNQSQDFSTTS<br>SHNSSERSGSLSGGKGGKKKKTKNSSKAQKNNGSTWANVPLPPPPVQPLPGTELGHYAAEQE<br>NGYDSDSWCPPLPVQTYLHQGMEDELEEEDEDRVPTPPVRGVASSPAISFGQQSTATLTPSR<br>EEMQPMLQAHLDELTRAYQFDIAKQTWHIQSNTPPPQPPAPPLGYVSGALISDLETDVPDED<br>ADDEEEPLEIPRPLRALDQTPGSSMDNLDSSVTGKAFSSSQRQRPTSPFSTDSNTSAAQNQS<br>QRPRPTKKHKGGRMDPQPVLPHRREGMPDDLPPPPDPPPGQGLRQQIGLSQHSGNVENSTER<br>KGSSLERQQAANLEDTKSSLDCPAKTVLEWQRQTQEDLWINSTERQEETRKAPHKQGVGSEESL<br>VPYSKPSFPSPGGHSSSGTSSSKGSTGPRKADVLRGSHQRNANDLLDIGYVGSNSQGQFTE |
| 5 | Human ROBO2 Ig 1,2 | PRIVEHPSDVIVSKGEPTTLNCKAEGRPTPTIEWYKDGERVETDKDDPRSHRMLLPSGSLFF<br>LRIVHGRRSKPDEGSYVCVARNYLGEAVSRNASLEVALLRDDFRQNPTDVVVAAGEPAILEC<br>QPPRGHPEPTIYWKKDKVRIDDKEERISIRGGKLMISNTRKSDAGMYTCVGTNMVGERDSDP<br>AELT |
| 6 | Cynomolgus ROBO2 Ig 1,2 | PRIVEHPSDVIVSKGEPTTLNCKAEGRPTPTIEWYKDGERVETDKDDPRSHRMLLPSGSLFF<br>LRIVHGRRSKPDEGSYVCVARNYLGEAVSRNASLEVALLRDDFRQNPTDVVVAAGEPAILEC<br>QPPRGHPEPTIYWKKDKVRIDDKEERISIRGGKLMISNTRKSDAGMYTCVGTNMVGERDSDP<br>AELT |
| 7 | Rat ROBO2 IG1,2 | PRIVEHPSDVIVSKGEPTTLNCKAEGRPTPTIEWYKDGERVETDKDDPRSHRMLLPSGSLFF<br>LRIVHGRRSKPDEGTYVCVARNYLGEAVSRNASLEVALLRDDFRQNPTDVVVAAGEPAILEC<br>QPPRGHPEPTIYWKKDKVRIDEKEERISIRGGKLMISNTRKSDAGMYTCVGTNMVGERDSDP<br>AELT |
| 8 | Mouse ROBO2 Ig 1,2 | PRIVEHPSDVIVSKGEPTTLNCKAEGRPTPTIEWYKDGERVETDKDDPRSHRMLLPSGSLFF<br>LRIVHGRRSKPDEGSYVCVARNYLGEAVSRNASLEVALLRDDFRQNPTDVVVAAGEPAILEC<br>QPPRGHPEPTIYWKKDKVRIDDKEERISIRGGKLMISNTRKSDAGMYTCVGTNMVGERDSDP<br>AELT |
| 9 | Human ROBO1 (Signal peptide underlined) | MKWKHVPFLVMISLLSLSPNHLFLA<br><br>QLIPDPEDVERGNDHGTPIPTSDNDDNSLGYTGSRLRQEDFPPRIVEHPSDLIVSKGEPATL<br>NCKAEGRPTPTIEWYKGGERVETDKDDPRSHRMLLPSGSLFFLRIVHGRKSRPDEGVYVCVA<br>RNYLGEAVSHNASLEVAILRDDFRQNPSDVMVAVGEPAVMECQPPRGHPEPTISWKKDGSPL<br>DDKDERITIRGGKLMITYTRKSDAGKYVCVGTNMVGERESEVAELTVLERPSFVKRPSNLAV<br>TVDDSAEFKCEARGDPVPTVRWRKDDGELPKSRYEIRDDHTLKIRKVTAGDMGSYTCVAENM<br>VGKAEASATLTVQEPPHFVVKPRDQVVALGRTVTFQCEATGNPQPAIFWRREGSQNLLFSYQ<br>PPQSSSRFSVSQTGDLTITNVQRSDVGYYICQTLNVAGSIITKAYLEVTDVIADRPPPVIRQ<br>GPVNQTVAVDGTFVLSCVATGSPVPTILWRKDGVLVSTQDSRIKQLENGVLQIRYAKLGDTG<br>RYTCIASTPSGEATWSAYIEVQEFGVPVQPPRPTDPNLIPSAPSKPEVTDVSRNTVTLSWQP<br>NLNSGATPTSYIIEAFSHASGSSWQTVAENVKTETSAIKGLKPNAIYLFLVRAANAYGISDP<br>SQISDPVKTQDVLPTSQGVDHKQVQRELGNAVLHLHNPTVLSSSSIEVHWTVDQQSQYIQGY<br>KILYRPSGANHGESDWLVFEVRTPAKNSVVIPDLRKGVNYEIKARPFFNEFQGADSEIKFAK<br>TLEEAPSAPPQGVTVSKNDGNGTAILVSWQPPPEDTQNGMVQEYKVWCLGNETRYHINKTVD<br>GSTFSVVIPFLVPGIRYSVEVAASTGAGSGVKSEPQFIQLDAHGNPVSPEDQVSLAQQISDV<br>VKQPAFIAGIGAACWIILMVFSIWLYRHRKKRNGLTSTYAGIRKVPSFTFTPTVTYQRGGEA<br>VSSGGRPGLLNISEPAAQPWLADTWPNTGNNHNDCSISCCTAGNGNSDSNLTTYSRPADCIA<br>NYNNQLDNKQTNLMLPESTVYGDVDLSNKINEMKTFNSPNLKDGRFVNPSGQPTPYATTQLI<br>QSNLSNNMNNGSGDSGEKHWKPLGQQKQEVAPVQVNIVEQNLKNKDYRANDTVPPTIPYNQS<br>YDQNTGGSYNSSDRGSSTSGSQGHKKGARTPKVPKQGGMNWADLLPPPPAHPPPHSNSEEYN<br>ISVDESYDQEMPCPVPPARMYLQQDELEEEEDERGPTPPVRGAASSPAAVSYSHQSTATLTP<br>SPQEELQPMLQDCPEETGHMQHQPDRRRQPVSPPPPPRPISPPHTYGYISGPLVSDMDTDAP<br>EEEEDEADMEVAKMQTRRLLLRGLEQTPASSVGDLESSVTGSMINGWGSASAEEDNISSGRSS<br>VSSSDGSFFTDADFAQAVAAAAEYAGLKVARRQMQDAAGRRHFHASQCPRPTSPVSTDSNMS<br>AAVMQKTRPAKKLKHQPGHLRRETYTDDLPPPPVPPPAIKSPTAQSKTQLEVRPVVVPKLPS<br>MDARTDRSSDRKGSSYKGREVLDGRQVVDMRTNPGDPREAQEQQNDGKGRGNKAAKRDLPPA<br>KTHLIQEDILPYCRPTFPTSNNPRDPSSSSSMSSRGSGSRQREQANVGRRNIAEMQVLGGYE<br>RGEDNNEELEETES |
| 10 | Cynomolgus ROBO1 (Signal peptide | MKWKHVPFLVIISLLSLSPNHLFLS<br><br>QLIPDPEDLERGKDNGTPIPTSENDDNSLGYTGSRLRQEDFPPRIVEHPSDLIVSKGEPATL<br>NCKAEGRPTPTIEWYKGGERVETDKDDPRSHRMLLPSGSLFFLRIVHGRKSRPDEGVYVCVA<br>RNYLGEAVSHNASLEVAILRDDFRQNPSDVMVAVGEPAVMECQPPRGHPEPTISWKKDGSPL |

TABLE 11-continued

SEQUENCES

| SEQ | DESCRIPTION | SEQUENCE |
|---|---|---|
| | underlined) | DDKDERITIRGGKLMITYTRKSDAGKYVCVGTNMVGERESEVAELTVLERPSFVKRPSNLAV
TVDDSAEFKCEARGDPVPTVRWRKDDGELPKSRYEIRDDHTLKIRKVMAGDMGSYTCVAENM
VGKAEASATLTVQEPPHFVVKPRDQVVALGRTVTFQCEATGNPQPAIFWRREGSQNLLFSYQ
PPQSSSRFSVSQTGDLTITNVQRSDVGYYICQTLNVAGSIITKAYLEVTDVIADRPPPVIRQ
GPVNQTVAVDGTLVLSCVATGSPVPTILWRKDGVLVSTQDSRIKQLENGVLQIRYAKLGDTG
RYTCIASTPSGEATWSAYIEVQEFGVPVQPPRPTDPNLIPSAPSKPEVTDVSRNTVTLSWQP
NLNSGATPTSYIIEAFSHASGSSWQTVAENVKTETFAIKGLKPNAIYLFLVRAANAYGISDP
SQISDPVKTQDVPPTSQGVDHKQVQRELGNVVLHLHNPTILSSSSIEVHWTVDQQSQYIQGY
KILYRPSGANHGESDWLVFEVRTPTKNSVVIPDLRKGVNYEIKARPFFNEFQGADSEIKFAK
TLEEGNAPPQGVTVSKNDGNGTAILVSWQPPPEGTQNGMVQEYKVWCLGNETRYHINKTVDG
STFSVVIPFLVPGIRYSVEVAASTGAGPGVKSEPQFIQLDSHGNPVSPEDQVSLAQQISDVV
KQPAFIAGIGAACWIILMVFSIWLYRHRKKRNGLTSTYAGIRKVPSFTFTPTVTYQRGGEAV
SSGGRPGLLNISEPATQPWLADTWPNTGNNHNDCSINCCTAGNGNSDSNLTTYSRPADCIAN
YNNQLDNKQTNLMLPESTVYGDVDLSNKINEMKTFNSPNLKDGRFVNPSGQPTPYATTQLIQ
SNLSNNMNNGSGDSGEKHWKPLGQQKQEVAPVQYNIMEQNKLNKDYRANDTIPPTIPYNQSY
DQNTGGSYNSSDRGSSTSGSQGHKKGARTPKVPKQGGMNWADLLPPPPAHPPPHSNSEEYNI
SVDESYDQEMPCPVPPARMYLQQDELEEEEDERGPTPVVRGAASSPAAVSYSHQSTATLTPS
PQEELQPMLQDCPEETGHMQHPPDRRRQPVSPPPPPPRPISPPHTYGYISGPLVSDMDTDAPE
EEEDEADMEVAKMQTRRLLLRGLEQTPASSVGDLESSVTGSMINGWGSASEEDNISSGRSSV
SSSDGSFFTDADFAQAVAAAAEYAGLKVARRQVQDAAGRRHFHASQCPRPTSPVSTDSNMSA
AIMQKTRPAKKPKHQPGHLRREAYTDDLPPPPVPPPAIKSPTVQSKTQLEVRPVVVPKLPSI
DARTERSSDRKGSSYKGREVLDGRPVVDVRTNPGDPREAQEQQNDGKGRGNKGAKRDLLPAK
THLVQEDILPYCRPTFPTSNNPRDPSSSSSMSSRGSGSRQREQANVGRRNIAEMQVLGGYER
GEDNNEELEVTGN |
| 11 | Rat ROBO1
(Signal
peptide
underlined) | <u>MKWKHLPLLVMISLLTLSKKHLLLA</u>
QLIPDPEDLERGNDNGTPAPTSDNDDNSLGYTGSRLRQEDFPPRIVEHPSDLIVSKGEPATL
NCKAEGRPTPTIEWYKGGERVETDKDDPRSHRMLLPSGSLFFLRIVHGRKSRPDEGVYICVA
RNYLGEAVSHNASLEVAILRDDFRQNPSDVMAVGEPAVMECQPPRGHPEPTISWKKDGSPL
DDKDERITIRGGKLMITYTRKSDAGKYVCVGTNMVGERESKVADVTVLERPSFVKRPSNLAV
TVDDSAEFKCEARGDPVPTFGWRKDDGELPKSRYEIRDDHTLKIRKVTAGDMGSYTCVAENM
VGKAEASATLTVQEPPHFVVKPRDQVVALGRTVTFQCEATGNPQPAIFWRREGSQNLLFSYQ
PPQSSSRFSVSQTGDLTVTNVQRSDVGYYICQTLNVAGSIITKAYLEVTDVIADRPPPVIRQ
GPVNQTVAVDGTLTLSCVATGSPVPTILWRKDGVLVSTQDSRIKQLESGVLQIRYAKLGDTG
RYTCTASTPSGEATWSAYIEVQEFGVPVQPPRPTDPNLIPSAPSKPEVTDVSKNTVTLLWQP
NLNSGATPTSYIIEAFSHASGSSWQTVAENVKTETFAIKGLKPNAIYLFLVRAANAYGISDP
SQISDPVKTQDVPPTTQGVDHKQVQRELGNVVLHLHNPTILSSSSVEVHWTVDQQSQYIQGY
KILYRPSGASHGESEWLVFEVRTPTKNSVVIPDLRKGVNYEIKARPFFNEFQGADSEIKFAK
TLEERPSAPPRSVTVSKNDGNGTAILVTWQPPPEDTQNGMVQEYKVWCLGNETRYHINKTVD
GSTFSVVIPFLVPGIRYSVEVAASTGAGPGVKSEPQFIQLDSHGNPVSPEDQVSLAQQISDV
VKQPAFIAGIGAACWIILMVFSIWLYRHRKKRNGLSSTYAGIRKVPSFTFTPTVTYQRGGEA
VSSGGRPGLLNISEPATQPWLADTWPNTGNSHNDCSINCCTASNGNSDSNLTTYSRPADCIA
NYNNQLDNKQTNLMLPESTVYGDVDLSNKINEMKTFNSPNLKDGRFVNPSGQPTPYATTQLI
QANLINNMNNGGGDSSEKHWKPPGQQKQEVAPIQYNIMEQNKLNKDYRANDTILPTIPYNHS
YDQNTGGSYNSSDRGSSTSGSQGHKKGARTPKAPKQGGMNWADLLPPPPAHPPPHSNSEEYS
MSVDESYDQEMPCPVPPARMYLQQDELEEEEAERGPTPVVRGAASSPAAVSYSHQSTATLTP
SPQEELQPMLQDCPEDLGHMPHPPDRRRQPVSPPPPPRPISPPHTYGYISGPLVSDMDTDAP
EEEEDEADMEVAKMQTRRLLLRGLEQTPASSVGDLESSVTGSMINGWGSASEEDNISSGRSS
VSSSDGSFFTDADFAQAVAAAAEYAGLKVARRQMQDAAGRRHFHASQCPRPTSPVSTDSNMS
AAVIQKARPTKKQKHQPGHLRREAYTDDLPPPPVPPPAIKSPSVQSKAQLEARPIMGPKLAS
IEARADRSSDRKGGSYKGREALDGRQVTDLRTSPGDPREAQEQPNEGKARGTKTAKRDLPPA
KTHLIPEDILPYCRPTFPTSNNPRDPSSSSSMSSRGSGSRQREQANVGRRNMAEMQVLGGFE
RGDENNEELEETES |
| 12 | Mouse ROBO1
(Signal
peptide
underlined) | <u>MIAEPAHFYLFGLICLCSG</u>
SRLRQEDFPPRIVEHPSDLIVSKGEPATLNCKAEGRPTPTIEWYKGGERVETDKDDPRSHRM
LLPSGSLFFLRIVHGRKSRPDEGVYICVARNYLGEAVSHNASLEVAILRDDFRQNPSDVMVA
VGEPAVMECQPPRGHPEPTISWKKDGSPLDDKDERITIRGGKLMITYTRKSDAGKYVCVGTN
MVGERESEVAELTVLERPSFVKRPSNLAVTVDDSAEFKCEARGDPVPTVRWRKDDGELPKSR
YEIRDDHTLKIRKVTAGDMGSYTCVAENMVGKAEASATLTVQEPPHFVVKPRDQVVALGRTV
TFQCEATGNPQPAIFWRREGSQNLLFSYQPPQSSSRFSVSQTGDLTITNVQRSDVGYYICQT
LNVAGSIITKAYLEVTDVIADRPPPVIRQGPVNQTVAVDGTLILSCVATGSPAPTILWRKDG
VLVSTQDSRIKQLESGVLQIRYAKLGDTGRYTCTASTPSGEATWSAYIEVQEFGVPVQPPRP
TDPNLIPSAPSKPEVTDVSKNTVTLSWQPNLNSGATPTSYIIEAFSHASGSSWQTAAENVKT
ETFAIKGLKPNAIYLFLVRAANAYGISDPSQISDPVKTQDVPPTSQGVDHKQVQRELGNVVL
HLHNPTILSSSSVEVHWTVDQQSQYIQGYKILYRPSGASHGESEWLVFEVRTPTKNSVVIPD
LRKGVNYEIKARPFFNEFQGADSEIKFAKTLEEAPSAPPRSVTVSKNDGNGTAILVTWQPPP
EDTQNGMVQEYKVWCLGNETKYHINKTVDGSTFSVVIPSLVPGIRYSVEVAASTGAGPGVKS
EPQFIQLDSHGNPVSPEDQVSLAQQISDVVRQPAFIAGIGAACWIILMVFSIWLYRHRKKRN
GLTSTYAGIRKVPSFTFTPTVTYQRGGEAVSSGGRPGLLNISEPATQPWLADTWPNTGNNHN
DCSINCCTAGNGNSDSNLTTYSRPADCIANYNNQLDNKQTNLMLPESTVYGDVDLSNKINEM
KTFNSPNLKDGRFVNPSGQPTPYATTQLIQANLSNNMNNGAGDSSEKHWKPPGQQKPEVAPI
QYNIMEQNKLNKDYRANDTIPPTIPYNQSYDQNTGGSYNSSDRGSSTSGSQGHKKGARTPKA
PKQGGMNWADLLPPPPAHPPPHSNSEEYNMSVDESYDQEMPCPVPPAPMYLQQDELQEEEDE
RGPTPVVRGAASSPAAVSYSHQSTATLTPSPQEELQPMLQDCPEDLGHMPHPPDRRRQPVSP
PPPPRPISPPHTYGYISGPLVSDMDTDAPEEEEDEADMEVAKMQTRRLLLRGLEQTPASSVG |

TABLE 11-continued

SEQUENCES

| SEQ | DESCRIPTION | SEQUENCE |
|---|---|---|
| | | DLESSVTGSMINGWGSASEEDNISSGRSSVSSSDGSFFTDADFAQAVAAAAEYAGLKVARRQ<br>MQDAAGRRHFHASQCPRPTSPVSTDSNMSAVVIQKARPAKKQKHQPGHLRREAYADDLPPPP<br>VPPPAIKSPTVQSKAQLEVRPVMVPKLASIEARTDRSSDRKGGSYKGREALDGRQVTDLRTN<br>PSDPREAQEQPNDGKGRGTRQPKRDLPPAKTHLGQEDILPYCRPTFPTSNNPRDPSSSSSMS<br>SRGSGSRQREQANVGRRNMAEMQVLGGFERGDENNEELEETES |
| 13 | Human ROBO1<br>Ig 1,2 | PRIVEHPSDLIVSKGEPATLNCKAEGRPTPTIEWYKGGERVETDKDDPRSHRMLLPSGSLFF<br>LRIVHGRKSRPDEGVYVCVARNYLGEAVSHNASLEVAILRDDFRQNPSDVMVAVGEPAVMEC<br>QPPRGHPEPTISWKKDGSPLDDKDERITIRGGKLMITYTRKSDAGKYVCVGTNMVGERESEV<br>AELT |
| 14 | CynomolgusROBO1<br>Ig 1,2 | PRIVEHPSDLIVSKGEPATLNCKAEGRPTPTIEWYKGGERVETDKDDPRSHRMLLPSGSLFF<br>LRIVHGRKSRPDEGVYVCVARNYLGEAVSHNASLEVAILRDDFRQNPSDVMVAVGEPAVMEC<br>QPPRGHPEPTISWKKDGSPLDDKDERITIRGGKLMITYTRKSDAGKYVCVGTNMVGERESEV<br>AELT |
| 15 | Rat ROBO1 Ig<br>1,2 | PRIVEHPSDLIVSKGEPATLNCKAEGRPTPTIEWYKGGERVETDKDDPRSHRMLLPSGSLFF<br>LRIVHGRKSRPDEGVYICVARNYLGEAVSHNASLEVAILRDDFRQNPSDVMVAVGEPAVMEC<br>QPPRGHPEPTISWKKDGSPLDDKDERITIRGGKLMITYTRKSDAGKYVCVGTNMVGERESKV<br>ADVT |
| 16 | MouseROBO1 Ig<br>1,2 | PRIVEHPSDLIVSKGEPATLNCKAEGRPTPTIEWYKGGERVETDKDDPRSHRMLLPSGSLFF<br>LRIVHGRKSRPDEGVYICVARNYLGEAVSHNASLEVAILRDDFRQNPSDVMVAVGEPAVMEC<br>QPPRGHPEPTISWKKDGSPLDDKDERITIRGGKLMITYTRKSDAGKYVCVGTNMVGERESEV<br>AELT |
| 17 | Human ROBO2<br>KSR mutant<br>(Signal<br>peptide<br>underlined) | MSLLMFTQLLLLCGFLYVRVDG<br>SRLRQEDFPPRIVEHPSDVIVSKGEPTTLNCKAEGRPTPTIEWYKDGERVETDKDDPRSHRM<br>LLPSGSLFFLRIVHGRKSRPDEGSYVCVARNYLGEAVSRNASLEVALLRDDFRQNPTDVVVA<br>AGEPAILECQPPRGHPEPTIYWKKDKVRIDDKEERISRGGKLMISNTRKSDAGMYTCVGTN<br>MVGERDSDPAELTVFERPTFLRRPINQVVLEEEAVEFRCQVQGDPQPTVRWKKDDADLPRGR<br>YDIKDDYTLRIKKTMSTDEGTYMCIAENRVGKMEASATLTVRAPPQFVVRPRDQIVAQGRTV<br>TFPCETKGNPQPAVFWQKEGSQNLLFPNQPQQPNSRCSVSPTGDLTITNIQRSDAGYYICQA<br>LTVAGSILAKAQLEVTDVLTDRPPPIILQGPANQTLAVDGTALLKCKATGDPLPVISWLKEG<br>FTFPGRDPRATIQEQGTLQIKNLRISDTGTYTCVATSSSGETSWSAVLDVTESGATISKNYD<br>LSDLPGPPSKPQVTDVTKNSVTLSWQPGTPGTLPASAYITEAFSQSVSNSWQTVANHVKTTL<br>YTVRGLRPNTIYLFMVRAINPQGLSDPSPMSDPVRTQDISPPAQGVDHRQVQKELGDVLVRL<br>HNPVVLTPTTVQVTWTVDRQPQFIQGYRVMYRQTSGLQATSSWQNLDAKVPTERSAVLVNLK<br>KGVTYEIKVRPYFNEFQGMDSESKTVRTTEEAPSAPPQSVTVLTVGSYNSTSISVSWDPPPP<br>DHQNGIIQEYKIWCLGNETRFTHINKTVDAAIRSVIIGGLFPGIQYRVEVAASTSAGVGVKSE<br>PQPIIIGRRNEVVITENNNSITEQITDVVKQPAFIAGIGGACWVILMGFSIWLYWRRKKRKG<br>LSNYAVTFQRGDGGLMSNGSRPGLLNAGDPSYPWLADSWPATSLPVNNSNSGPNEIGNFGRG<br>DVLPPVPGQGDKTATMLSDGAIYSSIDFTTKTSYNSSSQITQATPYATTQILHSNSIHELAV<br>DLPDPQWKSSIQQKTDLMGFGYSLPDQNKGNNGGKGGKKKNKNSSKPQKNNGSTWANVPLP<br>PPPVQPLPGTELEHYAVEQQENGYDSDSWCPPLPVQTYLHQGLEDELEEDDDRVPTPVRGV<br>ASSPAISFGQQSTATLTPSPREEMQPMLQAHLDELTRAYQFDIAKQTWHIQSNNQPPQPPVP<br>PLGYVSGALISDLETDVADDDADDEEEALEIPRPLRALDQTPGSSMDNLDSSVTGKAFTSSQ<br>RPRPTSPFSTDSNTSAALSQSQRPRPTKKHKGGRMDQQPALPHRREGMTDEEALVPYSKPSF<br>PSPGGHSSSGTASSKGSTGPRKTEVLRAGHQRNASDLLDIGYMGSNSQGQFTGEL |
| 18 | Human ROBO1<br>RSK Mutant<br>(Signal<br>peptide<br>underlined) | MKWKHVPFLVMISLLSLSPNHLFLA<br>QLIPDPEDVERGNDHGTPIPTSDNDDNSLGYTGSRLRQEDFPPRIVEHPSDLIVSKGEPATL<br>NCKAEGRPTPTIEWYKGGERVETDKDDPRSHRMLLPSGSLFFLRIVHGRKSRPDEGVYVCVA<br>RNYLGEAVSHNASLEVAILRDDFRQNPSDVMVAVGEPAVMECQPPRGHPEPTISWKKDGSPL<br>DDKDERITIRGGKLMITYTRKSDAGKYVCVGTNMVGERESEVAELTVLERPSFVKRPSNLAV<br>TVDDSAEFKCEARGDPVPTVRWKDDGELPKSRYEIRDDHTLKIRKVTAGDMGSYTCVAENM<br>VGKAEASATLTVQEPPHFVVKPRDQVVALGRTVTFQCEATGNPQPAIFWRREGSQNLLFSYQ<br>PPQSSSRFSVSQTGDLTITNVQRSDVGYYICQTLNVAGSIITKAYLEVTDVIADRPPPVIRQ<br>GPVNQTVAVDGTFVLSCVATGSPVPTILWRKDGVLVSTQDSRIKQLENGVLQIRYAKLGDTG<br>RYTCIASTPSGEATWSAYIEVQEFGVPVQPPRPTDPNLIPSAPSKPEVTDVSRNTVTLSWQP<br>NLNSGATPTSYITEAFSHASGSSWQTVAENVKTETSAIKGLKPNAIYLFLVRAANAYGISDP<br>SQISDPVKTQDVLPTSQGVDHKQVQRELGNAVLHLHNPTVLSSSSIEVHWTVDQQSQYIQGY<br>KILYRPSGANHGESDWLVFEVRTPAKNSVVIPDLRKGVNYEIKARPFFNEFQGADSEIKFAK<br>TLEEAPSAPPQGVTVSKNDGNGTAILVSWQPPPEDTQNGMVQEYKVWCLGNETRYHINKTVD<br>GSTFSVVIPFLVPGIRYSVEVAASTGAGSGVKSEPQFIQLDAHGNPVSPEDQVSLAQQISDV<br>VKQPAFIAGIGAACWIILMVFSIWLYRHRKKRNGLTSTSTYAGIRKVPSFTFTPTVTYQRGGEA<br>VSSGGRPGLLNISEPAAQPWLADTWPNTGNNHNDCSISCCTAGNGNSDSNLTTYSRPADCIA<br>NYNNQLDNKQTNLMLPESTVYGDVDLSNKINEMKTFNSPNLKDGRFVNPSGQPTPYATTQLI<br>QSNLSNNMNNGSGDSGEKHWKPLGQQKQEVAPVQYNIVEQNKLNKDYRANDTVPPTIPYNQS<br>YDQNTGGSYNSSDRGSSTSGSQGHKKGARTPKVPKQGGMNWADLLPPPPAHPPPHSNSEEYN<br>ISVDESYDQEMPCPVPPARMYLQQDELEEEEDERGPTPPVRGAASSPAAVSYSHQSTATLTP<br>SPQEELQPMLQDCPEETGHMQHQPDRRRQPVSPPPPPPRPISPPHTYGYISGPLVSDMDTDAP<br>EEEEDEADMEVAKMQTRRLLLRGLEQTPASSVGDLESSVTGSMINGWGSASEEDNISSGRSS<br>VSSSDGSFFTDADFAQAVAAAAEYAGLKVARRQMQDAAGRRHFHASQCPRPTSPVSTDSNMS<br>AAVMQKTRPAKKLKHQPGHLRRETYTDDLPPPPVPPPAIKSPTAQSKTQLEVRPVVVPKLPS<br>MDARTDRSSDRKGSSYKGREVLDGRQVVDMRTNPGDPREAQEQQNDGKGRGNKAAKRDLPPA<br>KTHLIQEDILPYCRPTFPTSNNPRDPSSSSSMSSRGSGSRQREQANVGRRNIAEMQVLGGYE<br>RGEDNNEELEETES |
| 19 | Human ROBO2<br>Ig 1,2 KSR | PRIVEHPSDVIVSKGEPTTLNCKAEGRPTPTIEWYKDGERVETDKDDPRSHRMLLPSGSLFF<br>LRIVHGKSRPDEGSYVCVARNYLGEAVSRNASLEVALLRDDFRQNPTDVVVAAGEPAILECQ |

TABLE 11-continued

SEQUENCES

| SEQ | DESCRIPTION | SEQUENCE |
|---|---|---|
|  | mutant | PPRGHPEPTIYWKKDKVRIDDKEERISIRGGKLMISNTRKSDAGMYTCVGTNMVGERDSDPAELT |
| 20 | Human ROBO1 Ig 1,2 RSK mutant | PRIVEHPSDLIVSKGEPATLNCKAEGRPTPTIEWYKGGERVETDKDDPRSHRMLLPSGSLFFLRIVHGRRSKPDEGVYVCVARNYLGEAVSHNASLEVAILRDDFRQNPSDVMVAVGEPAVMECQPPRGHPEPTISWKKDGSPLDDKDERITIRGGKLMITYTRKSDAGKYVCVGTNMVGERESEVAELT |
| 21 | Abcs35 VH NUCLEOTIDE. DASHED UNDERLINE: SIGNAL PEPTIDE | ATGGGATGGAGCTGTATCATCCTCTTCTTGGTAGCAACAGCTACAGGCGTGCACTCCGAGGTCCAGCTGGTGCAGTCTGGGGCTGAGGTGAAGAAGCCTGGGGCCTCAGTGAAGGTCTCCTGCAAGGCTTCTGGGTACACCTTCACCGGCTACTATATGCACTGGGTGCGACAGGCCCCTGGACAAGGGCTTGAGTGGATGGGATGGATCAATCCTAAGAATGGTGATACAGAGTTTCCACAGAAGTTTCAGGGCAGGGTCACCATGACCAGGGACACGTCCATCACCACAGCCTACATGGACCTGAGCAGGCTCAGATCTGACGACACGGCCGTGTATTACTGTGCGAGAGAAGTGGGGATGATGCTTTTGATATTTGGGGCCAAGGGACAATGGTCACCGTCTCGAGC |
| 22 | Abcs35 VH UNDERLINED: CDRS, with SIGNAL PEPTIDE | MGWSCIILFLVATATGVHSEVQLVQSGAEVKKPGASVKVSCKASGYTFTGYYMHWVRQAPGQGLEWMGWINPKNGDTEFPQKFQGRVTMTRDTSITTAYMDLSRLRSDDTAVYYCARESGDDAFDIWGQGTMVTVSS |
| 23 | Abcs 35 SIGNAL PEPTIDE | MGWSCIILFLVATATGVHS |
| 24 | Abcs35 CDRH1 | GYTFTGYYMH |
| 25 | Abcs35 CDRH2 | WINPKNGDTEFPQKFQG |
| 26 | Abcs35 CDRH3 | ESGDDAFDI |
| 27 | Abcs35 VL NUCLEOTIDE. DASHED UNDERLINE: SIGNAL PEPTIDE | ATGGGATGGAGCTGTATCATCCTCTTCTTGGTAGCAACAGCTACAGGCGTGCACTCCGACATCGTGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGTCGGTTGGTCTTTTTTCGGCGGAGGGACCAAGGTGGAGATCAAA |
| 28 | Abcs35 VL UNDERLINED: CDRS, with SIGNAL PEPTIDE | MGWSCIILFLVATATGVHSDIVMTQSPSSLSASVGDRVTITCRASQSISSYLNWYQQKPGKAPKLLIYAASSLQSGVPSRFSGSGSGTDFTLTISSLQPEDFATYYCQQSVGLFFGGGTKVEIK |
| 29 | Abcs35 CDRL1 | RASQSISSYLN |
| 30 | Abcs35 CDRL2 | AASSLQS |
| 31 | Abcs35 CDRL3 | QQSVGLF |
| 32 | Abcs35 VH UNDERLINED: CDRS | EVQLVQSGAEVKKPGASVKVSCKASGYTFTGYYMHWVRQAPGQGLEWMGWINPKNGDTEFPQKFQGRVTMTRDTSITTAYMDLSRLRSDDTAVYYCARESGDDAFDIWGQGTMVTVSS |
| 33 | Abcs35 JH | WGQGTMVTVSS |
| 34 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| 35 | HINGE | EPKSCDKTHTCPPCP |
| 36 | CH2 | APEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK |
| 37 | CH3 | GQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 38 | Abcs35 HC UNDERLINED: CDRS | EVQLVQSGAEVKKPGASVKVSCKASGYTFTGYYMHWVRQAPGQGLEWMGWINPKNGDTEFPQKFQGRVTMTRDTSITTAYMDLSRLRSDDTAVYYCARESGDDAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 39 | Abcs35 VL UNDERLINED: CDRS | DIVMTQSPSSLSASVGDRVTITCRASQSISSYLNWYQQKPGKAPKLLIYAASSLQSGVPSRFSGSGSGTDFTLTISSLQPEDFATYYCQQSVGLFFGGGTKVEIK |
| 40 | Abcs35 JK | FGGGTKVEIK |
| 41 | CL | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 42 | Abcs35 LC UNDERLINED: CDRS | DIVMTQSPSSLSASVGDRVTITCRASQSISSYLNWYQQKPGKAPKLLIYAASSLQSGVPSRFSGSGSGTDFTLTISSLQPEDFATYYCQQSVGLFFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 43 | 93H2 VH | EVQLVQSGAEVKKPGASVKVSCKASGYTFTGYYMHWVRQAPGQGLEWMGWINPNSGATNFPQKFQGRVTMTRDTSITTAYMDLSRLRSDDTAVYYCARESGDDAFDIWGQGTMVTVSS |
| 44 | 93H2 CDRH2 | WINPNSGATNFPQKFQG |
| 45 | 93H2 HC | EVQLVQSGAEVKKPGASVKVSCKASGYTFTGYYMHWVRQAPGQGLEWMGWINPNSGATNFPQKFQGRVTMTRDTSITTAYMDLSRLRSDDTAVYYCARESGDDAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKP |

TABLE 11-continued

SEQUENCES

| SEQ | DESCRIPTION | SEQUENCE |
|---|---|---|
| | | KDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEALH NHYTQKSLSLSPGK |
| 46 | 93H2 VL | DIVMTQSPSSLSASVGDRVTITCRASQSISSYLNWYQQKPGKAPKLLIYAASSLQSGVPSRF SGSGSGTDFTLTISSLQPEDFATYYCQQSYSTSFGGGTKVEIK |
| 47 | 93H2 CDRL3 | XSYSTS |
| 48 | 93H2 LC | DIVMTQSPSSLSASVGDRVTITCRASQSISSYLNWYQQKPGKAPKLLIYAASSLQSGVPSRF SGSGSGTDFTLTISSLQPEDFATYYCQQSYSTSFGGGTKVEIKRTVAAPSVFIFPPSDEQLK SGTASVVCLLNNFYPREAKVQWKVDNALQSGNSQESVTEQDSKDSTYSLSSTLTLSKADYEK HKVYACEVTHQGLSSPVTKSFNRGEC |
| 49 | Ab1 VH | EVQLVQSGAEVKKPGASVKVSCKASGYTFTGYDMH WVRQAPGQGLEWMGWINPNSGATNFPQKFQGRVTMTRDTSITTAYMDLSRLRSDDTAVYYCA RESGDDAFDIWGQGTMVTVSS |
| 50 | Ab1 CDRH1 | GYTFTGYDMH |
| 51 | Ab1 HC | EVQLVQSGAEVKKPGASVKVSCKASGYTFTGYDMH WVRQAPGQGLEWMGWINPNSGATNFPQKFQGRVTMTRDTSITTAYMDLSRLRSDDTAVYYCA RESGDDAFDIWGQGTMVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDKKVEPKSC DKTHTCPPCPAPEAAGAPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPR EPQVYTLPPSREEMTKNQVSLTCLVKGFYPSDIAVEWESNGQPENNYKTTPPVLDSDGSFFL YSKLTVDKSRWQQGNVFSCSVMHEALHNHYTQKSLSLSPGK |
| 52 | Ab1 VL | DIVMTQSPSSLSASVGDRVTITCRASQKISSYLNWYQQKPGKAPKLLIYAASSLQSGVPSRF SGSGSGTDFTLTISSLQPEDFATYYCQQSYSTSFGGGTKVEIK |
| 53 | Ab1 CDRL1 | RASQKISSYLN |
| 54 | Ab1 LC | DIVMTQSPSSLSASVGDRVTITCRASQKISSYLNWYQQKPGKAPKLLIYAASSLQSGVPSRF SGSGSGTDFTLTISSLQPEDFATYYCQQSYSTSFGGGTKVEIKRTVAAPSVFIFPPSDEQLK SGTASVVCLLNNFYPREAKVQWKVDNALQSGNSQESVTEQDSKDSTYSLSSTLTLSKADYEK HKVYACEVTHQGLSSPVTKSFNRGEC |
| 55 | Ab3 VH | EVQLVQSGAEVKKPGASVKVSCKASGYTFTGYYMHWVRQAPGQGLEWMGWINPKSGATNFPQ KFQGRVTMTRDTSITTAYMDLSRLRSDDTAVYYCARESGDDAFDIWGQGTMVTVSS |
| 56 | Ab3 CDRH2 | WINPKSGATNFPQKFQG |
| 57 | Ab3 HC | EVQLVQSGAEVKKPGASVKVSCKASGYTFTGYYMHWVRQAPGQGLEWMGWINPKSGATNFPQ KFQGRVTMTRDTSITTAYMDLSRLRSDDTAVYYCARESGDDAFDIWGQGTMVTVSSASTKGP SVFPLAPSSKSTSGGTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPEAAGAPSVFLFPPKP KDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEALH NHYTQKSLSLSPGK |
| 58 | Ab9 VL | DIVMTQSPSSLSASVGDRVTITCRASQRISSYLNWYQQKPGKAPKLLIYAASSLQSGVPSRF SGSGSGTDFTLTISSLQPEDFATYYCQQSYSTSFGGGTKVEIK |
| 59 | Ab9 CDRL1 | RASQRISSYLN |
| 60 | Ab9 LC | DIVMTQSPSSLSASVGDRVTITCRASQRISSYLNWYQQKPGKAPKLLIYAASSLQSGVPSRF SGSGSGTDFTLTISSLQPEDFATYYCQQSYSTSFGGGTKVEIKRTVAAPSVFIFPPSDEQLK SGTASVVCLLNNFYPREAKVQWKVDNALQSGNSQESVTEQDSKDSTYSLSSTLTLSKADYEK HKVYACEVTHQGLSSPVTKSFNRGEC |
| 61 | Ab13 VL | DIVMTQSPSSLSASVGDRVTITCRASQSISSYLNWYQQKPGKAPKLLIYAASSLQDGVPSRF SGSGSGTDFTLTISSLQPEDFATYYCQQSYSTSFGGGTKVEIK |
| 62 | Ab13 CDRL2 | AASSLQD |
| 63 | Ab13 LC | DIVMTQSPSSLSASVGDRVTITCRASQSISSYLNWYQQKPGKAPKLLIYAASSLQDGVPSRF SGSGSGTDFTLTISSLQPEDFATYYCQQSYSTSFGGGTKVEIKRTVAAPSVFIFPPSDEQLK SGTASVVCLLNNFYPREAKVQWKVDNALQSGNSQESVTEQDSKDSTYSLSSTLTLSKADYEK HKVYACEVTHQGLSSPVTKSFNRGEC |
| 64 | Ab17 VL | DIVMTQSPSSLSASVGDRVTITCRASQSISSYLNWYQQKPGKAPKLLIYAASSLQEGVPSRF SGSGSGTDFTLTISSLQPEDFATYYCQQSYSTSFGGGTKVEIK |
| 65 | Ab17 CDRL2 | AASSLQE |
| 66 | Ab17 LC | DIVMTQSPSSLSASVGDRVTITCRASQSISSYLNWYQQKPGKAPKLLIYAASSLQEGVPSRF SGSGSGTDFTLTISSLQPEDFATYYCQQSYSTSFGGGTKVEIKRTVAAPSVFIFPPSDEQLK SGTASVVCLLNNFYPREAKVQWKVDNALQSGNSQESVTEQDSKDSTYSLSSTLTLSKADYEK HKVYACEVTHQGLSSPVTKSFNRGEC |
| 67 | Ab21 VL | DIVMTQSPSSLSASVGDRVTITCRASQSISSYLNWYQQKPGKAPKLLIYAASSLQYGVPSRF SGSGSGTDFTLTISSLQPEDFATYYCQQSYSTSFGGGTKVEIK |
| 68 | Ab21 CDRL2 | AASSLQY |
| 69 | Ab21 LC | DIVMTQSPSSLSASVGDRVTITCRASQSISSYLNWYQQKPGKAPKLLIYAASSLQYGVPSRF SGSGSGTDFTLTISSLQPEDFATYYCQQSYSTSFGGGTKVEIKRTVAAPSVFIFPPSDEQLK SGTASVVCLLNNFYPREAKVQWKVDNALQSGNSQESVTEQDSKDSTYSLSSTLTLSKADYEK HKVYACEVTHQGLSSPVTKSFNRGEC |
| 70 | Ab22 VH | EVQLVQSGAEVKKPGASVKVSCKASGYTFTGYYMHWVRQAPGQGLEWMGWINPRSGATNFPQ KFQGRVTMTRDTSITTAYMDLSRLRSDDTAVYYCARESGDDAFDIWGQGTMVTVSS |
| 71 | Ab22 CDRH2 | WINPRSGATNFPQKFQG |
| 72 | Ab22 HC | EVQLVQSGAEVKKPGASVKVSCKASGYTFTGYYMHWVRQAPGQGLEWMGWINPRSGATNFPQ KFQGRVTMTRDTSITTAYMDLSRLRSDDTAVYYCARESGDDAFDIWGQGTMVTVSSASTKGP SVFPLAPSSKSTSGGTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPEAAGAPSVFLFPPKP |

TABLE 11-continued

SEQUENCES

| SEQ | DESCRIPTION | SEQUENCE |
|---|---|---|
| | | KDTLMISRTPEVTCVVVDVSHEDPEVKFNWYVDGVEVHNAKTKPREEQYNSTYRVVSVLTVL |
| | | HQDWLNGKEYKCKVSNKALPAPIEKTISKAKGQPREPQVYTLPPSREEMTKNQVSLTCLVKG |
| | | FYPSDIAVEWESNGQPENNYKTTPPVLDSDGSFFLYSKLTVDKSRWQQGNVFSCSVMHEALH |
| | | NHYTQKSLSLSPGK |
| 73 | Ab29 VH | EVQLVQSGAEVKKPGASVKVSCKASGYTFTGYYMHWVRQAPGQGLEWMGAIDPKSGTTMFPQ |
| | | KFQGRVTMTRDTSITTAYMDLSRLRSDDTAVYYCARESGDDAFDIWGQGTMVTVSS |
| 74 | Ab29 CDRH2 | AIDPKSGTTMFPQKFQG |
| 75 | Ab29 HC | EVQLVQSGAEVKKPGASVKVSCKASGYTFTGYYMHWVRQAPGQGLEWMGAIDPKSGTTMFPQ |
| | | KFQGRVTMTRDTSITTAYMDLSRLRSDDTAVYYCARESGDDAFDIWGQGTMVTVSSASTKGP |
| | | SVFPLAPSSKSTSGGTAALGCLVKDYFPEPVTVSWNSGALTSGVHTFPAVLQSSGLYSLSSV |
| | | VTVPSSSLGTQTYICNVNHKPSNTKVDKKVEPKSCDKTHTCPPCPAPEAAGAPSVFLFPPKP |
| | | KDTLMISRTPEVTCVVVDVSHEDPEVKFNWYVDGVEVHNAKTKPREEQYNSTYRVVSVLTVL |
| | | HQDWLNGKEYKCKVSNKALPAPIEKTISKAKGQPREPQVYTLPPSREEMTKNQVSLTCLVKG |
| | | FYPSDIAVEWESNGQPENNYKTTPPVLDSDGSFFLYSKLTVDKSRWQQGNVFSCSVMHEALH |
| | | NHYTQKSLSLSPGK |
| 76 | Ab32 VH | EVQLVQSGAEVKKPGASVKVSCKASGYTFTGYYMHWVRQAPGQGLEWMGAIDPKLGITIFPQ |
| | | KFQGRVTMTRDTSITTAYMDLSRLRSDDTAVYYCARESGDDAFDIWGQGTMVTVSS |
| 77 | Ab32 CDRH2 | AIDPKLGITIFPQKFQG |
| 78 | Ab32 HC | EVQLVQSGAEVKKPGASVKVSCKASGYTFTGYYMHWVRQAPGQGLEWMGAIDPKLGITIFPQ |
| | | KFQGRVTMTRDTSITTAYMDLSRLRSDDTAVYYCARESGDDAFDIWGQGTMVTVSSASTKGP |
| | | SVFPLAPSSKSTSGGTAALGCLVKDYFPEPVTVSWNSGALTSGVHTFPAVLQSSGLYSLSSV |
| | | VTVPSSSLGTQTYICNVNHKPSNTKVDKKVEPKSCDKTHTCPPCPAPEAAGAPSVFLFPPKP |
| | | KDTLMISRTPEVTCVVVDVSHEDPEVKFNWYVDGVEVHNAKTKPREEQYNSTYRVVSVLTVL |
| | | HQDWLNGKEYKCKVSNKALPAPIEKTISKAKGQPREPQVYTLPPSREEMTKNQVSLTCLVKG |
| | | FYPSDIAVEWESNGQPENNYKTTPPVLDSDGSFFLYSKLTVDKSRWQQGNVFSCSVMHEALH |
| | | NHYTQKSLSLSPGK |
| 79 | Ab45 VH | EVQLVQSGAEVKKPGASVKVSCKASGYTFTGYYMHWVRQAPGQGLEWMGMINPKSGFTAFPQ |
| | | KFQGRVTMTRDTSITTAYMDLSRLRSDDTAVYYCARESGDDAFDIWGQGTMVTVSS |
| 80 | Ab45 CDRH2 | MINPKSGFTAFPQKFQG |
| 81 | Ab45 HC | EVQLVQSGAEVKKPGASVKVSCKASGYTFTGYYMHWVRQAPGQGLEWMGMINPKSGFTAFPQ |
| | | KFQGRVTMTRDTSITTAYMDLSRLRSDDTAVYYCARESGDDAFDIWGQGTMVTVSSASTKGP |
| | | SVFPLAPSSKSTSGGTAALGCLVKDYFPEPVTVSWNSGALTSGVHTFPAVLQSSGLYSLSSV |
| | | VTVPSSSLGTQTYICNVNHKPSNTKVDKKVEPKSCDKTHTCPPCPAPEAAGAPSVFLFPPKP |
| | | KDTLMISRTPEVTCVVVDVSHEDPEVKFNWYVDGVEVHNAKTKPREEQYNSTYRVVSVLTVL |
| | | HQDWLNGKEYKCKVSNKALPAPIEKTISKAKGQPREPQVYTLPPSREEMTKNQVSLTCLVKG |
| | | FYPSDIAVEWESNGQPENNYKTTPPVLDSDGSFFLYSKLTVDKSRWQQGNVFSCSVMHEALH |
| | | NHYTQKSLSLSPGK |
| 82 | Ab46 VH | EVQLVQSGAEVKKPGASVKVSCKASGYTFTGYYMHWVRQAPGQGLEWMGAIDPKHGFTIFPQ |
| | | KFQGRVTMTRDTSITTAYMDLSRLRSDDTAVYYCARESGDDAFDIWGQGTMVTVSS |
| 83 | Ab46 CDRH2 | AIDPKHGFTIFPQKFQG |
| 84 | Ab46 HC | EVQLVQSGAEVKKPGASVKVSCKASGYTFTGYYMHWVRQAPGQGLEWMGAIDPKHGFTIFPQ |
| | | KFQGRVTMTRDTSITTAYMDLSRLRSDDTAVYYCARESGDDAFDIWGQGTMVTVSSASTKGP |
| | | SVFPLAPSSKSTSGGTAALGCLVKDYFPEPVTVSWNSGALTSGVHTFPAVLQSSGLYSLSSV |
| | | VTVPSSSLGTQTYICNVNHKPSNTKVDKKVEPKSCDKTHTCPPCPAPEAAGAPSVFLFPPKP |
| | | KDTLMISRTPEVTCVVVDVSHEDPEVKFNWYVDGVEVHNAKTKPREEQYNSTYRVVSVLTVL |
| | | HQDWLNGKEYKCKVSNKALPAPIEKTISKAKGQPREPQVYTLPPSREEMTKNQVSLTCLVKG |
| | | FYPSDIAVEWESNGQPENNYKTTPPVLDSDGSFFLYSKLTVDKSRWQQGNVFSCSVMHEALH |
| | | NHYTQKSLSLSPGK |
| 85 | Ab58 VH | EVQLVQSGAEVKKPGASVKVSCKASGYTFTGYYMHWVRQAPGQGLEWMGWINPKDGDTEFPQ |
| | | KFQGRVTMTRDTSITTAYMDLSRLRSDDTAVYYCARESGDDAFDIWGQGTMVTVSS |
| 86 | Ab58 CDRH2 | WINPKDGDTEFPQKFQG |
| 87 | Ab58 HC | EVQLVQSGAEVKKPGASVKVSCKASGYTFTGYYMHWVRQAPGQGLEWMGWINPKDGDTEFPQ |
| | | KFQGRVTMTRDTSITTAYMDLSRLRSDDTAVYYCARESGDDAFDIWGQGTMVTVSSASTKGP |
| | | SVFPLAPSSKSTSGGTAALGCLVKDYFPEPVTVSWNSGALTSGVHTFPAVLQSSGLYSLSSV |
| | | VTVPSSSLGTQTYICNVNHKPSNTKVDKKVEPKSCDKTHTCPPCPAPEAAGAPSVFLFPPKP |
| | | KDTLMISRTPEVTCVVVDVSHEDPEVKFNWYVDGVEVHNAKTKPREEQYNSTYRVVSVLTVL |
| | | HQDWLNGKEYKCKVSNKALPAPIEKTISKAKGQPREPQVYTLPPSREEMTKNQVSLTCLVKG |
| | | FYPSDIAVEWESNGQPENNYKTTPPVLDSDGSFFLYSKLTVDKSRWQQGNVFSCSVMHEALH |
| | | NHYTQKSLSLSPGK |
| 88 | Ab83 VH | EVQLVQSGAEVKKPGASVKVSCKASGYTFTGYYMHWVRQAPGQGLEWMGWINPRNGITSFPQ |
| | | KFQGRVTMTRDTSITTAYMDLSRLRSDDTAVYYCARESGDDAFDIWGQGTMVTVSS |
| 89 | Ab83 CDRH2 | WINPRNGITSFPQKFQG |
| 90 | Ab83 HC | EVQLVQSGAEVKKPGASVKVSCKASGYTFTGYYMHWVRQAPGQGLEWMGWINPRNGITSFPQ |
| | | KFQGRVTMTRDTSITTAYMDLSRLRSDDTAVYYCARESGDDAFDIWGQGTMVTVSSASTKGP |
| | | SVFPLAPSSKSTSGGTAALGCLVKDYFPEPVTVSWNSGALTSGVHTFPAVLQSSGLYSLSSV |
| | | VTVPSSSLGTQTYICNVNHKPSNTKVDKKVEPKSCDKTHTCPPCPAPEAAGAPSVFLFPPKP |
| | | KDTLMISRTPEVTCVVVDVSHEDPEVKFNWYVDGVEVHNAKTKPREEQYNSTYRVVSVLTVL |
| | | HQDWLNGKEYKCKVSNKALPAPIEKTISKAKGQPREPQVYTLPPSREEMTKNQVSLTCLVKG |
| | | FYPSDIAVEWESNGQPENNYKTTPPVLDSDGSFFLYSKLTVDKSRWQQGNVFSCSVMHEALH |
| | | NHYTQKSLSLSPGK |

TABLE 11-continued

SEQUENCES

| SEQ | DESCRIPTION | SEQUENCE |
|---|---|---|
| 91 | Ab112 VL | DIVMTQSPSSLSASVGDRVTITCRASQSISSYLNWYQQKPGKAPKLLIYAASSLQSGVPSRF<br>SGSGSGTDFTLTISSLQPEDFATYYCQQSVGLSFGGGTKVEIK |
| 92 | Ab112 CDRL3 | QQSVGLS |
| 93 | Ab112 LC | DIVMTQSPSSLSASVGDRVTITCRASQSISSYLNWYQQKPGKAPKLLIYAASSLQSGVPSRF<br>SGSGSGTDFTLTISSLQPEDFATYYCQQSVGLSFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 94 | Abcs1 VL | DIVMTQSPSSLSASVGDRVTITCRASQSISSYLNWYQQKPGKAPKLLIYAASSLQSGVPSRF<br>SGSGSGTDFTLTISSLQPEDFATYYCQQSLELGFGGGTKVEIK |
| 95 | Abcs1 CDRL3 | QQSLELG |
| 96 | Abcs1 LC | DIVMTQSPSSLSASVGDRVTITCRASQSISSYLNWYQQKPGKAPKLLIYAASSLQSGVPSRF<br>SGSGSGTDFTLTISSLQPEDFATYYCQQSLELGFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 97 | CTIR2-1 VL | DIVMTQSPSSLSASVGDRVTITCRASQSISSYLNWYQQKPGKAPKLLIYAASSLQYGVPSRF<br>SGSGSGTDFTLTISSLQPEDFATYYCQQSLELGFGGGTKVEIK |
| 98 | CTIR2-1 LC | DIVMTQSPSSLSASVGDRVTITCRASQSISSYLNWYQQKPGKAPKLLIYAASSLQYGVPSRF<br>SGSGSGTDFTLTISSLQPEDFATYYCQQSLELGFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 99 | CTIR2-2 VL | DIVMTQSPSSLSASVGDRVTITCRASQSISSYLNWYQQKPGKAPKLLIYAASSLQYGVPSRF<br>SGSGSGTDFTLTISSLQPEDFATYYCQQSVGLSFGGGTKVEIK |
| 100 | CTIR2-2 LC | DIVMTQSPSSLSASVGDRVTITCRASQSISSYLNWYQQKPGKAPKLLIYAASSLQYGVPSRF<br>SGSGSGTDFTLTISSLQPEDFATYYCQQSVGLSFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 101 | CTIR2-3 VL | DIVMTQSPSSLSASVGDRVTITCRASQSISSYLNWYQQKPGKAPKLLIYAASSLQYGVPSRF<br>SGSGSGTDFTLTISSLQPEDFATYYCQQSVGLFFGGGTKVEIK |
| 102 | CTIR2-3 LC | DIVMTQSPSSLSASVGDRVTITCRASQSISSYLNWYQQKPGKAPKLLIYAASSLQYGVPSRF<br>SGSGSGTDFTLTISSLQPEDFATYYCQQSVGLFFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 103 | CTIR2-4 VL | DIVMTQSPSSLSASVGDRVTITCRASQKISSYLNWYQQKPGKAPKLLIYAASSLQYGVPSRF<br>SGSGSGTDFTLTISSLQPEDFATYYCQQSYSTSFGGGTKVEIK |
| 104 | CTIR2-4 LC | DIVMTQSPSSLSASVGDRVTITCRASQKISSYLNWYQQKPGKAPKLLIYAASSLQYGVPSRF<br>SGSGSGTDFTLTISSLQPEDFATYYCQQSYSTSFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 105 | CTIR2-5 VL | DIVMTQSPSSLSASVGDRVTITCRASQKISSYLNWYQQKPGKAPKLLIYAASSLQSGVPSRF<br>SGSGSGTDFTLTISSLQPEDFATYYCQQSLELGFGGGTKVEIK |
| 106 | CTIR2-5 LC | DIVMTQSPSSLSASVGDRVTITCRASQKISSYLNWYQQKPGKAPKLLIYAASSLQSGVPSRF<br>SGSGSGTDFTLTISSLQPEDFATYYCQQSLELGFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 107 | CTIR2-6 VL | DIVMTQSPSSLSASVGDRVTITCRASQKISSYLNWYQQKPGKAPKLLIYAASSLQSGVPSRF<br>SGSGSGTDFTLTISSLQPEDFATYYCQQSVGLFFGGGTKVEIK |
| 108 | CTIR2-6 LC | DIVMTQSPSSLSASVGDRVTITCRASQKISSYLNWYQQKPGKAPKLLIYAASSLQSGVPSRF<br>SGSGSGTDFTLTISSLQPEDFATYYCQQSVGLFFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 109 | CTIR2-7 VL | DIVMTQSPSSLSASVGDRVTITCRASQKISSYLNWYQQKPGKAPKLLIYAASSLQYGVPSRF<br>SGSGSGTDFTLTISSLQPEDFATYYCQQSLELGFGGGTKVEIK |
| 110 | CTIR2-7 LC | DIVMTQSPSSLSASVGDRVTITCRASQKISSYLNWYQQKPGKAPKLLIYAASSLQYGVPSRF<br>SGSGSGTDFTLTISSLQPEDFATYYCQQSLELGFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 111 | CTIR2-8 VL | DIVMTQSPSSLSASVGDRVTITCRASQKISSYLNWYQQKPGKAPKLLIYAASSLQYGVPSRF<br>SGSGSGTDFTLTISSLQPEDFATYYCQQSVGLSFGGGTKVEIK |
| 112 | CTIR2-8 LC | DIVMTQSPSSLSASVGDRVTITCRASQKISSYLNWYQQKPGKAPKLLIYAASSLQYGVPSRF<br>SGSGSGTDFTLTISSLQPEDFATYYCQQSVGLSFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 113 | CTIR2-9 VL | DIVMTQSPSSLSASVGDRVTITCRASQKISSYLNWYQQKPGKAPKLLIYAASSLQYGVPSRF<br>SGSGSGTDFTLTISSLQPEDFATYYCQQSVGLFFGGGTKVEIK |
| 114 | CTIR2-9 LC | DIVMTQSPSSLSASVGDRVTITCRASQKISSYLNWYQQKPGKAPKLLIYAASSLQYGVPSRF<br>SGSGSGTDFTLTISSLQPEDFATYYCQQSVGLFFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 115 | CTIR2-10 VH | EVQLVQSGAEVKKPGASVKVSCKASGYTFRGYAMHWVRQAPGQGLEWMGWINPRSGVTEFPQ<br>KFQGRVTMTRDTSITTAYMDLSRLRSDDTAVYYCARESGDDAFDIWGQGTMVTVSS |
| 116 | CTIR2-10 CDRH1 | GYTFRGYAMH |
| 117 | CTIR2-10 CDRH2 | WINPRSGVTEFPQKFQG |
| 118 | CTIR2-10 HC | EVQLVQSGAEVKKPGASVKVSCKASGYTFRGYAMHWVRQAPGQGLEWMGWINPRSGVTEFPQ<br>KFQGRVTMTRDTSITTAYMDLSRLRSDDTAVYYCARESGDDAFDIWGQGTMVTVSSASTKGP |

TABLE 11-continued

SEQUENCES

| SEQ | DESCRIPTION | SEQUENCE |
|---|---|---|
| | | SVFPLAPSSKSTSGGTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPEAAGAPSVFLFPPKP KDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEALH NHYTQKSLSLSPGK |
| 119 | CTIR2-11 VH | EVQLVQSGAEVKKPGASVKVSCKASGYTFRGYAMHWVRQAPGQGLEWMGWIDPRTGLTKFPQ KFQGRVTMTRDTSITTAYMDLSRLRSDDTAVYYCARESGDDAFDIWGQGTMVTVSS |
| 120 | CTIR2-11 CDRH2 | WIDPRTGLTKFPQKFQG |
| 121 | CTIR2-11 HC | EVQLVQSGAEVKKPGASVKVSCKASGYTFRGYAMHWVRQAPGQGLEWMGWIDPRTGLTKFPQ KFQGRVTMTRDTSITTAYMDLSRLRSDDTAVYYCARESGDDAFDIWGQGTMVTVSSASTKGP SVFPLAPSSKSTSGGTAALGCLVKDYFPEPVTVSWNSGALTSGVHTFPAVLQSSGLYSLSSV VTVPSSSLGTQTYICNVNHKPSNTKVDKKVEPKSCDKTHTCPPCPAPEAAGAPSVFLFPPKP KDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEALH NHYTQKSLSLSPGK |
| 122 | ROBO2 ECD | SRLRQEDFPPRIVEHPSDVIVSKGEPTTLNCKAEGRPTPTIEWYKDGERVETDKDDPRSH RMLLPSGSLFFLRIVHGRRSKPDEGSYVCVARNYLGEAVSRNASLEVALLRDDFRQNPTD VVVAAGEPAILECQPPRGHPEPTIYWKKDKVRIDDKEERISIRGGKLMISNTRKSDAGMY TCVGTNMVGERDSDPAELTVFERPTFLRRPINQVVLEEEAVEFRCQVQGDPQPTVRWKKD DADLPRGRYDIKDDYTLRIKKTMSTDEGTYMCIAENRVGKMEASATLTVRAPPQFVVRPR DQIVAQGRTVTFPCETKGNPQPAVFWQKEGSQNLLFPNQPQQPNSRCSVSPTGDLTITNI QRSDAGYYICQALTVAGSILAKAQLEVTDVLTDRPPPIILQGPANQTLAVDGTALLKCKA TGDPLPVISWLKEGFTFPGRDPRATIQEQGTLQIKNLRISDTGTYTCVATSSSGETSWSA VLDVTESGATISKNYDLSDLPGPPSKPQVTDVTKNSVTLSWQPGTPGTLPASAYITEAFS QSVSNSWQTVANHVKTTLYTVRGLRPNTIYLFMVRAINPQGLSDPSPMSDPVRTQDISPPAQ GVDHRQVQKELGDVLVRLHNPVVLTPTTVQVTWTVDRQPQFIQGYRVMYRQTSGLQAT SSWQNLDAKVPTERSAVLVNLKKGVTYEIKVRPYFNEFQGMDSESKTVRTTEEAPSAPPQ SVTVLTVGSYNSTSISVSWDPPPPDHQNGIIQEYKIWCLGNETRFHINKTVDAAIRSVII GGLFPGIQYRVEVAASTSAGVGVKSEPQPIIIGRRNEVVITENNNSITEQITDVVKQP |
| 123 | ROBO1 ECD | QLIPDPEDVERGNDHGTPIPTSDNDDNSLGYTGSRLRQEDFPPRIVEHPSDLIVSKGEPA TLNCKAEGRPTPTIEWYKGGERVETDKDDPRSHRMLLPSGSLFFLRIVHGRKSRPDEGVY VCVARNYLGEAVSHNASLEVAILRDDFRQNPSDVMVAVGEPAVMECQPPRGHPEPTISWK KDGSPLDDKDERITIRGGKLMITYTRKSDAGKYVCVGTNMVGERESEVAELTVLERPSFV KRPSNLAVTVDDSAEFKCEARGDPVPTVRWKDDGELPKSRYEIRDDHTLKIRKVTAGDM GSYTCVAENMVGKAEASATLTVQEPPHFVVKPRDQVVALGRTVTFQCEATGNPQPAIFWR REGSQNLLFSYQPPQSSSRFSVSQTGDLTITNVQRSDVGYYICQTLNVAGSIITKAYLEV TDVIADRPPPVIRQGPVNQTVAVDGTFVLSCVATGSPVPTILWRKDGVLVSTQDSRIKQL ENGVLQIRYAKLGDTGRYTCIASTPSGEATWSAYIEVQEFGVPVQPPRPTDPNLIPSAPS KPEVTDVSRNTVTLSWQPNLNSGATPTSYITEAFSHASGSSWQTVAENVKTETSAIKGLK PNAIYLFLVRAANAYGISDPSQISDPVKTQDVLPTSQGVDHKQVQRELGNAVLHLHNPTV LSSSSSIEVHWTVDQQSQYIQGYKILYRPSGANHGESDWLVFEVRTPAKNSVVIPDLRKGV NYEIKARPFFNEFQGADSEIKFAKTLEEAPSAPPQGVTVSKNDGNGTAILVSWQPPPEDT QNGMVQEYKVWCLGNETRYHINKTVDGSTFSVVIPFLVPGIRYSVEVAASTGAGSGVKSE PQFIQLDAHGNPVSPEDQVSLAQQISDVVKQP |
| 124 | ROBO2 Ig1 | PRIVEHPSDVIVSKGEPTTLNCKAEGRPTPTIEWYKDGERVETDKDDPRSHRMLLPSGSLFF LRIVHGRRSKPDEGSYVCVARNYLGEAVSRNASLE |
| 125 | ROBO1 Ig1 | PRIVEHPSDLIVSKGEPATLNCKAEGRPTPTIEWYKGGERVETDKDDPRSHRMLLPSGSLFF LRIVHGRKSRPDEGVYVCVARNYLGEAVSHNASLE |
| 126 | Abcs35-B & Abcs35-I VH | EVQLVQSGAEVKKPGASVKVSCKASGYTFTGYYMHWVRQAPGQGLEWMGWINPKNGDTEFPQ KFQGRVTMTRDTSISTAYMDLSRLRSDDTAVYYCARESGDDAFDIWGQGTMVTVSS |
| 127 | Abcs35-C & Abcs35-J VH | EVQLVQSGAEVKKPGASVKVSCKASGYTFTGYYMHWVRQAPGQGLEWMGWINPKNGDTEFPQ KFQGRVTMTRDTSITTAYMELSRLRSDDTAVYYCARESGDDAFDIWGQGTMVTVSS |
| 128 | Abcs35-D & Abcs35-K VH | EVQLVQSGAEVKKPGASVKVSCKASGYTFTGYYMHWVRQAPGQGLEWMGWINPKNGDTEFPQ KFQGRVTMTRDTSISTAYMELSRLRSDDTAVYYCARESGDDAFDIWGQGTMVTVSS |
| 129 | Abcs35-E & Abcs35-L VH | QVQLVQSGAEVKKPGASVKVSCKASGYTFTGYYMHWVRQAPGQGLEWMGWINPKNGDTEFPQ KFQGRVTMTRDTSISTTAYMDLSRLRSDDTAVYYCARESGDDAFDIWGQGTMVTVSS |
| 130 | Abcs35-F & Abcs35-M VH | QVQLVQSGAEVKKPGASVKVSCKASGYTFTGYYMHWVRQAPGQGLEWMGWINPKNGDTEFPQ KFQGRVTMTRDTSISTAYMDLSRLRSDDTAVYYCARESGDDAFDIWGQGTMVTVSS |
| 131 | Abcs35-G & Abcs35-N VH | QVQLVQSGAEVKKPGASVKVSCKASGYTFTGYYMHWVRQAPGQGLEWMGWINPKNGDTEFPQ KFQGRVTMTRDTSISTTAYMDLSRLRSDDTAVYYCARESGDDAFDIWGQGTMVTVSS |
| 132 | Abcs35-H & Abcs35-O VH | QVQLVQSGAEVKKPGASVKVSCKASGYTFTGYYMHWVRQAPGQGLEWMGWINPKNGDTEFPQ KFQGRVTMTRDTSISTAYMELSRLRSDDTAVYYCARESGDDAFDIWGQGTMVTVSS |
| 133 | Abcs35-A, Abcs35-I, Abcs35-J, Abcs35-K, Abcs35-L, Abcs35-M, Abcs35-N, & Abcs35-O VL | DIQMTQSPSSLSASVGDRVTITCRASQSISSYLNWYQQKPGKAPKLLIYAASSLQSGVPSRF SGSGSGTDFTLTISSLQPEDFATYYCQQSVGLFFGGGTKVEIK |
| 134 | Abcs35-B & Abcs35-I HC | EVQLVQSGAEVKKPGASVKVSCKASGYTFTGYYMHWVRQAPGQGLEWMGWINPKNGDTEFPQ KFQGRVTMTRDTSISTAYMDLSRLRSDDTAVYYCARESGDDAFDIWGQGTMVTVSSASTKGP SVFPLAPSSKSTSGGTAALGCLVKDYFPEPVTVSWNSGALTSGVHTFPAVLQSSGLYSLSSV |

TABLE 11-continued

SEQUENCES

| SEQ | DESCRIPTION | SEQUENCE |
|---|---|---|
| | | VTVPSSSLGTQTYICNVNHKPSNTKVDKKVEPKSCDKTHTCPPCPAPEAAGAPSVFLFPPKP<br>KDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPGK |
| 135 | Abcs35-C & Abcs35-J HC | EVQLVQSGAEVKKPGASVKVSCKASGYTFTGYYMHWVRQAPGQGLEWMGWINPKNGDTEFPQ<br>KFQGRVTMTRDTSITTAYMELSRLRSDDTAVYYCARESGDDAFDIWGQGTMVTVSSASTKGP<br>SVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPEAAGAPSVFLFPPKP<br>KDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPGK |
| 136 | Abcs35-D & Abcs35-K HC | EVQLVQSGAEVKKPGASVKVSCKASGYTFTGYYMHWVRQAPGQGLEWMGWINPKNGDTEFPQ<br>KFQGRVTMTRDTSISTAYMELSRLRSDDTAVYYCARESGDDAFDIWGQGTMVTVSSASTKGP<br>SVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPEAAGAPSVFLFPPKP<br>KDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPGK |
| 137 | Abcs35-E & Abcs35-L HC | QVQLVQSGAEVKKPGASVKVSCKASGYTFTGYYMHWVRQAPGQGLEWMGWINPKNGDTEFPQ<br>KFQGRVTMTRDTSITTAYMDLSRLRSDDTAVYYCARESGDDAFDIWGQGTMVTVSSASTKGP<br>SVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPEAAGAPSVFLFPPKP<br>KDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPGK |
| 138 | Abcs35-F & Abcs35-M HC | QVQLVQSGAEVKKPGASVKVSCKASGYTFTGYYMHWVRQAPGQGLEWMGWINPKNGDTEFPQ<br>KFQGRVTMTRDTSISTAYMDLSRLRSDDTAVYYCARESGDDAFDIWGQGTMVTVSSASTKGP<br>SVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPEAAGAPSVFLFPPKP<br>KDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPGK |
| 139 | Abcs35-G & Abcs35-N HC | QVQLVQSGAEVKKPGASVKVSCKASGYTFTGYYMHWVRQAPGQGLEWMGWINPKNGDTEFPQ<br>KFQGRVTMTRDTSITTAYMELSRLRSDDTAVYYCARESGDDAFDIWGQGTMVTVSSASTKGP<br>SVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPEAAGAPSVFLFPPKP<br>KDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPGK |
| 140 | Abcs35-H & Abcs35-O HC | QVQLVQSGAEVKKPGASVKVSCKASGYTFTGYYMHWVRQAPGQGLEWMGWINPKNGDTEFPQ<br>KFQGRVTMTRDTSISTAYMELSRLRSDDTAVYYCARESGDDAFDIWGQGTMVTVSSASTKGP<br>SVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCDKTHTCPPCPAPEAAGAPSVFLFPPKP<br>KDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPGK |
| 141 | Abcs35-A,<br>Abcs35-I,<br>Abcs35-J,<br>Abcs35-K,<br>Abcs35-L,<br>Abcs35-M,<br>Abcs35-N, &<br>Abcs35-O LC | DIQMTQSPSSLSASVGDRVTITCRASQSISSYLNWYQQKPGKAPKLLIYAASSLQSGVPSRF<br>SGSGSGTDFTLTISSLQPEDFATYYCQQSVGLFFGGGTKVEIKRTVAAPSVFIFPPSDEQLK<br>SGTASVVCLLNNFYPREAKVQWKVDNALQSGNSQESVTEQDSKDSTYSLSSTLTLSKADYEK<br>HKVYACEVTHQGLSSPVTKSFNRGEC |
| 142 | Human SLIT2 | MRGVGWQMLSLSLGLVLAILNKVAPQACPA<br>QCSCSGSTVDCHGLALRSVPRNIPRNTERLDLNGNNITRITKTDFAGLRHLRVLQLMENK<br>ISTIERGAFQDLKELERLRLNRNHLQLFPELLFLGTAKLYRLDLSENQIQAIPRKAFRGA<br>VDIKNLQLDYNQISCIEDGAFRALRDLEVLTLNNNITRLSVASFNHMPKLRTFRLHSNN<br>LYCDCHLAWLSDWLRQRPRVGLYTQCMGPSHLRGHNVAEVQKREFVCSGHQSFMAPSCSV<br>LHCPAACTCSNNIVDCRGKGLTEIPTNLPETITEIRLEQNTIKVIPPGAFSPYKKLRRID<br>LSNNQISELAPDAFQGLRSLNSLVLYGNKITELPKSLFEGLFSLQLLLLNANKINCLRVD<br>AFQDLHNLNLLSLYDNKLQTIAKGTFSPLRAIQTMHLAQNPFICDCHLKWLADYLHTNPI<br>ETSGARCTSPRRLANKRIGQIKSKKFRCSAKEQYFIPGTEDYRSKLSGDCFADLACPEKC<br>RCEGTTVDCSNQKLNKIPEHIPQYTAELRLNNNEFTVLEATGIFFKKLPQLRKINFSNNKI<br>TDIEEGAFEGASGVNEILLTSNRLENVQHKMFKGLESLKTLMLRSNRITCVGNDSFIGLS<br>SVRLLSLYDNQITTVAPGAFDTLHSLSTLNLLANPFNCNCYLAWLGEWLRKKRIVTGNPR<br>CQKPYFLKEIPIQDVAIQDFTCDDGNDDNSCSPLSRCPTECTCLDTVVRCSNKGLKVLPK<br>GIPRDVTELYLDGNQFTLVPKELSNYKHLTLIDLSNNRISTLSNQSFSNMTQLLTLILSY<br>NRLRCIPPRTFDGLKSLRLLSLHGNDISVVPEGAFNDLSALSHLAIGANPLYCDCNMQWL |

TABLE 11-continued

SEQUENCES

| SEQ | DESCRIPTION | SEQUENCE |
|---|---|---|
| | | SDWVKSEYKEPGIARCAGPGEMADKLLLTTPSKKFTCQGPVDVNILAKCNPCLSNPCKND GTCNSDPVDFYRCTCPYGFKGQDCDVPIHACISNPCKHGGTCHLKEGEEDGFWCICADGF EGENCEVNVDDCEDNDCENNSTCVDGINNYTCLCPPEYTGELCEEKLDFCAQDLNPCQHD SKCILTPKGFKCDCTPGYVGEHCDIDFDDCQDNKCKNGAHCTDAVNGYTCICPEGYSGLF CEFSPPMVLPRTSPCDNFDCQNGAQCIVRINEPICQCLPGYQGEKCEKLVSVNFINKESY LQIPSAKVRPQTNITLQIATDEDSGILLYKGDKDHIAVELYRGRVRASYDTGSHPASAIY SVETINDGNFHIVELLALDQSLSLSVDGGNPKIITNLSKQSTLNFDSPLYVGGMPGKSNV ASLRQAPGQNGTSFHGCIRNLYINSELQDFQKVPMQTGILPGCEPCHKKVCAHGTCQPSS QAGFTCECQEGWMGPLCDQRTNDPCLGNKCVHGTCLPINAFSYSCKCLEGHGGVLCDEEE DLFNPCQAIKCKHGKCRLSGLGQPYCECSSGYTGDSCDREISCRGERIRDYYQKQQGYAA CQTTKKVSRLECRGGCAGGQCCGPLRSKRRKYSFECTDGSSFVDEVEKVVKCGCTRCVS |
| 143 | Abcs35-J VH nucleic acid | GAGGTCCAGCTGGTGCAGTCTGGGGCTGAGGTGAAGAAGCCTGGGGCCTCAGTGAAGGTCTC CTGCAAGGCTTCTGGGTACACCTTCACCGGCTACTATATGCACTGGGTGCGACAGGCCCCTG GACAAGGGCTTGAGTGGATGGGATGGATCAATCCTAAGAATGGTGATACAGAGTTTCCACAG AAGTTTCAGGGCAGGGTCACCATGACCAGGGACACGTCCATCACCACAGCCTACATGGAGCT GAGCAGGCTCAGATCTGACGACACGGCCGTGTATTACTGTGCGAGAGAAAGTGGGGATGATG CTTTTGATATTTGGGGCCAAGGGACAATGGTCACCGTCTCGAGC |
| 144 | Abcs35-J VL nucleic acid | GACATCCAGATGACCCAGTCTCCATCCTCCCTGTCTGCATCTGTAGGAGACAGAGTCACCAT CACTTGCCGGGCAAGTCAGAGCATTAGCAGCTATTTAAATTGGTATCAGCAGAAACCAGGGA AAGCCCCTAAGCTCCTGATCTATGCTGCATCCAGTTTGCAAAGTGGGGTCCCATCAAGGTTC AGTGGCAGTGGATCTGGGACAGATTTCACTCTCACCATCAGCAGTCTGCAACCTGAAGATTT TGCAACTTACTACTGTCAACAGTCGGTTGGTCTTTTTTCGGCGGAGGGACCAAGGTGGAGA TCAAA |
| 145 | Abcs35 VH nucleic acid | GAGGTCCAGCTGGTGCAGTCTGGGGCTGAGGTGAAGAAGCCTGGGGCCTCAGTGAAGGTCTC CTGCAAGGCTTCTGGGTACACCTTCACCGGCTACTATATGCACTGGGTGCGACAGGCCCCTG GACAAGGGCTTGAGTGGATGGGATGGATCAATCCTAAGAATGGTGATACAGAGTTTCCACAG AAGTTTCAGGGCAGGGTCACCATGACCAGGGACACGTCCATCACCACAGCCTACATGGACCT GAGCAGGCTCAGATCTGACGACACGGCCGTGTATTACTGTGCGAGAGAAAGTGGGGATGATG CTTTTGATATTTGGGGCCAAGGGACAATGGTCACCGTCTCGAGC |
| 146 | Abcs35 VL nucleic acid | GACATCGTGATGACCCAGTCTCCATCCTCCCTGTCTGCATCTGTAGGAGACAGAGTCACCAT CACTTGCCGGGCAAGTCAGAGCATTAGCAGCTATTTAAATTGGTATCAGCAGAAACCAGGGA AAGCCCCTAAGCTCCTGATCTATGCTGCATCCAGTTTGCAAAGTGGGGTCCCATCAAGGTTC AGTGGCAGTGGATCTGGGACAGATTTCACTCTCACCATCAGCAGTCTGCAACCTGAAGATTT TGCAACTTACTACTGTCAACAGTCGGTTGGTCTTTTTTCGGCGGAGGGACCAAGGTGGAGA TCAAA |

CDR sequences in this Table are defined as follows (residue numbering according to Kabat):
CDR-H1: H26-H35B; CDR-H2: H50-H65; CDR-H3: H95-H102;
CDR-L1: L24-L34; CDR-L2: L50-L56; CDR-L3: L89-L97.

TABLE 12

SEQUENCE ID Assignment

| | Heavy Chain (HC) | | | | | | | | | | Light Chain (LC) | | | | | | |
|---|---|---|---|---|---|---|---|---|---|---|---|---|---|---|---|---|---|
| Anti-body | HC CDR1 | HC CDR2 | HC CDR3 | $J_H$ | $V_H$ | CH1 | HINGE | $C_H2$ | $C_H3$ | HC | LC CDR1 | LC CDR2 | LC CDR3 | JK | $V_L$ | $C_L$ | LC |
| Abcs35 | 24 | 25 | 26 | 33 | 32 | 34 | 35 | 36 | 37 | 38 | 29 | 30 | 31 | 40 | 39 | 41 | 42 |
| 93H2 | 24 | 44 | 26 | 33 | 43 | 34 | 35 | 36 | 37 | 45 | 29 | 30 | 47 | 40 | 46 | 41 | 48 |
| Ab1 | 50 | 44 | 26 | 33 | 49 | 34 | 35 | 36 | 37 | 51 | 53 | 30 | 47 | 40 | 52 | 41 | 54 |
| Ab3 | 24 | 56 | 26 | 33 | 55 | 34 | 35 | 36 | 37 | 57 | 53 | 30 | 47 | 40 | 52 | 41 | 54 |
| Ab9 | 50 | 44 | 26 | 33 | 49 | 34 | 35 | 36 | 37 | 51 | 59 | 30 | 47 | 40 | 58 | 41 | 60 |
| Ab13 | 50 | 44 | 26 | 33 | 49 | 34 | 35 | 36 | 37 | 51 | 29 | 62 | 47 | 40 | 61 | 41 | 63 |
| Ab17 | 50 | 44 | 26 | 33 | 49 | 34 | 35 | 36 | 37 | 51 | 29 | 65 | 47 | 40 | 64 | 41 | 66 |
| Ab21 | 50 | 44 | 26 | 33 | 49 | 34 | 35 | 36 | 37 | 51 | 29 | 68 | 47 | 40 | 67 | 41 | 69 |
| Ab22 | 24 | 71 | 26 | 33 | 70 | 34 | 35 | 36 | 37 | 72 | 29 | 68 | 47 | 40 | 67 | 41 | 69 |
| Ab25 | 50 | 44 | 26 | 33 | 49 | 34 | 35 | 36 | 37 | 51 | 29 | 30 | 47 | 40 | 46 | 41 | 48 |
| Ab29 | 24 | 74 | 26 | 33 | 73 | 34 | 35 | 36 | 37 | 75 | 29 | 30 | 47 | 40 | 46 | 41 | 48 |
| Ab32 | 24 | 77 | 26 | 33 | 76 | 34 | 35 | 36 | 37 | 78 | 29 | 30 | 47 | 40 | 46 | 41 | 48 |
| Ab40 | 24 | 44 | 26 | 33 | 43 | 34 | 35 | 36 | 37 | 45 | 29 | 30 | 95 | 40 | 94 | 41 | 96 |
| Ab45 | 24 | 60 | 26 | 33 | 79 | 34 | 35 | 36 | 37 | 81 | 29 | 30 | 47 | 40 | 46 | 41 | 48 |
| Ab46 | 24 | 83 | 26 | 33 | 82 | 34 | 35 | 36 | 37 | 84 | 29 | 30 | 47 | 40 | 46 | 41 | 48 |
| Ab58 | 24 | 86 | 26 | 33 | 85 | 34 | 35 | 36 | 37 | 87 | 29 | 30 | 47 | 40 | 46 | 41 | 48 |
| Ab83 | 24 | 89 | 26 | 33 | 88 | 34 | 35 | 36 | 37 | 90 | 29 | 30 | 47 | 40 | 46 | 41 | 48 |
| Ab96 | 24 | 25 | 26 | 33 | 32 | 34 | 35 | 36 | 37 | 38 | 29 | 30 | 47 | 40 | 46 | 41 | 48 |
| Ab112 | 24 | 44 | 26 | 33 | 43 | 34 | 35 | 36 | 37 | 45 | 29 | 30 | 92 | 40 | 91 | 41 | 93 |
| Ab123 | 24 | 44 | 26 | 33 | 43 | 34 | 35 | 36 | 37 | 45 | 29 | 30 | 31 | 40 | 39 | 41 | 42 |
| Abcs1 | 24 | 74 | 26 | 33 | 73 | 34 | 35 | 36 | 37 | 75 | 29 | 30 | 95 | 40 | 94 | 41 | 96 |
| Abcs2 | 24 | 77 | 26 | 33 | 76 | 34 | 35 | 36 | 37 | 78 | 29 | 30 | 95 | 40 | 94 | 41 | 96 |
| Abcs4 | 24 | 83 | 26 | 33 | 82 | 34 | 35 | 36 | 37 | 84 | 29 | 30 | 95 | 40 | 94 | 41 | 96 |
| Abcs5 | 24 | 25 | 26 | 33 | 32 | 34 | 35 | 36 | 37 | 38 | 29 | 30 | 95 | 40 | 94 | 41 | 96 |
| Abcs12 | 24 | 89 | 26 | 33 | 88 | 34 | 35 | 36 | 37 | 90 | 29 | 30 | 95 | 40 | 94 | 41 | 96 |

TABLE 12-continued

SEQUENCE ID Assignment

| | Heavy Chain (HC) | | | | | | | | | Light Chain (LC) | | | | | | |
|---|---|---|---|---|---|---|---|---|---|---|---|---|---|---|---|---|
| Anti-body | HC CDR1 | HC CDR2 | HC CDR3 | $J_H$ | $V_H$ | CH1 | HINGE | $C_H2$ | $C_H3$ | HC | LC CDR1 | LC CDR2 | LC CDR3 | JK | $V_L$ | $C_L$ | LC |
| Abcs20 | 24 | 25 | 26 | 33 | 32 | 34 | 35 | 36 | 37 | 38 | 29 | 30 | 92 | 40 | 91 | 41 | 93 |
| Abcs25 | 24 | 86 | 26 | 33 | 85 | 34 | 35 | 36 | 37 | 87 | 29 | 30 | 92 | 40 | 91 | 41 | 93 |
| Abcs40 | 24 | 86 | 26 | 33 | 85 | 34 | 35 | 36 | 37 | 87 | 29 | 30 | 31 | 40 | 39 | 41 | 42 |
| Abcs50 | 24 | 25 | 26 | 33 | 32 | 34 | 35 | 36 | 37 | 38 | 29 | 68 | 47 | 40 | 67 | 41 | 69 |
| Abcs55 | 24 | 86 | 26 | 33 | 85 | 34 | 35 | 36 | 37 | 87 | 29 | 68 | 47 | 40 | 67 | 41 | 69 |
| CTIR2-1 | 24 | 71 | 26 | 33 | 70 | 34 | 35 | 36 | 37 | 72 | 29 | 68 | 95 | 40 | 97 | 41 | 98 |
| CTIR2-2 | 24 | 71 | 26 | 33 | 70 | 34 | 35 | 36 | 37 | 72 | 29 | 68 | 92 | 40 | 99 | 41 | 100 |
| CTIR2-3 | 24 | 71 | 26 | 33 | 70 | 34 | 35 | 36 | 37 | 72 | 29 | 68 | 31 | 40 | 101 | 41 | 102 |
| CTIR2-4 | 24 | 56 | 26 | 33 | 55 | 34 | 35 | 36 | 37 | 57 | 53 | 68 | 47 | 40 | 103 | 41 | 104 |
| CTIR2-5 | 24 | 56 | 26 | 33 | 55 | 34 | 35 | 36 | 37 | 57 | 53 | 30 | 95 | 40 | 105 | 41 | 106 |
| CTIR2-6 | 24 | 56 | 26 | 33 | 55 | 34 | 35 | 36 | 37 | 57 | 53 | 30 | 31 | 40 | 107 | 41 | 108 |
| CTIR2-7 | 24 | 56 | 26 | 33 | 55 | 34 | 35 | 36 | 37 | 57 | 53 | 68 | 95 | 40 | 109 | 41 | 110 |
| CTIR2-8 | 24 | 56 | 26 | 33 | 55 | 34 | 35 | 36 | 37 | 57 | 53 | 68 | 92 | 40 | 111 | 41 | 112 |
| CTIR2-9 | 24 | 56 | 26 | 33 | 55 | 34 | 35 | 36 | 37 | 57 | 53 | 68 | 31 | 40 | 113 | 41 | 114 |
| CTIR2-10 | 116 | 117 | 26 | 33 | 115 | 34 | 35 | 36 | 37 | 118 | 29 | 30 | 47 | 40 | 46 | 41 | 48 |
| CTIR2-11 | 116 | 120 | 26 | 33 | 119 | 34 | 35 | 36 | 37 | 121 | 29 | 30 | 47 | 40 | 46 | 41 | 48 |
| CTIR2-12 | 116 | 120 | 26 | 33 | 119 | 34 | 35 | 36 | 37 | 121 | 53 | 30 | 47 | 40 | 52 | 41 | 54 |
| CTIR2-13 | 116 | 120 | 26 | 33 | 119 | 34 | 35 | 36 | 37 | 121 | 53 | 68 | 47 | 40 | 103 | 41 | 104 |
| CTIR2-14 | 116 | 120 | 26 | 33 | 119 | 34 | 35 | 36 | 37 | 121 | 53 | 68 | 95 | 40 | 109 | 41 | 110 |
| CTIR2-15 | 116 | 120 | 26 | 33 | 119 | 34 | 35 | 36 | 37 | 121 | 53 | 68 | 92 | 40 | 111 | 41 | 112 |
| CTIR2-16 | 116 | 120 | 26 | 33 | 119 | 34 | 35 | 36 | 37 | 121 | 53 | 68 | 31 | 40 | 113 | 41 | 114 |
| Abcs35-A | 24 | 25 | 26 | 33 | 32 | 34 | 35 | 36 | 37 | 38 | 29 | 30 | 31 | 40 | 133 | 41 | 141 |
| Abcs35-B | 24 | 25 | 26 | 33 | 126 | 34 | 35 | 36 | 37 | 134 | 29 | 30 | 31 | 40 | 39 | 41 | 42 |
| Abcs35-C | 24 | 25 | 26 | 33 | 127 | 34 | 35 | 36 | 37 | 135 | 29 | 30 | 31 | 40 | 39 | 41 | 42 |
| Abcs35-D | 24 | 25 | 26 | 33 | 128 | 34 | 35 | 36 | 37 | 136 | 29 | 30 | 31 | 40 | 39 | 41 | 42 |
| Abcs35-E | 24 | 25 | 26 | 33 | 129 | 34 | 35 | 36 | 37 | 137 | 29 | 30 | 31 | 40 | 39 | 41 | 42 |
| Abcs35-F | 24 | 25 | 26 | 33 | 130 | 34 | 35 | 36 | 37 | 138 | 29 | 30 | 31 | 40 | 39 | 41 | 42 |
| Abcs35-G | 24 | 25 | 26 | 33 | 131 | 34 | 35 | 36 | 37 | 139 | 29 | 30 | 31 | 40 | 39 | 41 | 42 |
| Abcs35-H | 24 | 25 | 26 | 33 | 132 | 34 | 35 | 36 | 37 | 140 | 29 | 30 | 31 | 40 | 39 | 41 | 42 |
| Abcs35-I | 24 | 25 | 26 | 33 | 126 | 34 | 35 | 36 | 37 | 134 | 29 | 30 | 31 | 40 | 133 | 41 | 141 |
| Abcs35-J | 24 | 25 | 26 | 33 | 127 | 34 | 35 | 36 | 37 | 135 | 29 | 30 | 31 | 40 | 133 | 41 | 141 |
| Abcs35-K | 24 | 25 | 26 | 33 | 128 | 34 | 35 | 36 | 37 | 136 | 29 | 30 | 31 | 40 | 133 | 41 | 141 |
| Abcs35-L | 24 | 25 | 26 | 33 | 129 | 34 | 35 | 36 | 37 | 137 | 29 | 30 | 31 | 40 | 133 | 41 | 141 |
| Abcs35-M | 24 | 25 | 26 | 33 | 130 | 34 | 35 | 36 | 37 | 138 | 29 | 30 | 31 | 40 | 133 | 41 | 141 |
| Abcs35-N | 24 | 25 | 26 | 33 | 131 | 34 | 35 | 36 | 37 | 139 | 29 | 30 | 31 | 40 | 133 | 41 | 141 |
| Abcs35-O | 24 | 25 | 26 | 33 | 132 | 34 | 35 | 36 | 37 | 148 | 29 | 30 | 31 | 40 | 133 | 41 | 141 |

The invention claimed is:

1. An isolated antibody, or antigen-binding fragment thereof, that specifically binds ROBO2, comprising:
   (i) a heavy chain variable region (VH) that comprises:
      (a) a VH complementarity determining region one (CDR-H1) comprising the amino acid sequence of SEQ ID NO: 24,
      (b) a VH CDR-H2 comprising the amino acid sequence of SEQ ID NO: 25 or 44; and
      (c) a VH CDR-H3 comprising the amino acid sequence of SEQ ID NO: 26; and
   (ii) a light chain variable region (VL) that comprises:
      (a) a VL complementarity determining region one (CDR-L1) comprising the amino acid sequence of SEQ ID NO: 29,
      (b) a VL CDR-L2 comprising the amino acid sequence of SEQ ID NO: 30; and
      (c) a VL CDR-L3 comprising the amino acid sequence of SEQ ID NO: 31 or 47.

2. The antibody, or antigen binding fragment thereof, of claim 1, further comprising:
   (1) a VL framework sequence; and
   (2) a VH framework sequence,
   wherein the VL framework sequence is at least 90%, 91%, 92%, 93%, 94%, 95%, 96%, 97%, 98%, 99%, or 100% identical to a human germline VL framework sequence and the VH framework sequence is at least 90%, 91%, 92%, 93%, 94%, 95%, 96%, 97%, 98%, 99%, or 100% identical to a human germline VH framework sequence,
   wherein said human germline VL framework sequence is the framework sequence of: DPK9, DPK12, DPK18, DPK24, HK102_V1, DPK1, DPK8, DPK3, DPK21, Vg_38K, DPK22, DPK15, DPL16, DPL8, V1-22, Vλ consensus, Vλ1 consensus, Vλ3 consensus, $V_K$ consensus, $V_K1$ consensus, $V_K2$ consensus, or $V_K3$ consensus, and
   wherein said human germline VH framework sequence is the framework sequence of: DP54, DP47, DP50, DP31, DP46, DP71, DP75, DP10, DP7, DP49, DP51, DP38, DP79, DP78, DP73, VH3 consensus, VH5 consensus, VH1 consensus, or VH4 consensus.

3. The antibody, or antigen binding fragment thereof, of claim 1, comprising (i) a VH comprising an amino acid sequence at least 90% identical to any one of SEQ ID NOs:32, 43, 126, 127, 128, 129, 130, 131, and 132; and (ii) a VL comprising an amino acid sequence at least 90% identical to any one of SEQ ID NOs:39, 46, and 133.

4. The antibody, or antigen binding fragment thereof, of claim 1, comprising (i) a VH comprising the amino acid sequence selected from the group consisting of SEQ ID NOs:32, 43, and 126-132, and (ii) a VL comprising the amino acid sequence selected from the group consisting of SEQ ID NOs.:39, 46, and 133.

5. The antibody, or antigen binding fragment thereof, of claim 1, comprising (i) a VH comprising the amino acid sequence of SEQ ID NO:127, and (ii) a VL comprising the amino acid sequence of SEQ ID NO:133.

6. The antibody, or antigen binding fragment thereof, of claim 1, comprising an Fc domain, wherein the Fc domain is the Fc domain of an IgA1 IgA2, IgD, IgE, IgM, IgG1, IgG2, IgG3, or IgG4.

7. The antibody, or antigen binding fragment thereof, of claim 1, comprising (i) a heavy chain comprising an amino acid sequence at least 90% identical to any one of SEQ ID NOs:38, 45, 134, 135, 136, 137, 138, 139, and 140; and (ii) a light chain comprising an amino acid sequence at least 90% identical to any one of SEQ ID NOs :42, 48, and 141.

8. The antibody, or antigen binding fragment thereof, of claim 1, comprising (i) a heavy chain comprising the amino acid sequence selected from the group consisting of SEQ ID NOs: 38, 45, 134, 135, 136, 137, 138, 139, and 140, and (ii) a light chain comprising the amino acid sequence selected from the group consisting of SEQ ID NOs: 42, 48, and 141.

9. The antibody, or antigen binding fragment thereof, of claim 1, comprising (i) a heavy chain comprising the amino acid sequence of SEQ ID NO: 135, and (ii) a light chain comprising the amino acid sequence of SEQ ID NO. 141.

10. The antibody, or antigen binding fragment thereof, of claim 1, comprising the VH sequence encoded by:
   a. the insert in the plasmid deposited at the ATCC and having ATCC Accession No. PTA-123265;
   b. the insert in the plasmid deposited at the ATCC and having ATCC Accession No. PTA-123700;
   c. the isolated nucleic acid comprising the sequence of SEQ ID NO:143; or
   d. the isolated nucleic acid comprising the sequence of SEQ ID NO:145;
   and further comprising the VL sequence encoded by:
   a. the insert in the plasmid deposited at the ATCC and having ATCC Accession No. PTA-123266;
   b. the insert in the plasmid deposited at the ATCC and having ATCC Accession No. PTA-123701;
   c. the isolated nucleic acid comprising the sequence of SEQ ID NO:144; or
   d. the isolated nucleic acid comprising the sequence of SEQ ID NO:146.

11. An isolated nucleic acid molecule, comprising one or more nucleotide sequences encoding the antibody, or antigen binding fragment thereof, of claim 1.

12. A vector comprising the nucleic acid molecule of claim 11.

13. A host cell comprising the nucleic acid molecule of claim 11.

14. A host cell comprising the vector of claim 12.

15. The isolated nucleic acid of claim 11, wherein the one or more nucleotide sequences are selected from the group consisting of:
   (i) the sequence of SEQ ID NO: 143;
   (ii) the sequence of SEQ ID NO: 144;
   (iii) the sequence of SEQ ID NO: 145; and
   (iv) the sequence of SEQ ID NO: 146.

16. A pharmaceutical composition comprising the antibody, or antigen binding fragment thereof, of claim 1, and a pharmaceutically acceptable carrier or excipient.

17. A method of reducing proteinuria, comprising administering to a subject in need thereof a therapeutically effective amount of the antibody, or antigen binding fragment thereof, of claim 1, or the pharmaceutical composition of claim 16.

18. The method of claim 17, wherein said subject suffers from a renal disease, wherein said renal disease is a glomerular disease, Focal Segmental Glomerular Sclerosis (FSGS), or nephropathy.

19. The method of claim 17, wherein said subject is susceptible to a renal disease, wherein said renal disease is a glomerular disease, Focal Segmental Glomerular Sclerosis (FSGS), or nephropathy.

20. A method of preserving podocyte function, comprising administering to a subject in need thereof a therapeutically effective amount of the antibody, or antigen binding fragment thereof, of claim 1, or the pharmaceutical composition of claim 16.

21. The method of claim 20, wherein said subject suffers from a renal disease, wherein said renal disease is a glomerular disease, Focal Segmental Glomerular Sclerosis (FSGS), or nephropathy.

22. The method of claim 20, wherein said subject is susceptible to a renal disease, wherein said renal disease is a glomerular disease, Focal Segmental Glomerular Sclerosis (FSGS), or nephropathy.

* * * * *

SEQUENCE LISTING

```
<160> NUMBER OF SEQ ID NOS: 146

<210> SEQ ID NO 1
<211> LENGTH: 1378
<212> TYPE: PRT
<213> ORGANISM: Homo sapiens

<400> SEQUENCE: 1
```

Met Ser Leu Leu Met Phe Thr Gln Leu Leu Leu Cys Gly Phe Leu Tyr
1               5                   10                  15

Val Arg Val Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
        35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

His Gly Arg Arg Ser Lys Pro Asp Glu Gly Ser Tyr Val Cys Val Ala
            100                 105                 110

```
Arg Asn Tyr Leu Gly Glu Ala Val Ser Arg Asn Ala Ser Leu Glu Val
            115                 120                 125

Ala Leu Leu Arg Asp Asp Phe Arg Gln Asn Pro Thr Asp Val Val Val
130                 135                 140

Ala Ala Gly Glu Pro Ala Ile Leu Glu Cys Gln Pro Pro Arg Gly His
        145                 150                 155             160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
                    180                 185                 190

Thr Arg Lys Ser Asp Ala Gly Met Tyr Thr Cys Val Gly Thr Asn Met
                195                 200                 205

Val Gly Glu Arg Asp Ser Asp Pro Ala Glu Leu Thr Val Phe Glu Arg
        210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                    245                 250                 255

Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Thr Met Ser Thr Asp Glu
                275                 280                 285

Gly Thr Tyr Met Cys Ile Ala Glu Asn Arg Val Gly Lys Met Glu Ala
        290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                    325                 330                 335

Thr Lys Gly Asn Pro Gln Pro Ala Val Phe Trp Gln Lys Glu Gly Ser
            340                 345                 350

Gln Asn Leu Leu Phe Pro Asn Gln Pro Gln Pro Asn Ser Arg Cys
                355                 360                 365

Ser Val Ser Pro Thr Gly Asp Leu Thr Ile Thr Asn Ile Gln Arg Ser
370                 375                 380

Asp Ala Gly Tyr Tyr Ile Cys Gln Ala Leu Thr Val Ala Gly Ser Ile
385                 390                 395                 400

Leu Ala Lys Ala Gln Leu Glu Val Thr Asp Val Leu Thr Asp Arg Pro
                405                 410                 415

Pro Pro Ile Ile Leu Gln Gly Pro Ala Asn Gln Thr Leu Ala Val Asp
            420                 425                 430

Gly Thr Ala Leu Leu Lys Cys Lys Ala Thr Gly Asp Pro Leu Pro Val
        435                 440                 445

Ile Ser Trp Leu Lys Glu Gly Phe Thr Phe Pro Gly Arg Asp Pro Arg
450                 455                 460

Ala Thr Ile Gln Glu Gln Gly Thr Leu Gln Ile Lys Asn Leu Arg Ile
465                 470                 475                 480

Ser Asp Thr Gly Thr Tyr Thr Cys Val Ala Thr Ser Ser Ser Gly Glu
                485                 490                 495

Thr Ser Trp Ser Ala Val Leu Asp Val Thr Glu Ser Gly Ala Thr Ile
            500                 505                 510

Ser Lys Asn Tyr Asp Leu Ser Asp Leu Pro Gly Pro Pro Ser Lys Pro
        515                 520                 525
```

```
Gln Val Thr Asp Val Thr Lys Asn Ser Val Thr Leu Ser Trp Gln Pro
    530                 535                 540
Gly Thr Pro Gly Thr Leu Pro Ala Ser Ala Tyr Ile Ile Glu Ala Phe
545                 550                 555                 560
Ser Gln Ser Val Ser Asn Ser Trp Gln Thr Val Ala Asn His Val Lys
                565                 570                 575
Thr Thr Leu Tyr Thr Val Arg Gly Leu Arg Pro Asn Thr Ile Tyr Leu
            580                 585                 590
Phe Met Val Arg Ala Ile Asn Pro Gln Gly Leu Ser Asp Pro Ser Pro
        595                 600                 605
Met Ser Asp Pro Val Arg Thr Gln Asp Ile Ser Pro Pro Ala Gln Gly
    610                 615                 620
Val Asp His Arg Gln Val Gln Lys Glu Leu Gly Asp Val Leu Val Arg
625                 630                 635                 640
Leu His Asn Pro Val Val Leu Thr Pro Thr Thr Val Gln Val Thr Trp
                645                 650                 655
Thr Val Asp Arg Gln Pro Gln Phe Ile Gln Gly Tyr Arg Val Met Tyr
            660                 665                 670
Arg Gln Thr Ser Gly Leu Gln Ala Thr Ser Ser Trp Gln Asn Leu Asp
        675                 680                 685
Ala Lys Val Pro Thr Glu Arg Ser Ala Val Leu Val Asn Leu Lys Lys
    690                 695                 700
Gly Val Thr Tyr Glu Ile Lys Val Arg Pro Tyr Phe Asn Glu Phe Gln
705                 710                 715                 720
Gly Met Asp Ser Glu Ser Lys Thr Val Arg Thr Thr Glu Glu Ala Pro
                725                 730                 735
Ser Ala Pro Pro Gln Ser Val Thr Val Leu Thr Val Gly Ser Tyr Asn
            740                 745                 750
Ser Thr Ser Ile Ser Val Ser Trp Asp Pro Pro Pro Asp His Gln
        755                 760                 765
Asn Gly Ile Ile Gln Glu Tyr Lys Ile Trp Cys Leu Gly Asn Glu Thr
    770                 775                 780
Arg Phe His Ile Asn Lys Thr Val Asp Ala Ala Ile Arg Ser Val Ile
785                 790                 795                 800
Ile Gly Gly Leu Phe Pro Gly Ile Gln Tyr Arg Val Glu Val Ala Ala
                805                 810                 815
Ser Thr Ser Ala Gly Val Gly Val Lys Ser Glu Pro Gln Pro Ile Ile
            820                 825                 830
Ile Gly Arg Arg Asn Glu Val Val Ile Thr Glu Asn Asn Ser Ile
        835                 840                 845
Thr Glu Gln Ile Thr Asp Val Val Lys Gln Pro Ala Phe Ile Ala Gly
    850                 855                 860
Ile Gly Gly Ala Cys Trp Val Ile Leu Met Gly Phe Ser Ile Trp Leu
865                 870                 875                 880
Tyr Trp Arg Arg Lys Lys Arg Lys Gly Leu Ser Asn Tyr Ala Val Thr
                885                 890                 895
Phe Gln Arg Gly Asp Gly Gly Leu Met Ser Asn Gly Ser Arg Pro Gly
            900                 905                 910
Leu Leu Asn Ala Gly Asp Pro Ser Tyr Pro Trp Leu Ala Asp Ser Trp
        915                 920                 925
Pro Ala Thr Ser Leu Pro Val Asn Asn Ser Asn Ser Gly Pro Asn Glu
    930                 935                 940
Ile Gly Asn Phe Gly Arg Gly Asp Val Leu Pro Pro Val Pro Gly Gln
```

```
                945                 950                 955                 960
          Gly Asp Lys Thr Ala Thr Met Leu Ser Asp Gly Ala Ile Tyr Ser Ser
                          965                 970                 975
          Ile Asp Phe Thr Thr Lys Thr Ser Tyr Asn Ser Ser Ser Gln Ile Thr
                                  980                 985                 990
          Gln Ala Thr Pro Tyr Ala Thr Thr Gln Ile Leu His Ser Asn Ser Ile
                          995                 1000                1005
          His Glu Leu Ala Val Asp Leu Pro Asp Pro Gln Trp Lys Ser Ser
                  1010                1015                1020
          Ile Gln Gln Lys Thr Asp Leu Met Gly Phe Gly Tyr Ser Leu Pro
                  1025                1030                1035
          Asp Gln Asn Lys Gly Asn Asn Gly Gly Lys Gly Lys Lys Lys
                  1040                1045                1050
          Lys Asn Lys Asn Ser Ser Lys Pro Gln Lys Asn Asn Gly Ser Thr
                  1055                1060                1065
          Trp Ala Asn Val Pro Leu Pro Pro Pro Val Gln Pro Leu Pro
                  1070                1075                1080
          Gly Thr Glu Leu Glu His Tyr Ala Val Glu Gln Glu Asn Gly
                  1085                1090                1095
          Tyr Asp Ser Asp Ser Trp Cys Pro Pro Leu Pro Val Gln Thr Tyr
                  1100                1105                1110
          Leu His Gln Gly Leu Glu Asp Glu Leu Glu Glu Asp Asp Asp Arg
                  1115                1120                1125
          Val Pro Thr Pro Pro Val Arg Gly Val Ala Ser Ser Pro Ala Ile
                  1130                1135                1140
          Ser Phe Gly Gln Gln Ser Thr Ala Thr Leu Thr Pro Ser Pro Arg
                  1145                1150                1155
          Glu Glu Met Gln Pro Met Leu Gln Ala His Leu Asp Glu Leu Thr
                  1160                1165                1170
          Arg Ala Tyr Gln Phe Asp Ile Ala Lys Gln Thr Trp His Ile Gln
                  1175                1180                1185
          Ser Asn Asn Gln Pro Pro Gln Pro Pro Val Pro Pro Leu Gly Tyr
                  1190                1195                1200
          Val Ser Gly Ala Leu Ile Ser Asp Leu Glu Thr Asp Val Ala Asp
                  1205                1210                1215
          Asp Asp Ala Asp Glu Glu Glu Ala Leu Glu Ile Pro Arg Pro
                  1220                1225                1230
          Leu Arg Ala Leu Asp Gln Thr Pro Gly Ser Ser Met Asp Asn Leu
                  1235                1240                1245
          Asp Ser Ser Val Thr Gly Lys Ala Phe Thr Ser Ser Gln Arg Pro
                  1250                1255                1260
          Arg Pro Thr Ser Pro Phe Ser Thr Asp Ser Asn Thr Ser Ala Ala
                  1265                1270                1275
          Leu Ser Gln Ser Gln Arg Pro Arg Pro Thr Lys Lys His Lys Gly
                  1280                1285                1290
          Gly Arg Met Asp Gln Gln Pro Ala Leu Pro His Arg Arg Glu Gly
                  1295                1300                1305
          Met Thr Asp Glu Glu Ala Leu Val Pro Tyr Ser Lys Pro Ser Phe
                  1310                1315                1320
          Pro Ser Pro Gly Gly His Ser Ser Ser Gly Thr Ala Ser Ser Lys
                  1325                1330                1335
          Gly Ser Thr Gly Pro Arg Lys Thr Glu Val Leu Arg Ala Gly His
                  1340                1345                1350
```

-continued

Gln Arg Asn Ala Ser Asp Leu Leu Asp Ile Gly Tyr Met Gly Ser
    1355                1360                1365

Asn Ser Gln Gly Gln Phe Thr Gly Glu Leu
    1370                1375

<210> SEQ ID NO 2
<211> LENGTH: 1378
<212> TYPE: PRT
<213> ORGANISM: Macaca fascicularis

<400> SEQUENCE: 2

Met Ser Leu Leu Met Phe Thr Gln Leu Met Leu Cys Gly Phe Leu Tyr
1               5                   10                  15

Val Arg Val Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
        35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

His Gly Arg Arg Ser Lys Pro Asp Glu Gly Ser Tyr Val Cys Val Ala
            100                 105                 110

Arg Asn Tyr Leu Gly Glu Ala Val Ser Arg Asn Ala Ser Leu Glu Val
        115                 120                 125

Ala Leu Leu Arg Asp Asp Phe Arg Gln Asn Pro Thr Asp Val Val Val
    130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
            180                 185                 190

Thr Arg Lys Ser Asp Ala Gly Met Tyr Thr Cys Val Gly Thr Asn Met
        195                 200                 205

Val Gly Glu Arg Asp Ser Asp Pro Ala Glu Leu Thr Val Phe Glu Arg
    210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                245                 250                 255

Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Thr Met Ser Thr Asp Glu
        275                 280                 285

Gly Thr Tyr Met Cys Ile Ala Glu Asn Arg Val Gly Lys Met Glu Ala
    290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                325                 330                 335

Thr Lys Gly Asn Pro Gln Pro Ala Val Phe Trp Gln Lys Glu Gly Ser

```
                340             345             350
Gln Asn Leu Leu Phe Pro Asn Gln Pro Gln Pro Asn Ser Arg Cys
            355                 360             365

Ser Val Ser Pro Thr Gly Asp Leu Thr Ile Thr Asn Ile Gln Arg Ser
    370             375             380

Asp Ala Gly Tyr Tyr Ile Cys Gln Ala Leu Thr Val Ala Gly Ser Ile
385             390             395             400

Leu Ala Lys Ala Gln Leu Glu Val Thr Asp Val Leu Thr Asp Arg Pro
                405             410             415

Pro Pro Ile Ile Leu Gln Gly Pro Ala Asn Gln Thr Leu Ala Val Asp
            420             425             430

Gly Thr Ala Leu Leu Lys Cys Lys Ala Thr Gly Asp Pro Leu Pro Val
        435             440             445

Ile Ser Trp Leu Lys Glu Gly Phe Thr Phe Leu Ser Arg Asp Pro Arg
    450             455             460

Ala Thr Ile Gln Glu Gln Gly Thr Leu Gln Ile Lys Asn Leu Arg Ile
465             470             475             480

Ser Asp Thr Gly Thr Tyr Thr Cys Val Ala Thr Ser Ser Ser Gly Glu
                485             490             495

Thr Ser Trp Ser Ala Val Leu Asp Val Thr Glu Ser Gly Ala Thr Ile
        500             505             510

Ser Lys Asn Tyr Asp Leu Asn Asp Leu Pro Gly Pro Pro Ser Lys Pro
    515             520             525

Gln Val Thr Asp Val Thr Lys Asn Ser Val Thr Leu Ser Trp Gln Pro
                530             535             540

Gly Thr Pro Gly Thr Leu Pro Ala Ser Ala Tyr Ile Ile Glu Ala Phe
545             550             555             560

Ser Gln Ser Val Ser Asn Ser Trp Gln Thr Val Ala Asn His Val Lys
                565             570             575

Thr Thr Leu Tyr Thr Val Arg Gly Leu Arg Pro Asn Thr Ile Tyr Leu
            580             585             590

Phe Met Val Arg Ala Ile Asn Pro Gln Gly Leu Ser Asp Pro Ser Pro
            595             600             605

Met Ser Asp Pro Val Arg Thr Gln Asp Ile Ser Pro Pro Ala Gln Gly
        610             615             620

Val Asp His Arg Gln Val Gln Lys Glu Leu Gly Asp Val Leu Val Arg
625             630             635             640

Leu His Asn Pro Val Val Leu Thr Pro Thr Thr Val Gln Val Thr Trp
                645             650             655

Thr Val Asp Arg Gln Pro Gln Phe Ile Gln Gly Tyr Arg Val Met Tyr
            660             665             670

Arg Gln Thr Ser Gly Leu Gln Ala Thr Ser Ser Trp Gln Asn Leu Asp
        675             680             685

Ala Lys Val Pro Asn Glu Arg Ser Ala Val Leu Val Asn Leu Lys Lys
    690             695             700

Gly Val Thr Tyr Glu Ile Lys Val Arg Pro Tyr Phe Asn Glu Phe Gln
705             710             715             720

Gly Met Asp Ser Glu Ser Lys Thr Val Arg Thr Thr Glu Glu Ala Pro
                725             730             735

Ser Ala Pro Pro Gln Ser Val Thr Val Leu Thr Val Gly Ser Tyr Asn
            740             745             750

Ser Thr Ser Ile Ser Val Ser Trp Asp Pro Pro Pro Pro Asp His Gln
        755             760             765
```

```
Asn Gly Ile Leu Gln Glu Tyr Lys Ile Trp Cys Leu Gly Asn Glu Thr
770                 775                 780

Arg Phe His Ile Asn Lys Thr Val Asp Ala Ala Ile Arg Ser Val Ile
785                 790                 795                 800

Ile Gly Gly Leu Phe Pro Gly Ile Gln Tyr Arg Val Glu Val Ala Ala
                805                 810                 815

Ser Thr Ser Ala Gly Val Gly Val Lys Ser Glu Pro Gln Pro Ile Ile
            820                 825                 830

Ile Gly Arg Arg Asn Glu Val Val Ile Thr Glu Asn Asn Ser Ile
        835                 840                 845

Thr Glu Gln Ile Thr Asp Val Val Lys Gln Pro Ala Phe Ile Ala Gly
850                 855                 860

Ile Gly Gly Ala Cys Trp Val Ile Leu Met Gly Phe Ser Ile Trp Leu
865                 870                 875                 880

Tyr Trp Arg Arg Lys Lys Arg Lys Gly Leu Ser Asn Tyr Ala Val Thr
                885                 890                 895

Phe Gln Arg Gly Asp Gly Gly Leu Met Thr Asn Gly Ser Arg Pro Gly
                900                 905                 910

Leu Leu Asn Ala Gly Asp Pro Ser Tyr Pro Trp Leu Ala Asp Ser Trp
            915                 920                 925

Pro Ala Thr Ser Leu Pro Val Asn Asn Ser Asn Ser Gly Pro Asn Asp
930                 935                 940

Ile Gly Asn Phe Gly Arg Gly Asp Val Leu Pro Val Pro Gly Gln
945                 950                 955                 960

Gly Asp Lys Thr Ala Thr Met Leu Ser Asp Gly Ala Ile Tyr Ser Ser
                965                 970                 975

Ile Asp Phe Thr Thr Lys Thr Thr Tyr Asn Ser Ser Gln Ile Thr
            980                 985                 990

Gln Ala Thr Pro Tyr Ala Thr Thr Gln Ile Leu His Ser Asn Ser Ile
        995                 1000                1005

His Glu Leu Ala Val Asp Leu Pro Asp Pro Gln Trp Lys Ser Ser
    1010                1015                1020

Ile Gln Gln Lys Thr Asp Leu Met Gly Phe Gly Tyr Ser Leu Pro
    1025                1030                1035

Asp Gln Asn Lys Gly Asn Asn Gly Gly Lys Gly Lys Lys Lys
    1040                1045                1050

Lys Asn Lys Asn Ser Ser Lys Pro Gln Lys Asn Asn Gly Ser Thr
    1055                1060                1065

Trp Ala Asn Val Pro Leu Pro Pro Pro Val Gln Pro Leu Pro
    1070                1075                1080

Gly Thr Glu Leu Glu His Tyr Ala Ala Glu Gln Gln Glu Asn Gly
    1085                1090                1095

Tyr Asp Ser Asp Ser Trp Cys Pro Pro Leu Pro Val Gln Thr Tyr
    1100                1105                1110

Leu His Gln Gly Leu Glu Asp Glu Leu Glu Asp Asp Asp Arg
    1115                1120                1125

Val Pro Thr Pro Pro Val Arg Gly Val Ala Ser Pro Ala Ile
    1130                1135                1140

Ser Phe Gly Gln Gln Ser Thr Ala Thr Leu Thr Pro Ser Pro Arg
    1145                1150                1155

Glu Glu Met Gln Pro Met Leu Gln Ala His Leu Asp Glu Leu Thr
    1160                1165                1170
```

```
Arg Ala Tyr Gln Phe Asp Ile Ala Lys Gln Thr Trp His Ile Gln
    1175                1180                1185

Ser Asn Asn Gln Pro Pro Gln Pro Pro Val Pro Pro Leu Gly Tyr
    1190                1195                1200

Val Ser Gly Ala Leu Ile Ser Asp Leu Glu Thr Asp Val Pro Asp
    1205                1210                1215

Asp Asp Ala Asp Asp Glu Glu Ala Leu Glu Ile Pro Arg Pro
    1220                1225                1230

Leu Arg Ala Leu Asp Gln Thr Pro Gly Ser Ser Met Asp Asn Leu
    1235                1240                1245

Asp Ser Ser Val Thr Gly Lys Ala Phe Thr Ser Ser Gln Arg Pro
    1250                1255                1260

Arg Pro Thr Ser Pro Phe Ser Thr Asp Ser Asn Thr Ser Ala Ala
    1265                1270                1275

Val Ser Gln Ser Gln Arg Pro Arg Pro Thr Lys Lys His Lys Gly
    1280                1285                1290

Gly Arg Met Asp Gln Gln Pro Ala Leu Pro His Arg Arg Glu Gly
    1295                1300                1305

Met Thr Asp Glu Glu Ala Leu Val Pro Tyr Ser Lys Pro Ser Phe
    1310                1315                1320

Pro Ser Pro Gly Gly His Ser Ser Ser Gly Thr Ala Ser Ser Lys
    1325                1330                1335

Gly Ser Thr Gly Pro Arg Lys Ala Glu Val Leu Arg Ala Gly His
    1340                1345                1350

Gln Arg Asn Ala Ser Asp Leu Leu Asp Ile Gly Tyr Met Gly Ser
    1355                1360                1365

Asn Ser Gln Gly Gln Phe Thr Gly Glu Leu
    1370                1375

<210> SEQ ID NO 3
<211> LENGTH: 1377
<212> TYPE: PRT
<213> ORGANISM: Rattus sp.

<400> SEQUENCE: 3

Met Thr Pro Leu Met Phe Thr Leu Leu Leu Phe Gly Phe Leu Cys
1               5                   10                  15

Ile Arg Thr Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
            35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

His Gly Arg Arg Ser Lys Pro Asp Glu Gly Thr Tyr Val Cys Val Ala
            100                 105                 110

Arg Asn Tyr Leu Gly Glu Ala Val Ser Arg Asn Ala Ser Leu Glu Val
            115                 120                 125

Ala Leu Leu Arg Asp Asp Phe Arg Gln Asn Pro Thr Asp Val Val Val
    130                 135                 140

Ala Ala Gly Glu Pro Ala Ile Leu Glu Cys Gln Pro Pro Arg Gly His
145                 150                 155                 160
```

-continued

```
Pro Glu Pro Thr Ile Tyr Trp Lys Lys Asp Lys Val Arg Ile Asp Glu
            165                 170                 175

Lys Glu Glu Arg Ile Ser Ile Arg Gly Gly Lys Leu Met Ile Ser Asn
        180                 185                 190

Thr Arg Lys Ser Asp Ala Gly Met Tyr Thr Cys Val Gly Thr Asn Met
    195                 200                 205

Val Gly Glu Arg Asp Ser Asp Pro Ala Glu Leu Thr Val Phe Glu Arg
210                 215                 220

Pro Thr Phe Leu Arg Arg Pro Ile Asn Gln Val Val Leu Glu Asp Glu
225                 230                 235                 240

Pro Ala Glu Phe Arg Cys Gln Val Gln Gly Asp Pro Gln Pro Thr Val
                245                 250                 255

Arg Trp Lys Lys Asp Asp Ala Asp Leu Pro Arg Gly Arg Tyr Asp Ile
                260                 265                 270

Lys Asp Asp Tyr Thr Leu Arg Ile Lys Lys Ala Ile Ser Ala Asp Glu
            275                 280                 285

Gly Thr Tyr Val Cys Ile Ala Glu Asn Arg Val Gly Lys Val Glu Ala
        290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                325                 330                 335

Thr Lys Gly Asn Pro Gln Pro Ala Val Phe Trp Gln Lys Glu Gly Ser
                340                 345                 350

Gln Asn Leu Leu Phe Pro Asn Gln Pro Gln Pro Asn Ser Arg Cys
            355                 360                 365

Ser Val Ser Pro Thr Gly Asp Leu Thr Ile Thr Asn Ile Gln Arg Ser
        370                 375                 380

Asp Ala Gly Tyr Tyr Ile Cys Gln Ala Leu Thr Val Ala Gly Ser Ile
385                 390                 395                 400

Leu Ala Lys Ala Gln Leu Glu Val Thr Asp Val Leu Thr Asp Arg Pro
                405                 410                 415

Pro Pro Ile Ile Leu Gln Gly Pro Ile Asn Gln Thr Leu Ala Val Asp
                420                 425                 430

Gly Thr Ala Leu Leu Lys Cys Lys Ala Thr Gly Glu Pro Leu Pro Val
            435                 440                 445

Ile Ser Trp Leu Lys Glu Gly Phe Thr Phe Leu Gly Arg Asp Pro Arg
450                 455                 460

Ala Thr Ile Gln Asp Gln Gly Thr Leu Gln Ile Lys Asn Leu Arg Ile
465                 470                 475                 480

Ser Asp Thr Gly Thr Tyr Thr Cys Val Ala Thr Ser Ser Ser Gly Glu
                485                 490                 495

Thr Ser Trp Ser Ala Val Leu Asp Val Thr Glu Ser Gly Ala Thr Ile
                500                 505                 510

Ser Lys Asn Tyr Asp Thr Asn Asp Leu Pro Gly Pro Pro Ser Lys Pro
            515                 520                 525

Gln Val Thr Asp Val Thr Lys Asn Ser Val Thr Leu Ser Trp Gln Pro
        530                 535                 540

Gly Thr Pro Gly Val Leu Pro Ala Ser Ala Tyr Ile Ile Glu Ala Phe
545                 550                 555                 560

Ser Gln Ser Val Ser Asn Ser Trp Gln Thr Val Ala Asn His Val Lys
                565                 570                 575
```

-continued

```
Thr Thr Leu Tyr Thr Val Arg Gly Leu Arg Pro Asn Thr Ile Tyr Leu
            580                 585                 590

Phe Met Val Arg Ala Ile Asn Pro Gln Gly Leu Ser Asp Pro Ser Pro
        595                 600                 605

Met Ser Asp Pro Val Arg Thr Gln Asp Ile Ser Pro Pro Ala Gln Gly
    610                 615                 620

Val Asp His Arg Gln Val Gln Lys Glu Leu Gly Asp Val Thr Val Arg
625                 630                 635                 640

Leu His Asn Pro Val Leu Thr Pro Thr Thr Val Gln Val Thr Trp
                645                 650                 655

Thr Val Asp Arg Gln Pro Gln Phe Ile Gln Gly Tyr Arg Val Met Tyr
            660                 665                 670

Arg Gln Thr Ser Gly Leu Gln Ala Ser Thr Val Trp Gln Asn Leu Asp
        675                 680                 685

Ala Lys Val Pro Thr Glu Arg Ser Ala Val Leu Val Asn Leu Lys Lys
    690                 695                 700

Gly Val Thr Tyr Glu Ile Lys Val Arg Pro Tyr Phe Asn Glu Phe Gln
705                 710                 715                 720

Gly Met Asp Ser Glu Ser Lys Thr Ile Arg Thr Thr Glu Glu Ala Pro
                725                 730                 735

Ser Ala Pro Pro Gln Ser Val Thr Val Leu Thr Val Gly Ser His Asn
            740                 745                 750

Ser Thr Ser Ile Ser Val Ser Trp Asp Pro Pro Ala Asp His Gln
        755                 760                 765

Asn Gly Ile Ile Gln Glu Tyr Lys Ile Trp Cys Leu Gly Asn Glu Thr
    770                 775                 780

Arg Phe His Ile Asn Lys Thr Val Asp Ala Thr Ile Arg Ser Val Val
785                 790                 795                 800

Ile Gly Gly Leu Phe Pro Gly Ile Gln Tyr Arg Val Glu Val Ala Ala
                805                 810                 815

Ser Thr Ser Ala Gly Val Gly Val Lys Ser Glu Pro Gln Pro Ile Ile
            820                 825                 830

Ile Gly Gly Arg Asn Glu Val Val Ile Thr Glu Asn Asn Ser Ile
        835                 840                 845

Thr Glu Gln Ile Thr Asp Val Val Lys Gln Pro Ala Phe Ile Ala Gly
    850                 855                 860

Ile Gly Gly Ala Cys Trp Val Ile Leu Met Gly Phe Ser Ile Trp Leu
865                 870                 875                 880

Tyr Trp Arg Arg Lys Arg Lys Gly Leu Ser Asn Tyr Ala Val Thr
                885                 890                 895

Phe Gln Arg Gly Asp Gly Gly Leu Met Ser Asn Gly Ser Arg Pro Gly
            900                 905                 910

Leu Leu Asn Thr Gly Asp Pro Ser Tyr Pro Trp Leu Ala Asp Ser Trp
        915                 920                 925

Pro Ala Thr Ser Leu Pro Val Asn Asn Ser Asn Ser Gly Pro Asn Glu
    930                 935                 940

Ile Gly Asn Phe Gly Arg Gly Asp Val Leu Pro Val Pro Gly Gln
945                 950                 955                 960

Gly Asp Lys Thr Ala Thr Met Leu Ser Asp Gly Ala Ile Tyr Ser Ser
                965                 970                 975

Ile Asp Phe Thr Thr Lys Thr Thr Tyr Asn Ser Ser Ser Gln Ile Thr
            980                 985                 990

Gln Ala Thr Pro Tyr Ala Thr Thr  Gln Ile Leu His Ser  Asn Ser Ile
```

```
                995              1000              1005
His  Glu  Leu  Ala  Val  Asp  Leu  Pro  Asp  Pro  Gln  Trp  Lys  Ser  Ser
     1010                1015                1020

Val  Gln  Gln  Lys  Ser  Asp  Leu  Met  Gly  Phe  Ala  Tyr  Ser  Leu  Pro
     1025                1030                1035

Asp  Gln  Asn  Lys  Gly  Asn  Asn  Gly  Gly  Lys  Gly  Gly  Lys  Lys  Lys
     1040                1045                1050

Lys  Thr  Lys  Asn  Ser  Ser  Lys  Ala  Gln  Lys  Asn  Asn  Gly  Ser  Thr
     1055                1060                1065

Trp  Ala  Asn  Val  Pro  Leu  Pro  Pro  Pro  Val  Gln  Pro  Leu  Pro
     1070                1075                1080

Gly  Thr  Glu  Leu  Gly  His  Tyr  Pro  Ala  Glu  Gln  Glu  Asn  Gly  Tyr
     1085                1090                1095

Asp  Ser  Asp  Ser  Trp  Cys  Pro  Pro  Leu  Pro  Val  Gln  Thr  Tyr  Leu
     1100                1105                1110

His  Gln  Gly  Met  Glu  Asp  Glu  Leu  Glu  Glu  Asp  Glu  Asp  Arg  Val
     1115                1120                1125

Pro  Thr  Pro  Pro  Val  Arg  Gly  Val  Ala  Ser  Ser  Pro  Ala  Ile  Ser
     1130                1135                1140

Phe  Gly  Gln  Gln  Ser  Thr  Ala  Thr  Leu  Thr  Pro  Ser  Pro  Arg  Glu
     1145                1150                1155

Glu  Met  Gln  Pro  Met  Leu  Gln  Ala  His  Leu  Asp  Glu  Leu  Thr  Arg
     1160                1165                1170

Ala  Tyr  Gln  Phe  Asp  Ile  Ala  Lys  Gln  Thr  Trp  His  Ile  Gln  Ser
     1175                1180                1185

Asn  Thr  Pro  Pro  Pro  Gln  Pro  Pro  Val  Pro  Pro  Leu  Gly  Tyr  Ala
     1190                1195                1200

Ser  Gly  Ala  Leu  Ile  Ser  Asp  Leu  Glu  Thr  Asp  Val  Pro  Asp  Glu
     1205                1210                1215

Asp  Ala  Asp  Asp  Glu  Glu  Glu  Pro  Leu  Glu  Ile  Pro  Arg  Pro  Leu
     1220                1225                1230

Arg  Ala  Leu  Asp  Gln  Thr  Pro  Gly  Ser  Ser  Met  Asp  Asn  Leu  Asp
     1235                1240                1245

Ser  Ser  Val  Thr  Gly  Lys  Ala  Phe  Thr  Ser  Ser  Gln  Arg  Gln  Arg
     1250                1255                1260

Pro  Thr  Ser  Pro  Phe  Ser  Thr  Asp  Ser  Asn  Thr  Ser  Ala  Ala  Gln
     1265                1270                1275

Asn  Gln  Ser  Gln  Arg  Pro  Arg  Pro  Thr  Lys  Lys  His  Lys  Gly  Gly
     1280                1285                1290

Arg  Met  Asp  Pro  Gln  Pro  Val  Leu  Pro  His  Arg  Arg  Glu  Gly  Met
     1295                1300                1305

Pro  Asp  Glu  Glu  Ser  Leu  Val  Pro  Tyr  Ser  Lys  Pro  Ser  Phe  Pro
     1310                1315                1320

Ser  Pro  Gly  Gly  His  Ser  Ser  Ser  Gly  Thr  Ala  Ser  Ser  Lys  Gly
     1325                1330                1335

Ser  Thr  Gly  Pro  Arg  Lys  Ala  Glu  Ile  Leu  Arg  Gly  Ser  His  Gln
     1340                1345                1350

Arg  Asn  Ala  Asn  Asp  Leu  Leu  Asp  Ile  Gly  Tyr  Val  Gly  Ser  Asn
     1355                1360                1365

Ser  Gln  Gly  Gln  Phe  Thr  Gly  Glu  Leu
     1370                1375

<210> SEQ ID NO 4
```

<211> LENGTH: 1508
<212> TYPE: PRT
<213> ORGANISM: Mus sp.

<400> SEQUENCE: 4

```
Met Asn Pro Leu Met Phe Thr Leu Leu Leu Phe Gly Phe Leu Cys
1               5                   10                  15

Ile Gln Ile Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
        35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

His Gly Arg Arg Ser Lys Pro Asp Glu Gly Ser Tyr Val Cys Val Ala
            100                 105                 110

Arg Asn Tyr Leu Gly Glu Ala Val Ser Arg Asn Ala Ser Leu Glu Val
        115                 120                 125

Ala Leu Leu Arg Asp Asp Phe Arg Gln Asn Pro Thr Asp Val Val Val
    130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
            180                 185                 190

Thr Arg Lys Ser Asp Ala Gly Met Tyr Thr Cys Val Gly Thr Asn Met
        195                 200                 205

Val Gly Glu Arg Asp Ser Asp Pro Ala Glu Leu Thr Val Phe Glu Arg
    210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                245                 250                 255

Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Ala Met Ser Thr Asp Glu
        275                 280                 285

Gly Thr Tyr Val Cys Ile Ala Glu Asn Arg Val Gly Lys Val Glu Ala
    290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                325                 330                 335

Thr Lys Gly Asn Pro Gln Pro Ala Val Phe Trp Gln Lys Glu Gly Ser
            340                 345                 350

Gln Asn Leu Leu Phe Pro Asn Gln Pro Gln Pro Asn Ser Arg Cys
        355                 360                 365

Ser Val Ser Pro Thr Gly Asp Leu Thr Ile Thr Asn Ile Gln Arg Ser
    370                 375                 380

Asp Ala Gly Tyr Tyr Ile Cys Gln Ala Leu Thr Val Ala Gly Ser Ile
```

-continued

```
        385                 390                 395                 400
Leu Ala Lys Ala Gln Leu Glu Val Thr Asp Val Leu Thr Asp Arg Pro
                405                 410                 415
Pro Pro Ile Ile Leu Gln Gly Pro Ile Asn Gln Thr Leu Ala Val Asp
                420                 425                 430
Gly Thr Ala Leu Leu Lys Cys Lys Ala Thr Gly Glu Pro Leu Pro Val
                435                 440                 445
Ile Ser Trp Leu Lys Glu Gly Phe Thr Phe Leu Gly Arg Asp Pro Arg
            450                 455                 460
Ala Thr Ile Gln Asp Gln Gly Thr Leu Gln Ile Lys Asn Leu Arg Ile
465                 470                 475                 480
Ser Asp Thr Gly Thr Tyr Thr Cys Val Ala Thr Ser Ser Ser Gly Glu
                    485                 490                 495
Thr Ser Trp Ser Ala Val Leu Asp Val Thr Glu Ser Gly Ala Thr Ile
                500                 505                 510
Ser Lys Asn Tyr Asp Met Asn Asp Leu Pro Gly Pro Pro Ser Lys Pro
            515                 520                 525
Gln Val Thr Asp Val Ser Lys Asn Ser Val Thr Leu Ser Trp Gln Pro
        530                 535                 540
Gly Thr Pro Gly Val Leu Pro Ala Ser Ala Tyr Ile Ile Glu Ala Phe
545                 550                 555                 560
Ser Gln Ser Val Ser Asn Ser Trp Gln Thr Val Ala Asn His Val Lys
                565                 570                 575
Thr Thr Leu Tyr Thr Val Arg Gly Leu Arg Pro Asn Thr Ile Tyr Leu
                580                 585                 590
Phe Met Val Arg Ala Ile Asn Pro Gln Gly Leu Ser Asp Pro Ser Pro
            595                 600                 605
Met Ser Asp Pro Val Arg Thr Gln Asp Ile Ser Pro Pro Ala Gln Gly
        610                 615                 620
Val Asp His Arg Gln Val Gln Lys Glu Leu Gly Asp Val Val Val Arg
625                 630                 635                 640
Leu His Asn Pro Val Val Leu Thr Pro Thr Thr Val Gln Val Thr Trp
                645                 650                 655
Thr Val Asp Arg Gln Pro Gln Phe Ile Gln Gly Tyr Arg Val Met Tyr
                660                 665                 670
Arg Gln Thr Ser Gly Leu Gln Ala Ser Thr Val Trp Gln Asn Leu Asp
            675                 680                 685
Ala Lys Val Pro Thr Glu Arg Ser Ala Val Leu Val Asn Leu Lys Lys
        690                 695                 700
Gly Val Thr Tyr Glu Ile Lys Val Arg Pro Tyr Phe Asn Glu Phe Gln
705                 710                 715                 720
Gly Met Asp Ser Glu Ser Lys Thr Val Arg Thr Thr Glu Glu Ala Pro
                725                 730                 735
Ser Ala Pro Pro Gln Ser Val Thr Val Leu Thr Val Gly Ser His Asn
                740                 745                 750
Ser Thr Ser Ile Ser Val Ser Trp Asp Pro Pro Ala Asp His Gln
            755                 760                 765
Asn Gly Ile Ile Gln Glu Tyr Lys Ile Trp Cys Leu Gly Asn Glu Thr
        770                 775                 780
Arg Phe His Ile Asn Lys Thr Val Asp Ala Ala Ile Arg Ser Val Val
785                 790                 795                 800
Ile Gly Gly Leu Phe Pro Gly Ile Gln Tyr Arg Val Glu Val Ala Ala
                805                 810                 815
```

Ser Thr Ser Ala Gly Val Gly Val Lys Ser Glu Pro Gln Pro Ile Ile
          820                 825                 830

Ile Gly Gly Arg Asn Glu Val Val Ile Thr Glu Asn Asn Ser Ile
          835                 840                 845

Thr Glu Gln Ile Thr Asp Val Val Lys Gln Pro Ala Phe Ile Ala Gly
          850                 855                 860

Ile Gly Gly Ala Cys Trp Val Ile Leu Met Gly Phe Ser Ile Trp Leu
865                 870                 875                 880

Tyr Trp Arg Arg Lys Lys Arg Lys Gly Leu Ser Asn Tyr Ala Val Thr
                    885                 890                 895

Phe Gln Arg Gly Asp Gly Gly Leu Met Ser Asn Gly Ser Arg Pro Gly
              900                 905                 910

Leu Leu Asn Ala Gly Asp Pro Asn Tyr Pro Trp Leu Ala Asp Ser Trp
          915                 920                 925

Pro Ala Thr Ser Leu Pro Val Asn Asn Ser Asn Ser Gly Pro Asn Glu
          930                 935                 940

Ile Gly Asn Phe Gly Arg Gly Asp Val Leu Pro Val Pro Gly Gln
945                 950                 955                 960

Gly Asp Lys Thr Ala Thr Met Leu Ser Asp Gly Ala Ile Tyr Ser Ser
                    965                 970                 975

Ile Asp Phe Thr Thr Lys Thr Thr Tyr Asn Ser Ser Ser Gln Ile Thr
                    980                 985                 990

Gln Ala Thr Pro Tyr Ala Thr Thr  Gln Ile Leu His Ser  Asn Ser Ile
          995                 1000                 1005

His Glu  Leu Ala Val Asp Leu  Pro Asp Pro Gln Trp  Lys Ser Ser
    1010                 1015                 1020

Val Gln  Gln Lys Thr Asp Leu  Met Gly Phe Gly Tyr  Ser Leu Pro
    1025                 1030                 1035

Asp Gln  Asn Lys Gly Asn Asn  Ala Leu Leu Tyr Ile  Pro Asp Tyr
    1040                 1045                 1050

Arg Leu  Ala Glu Gly Leu Ser  Asn Arg Met Pro His  Asn Gln Ser
    1055                 1060                 1065

Gln Asp  Phe Ser Thr Thr Ser  Ser His Asn Ser Ser  Glu Arg Ser
    1070                 1075                 1080

Gly Ser  Leu Ser Gly Gly Lys  Gly Gly Lys Lys Lys  Lys Thr Lys
    1085                 1090                 1095

Asn Ser  Ser Lys Ala Gln Lys  Asn Asn Gly Ser Thr  Trp Ala Asn
    1100                 1105                 1110

Val Pro  Leu Pro Pro Pro Pro  Val Gln Pro Leu Pro  Gly Thr Glu
    1115                 1120                 1125

Leu Gly  His Tyr Ala Ala Glu  Gln Glu Asn Gly Tyr  Asp Ser Asp
    1130                 1135                 1140

Ser Trp  Cys Pro Pro Leu Pro  Val Gln Thr Tyr Leu  His Gln Gly
    1145                 1150                 1155

Met Glu  Asp Glu Leu Glu Glu  Asp Glu Asp Arg Val  Pro Thr Pro
    1160                 1165                 1170

Pro Val  Arg Gly Val Ala Ser  Ser Pro Ala Ile Ser  Phe Gly Gln
    1175                 1180                 1185

Gln Ser  Thr Ala Thr Leu Thr  Pro Ser Pro Arg Glu  Glu Met Gln
    1190                 1195                 1200

Pro Met  Leu Gln Ala His Leu  Asp Glu Leu Thr Arg  Ala Tyr Gln
    1205                 1210                 1215

```
Phe Asp Ile Ala Lys Gln Thr Trp His Ile Gln Ser Asn Thr Pro
1220                1225                1230

Pro Pro Gln Pro Pro Ala Pro Pro Leu Gly Tyr Val Ser Gly Ala
    1235                1240                1245

Leu Ile Ser Asp Leu Glu Thr Asp Val Pro Asp Glu Asp Ala Asp
1250                1255                1260

Asp Glu Glu Glu Pro Leu Glu Ile Pro Arg Pro Leu Arg Ala Leu
    1265                1270                1275

Asp Gln Thr Pro Gly Ser Ser Met Asp Asn Leu Asp Ser Ser Val
1280                1285                1290

Thr Gly Lys Ala Phe Ser Ser Gln Arg Gln Arg Pro Thr Ser
    1295                1300                1305

Pro Phe Ser Thr Asp Ser Asn Thr Ser Ala Ala Gln Asn Gln Ser
1310                1315                1320

Gln Arg Pro Arg Pro Thr Lys Lys His Lys Gly Gly Arg Met Asp
    1325                1330                1335

Pro Gln Pro Val Leu Pro His Arg Arg Glu Gly Met Pro Asp Asp
1340                1345                1350

Leu Pro Pro Pro Pro Asp Pro Pro Gly Gln Gly Leu Arg Gln
    1355                1360                1365

Gln Ile Gly Leu Ser Gln His Ser Gly Asn Val Glu Asn Ser Thr
1370                1375                1380

Glu Arg Lys Gly Ser Ser Leu Glu Arg Gln Gln Ala Ala Asn Leu
    1385                1390                1395

Glu Asp Thr Lys Ser Ser Leu Asp Cys Pro Ala Lys Thr Val Leu
1400                1405                1410

Glu Trp Gln Arg Gln Thr Gln Asp Trp Ile Asn Ser Thr Glu Arg
    1415                1420                1425

Gln Glu Glu Thr Arg Lys Ala Pro His Lys Gln Gly Val Gly Ser
1430                1435                1440

Glu Glu Ser Leu Val Pro Tyr Ser Lys Pro Ser Phe Pro Ser Pro
    1445                1450                1455

Gly Gly His Ser Ser Ser Gly Thr Ser Ser Ser Lys Gly Ser Thr
1460                1465                1470

Gly Pro Arg Lys Ala Asp Val Leu Arg Gly Ser His Gln Arg Asn
    1475                1480                1485

Ala Asn Asp Leu Leu Asp Ile Gly Tyr Val Gly Ser Asn Ser Gln
1490                1495                1500

Gly Gln Phe Thr Glu
    1505

<210> SEQ ID NO 5
<211> LENGTH: 190
<212> TYPE: PRT
<213> ORGANISM: Homo sapiens

<400> SEQUENCE: 5

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60
```

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu Val Ala Leu Leu Arg Asp Asp Phe Arg Gln Asn Pro Thr Asp Val
            100                 105                 110

Val Val Ala Ala Gly Glu Pro Ala Ile Leu Glu Cys Gln Pro Pro Arg
            115                 120                 125

Gly His Pro Glu Pro Thr Ile Tyr Trp Lys Lys Asp Lys Val Arg Ile
        130                 135                 140

Asp Asp Lys Glu Glu Arg Ile Ser Ile Arg Gly Gly Lys Leu Met Ile
145                 150                 155                 160

Ser Asn Thr Arg Lys Ser Asp Ala Gly Met Tyr Thr Cys Val Gly Thr
                165                 170                 175

Asn Met Val Gly Glu Arg Asp Ser Asp Pro Ala Glu Leu Thr
            180                 185                 190

<210> SEQ ID NO 6
<211> LENGTH: 190
<212> TYPE: PRT
<213> ORGANISM: Macaca fascicularis

<400> SEQUENCE: 6

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu Val Ala Leu Leu Arg Asp Asp Phe Arg Gln Asn Pro Thr Asp Val
            100                 105                 110

Val Val Ala Ala Gly Glu Pro Ala Ile Leu Glu Cys Gln Pro Pro Arg
            115                 120                 125

Gly His Pro Glu Pro Thr Ile Tyr Trp Lys Lys Asp Lys Val Arg Ile
        130                 135                 140

Asp Asp Lys Glu Glu Arg Ile Ser Ile Arg Gly Gly Lys Leu Met Ile
145                 150                 155                 160

Ser Asn Thr Arg Lys Ser Asp Ala Gly Met Tyr Thr Cys Val Gly Thr
                165                 170                 175

Asn Met Val Gly Glu Arg Asp Ser Asp Pro Ala Glu Leu Thr
            180                 185                 190

<210> SEQ ID NO 7
<211> LENGTH: 190
<212> TYPE: PRT
<213> ORGANISM: Rattus sp.

<400> SEQUENCE: 7

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Arg Ser Lys Pro Asp Glu Gly Thr Tyr Val Cys
65                  70                  75                  80

Val Ala Arg Asn Tyr Leu Gly Glu Ala Val Ser Arg Asn Ala Ser Leu
                85                  90                  95

Glu Val Ala Leu Leu Arg Asp Asp Phe Arg Gln Asn Pro Thr Asp Val
            100                 105                 110

Val Val Ala Ala Gly Glu Pro Ala Ile Leu Glu Cys Gln Pro Pro Arg
        115                 120                 125

Gly His Pro Glu Pro Thr Ile Tyr Trp Lys Lys Asp Lys Val Arg Ile
    130                 135                 140

Asp Glu Lys Glu Glu Arg Ile Ser Ile Arg Gly Gly Lys Leu Met Ile
145                 150                 155                 160

Ser Asn Thr Arg Lys Ser Asp Ala Gly Met Tyr Thr Cys Val Gly Thr
                165                 170                 175

Asn Met Val Gly Glu Arg Asp Ser Asp Pro Ala Glu Leu Thr
            180                 185                 190

<210> SEQ ID NO 8
<211> LENGTH: 190
<212> TYPE: PRT
<213> ORGANISM: Mus sp.

<400> SEQUENCE: 8

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu Val Ala Leu Leu Arg Asp Asp Phe Arg Gln Asn Pro Thr Asp Val
            100                 105                 110

Val Val Ala Ala Gly Glu Pro Ala Ile Leu Glu Cys Gln Pro Pro Arg
        115                 120                 125

Gly His Pro Glu Pro Thr Ile Tyr Trp Lys Lys Asp Lys Val Arg Ile
    130                 135                 140

Asp Asp Lys Glu Glu Arg Ile Ser Ile Arg Gly Gly Lys Leu Met Ile
145                 150                 155                 160

Ser Asn Thr Arg Lys Ser Asp Ala Gly Met Tyr Thr Cys Val Gly Thr
                165                 170                 175

Asn Met Val Gly Glu Arg Asp Ser Asp Pro Ala Glu Leu Thr
            180                 185                 190

-continued

```
<210> SEQ ID NO 9
<211> LENGTH: 1651
<212> TYPE: PRT
<213> ORGANISM: Homo sapiens

<400> SEQUENCE: 9
```

Met Lys Trp Lys His Val Pro Phe Leu Val Met Ile Ser Leu Leu Ser
1               5                   10                  15

Leu Ser Pro Asn His Leu Phe Leu Ala Gln Leu Ile Pro Asp Pro Glu
            20                  25                  30

Asp Val Glu Arg Gly Asn Asp His Gly Thr Pro Ile Pro Thr Ser Asp
        35                  40                  45

Asn Asp Asp Asn Ser Leu Gly Tyr Thr Gly Ser Arg Leu Arg Gln Glu
    50                  55                  60

Asp Phe Pro Pro Arg Ile Val Glu His Pro Ser Asp Leu Ile Val Ser
65                  70                  75                  80

Lys Gly Glu Pro Ala Thr Leu Asn Cys Lys Ala Glu Gly Arg Pro Thr
                85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Lys Ser Arg Pro Asp Glu Gly Val
    130                 135                 140

Tyr Val Cys Val Ala Arg Asn Tyr Leu Gly Glu Ala Val Ser His Asn
145                 150                 155                 160

Ala Ser Leu Glu Val Ala Ile Leu Arg Asp Asp Phe Arg Gln Asn Pro
                165                 170                 175

Ser Asp Val Met Val Ala Val Gly Glu Pro Ala Val Met Glu Cys Gln
            180                 185                 190

Pro Pro Arg Gly His Pro Glu Pro Thr Ile Ser Trp Lys Lys Asp Gly
        195                 200                 205

Ser Pro Leu Asp Asp Lys Asp Glu Arg Ile Thr Ile Arg Gly Gly Lys
    210                 215                 220

Leu Met Ile Thr Tyr Thr Arg Lys Ser Asp Ala Gly Lys Tyr Val Cys
225                 230                 235                 240

Val Gly Thr Asn Met Val Gly Glu Arg Glu Ser Glu Val Ala Glu Leu
                245                 250                 255

Thr Val Leu Glu Arg Pro Ser Phe Val Lys Arg Pro Ser Asn Leu Ala
            260                 265                 270

Val Thr Val Asp Asp Ser Ala Glu Phe Lys Cys Glu Ala Arg Gly Asp
        275                 280                 285

Pro Val Pro Thr Val Arg Trp Arg Lys Asp Asp Gly Glu Leu Pro Lys
    290                 295                 300

Ser Arg Tyr Glu Ile Arg Asp Asp His Thr Leu Lys Ile Arg Lys Val
305                 310                 315                 320

Thr Ala Gly Asp Met Gly Ser Tyr Thr Cys Val Ala Glu Asn Met Val
                325                 330                 335

Gly Lys Ala Glu Ala Ser Ala Thr Leu Thr Val Gln Glu Pro Pro His
            340                 345                 350

Phe Val Val Lys Pro Arg Asp Gln Val Val Ala Leu Gly Arg Thr Val
        355                 360                 365

Thr Phe Gln Cys Glu Ala Thr Gly Asn Pro Gln Pro Ala Ile Phe Trp
    370                 375                 380

```
Arg Arg Glu Gly Ser Gln Asn Leu Leu Phe Ser Tyr Gln Pro Pro Gln
385                 390                 395                 400

Ser Ser Ser Arg Phe Ser Val Ser Gln Thr Gly Asp Leu Thr Ile Thr
                405                 410                 415

Asn Val Gln Arg Ser Asp Val Gly Tyr Tyr Ile Cys Gln Thr Leu Asn
            420                 425                 430

Val Ala Gly Ser Ile Ile Thr Lys Ala Tyr Leu Glu Val Thr Asp Val
        435                 440                 445

Ile Ala Asp Arg Pro Pro Val Ile Arg Gln Gly Pro Val Asn Gln
    450                 455                 460

Thr Val Ala Val Asp Gly Thr Phe Val Leu Ser Cys Val Ala Thr Gly
465                 470                 475                 480

Ser Pro Val Pro Thr Ile Leu Trp Arg Lys Asp Gly Val Leu Val Ser
                485                 490                 495

Thr Gln Asp Ser Arg Ile Lys Gln Leu Glu Asn Gly Val Leu Gln Ile
            500                 505                 510

Arg Tyr Ala Lys Leu Gly Asp Thr Gly Arg Tyr Thr Cys Ile Ala Ser
        515                 520                 525

Thr Pro Ser Gly Glu Ala Thr Trp Ser Ala Tyr Ile Glu Val Gln Glu
530                 535                 540

Phe Gly Val Pro Val Gln Pro Pro Arg Pro Thr Asp Pro Asn Leu Ile
545                 550                 555                 560

Pro Ser Ala Pro Ser Lys Pro Glu Val Thr Asp Val Ser Arg Asn Thr
                565                 570                 575

Val Thr Leu Ser Trp Gln Pro Asn Leu Asn Ser Gly Ala Thr Pro Thr
            580                 585                 590

Ser Tyr Ile Ile Glu Ala Phe Ser His Ala Ser Gly Ser Ser Trp Gln
        595                 600                 605

Thr Val Ala Glu Asn Val Lys Thr Glu Thr Ser Ala Ile Lys Gly Leu
610                 615                 620

Lys Pro Asn Ala Ile Tyr Leu Phe Leu Val Arg Ala Ala Asn Ala Tyr
625                 630                 635                 640

Gly Ile Ser Asp Pro Ser Gln Ile Ser Asp Pro Val Lys Thr Gln Asp
                645                 650                 655

Val Leu Pro Thr Ser Gln Gly Val Asp His Lys Gln Val Gln Arg Glu
            660                 665                 670

Leu Gly Asn Ala Val Leu His Leu His Asn Pro Thr Val Leu Ser Ser
        675                 680                 685

Ser Ser Ile Glu Val His Trp Thr Val Asp Gln Gln Ser Gln Tyr Ile
        690                 695                 700

Gln Gly Tyr Lys Ile Leu Tyr Arg Pro Ser Gly Ala Asn His Gly Glu
705                 710                 715                 720

Ser Asp Trp Leu Val Phe Glu Val Arg Thr Pro Ala Lys Asn Ser Val
                725                 730                 735

Val Ile Pro Asp Leu Arg Lys Gly Val Asn Tyr Glu Ile Lys Ala Arg
            740                 745                 750

Pro Phe Phe Asn Glu Phe Gln Gly Ala Asp Ser Glu Ile Lys Phe Ala
        755                 760                 765

Lys Thr Leu Glu Glu Ala Pro Ser Ala Pro Pro Gln Gly Val Thr Val
        770                 775                 780

Ser Lys Asn Asp Gly Asn Gly Thr Ala Ile Leu Val Ser Trp Gln Pro
785                 790                 795                 800

Pro Pro Glu Asp Thr Gln Asn Gly Met Val Gln Glu Tyr Lys Val Trp
```

```
                805                 810                 815
Cys Leu Gly Asn Glu Thr Arg Tyr His Ile Asn Lys Thr Val Asp Gly
            820                 825                 830

Ser Thr Phe Ser Val Val Ile Pro Phe Leu Val Pro Gly Ile Arg Tyr
            835                 840                 845

Ser Val Glu Val Ala Ala Ser Thr Gly Ala Gly Ser Gly Val Lys Ser
            850                 855                 860

Glu Pro Gln Phe Ile Gln Leu Asp Ala His Gly Asn Pro Val Ser Pro
865                 870                 875                 880

Glu Asp Gln Val Ser Leu Ala Gln Gln Ile Ser Asp Val Val Lys Gln
                885                 890                 895

Pro Ala Phe Ile Ala Gly Ile Gly Ala Ala Cys Trp Ile Ile Leu Met
                900                 905                 910

Val Phe Ser Ile Trp Leu Tyr Arg His Arg Lys Arg Asn Gly Leu
            915                 920                 925

Thr Ser Thr Tyr Ala Gly Ile Arg Lys Val Pro Ser Phe Thr Phe Thr
            930                 935                 940

Pro Thr Val Thr Tyr Gln Arg Gly Gly Glu Ala Val Ser Ser Gly Gly
945                 950                 955                 960

Arg Pro Gly Leu Leu Asn Ile Ser Glu Pro Ala Ala Gln Pro Trp Leu
                965                 970                 975

Ala Asp Thr Trp Pro Asn Thr Gly Asn Asn His Asn Asp Cys Ser Ile
            980                 985                 990

Ser Cys Cys Thr Ala Gly Asn Gly Asn Ser Asp Ser Asn Leu Thr Thr
            995                 1000                1005

Tyr Ser Arg Pro Ala Asp Cys Ile Ala Asn Tyr Asn Asn Gln Leu
    1010                1015                1020

Asp Asn Lys Gln Thr Asn Leu Met Leu Pro Glu Ser Thr Val Tyr
    1025                1030                1035

Gly Asp Val Asp Leu Ser Asn Lys Ile Asn Glu Met Lys Thr Phe
    1040                1045                1050

Asn Ser Pro Asn Leu Lys Asp Gly Arg Phe Val Asn Pro Ser Gly
    1055                1060                1065

Gln Pro Thr Pro Tyr Ala Thr Thr Gln Leu Ile Gln Ser Asn Leu
    1070                1075                1080

Ser Asn Asn Met Asn Asn Gly Ser Gly Asp Ser Gly Glu Lys His
    1085                1090                1095

Trp Lys Pro Leu Gly Gln Gln Lys Gln Glu Val Ala Pro Val Gln
    1100                1105                1110

Tyr Asn Ile Val Glu Gln Asn Lys Leu Asn Lys Asp Tyr Arg Ala
    1115                1120                1125

Asn Asp Thr Val Pro Pro Thr Ile Pro Tyr Asn Gln Ser Tyr Asp
    1130                1135                1140

Gln Asn Thr Gly Gly Ser Tyr Asn Ser Ser Asp Arg Gly Ser Ser
    1145                1150                1155

Thr Ser Gly Ser Gln Gly His Lys Lys Gly Ala Arg Thr Pro Lys
    1160                1165                1170

Val Pro Lys Gln Gly Gly Met Asn Trp Ala Asp Leu Leu Pro Pro
    1175                1180                1185

Pro Pro Ala His Pro Pro Pro His Ser Asn Ser Glu Glu Tyr Asn
    1190                1195                1200

Ile Ser Val Asp Glu Ser Tyr Asp Gln Glu Met Pro Cys Pro Val
    1205                1210                1215
```

-continued

Pro Pro Ala Arg Met Tyr Leu Gln Gln Asp Glu Leu Glu Glu Glu
    1220            1225            1230

Glu Asp Glu Arg Gly Pro Thr Pro Pro Val Arg Gly Ala Ala Ser
    1235            1240            1245

Ser Pro Ala Ala Val Ser Tyr Ser His Gln Ser Thr Ala Thr Leu
    1250            1255            1260

Thr Pro Ser Pro Gln Glu Glu Leu Gln Pro Met Leu Gln Asp Cys
    1265            1270            1275

Pro Glu Glu Thr Gly His Met Gln His Gln Pro Asp Arg Arg Arg
    1280            1285            1290

Gln Pro Val Ser Pro Pro Pro Pro Arg Pro Ile Ser Pro Pro
    1295            1300            1305

His Thr Tyr Gly Tyr Ile Ser Gly Pro Leu Val Ser Asp Met Asp
    1310            1315            1320

Thr Asp Ala Pro Glu Glu Glu Asp Glu Ala Asp Met Glu Val
    1325            1330            1335

Ala Lys Met Gln Thr Arg Arg Leu Leu Leu Arg Gly Leu Glu Gln
    1340            1345            1350

Thr Pro Ala Ser Ser Val Gly Asp Leu Glu Ser Ser Val Thr Gly
    1355            1360            1365

Ser Met Ile Asn Gly Trp Gly Ser Ala Ser Glu Glu Asp Asn Ile
    1370            1375            1380

Ser Ser Gly Arg Ser Ser Val Ser Ser Ser Asp Gly Ser Phe Phe
    1385            1390            1395

Thr Asp Ala Asp Phe Ala Gln Ala Val Ala Ala Ala Ala Glu Tyr
    1400            1405            1410

Ala Gly Leu Lys Val Ala Arg Arg Gln Met Gln Asp Ala Ala Gly
    1415            1420            1425

Arg Arg His Phe His Ala Ser Gln Cys Pro Arg Pro Thr Ser Pro
    1430            1435            1440

Val Ser Thr Asp Ser Asn Met Ser Ala Ala Val Met Gln Lys Thr
    1445            1450            1455

Arg Pro Ala Lys Lys Leu Lys His Gln Pro Gly His Leu Arg Arg
    1460            1465            1470

Glu Thr Tyr Thr Asp Asp Leu Pro Pro Pro Val Pro Pro Pro
    1475            1480            1485

Ala Ile Lys Ser Pro Thr Ala Gln Ser Lys Thr Gln Leu Glu Val
    1490            1495            1500

Arg Pro Val Val Val Pro Lys Leu Pro Ser Met Asp Ala Arg Thr
    1505            1510            1515

Asp Arg Ser Ser Asp Arg Lys Gly Ser Ser Tyr Lys Gly Arg Glu
    1520            1525            1530

Val Leu Asp Gly Arg Gln Val Val Asp Met Arg Thr Asn Pro Gly
    1535            1540            1545

Asp Pro Arg Glu Ala Gln Glu Gln Gln Asn Asp Gly Lys Gly Arg
    1550            1555            1560

Gly Asn Lys Ala Ala Lys Arg Asp Leu Pro Pro Ala Lys Thr His
    1565            1570            1575

Leu Ile Gln Glu Asp Ile Leu Pro Tyr Cys Arg Pro Thr Phe Pro
    1580            1585            1590

Thr Ser Asn Asn Pro Arg Asp Pro Ser Ser Ser Ser Met Ser
    1595            1600            1605

```
Ser Arg Gly Ser Gly Ser Arg Gln Arg Glu Gln Ala Asn Val Gly
    1610                1615                1620

Arg Arg Asn Ile Ala Glu Met Gln Val Leu Gly Gly Tyr Glu Arg
    1625                1630                1635

Gly Glu Asp Asn Asn Glu Glu Leu Glu Glu Thr Glu Ser
    1640                1645                1650

<210> SEQ ID NO 10
<211> LENGTH: 1650
<212> TYPE: PRT
<213> ORGANISM: Macaca fascicularis

<400> SEQUENCE: 10

Met Lys Trp Lys His Val Pro Phe Leu Val Ile Ile Ser Leu Leu Ser
1               5                   10                  15

Leu Ser Pro Asn His Leu Phe Leu Ser Gln Leu Ile Pro Asp Pro Glu
            20                  25                  30

Asp Leu Glu Arg Gly Lys Asp Asn Gly Thr Pro Ile Pro Thr Ser Glu
        35                  40                  45

Asn Asp Asp Asn Ser Leu Gly Tyr Thr Gly Ser Arg Leu Arg Gln Glu
    50                  55                  60

Asp Phe Pro Pro Arg Ile Val Glu His Pro Ser Asp Leu Ile Val Ser
65                  70                  75                  80

Lys Gly Glu Pro Ala Thr Leu Asn Cys Lys Ala Glu Gly Arg Pro Thr
                85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Lys Ser Arg Pro Asp Glu Gly Val
    130                 135                 140

Tyr Val Cys Val Ala Arg Asn Tyr Leu Gly Glu Ala Val Ser His Asn
145                 150                 155                 160

Ala Ser Leu Glu Val Ala Ile Leu Arg Asp Asp Phe Arg Gln Asn Pro
                165                 170                 175

Ser Asp Val Met Val Ala Val Gly Glu Pro Ala Val Met Glu Cys Gln
            180                 185                 190

Pro Pro Arg Gly His Pro Glu Pro Thr Ile Ser Trp Lys Lys Asp Gly
        195                 200                 205

Ser Pro Leu Asp Asp Lys Asp Glu Arg Ile Thr Ile Arg Gly Gly Lys
    210                 215                 220

Leu Met Ile Thr Tyr Thr Arg Lys Ser Asp Ala Gly Lys Tyr Val Cys
225                 230                 235                 240

Val Gly Thr Asn Met Val Gly Glu Arg Glu Ser Glu Val Ala Glu Leu
                245                 250                 255

Thr Val Leu Glu Arg Pro Ser Phe Val Lys Arg Pro Ser Asn Leu Ala
            260                 265                 270

Val Thr Val Asp Asp Ser Ala Glu Phe Lys Cys Glu Ala Arg Gly Asp
        275                 280                 285

Pro Val Pro Thr Val Arg Trp Arg Lys Asp Asp Gly Glu Leu Pro Lys
    290                 295                 300

Ser Arg Tyr Glu Ile Arg Asp Asp His Thr Leu Lys Ile Arg Lys Val
305                 310                 315                 320

Met Ala Gly Asp Met Gly Ser Tyr Thr Cys Val Ala Glu Asn Met Val
                325                 330                 335
```

```
Gly Lys Ala Glu Ala Ser Ala Thr Leu Thr Val Gln Glu Pro Pro His
            340                 345                 350

Phe Val Val Lys Pro Arg Asp Gln Val Val Ala Leu Gly Arg Thr Val
            355                 360                 365

Thr Phe Gln Cys Glu Ala Thr Gly Asn Pro Gln Pro Ala Ile Phe Trp
370                 375                 380

Arg Arg Glu Gly Ser Gln Asn Leu Leu Phe Ser Tyr Gln Pro Pro Gln
385                 390                 395                 400

Ser Ser Ser Arg Phe Ser Val Ser Gln Thr Gly Asp Leu Thr Ile Thr
                405                 410                 415

Asn Val Gln Arg Ser Asp Val Gly Tyr Tyr Ile Cys Gln Thr Leu Asn
            420                 425                 430

Val Ala Gly Ser Ile Ile Thr Lys Ala Tyr Leu Glu Val Thr Asp Val
            435                 440                 445

Ile Ala Asp Arg Pro Pro Val Ile Arg Gln Gly Pro Val Asn Gln
450                 455                 460

Thr Val Ala Val Asp Gly Thr Leu Val Leu Ser Cys Val Ala Thr Gly
465                 470                 475                 480

Ser Pro Val Pro Thr Ile Leu Trp Arg Lys Asp Gly Val Leu Val Ser
                485                 490                 495

Thr Gln Asp Ser Arg Ile Lys Gln Leu Glu Asn Gly Val Leu Gln Ile
                500                 505                 510

Arg Tyr Ala Lys Leu Gly Asp Thr Gly Arg Tyr Thr Cys Ile Ala Ser
            515                 520                 525

Thr Pro Ser Gly Glu Ala Thr Trp Ser Ala Tyr Ile Glu Val Gln Glu
            530                 535                 540

Phe Gly Val Pro Val Gln Pro Pro Arg Pro Thr Asp Pro Asn Leu Ile
545                 550                 555                 560

Pro Ser Ala Pro Ser Lys Pro Glu Val Thr Asp Val Ser Arg Asn Thr
                565                 570                 575

Val Thr Leu Ser Trp Gln Pro Asn Leu Asn Ser Gly Ala Thr Pro Thr
                580                 585                 590

Ser Tyr Ile Ile Glu Ala Phe Ser His Ala Ser Gly Ser Ser Trp Gln
            595                 600                 605

Thr Val Ala Glu Asn Val Lys Thr Glu Thr Phe Ala Ile Lys Gly Leu
            610                 615                 620

Lys Pro Asn Ala Ile Tyr Leu Phe Leu Val Arg Ala Ala Asn Ala Tyr
625                 630                 635                 640

Gly Ile Ser Asp Pro Ser Gln Ile Ser Asp Pro Val Lys Thr Gln Asp
                645                 650                 655

Val Pro Pro Thr Ser Gln Gly Val Asp His Lys Gln Val Gln Arg Glu
                660                 665                 670

Leu Gly Asn Val Val Leu His Leu His Asn Pro Thr Ile Leu Ser Ser
            675                 680                 685

Ser Ser Ile Glu Val His Trp Thr Val Asp Gln Gln Ser Gln Tyr Ile
            690                 695                 700

Gln Gly Tyr Lys Ile Leu Tyr Arg Pro Ser Gly Ala Asn His Gly Glu
705                 710                 715                 720

Ser Asp Trp Leu Val Phe Glu Val Arg Thr Pro Thr Lys Asn Ser Val
                725                 730                 735

Val Ile Pro Asp Leu Arg Lys Gly Val Asn Tyr Glu Ile Lys Ala Arg
            740                 745                 750
```

```
Pro Phe Phe Asn Glu Phe Gln Gly Ala Asp Ser Glu Ile Lys Phe Ala
            755                 760                 765

Lys Thr Leu Glu Glu Gly Asn Ala Pro Pro Gln Gly Val Thr Val Ser
    770                 775                 780

Lys Asn Asp Gly Asn Gly Thr Ala Ile Leu Val Ser Trp Gln Pro Pro
785                 790                 795                 800

Pro Glu Gly Thr Gln Asn Gly Met Val Gln Glu Tyr Lys Val Trp Cys
                805                 810                 815

Leu Gly Asn Glu Thr Arg Tyr His Ile Asn Lys Thr Val Asp Gly Ser
            820                 825                 830

Thr Phe Ser Val Val Ile Pro Phe Leu Val Pro Gly Ile Arg Tyr Ser
        835                 840                 845

Val Glu Val Ala Ala Ser Thr Gly Ala Gly Pro Gly Val Lys Ser Glu
    850                 855                 860

Pro Gln Phe Ile Gln Leu Asp Ser His Gly Asn Pro Val Ser Pro Glu
865                 870                 875                 880

Asp Gln Val Ser Leu Ala Gln Gln Ile Ser Asp Val Val Lys Gln Pro
                885                 890                 895

Ala Phe Ile Ala Gly Ile Gly Ala Ala Cys Trp Ile Ile Leu Met Val
            900                 905                 910

Phe Ser Ile Trp Leu Tyr Arg His Arg Lys Lys Arg Asn Gly Leu Thr
        915                 920                 925

Ser Thr Tyr Ala Gly Ile Arg Lys Val Pro Ser Phe Thr Phe Thr Pro
    930                 935                 940

Thr Val Thr Tyr Gln Arg Gly Gly Glu Ala Val Ser Ser Gly Gly Arg
945                 950                 955                 960

Pro Gly Leu Leu Asn Ile Ser Glu Pro Ala Thr Gln Pro Trp Leu Ala
                965                 970                 975

Asp Thr Trp Pro Asn Thr Gly Asn Asn His Asn Asp Cys Ser Ile Asn
            980                 985                 990

Cys Cys Thr Ala Gly Asn Gly Asn Ser Asp Ser Asn Leu Thr Thr Tyr
        995                1000                1005

Ser Arg Pro Ala Asp Cys Ile Ala Asn Tyr Asn Asn Gln Leu Asp
   1010                1015                1020

Asn Lys Gln Thr Asn Leu Met Leu Pro Glu Ser Thr Val Tyr Gly
   1025                1030                1035

Asp Val Asp Leu Ser Asn Lys Ile Asn Glu Met Lys Thr Phe Asn
   1040                1045                1050

Ser Pro Asn Leu Lys Asp Gly Arg Phe Val Asn Pro Ser Gly Gln
   1055                1060                1065

Pro Thr Pro Tyr Ala Thr Thr Gln Leu Ile Gln Ser Asn Leu Ser
   1070                1075                1080

Asn Asn Met Asn Asn Gly Ser Gly Asp Ser Gly Glu Lys His Trp
   1085                1090                1095

Lys Pro Leu Gly Gln Gln Lys Gln Glu Val Ala Pro Val Gln Tyr
   1100                1105                1110

Asn Ile Met Glu Gln Asn Lys Leu Asn Lys Asp Tyr Arg Ala Asn
   1115                1120                1125

Asp Thr Ile Pro Pro Thr Ile Pro Tyr Asn Gln Ser Tyr Asp Gln
   1130                1135                1140

Asn Thr Gly Gly Ser Tyr Asn Ser Ser Asp Arg Gly Ser Ser Thr
   1145                1150                1155

Ser Gly Ser Gln Gly His Lys Lys Gly Ala Arg Thr Pro Lys Val
```

-continued

|      | 1160 |      |      | 1165 |      |      | 1170 |      |      |      |
|------|------|------|------|------|------|------|------|------|------|------|
| Pro  | Lys  | Gln  | Gly  | Gly  | Met  | Asn  | Trp  | Ala  | Asp  | Leu  | Leu  | Pro  | Pro  | Pro  |
|      | 1175 |      |      |      | 1180 |      |      |      | 1185 |

Pro Lys Gln Gly Gly Met Asn Trp Ala Asp Leu Leu Pro Pro Pro
         1175                1180                1185

Pro Ala His Pro Pro His Ser Asn Ser Glu Glu Tyr Asn Ile
         1190                1195                1200

Ser Val Asp Glu Ser Tyr Asp Gln Glu Met Pro Cys Pro Val Pro
         1205                1210                1215

Pro Ala Arg Met Tyr Leu Gln Gln Asp Glu Leu Glu Glu Glu
         1220                1225                1230

Asp Glu Arg Gly Pro Thr Pro Pro Val Arg Gly Ala Ala Ser Ser
         1235                1240                1245

Pro Ala Ala Val Ser Tyr Ser His Gln Ser Thr Ala Thr Leu Thr
         1250                1255                1260

Pro Ser Pro Gln Glu Glu Leu Gln Pro Met Leu Gln Asp Cys Pro
         1265                1270                1275

Glu Glu Thr Gly His Met Gln His Pro Pro Asp Arg Arg Arg Gln
         1280                1285                1290

Pro Val Ser Pro Pro Pro Pro Arg Pro Ile Ser Pro Pro His
         1295                1300                1305

Thr Tyr Gly Tyr Ile Ser Gly Pro Leu Val Ser Asp Met Asp Thr
         1310                1315                1320

Asp Ala Pro Glu Glu Glu Asp Glu Ala Asp Met Glu Val Ala
         1325                1330                1335

Lys Met Gln Thr Arg Arg Leu Leu Leu Arg Gly Leu Glu Gln Thr
         1340                1345                1350

Pro Ala Ser Ser Val Gly Asp Leu Glu Ser Ser Val Thr Gly Ser
         1355                1360                1365

Met Ile Asn Gly Trp Gly Ser Ala Ser Glu Glu Asp Asn Ile Ser
         1370                1375                1380

Ser Gly Arg Ser Ser Val Ser Ser Ser Asp Gly Ser Phe Phe Thr
         1385                1390                1395

Asp Ala Asp Phe Ala Gln Ala Val Ala Ala Ala Glu Tyr Ala
         1400                1405                1410

Gly Leu Lys Val Ala Arg Arg Gln Val Gln Asp Ala Ala Gly Arg
         1415                1420                1425

Arg His Phe His Ala Ser Gln Cys Pro Arg Pro Thr Ser Pro Val
         1430                1435                1440

Ser Thr Asp Ser Asn Met Ser Ala Ala Ile Met Gln Lys Thr Arg
         1445                1450                1455

Pro Ala Lys Lys Pro Lys His Gln Pro Gly His Leu Arg Arg Glu
         1460                1465                1470

Ala Tyr Thr Asp Asp Leu Pro Pro Pro Val Pro Pro Pro Ala
         1475                1480                1485

Ile Lys Ser Pro Thr Val Gln Ser Lys Thr Gln Leu Glu Val Arg
         1490                1495                1500

Pro Val Val Val Pro Lys Leu Pro Ser Ile Asp Ala Arg Thr Glu
         1505                1510                1515

Arg Ser Ser Asp Arg Lys Gly Ser Ser Tyr Lys Gly Arg Glu Val
         1520                1525                1530

Leu Asp Gly Arg Pro Val Val Asp Val Arg Thr Asn Pro Gly Asp
         1535                1540                1545

Pro Arg Glu Ala Gln Glu Gln Gln Asn Asp Gly Lys Gly Arg Gly
         1550                1555                1560

-continued

Asn Lys Gly Ala Lys Arg Asp Leu Leu Pro Ala Lys Thr His Leu
1565                 1570                1575

Val Gln Glu Asp Ile Leu Pro Tyr Cys Arg Pro Thr Phe Pro Thr
1580             1585                1590

Ser Asn Asn Pro Arg Asp Pro Ser Ser Ser Ser Met Ser Ser
1595                 1600                1605

Arg Gly Ser Gly Ser Arg Gln Arg Glu Gln Ala Asn Val Gly Arg
1610                 1615                1620

Arg Asn Ile Ala Glu Met Gln Val Leu Gly Gly Tyr Glu Arg Gly
1625                 1630                1635

Glu Asp Asn Asn Glu Glu Leu Glu Val Thr Gly Asn
1640                 1645                1650

<210> SEQ ID NO 11
<211> LENGTH: 1651
<212> TYPE: PRT
<213> ORGANISM: Rattus sp.

<400> SEQUENCE: 11

Met Lys Trp Lys His Leu Pro Leu Leu Val Met Ile Ser Leu Leu Thr
1               5                   10                  15

Leu Ser Lys Lys His Leu Leu Leu Ala Gln Leu Ile Pro Asp Pro Glu
                20                  25                  30

Asp Leu Glu Arg Gly Asn Asp Asn Gly Thr Pro Ala Pro Thr Ser Asp
            35                  40                  45

Asn Asp Asp Asn Ser Leu Gly Tyr Thr Gly Ser Arg Leu Arg Gln Glu
50                  55                  60

Asp Phe Pro Pro Arg Ile Val Glu His Pro Ser Asp Leu Ile Val Ser
65                  70                  75                  80

Lys Gly Glu Pro Ala Thr Leu Asn Cys Lys Ala Glu Gly Arg Pro Thr
                85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Lys Ser Arg Pro Asp Glu Gly Val
130                 135                 140

Tyr Ile Cys Val Ala Arg Asn Tyr Leu Gly Glu Ala Val Ser His Asn
145                 150                 155                 160

Ala Ser Leu Glu Val Ala Ile Leu Arg Asp Asp Phe Arg Gln Asn Pro
                165                 170                 175

Ser Asp Val Met Val Ala Val Gly Glu Pro Ala Val Met Glu Cys Gln
            180                 185                 190

Pro Pro Arg Gly His Pro Glu Pro Thr Ile Ser Trp Lys Lys Asp Gly
        195                 200                 205

Ser Pro Leu Asp Asp Lys Asp Glu Arg Ile Thr Ile Arg Gly Gly Lys
210                 215                 220

Leu Met Ile Thr Tyr Thr Arg Lys Ser Asp Ala Gly Lys Tyr Val Cys
225                 230                 235                 240

Val Gly Thr Asn Met Val Gly Glu Arg Glu Ser Lys Val Ala Asp Val
                245                 250                 255

Thr Val Leu Glu Arg Pro Ser Phe Val Lys Arg Pro Ser Asn Leu Ala
            260                 265                 270

Val Thr Val Asp Asp Ser Ala Glu Phe Lys Cys Glu Ala Arg Gly Asp

-continued

```
            275                 280                 285
Pro Val Pro Thr Phe Gly Trp Arg Lys Asp Asp Gly Glu Leu Pro Lys
290                 295                 300
Ser Arg Tyr Glu Ile Arg Asp His Thr Leu Lys Ile Arg Lys Val
305                 310                 315                 320
Thr Ala Gly Asp Met Gly Ser Tyr Thr Cys Val Ala Glu Asn Met Val
                    325                 330                 335
Gly Lys Ala Glu Ala Ser Ala Thr Leu Thr Val Gln Glu Pro Pro His
                340                 345                 350
Phe Val Val Lys Pro Arg Asp Gln Val Val Ala Leu Gly Arg Thr Val
                355                 360                 365
Thr Phe Gln Cys Glu Ala Thr Gly Asn Pro Gln Pro Ala Ile Phe Trp
370                 375                 380
Arg Arg Glu Gly Ser Gln Asn Leu Leu Phe Ser Tyr Gln Pro Pro Gln
385                 390                 395                 400
Ser Ser Ser Arg Phe Ser Val Ser Gln Thr Gly Asp Leu Thr Val Thr
                405                 410                 415
Asn Val Gln Arg Ser Asp Val Gly Tyr Tyr Ile Cys Gln Thr Leu Asn
                420                 425                 430
Val Ala Gly Ser Ile Ile Thr Lys Ala Tyr Leu Glu Val Thr Asp Val
                435                 440                 445
Ile Ala Asp Arg Pro Pro Val Ile Arg Gln Gly Pro Val Asn Gln
450                 455                 460
Thr Val Ala Val Asp Gly Thr Leu Thr Leu Ser Cys Val Ala Thr Gly
465                 470                 475                 480
Ser Pro Val Pro Thr Ile Leu Trp Arg Lys Asp Gly Val Leu Val Ser
                485                 490                 495
Thr Gln Asp Ser Arg Ile Lys Gln Leu Glu Ser Gly Val Leu Gln Ile
                500                 505                 510
Arg Tyr Ala Lys Leu Gly Asp Thr Gly Arg Tyr Thr Cys Thr Ala Ser
                515                 520                 525
Thr Pro Ser Gly Glu Ala Thr Trp Ser Ala Tyr Ile Glu Val Gln Glu
530                 535                 540
Phe Gly Val Pro Val Gln Pro Pro Arg Pro Thr Asp Pro Asn Leu Ile
545                 550                 555                 560
Pro Ser Ala Pro Ser Lys Pro Glu Val Thr Asp Val Ser Lys Asn Thr
                565                 570                 575
Val Thr Leu Leu Trp Gln Pro Asn Leu Asn Ser Gly Ala Thr Pro Thr
                580                 585                 590
Ser Tyr Ile Ile Glu Ala Phe Ser His Ala Ser Gly Ser Ser Trp Gln
                595                 600                 605
Thr Val Ala Glu Asn Val Lys Thr Glu Thr Phe Ala Ile Lys Gly Leu
                610                 615                 620
Lys Pro Asn Ala Ile Tyr Leu Phe Leu Val Arg Ala Ala Asn Ala Tyr
625                 630                 635                 640
Gly Ile Ser Asp Pro Ser Gln Ile Ser Asp Pro Val Lys Thr Gln Asp
                645                 650                 655
Val Pro Pro Thr Thr Gln Gly Val Asp His Lys Gln Val Gln Arg Glu
                660                 665                 670
Leu Gly Asn Val Val Leu His Leu His Asn Pro Thr Ile Leu Ser Ser
                675                 680                 685
Ser Ser Val Glu Val His Trp Thr Val Asp Gln Gln Ser Gln Tyr Ile
                690                 695                 700
```

```
Gln Gly Tyr Lys Ile Leu Tyr Arg Pro Ser Gly Ala Ser His Gly Glu
705                 710                 715                 720

Ser Glu Trp Leu Val Phe Glu Val Arg Thr Pro Thr Lys Asn Ser Val
            725                 730                 735

Val Ile Pro Asp Leu Arg Lys Gly Val Asn Tyr Glu Ile Lys Ala Arg
        740                 745                 750

Pro Phe Phe Asn Glu Phe Gln Gly Ala Asp Ser Glu Ile Lys Phe Ala
        755                 760                 765

Lys Thr Leu Glu Glu Arg Pro Ser Ala Pro Arg Ser Val Thr Val
770                 775                 780

Ser Lys Asn Asp Gly Asn Gly Thr Ala Ile Leu Val Thr Trp Gln Pro
785                 790                 795                 800

Pro Pro Glu Asp Thr Gln Asn Gly Met Val Gln Glu Tyr Lys Val Trp
            805                 810                 815

Cys Leu Gly Asn Glu Thr Arg Tyr His Ile Asn Lys Thr Val Asp Gly
        820                 825                 830

Ser Thr Phe Ser Val Val Ile Pro Phe Leu Val Pro Gly Ile Arg Tyr
        835                 840                 845

Ser Val Glu Val Ala Ala Ser Thr Gly Ala Gly Pro Gly Val Lys Ser
850                 855                 860

Glu Pro Gln Phe Ile Gln Leu Asp Ser His Gly Asn Pro Val Ser Pro
865                 870                 875                 880

Glu Asp Gln Val Ser Leu Ala Gln Gln Ile Ser Asp Val Val Lys Gln
            885                 890                 895

Pro Ala Phe Ile Ala Gly Ile Gly Ala Ala Cys Trp Ile Ile Leu Met
        900                 905                 910

Val Phe Ser Ile Trp Leu Tyr Arg His Arg Lys Lys Arg Asn Gly Leu
        915                 920                 925

Ser Ser Thr Tyr Ala Gly Ile Arg Lys Val Pro Ser Phe Thr Phe Thr
930                 935                 940

Pro Thr Val Thr Tyr Gln Arg Gly Gly Glu Ala Val Ser Ser Gly Gly
945                 950                 955                 960

Arg Pro Gly Leu Leu Asn Ile Ser Glu Pro Ala Thr Gln Pro Trp Leu
            965                 970                 975

Ala Asp Thr Trp Pro Asn Thr Gly Asn Ser His Asn Asp Cys Ser Ile
        980                 985                 990

Asn Cys Cys Thr Ala Ser Asn Gly  Asn Ser Asp Ser Asn  Leu Thr Thr
        995                 1000                1005

Tyr Ser  Arg Pro Ala Asp Cys  Ile Ala Asn Tyr Asn  Asn Gln Leu
    1010                1015                1020

Asp Asn Lys Gln Thr Asn Leu  Met Leu Pro Glu Ser  Thr Val Tyr
        1025                1030                1035

Gly Asp  Val Asp Leu Ser Asn  Lys Ile Asn Glu Met  Lys Thr Phe
        1040                1045                1050

Asn Ser  Pro Asn Leu Lys Asp  Gly Arg Phe Val Asn  Pro Ser Gly
        1055                1060                1065

Gln Pro  Thr Pro Tyr Ala Thr  Thr Gln Leu Ile Gln  Ala Asn Leu
        1070                1075                1080

Ile Asn  Asn Met Asn Asn Gly  Gly Gly Asp Ser Ser  Glu Lys His
        1085                1090                1095

Trp Lys  Pro Pro Gly Gln Gln  Lys Gln Glu Val Ala  Pro Ile Gln
        1100                1105                1110
```

-continued

Tyr Asn Ile Met Glu Gln Asn Lys Leu Asn Lys Asp Tyr Arg Ala
1115                1120                1125

Asn Asp Thr Ile Leu Pro Thr Ile Pro Tyr Asn His Ser Tyr Asp
1130                1135                1140

Gln Asn Thr Gly Gly Ser Tyr Asn Ser Ser Asp Arg Gly Ser Ser
1145                1150                1155

Thr Ser Gly Ser Gln Gly His Lys Lys Gly Ala Arg Thr Pro Lys
1160                1165                1170

Ala Pro Lys Gln Gly Gly Met Asn Trp Ala Asp Leu Leu Pro Pro
1175                1180                1185

Pro Pro Ala His Pro Pro His Ser Asn Ser Glu Glu Tyr Ser
1190                1195                1200

Met Ser Val Asp Glu Ser Tyr Asp Gln Glu Met Pro Cys Pro Val
1205                1210                1215

Pro Pro Ala Arg Met Tyr Leu Gln Gln Asp Glu Leu Glu Glu Glu
1220                1225                1230

Glu Ala Glu Arg Gly Pro Thr Pro Pro Val Arg Gly Ala Ala Ser
1235                1240                1245

Ser Pro Ala Ala Val Ser Tyr Ser His Gln Ser Thr Ala Thr Leu
1250                1255                1260

Thr Pro Ser Pro Gln Glu Glu Leu Gln Pro Met Leu Gln Asp Cys
1265                1270                1275

Pro Glu Asp Leu Gly His Met Pro His Pro Pro Asp Arg Arg Arg
1280                1285                1290

Gln Pro Val Ser Pro Pro Pro Pro Arg Pro Ile Ser Pro Pro
1295                1300                1305

His Thr Tyr Gly Tyr Ile Ser Gly Pro Leu Val Ser Asp Met Asp
1310                1315                1320

Thr Asp Ala Pro Glu Glu Glu Asp Glu Ala Asp Met Glu Val
1325                1330                1335

Ala Lys Met Gln Thr Arg Arg Leu Leu Leu Arg Gly Leu Glu Gln
1340                1345                1350

Thr Pro Ala Ser Ser Val Gly Asp Leu Glu Ser Ser Val Thr Gly
1355                1360                1365

Ser Met Ile Asn Gly Trp Gly Ser Ala Ser Glu Glu Asp Asn Ile
1370                1375                1380

Ser Ser Gly Arg Ser Ser Val Ser Ser Ser Asp Gly Ser Phe Phe
1385                1390                1395

Thr Asp Ala Asp Phe Ala Gln Ala Val Ala Ala Ala Glu Tyr
1400                1405                1410

Ala Gly Leu Lys Val Ala Arg Arg Gln Met Gln Asp Ala Ala Gly
1415                1420                1425

Arg Arg His Phe His Ala Ser Gln Cys Pro Arg Pro Thr Ser Pro
1430                1435                1440

Val Ser Thr Asp Ser Asn Met Ser Ala Ala Val Ile Gln Lys Ala
1445                1450                1455

Arg Pro Thr Lys Lys Gln Lys His Gln Pro Gly His Leu Arg Arg
1460                1465                1470

Glu Ala Tyr Thr Asp Asp Leu Pro Pro Pro Pro Val Pro Pro Pro
1475                1480                1485

Ala Ile Lys Ser Pro Ser Val Gln Ser Lys Ala Gln Leu Glu Ala
1490                1495                1500

Arg Pro Ile Met Gly Pro Lys Leu Ala Ser Ile Glu Ala Arg Ala

```
                  1505                1510                1515

Asp Arg Ser Ser Asp Arg Lys Gly Gly Ser Tyr Lys Gly Arg Glu
        1520                1525                1530

Ala Leu Asp Gly Arg Gln Val Thr Asp Leu Arg Thr Ser Pro Gly
    1535                1540                1545

Asp Pro Arg Glu Ala Gln Glu Gln Pro Asn Glu Gly Lys Ala Arg
1550                1555                1560

Gly Thr Lys Thr Ala Lys Arg Asp Leu Pro Pro Ala Lys Thr His
    1565                1570                1575

Leu Ile Pro Glu Asp Ile Leu Pro Tyr Cys Arg Pro Thr Phe Pro
1580                1585                1590

Thr Ser Asn Asn Pro Arg Asp Pro Ser Ser Ser Ser Met Ser
    1595                1600                1605

Ser Arg Gly Ser Gly Ser Arg Gln Arg Glu Gln Ala Asn Val Gly
    1610                1615                1620

Arg Arg Asn Met Ala Glu Met Gln Val Leu Gly Gly Phe Glu Arg
    1625                1630                1635

Gly Asp Glu Asn Asn Glu Glu Leu Glu Glu Thr Glu Ser
    1640                1645                1650

<210> SEQ ID NO 12
<211> LENGTH: 1612
<212> TYPE: PRT
<213> ORGANISM: Mus sp.

<400> SEQUENCE: 12

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220
```

-continued

```
Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
            245                 250                 255

Arg Lys Asp Asp Gly Glu Leu Pro Lys Ser Arg Tyr Glu Ile Arg Asp
        260                 265                 270

Asp His Thr Leu Lys Ile Arg Lys Val Thr Ala Gly Asp Met Gly Ser
    275                 280                 285

Tyr Thr Cys Val Ala Glu Asn Met Val Gly Lys Ala Glu Ala Ser Ala
290                 295                 300

Thr Leu Thr Val Gln Glu Pro Pro His Phe Val Lys Pro Arg Asp
305                 310                 315                 320

Gln Val Val Ala Leu Gly Arg Thr Val Thr Phe Gln Cys Glu Ala Thr
            325                 330                 335

Gly Asn Pro Gln Pro Ala Ile Phe Trp Arg Arg Glu Gly Ser Gln Asn
        340                 345                 350

Leu Leu Phe Ser Tyr Gln Pro Gln Ser Ser Arg Phe Ser Val
    355                 360                 365

Ser Gln Thr Gly Asp Leu Thr Ile Thr Asn Val Gln Arg Ser Asp Val
370                 375                 380

Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro Pro
            405                 410                 415

Val Ile Arg Gln Gly Pro Val Asn Gln Thr Val Ala Val Asp Gly Thr
        420                 425                 430

Leu Ile Leu Ser Cys Val Ala Thr Gly Ser Pro Ala Pro Thr Ile Leu
    435                 440                 445

Trp Arg Lys Asp Gly Val Leu Val Ser Thr Gln Asp Ser Arg Ile Lys
450                 455                 460

Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
            485                 490                 495

Trp Ser Ala Tyr Ile Glu Val Gln Glu Phe Gly Val Pro Val Gln Pro
        500                 505                 510

Pro Arg Pro Thr Asp Pro Asn Leu Ile Pro Ser Ala Pro Ser Lys Pro
    515                 520                 525

Glu Val Thr Asp Val Ser Lys Asn Thr Val Thr Leu Ser Trp Gln Pro
530                 535                 540

Asn Leu Asn Ser Gly Ala Thr Pro Thr Ser Tyr Ile Ile Glu Ala Phe
545                 550                 555                 560

Ser His Ala Ser Gly Ser Ser Trp Gln Thr Ala Ala Glu Asn Val Lys
            565                 570                 575

Thr Glu Thr Phe Ala Ile Lys Gly Leu Lys Pro Asn Ala Ile Tyr Leu
        580                 585                 590

Phe Leu Val Arg Ala Ala Asn Ala Tyr Gly Ile Ser Asp Pro Ser Gln
    595                 600                 605

Ile Ser Asp Pro Val Lys Thr Gln Asp Val Pro Pro Thr Ser Gln Gly
610                 615                 620

Val Asp His Lys Gln Val Gln Arg Glu Leu Gly Asn Val Val Leu His
625                 630                 635                 640

Leu His Asn Pro Thr Ile Leu Ser Ser Ser Ser Val Glu Val His Trp
```

-continued

```
              645                 650                 655
Thr Val Asp Gln Gln Ser Gln Tyr Ile Gln Gly Tyr Lys Ile Leu Tyr
              660                 665                 670

Arg Pro Ser Gly Ala Ser His Gly Glu Ser Glu Trp Leu Val Phe Glu
              675                 680                 685

Val Arg Thr Pro Thr Lys Asn Ser Val Val Ile Pro Asp Leu Arg Lys
              690                 695                 700

Gly Val Asn Tyr Glu Ile Lys Ala Arg Pro Phe Phe Asn Glu Phe Gln
              705                 710                 715                 720

Gly Ala Asp Ser Glu Ile Lys Phe Ala Lys Thr Leu Glu Glu Ala Pro
              725                 730                 735

Ser Ala Pro Pro Arg Ser Val Thr Val Ser Lys Asn Asp Gly Asn Gly
              740                 745                 750

Thr Ala Ile Leu Val Thr Trp Gln Pro Pro Glu Asp Thr Gln Asn
              755                 760                 765

Gly Met Val Gln Glu Tyr Lys Val Trp Cys Leu Gly Asn Glu Thr Lys
              770                 775                 780

Tyr His Ile Asn Lys Thr Val Asp Gly Ser Thr Phe Ser Val Val Ile
              785                 790                 795                 800

Pro Ser Leu Val Pro Gly Ile Arg Tyr Ser Val Glu Val Ala Ala Ser
              805                 810                 815

Thr Gly Ala Gly Pro Gly Val Lys Ser Glu Pro Gln Phe Ile Gln Leu
              820                 825                 830

Asp Ser His Gly Asn Pro Val Ser Pro Glu Asp Gln Val Ser Leu Ala
              835                 840                 845

Gln Gln Ile Ser Asp Val Val Arg Gln Pro Ala Phe Ile Ala Gly Ile
              850                 855                 860

Gly Ala Ala Cys Trp Ile Ile Leu Met Val Phe Ser Ile Trp Leu Tyr
              865                 870                 875                 880

Arg His Arg Lys Lys Arg Asn Gly Leu Thr Ser Thr Tyr Ala Gly Ile
              885                 890                 895

Arg Lys Val Pro Ser Phe Thr Phe Thr Pro Thr Val Thr Tyr Gln Arg
              900                 905                 910

Gly Gly Glu Ala Val Ser Ser Gly Arg Pro Gly Leu Leu Asn Ile
              915                 920                 925

Ser Glu Pro Ala Thr Gln Pro Trp Leu Ala Asp Thr Trp Pro Asn Thr
              930                 935                 940

Gly Asn Asn His Asn Asp Cys Ser Ile Asn Cys Cys Thr Ala Gly Asn
              945                 950                 955                 960

Gly Asn Ser Asp Ser Asn Leu Thr Thr Tyr Ser Arg Pro Ala Asp Cys
              965                 970                 975

Ile Ala Asn Tyr Asn Asn Gln Leu Asp Asn Lys Gln Thr Asn Leu Met
              980                 985                 990

Leu Pro Glu Ser Thr Val Tyr Gly Asp Val Asp Leu Ser Asn Lys Ile
              995                 1000                1005

Asn Glu Met Lys Thr Phe Asn Ser Pro Asn Leu Lys Asp Gly Arg
              1010                1015                1020

Phe Val Asn Pro Ser Gly Gln Pro Thr Pro Tyr Ala Thr Thr Gln
              1025                1030                1035

Leu Ile Gln Ala Asn Leu Ser Asn Asn Met Asn Asn Gly Ala Gly
              1040                1045                1050

Asp Ser Ser Glu Lys His Trp Lys Pro Pro Gly Gln Gln Lys Pro
              1055                1060                1065
```

```
Glu Val Ala Pro Ile Gln Tyr Asn Ile Met Glu Gln Asn Lys Leu
    1070                1075                1080

Asn Lys Asp Tyr Arg Ala Asn Asp Thr Ile Pro Pro Thr Ile Pro
    1085                1090                1095

Tyr Asn Gln Ser Tyr Asp Gln Asn Thr Gly Gly Ser Tyr Asn Ser
    1100                1105                1110

Ser Asp Arg Gly Ser Ser Thr Ser Gly Ser Gln Gly His Lys Lys
    1115                1120                1125

Gly Ala Arg Thr Pro Lys Ala Pro Lys Gln Gly Gly Met Asn Trp
    1130                1135                1140

Ala Asp Leu Leu Pro Pro Pro Ala His Pro Pro Pro His Ser
    1145                1150                1155

Asn Ser Glu Glu Tyr Asn Met Ser Val Asp Glu Ser Tyr Asp Gln
    1160                1165                1170

Glu Met Pro Cys Pro Val Pro Pro Ala Pro Met Tyr Leu Gln Gln
    1175                1180                1185

Asp Glu Leu Gln Glu Glu Glu Asp Glu Arg Gly Pro Thr Pro Pro
    1190                1195                1200

Val Arg Gly Ala Ala Ser Ser Pro Ala Ala Val Ser Tyr Ser His
    1205                1210                1215

Gln Ser Thr Ala Thr Leu Thr Pro Ser Pro Gln Glu Glu Leu Gln
    1220                1225                1230

Pro Met Leu Gln Asp Cys Pro Glu Asp Leu Gly His Met Pro His
    1235                1240                1245

Pro Pro Asp Arg Arg Arg Gln Pro Val Ser Pro Pro Pro Pro
    1250                1255                1260

Arg Pro Ile Ser Pro Pro His Thr Tyr Gly Tyr Ile Ser Gly Pro
    1265                1270                1275

Leu Val Ser Asp Met Asp Thr Asp Ala Pro Glu Glu Glu Glu Asp
    1280                1285                1290

Glu Ala Asp Met Glu Val Ala Lys Met Gln Thr Arg Arg Leu Leu
    1295                1300                1305

Leu Arg Gly Leu Glu Gln Thr Pro Ala Ser Ser Val Gly Asp Leu
    1310                1315                1320

Glu Ser Ser Val Thr Gly Ser Met Ile Asn Gly Trp Gly Ser Ala
    1325                1330                1335

Ser Glu Glu Asp Asn Ile Ser Ser Gly Arg Ser Ser Val Ser Ser
    1340                1345                1350

Ser Asp Gly Ser Phe Phe Thr Asp Ala Asp Phe Ala Gln Ala Val
    1355                1360                1365

Ala Ala Ala Ala Glu Tyr Ala Gly Leu Lys Val Ala Arg Arg Gln
    1370                1375                1380

Met Gln Asp Ala Ala Gly Arg Arg His Phe His Ala Ser Gln Cys
    1385                1390                1395

Pro Arg Pro Thr Ser Pro Val Ser Thr Asp Ser Asn Met Ser Ala
    1400                1405                1410

Val Val Ile Gln Lys Ala Arg Pro Ala Lys Lys Gln Lys His Gln
    1415                1420                1425

Pro Gly His Leu Arg Arg Glu Ala Tyr Ala Asp Asp Leu Pro Pro
    1430                1435                1440

Pro Pro Val Pro Pro Ala Ile Lys Ser Pro Thr Val Gln Ser
    1445                1450                1455
```

Lys Ala Gln Leu Glu Val Arg Pro Val Met Val Pro Lys Leu Ala
1460            1465            1470

Ser Ile Glu Ala Arg Thr Asp Arg Ser Ser Asp Arg Lys Gly Gly
1475            1480            1485

Ser Tyr Lys Gly Arg Glu Ala Leu Asp Gly Arg Gln Val Thr Asp
1490            1495            1500

Leu Arg Thr Asn Pro Ser Asp Pro Arg Glu Ala Gln Glu Gln Pro
1505            1510            1515

Asn Asp Gly Lys Gly Arg Gly Thr Arg Gln Pro Lys Arg Asp Leu
1520            1525            1530

Pro Pro Ala Lys Thr His Leu Gly Gln Glu Asp Ile Leu Pro Tyr
1535            1540            1545

Cys Arg Pro Thr Phe Pro Thr Ser Asn Asn Pro Arg Asp Pro Ser
1550            1555            1560

Ser Ser Ser Ser Met Ser Ser Arg Gly Ser Gly Ser Arg Gln Arg
1565            1570            1575

Glu Gln Ala Asn Val Gly Arg Arg Asn Met Ala Glu Met Gln Val
1580            1585            1590

Leu Gly Gly Phe Glu Arg Gly Asp Glu Asn Asn Glu Glu Leu Glu
1595            1600            1605

Glu Thr Glu Ser
1610

<210> SEQ ID NO 13
<211> LENGTH: 190
<212> TYPE: PRT
<213> ORGANISM: Homo sapiens

<400> SEQUENCE: 13

Pro Arg Ile Val Glu His Pro Ser Asp Leu Ile Val Ser Lys Gly Glu
1               5                   10                  15

Pro Ala Thr Leu Asn Cys Lys Ala Glu Gly Arg Pro Thr Pro Thr Ile
                20                  25                  30

Glu Trp Tyr Lys Gly Gly Glu Arg Val Glu Thr Asp Lys Asp Asp Pro
            35                  40                  45

Arg Ser His Arg Met Leu Leu Pro Ser Gly Ser Leu Phe Phe Leu Arg
        50                  55                  60

Ile Val His Gly Arg Lys Ser Arg Pro Asp Glu Gly Val Tyr Val Cys
65                  70                  75                  80

Val Ala Arg Asn Tyr Leu Gly Glu Ala Val Ser His Asn Ala Ser Leu
                85                  90                  95

Glu Val Ala Ile Leu Arg Asp Asp Phe Arg Gln Asn Pro Ser Asp Val
            100                 105                 110

Met Val Ala Val Gly Glu Pro Ala Val Met Glu Cys Gln Pro Pro Arg
        115                 120                 125

Gly His Pro Glu Pro Thr Ile Ser Trp Lys Lys Asp Gly Ser Pro Leu
    130                 135                 140

Asp Asp Lys Asp Glu Arg Ile Thr Ile Arg Gly Gly Lys Leu Met Ile
145                 150                 155                 160

Thr Tyr Thr Arg Lys Ser Asp Ala Gly Lys Tyr Val Cys Val Gly Thr
                165                 170                 175

Asn Met Val Gly Glu Arg Glu Ser Glu Val Ala Glu Leu Thr
            180                 185                 190

<210> SEQ ID NO 14

```
<211> LENGTH: 190
<212> TYPE: PRT
<213> ORGANISM: Macaca fascicularis

<400> SEQUENCE: 14

Pro Arg Ile Val Glu His Pro Ser Asp Leu Ile Val Ser Lys Gly Glu
1               5                   10                  15

Pro Ala Thr Leu Asn Cys Lys Ala Glu Gly Arg Pro Thr Pro Thr Ile
            20                  25                  30

Glu Trp Tyr Lys Gly Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Lys Ser Arg Pro Asp Glu Gly Val Tyr Val Cys
65                  70                  75                  80

Val Ala Arg Asn Tyr Leu Gly Glu Ala Val Ser His Asn Ala Ser Leu
                85                  90                  95

Glu Val Ala Ile Leu Arg Asp Asp Phe Arg Gln Asn Pro Ser Asp Val
            100                 105                 110

Met Val Ala Val Gly Glu Pro Ala Val Met Glu Cys Gln Pro Pro Arg
        115                 120                 125

Gly His Pro Glu Pro Thr Ile Ser Trp Lys Lys Asp Gly Ser Pro Leu
    130                 135                 140

Asp Asp Lys Asp Glu Arg Ile Thr Ile Arg Gly Gly Lys Leu Met Ile
145                 150                 155                 160

Thr Tyr Thr Arg Lys Ser Asp Ala Gly Lys Tyr Val Cys Val Gly Thr
                165                 170                 175

Asn Met Val Gly Glu Arg Glu Ser Glu Val Ala Glu Leu Thr
            180                 185                 190

<210> SEQ ID NO 15
<211> LENGTH: 190
<212> TYPE: PRT
<213> ORGANISM: Rattus sp.

<400> SEQUENCE: 15

Pro Arg Ile Val Glu His Pro Ser Asp Leu Ile Val Ser Lys Gly Glu
1               5                   10                  15

Pro Ala Thr Leu Asn Cys Lys Ala Glu Gly Arg Pro Thr Pro Thr Ile
            20                  25                  30

Glu Trp Tyr Lys Gly Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Lys Ser Arg Pro Asp Glu Gly Val Tyr Ile Cys
65                  70                  75                  80

Val Ala Arg Asn Tyr Leu Gly Glu Ala Val Ser His Asn Ala Ser Leu
                85                  90                  95

Glu Val Ala Ile Leu Arg Asp Asp Phe Arg Gln Asn Pro Ser Asp Val
            100                 105                 110

Met Val Ala Val Gly Glu Pro Ala Val Met Glu Cys Gln Pro Pro Arg
        115                 120                 125

Gly His Pro Glu Pro Thr Ile Ser Trp Lys Lys Asp Gly Ser Pro Leu
    130                 135                 140

Asp Asp Lys Asp Glu Arg Ile Thr Ile Arg Gly Gly Lys Leu Met Ile
145                 150                 155                 160
```

Thr Tyr Thr Arg Lys Ser Asp Ala Gly Lys Tyr Val Cys Val Gly Thr
                165                 170                 175

Asn Met Val Gly Glu Arg Glu Ser Lys Val Ala Asp Val Thr
        180                 185                 190

<210> SEQ ID NO 16
<211> LENGTH: 190
<212> TYPE: PRT
<213> ORGANISM: Mus sp.

<400> SEQUENCE: 16

Pro Arg Ile Val Glu His Pro Ser Asp Leu Ile Val Ser Lys Gly Glu
1               5                   10                  15

Pro Ala Thr Leu Asn Cys Lys Ala Glu Gly Arg Pro Thr Pro Thr Ile
            20                  25                  30

Glu Trp Tyr Lys Gly Gly Glu Arg Val Glu Thr Asp Lys Asp Asp Pro
        35                  40                  45

Arg Ser His Arg Met Leu Leu Pro Ser Gly Ser Leu Phe Phe Leu Arg
50                  55                  60

Ile Val His Gly Arg Lys Ser Arg Pro Asp Glu Gly Val Tyr Ile Cys
65                  70                  75                  80

Val Ala Arg Asn Tyr Leu Gly Glu Ala Val Ser His Asn Ala Ser Leu
                85                  90                  95

Glu Val Ala Ile Leu Arg Asp Asp Phe Arg Gln Asn Pro Ser Asp Val
            100                 105                 110

Met Val Ala Val Gly Glu Pro Ala Val Met Glu Cys Gln Pro Pro Arg
        115                 120                 125

Gly His Pro Glu Pro Thr Ile Ser Trp Lys Lys Asp Gly Ser Pro Leu
130                 135                 140

Asp Asp Lys Asp Glu Arg Ile Thr Ile Arg Gly Gly Lys Leu Met Ile
145                 150                 155                 160

Thr Tyr Thr Arg Lys Ser Asp Ala Gly Lys Tyr Val Cys Val Gly Thr
                165                 170                 175

Asn Met Val Gly Glu Arg Glu Ser Glu Val Ala Glu Leu Thr
        180                 185                 190

<210> SEQ ID NO 17
<211> LENGTH: 1378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ser Leu Leu Met Phe Thr Gln Leu Leu Leu Cys Gly Phe Leu Tyr
1               5                   10                  15

Val Arg Val Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
        35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

-continued

```
His Gly Arg Lys Ser Arg Pro Asp Glu Gly Ser Tyr Val Cys Val Ala
            100                 105                 110

Arg Asn Tyr Leu Gly Glu Ala Val Ser Arg Asn Ala Ser Leu Glu Val
            115                 120                 125

Ala Leu Leu Arg Asp Asp Phe Arg Gln Asn Pro Thr Asp Val Val Val
145             130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
            180                 185                 190

Thr Arg Lys Ser Asp Ala Gly Met Tyr Thr Cys Val Gly Thr Asn Met
            195                 200                 205

Val Gly Glu Arg Asp Ser Asp Pro Ala Glu Leu Thr Val Phe Glu Arg
            210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                245                 250                 255

Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Thr Met Ser Thr Asp Glu
            275                 280                 285

Gly Thr Tyr Met Cys Ile Ala Glu Asn Arg Val Gly Lys Met Glu Ala
            290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                325                 330                 335

Thr Lys Gly Asn Pro Gln Pro Ala Val Phe Trp Gln Lys Glu Gly Ser
            340                 345                 350

Gln Asn Leu Leu Phe Pro Asn Gln Pro Gln Pro Asn Ser Arg Cys
            355                 360                 365

Ser Val Ser Pro Thr Gly Asp Leu Thr Ile Thr Asn Ile Gln Arg Ser
370                 375                 380

Asp Ala Gly Tyr Tyr Ile Cys Gln Ala Leu Thr Val Ala Gly Ser Ile
385                 390                 395                 400

Leu Ala Lys Ala Gln Leu Glu Val Thr Asp Val Leu Thr Asp Arg Pro
                405                 410                 415

Pro Pro Ile Ile Leu Gln Gly Pro Ala Asn Gln Thr Leu Ala Val Asp
            420                 425                 430

Gly Thr Ala Leu Leu Lys Cys Lys Ala Thr Gly Asp Pro Leu Pro Val
            435                 440                 445

Ile Ser Trp Leu Lys Glu Gly Phe Thr Phe Pro Gly Arg Asp Pro Arg
            450                 455                 460

Ala Thr Ile Gln Glu Gln Gly Thr Leu Gln Ile Lys Asn Leu Arg Ile
465                 470                 475                 480

Ser Asp Thr Gly Thr Tyr Thr Cys Val Ala Thr Ser Ser Ser Gly Glu
                485                 490                 495

Thr Ser Trp Ser Ala Val Leu Asp Val Thr Glu Ser Gly Ala Thr Ile
            500                 505                 510
```

```
Ser Lys Asn Tyr Asp Leu Ser Asp Leu Pro Gly Pro Pro Ser Lys Pro
            515                 520                 525

Gln Val Thr Asp Val Thr Lys Asn Ser Val Thr Leu Ser Trp Gln Pro
530                 535                 540

Gly Thr Pro Gly Thr Leu Pro Ala Ser Ala Tyr Ile Ile Glu Ala Phe
545                 550                 555                 560

Ser Gln Ser Val Ser Asn Ser Trp Gln Thr Val Ala Asn His Val Lys
            565                 570                 575

Thr Thr Leu Tyr Thr Val Arg Gly Leu Arg Pro Asn Thr Ile Tyr Leu
            580                 585                 590

Phe Met Val Arg Ala Ile Asn Pro Gln Gly Leu Ser Asp Pro Ser Pro
            595                 600                 605

Met Ser Asp Pro Val Arg Thr Gln Asp Ile Ser Pro Pro Ala Gln Gly
            610                 615                 620

Val Asp His Arg Gln Val Gln Lys Glu Leu Gly Asp Val Leu Val Arg
625                 630                 635                 640

Leu His Asn Pro Val Val Leu Thr Pro Thr Thr Val Gln Val Thr Trp
                    645                 650                 655

Thr Val Asp Arg Gln Pro Gln Phe Ile Gln Gly Tyr Arg Val Met Tyr
            660                 665                 670

Arg Gln Thr Ser Gly Leu Gln Ala Thr Ser Ser Trp Gln Asn Leu Asp
            675                 680                 685

Ala Lys Val Pro Thr Glu Arg Ser Ala Val Leu Val Asn Leu Lys Lys
            690                 695                 700

Gly Val Thr Tyr Glu Ile Lys Val Arg Pro Tyr Phe Asn Glu Phe Gln
705                 710                 715                 720

Gly Met Asp Ser Glu Ser Lys Thr Val Arg Thr Thr Glu Glu Ala Pro
                    725                 730                 735

Ser Ala Pro Pro Gln Ser Val Thr Val Leu Thr Val Gly Ser Tyr Asn
                    740                 745                 750

Ser Thr Ser Ile Ser Val Ser Trp Asp Pro Pro Pro Asp His Gln
            755                 760                 765

Asn Gly Ile Ile Gln Glu Tyr Lys Ile Trp Cys Leu Gly Asn Glu Thr
770                 775                 780

Arg Phe His Ile Asn Lys Thr Val Asp Ala Ala Ile Arg Ser Val Ile
785                 790                 795                 800

Ile Gly Gly Leu Phe Pro Gly Ile Gln Tyr Arg Val Glu Val Ala Ala
                    805                 810                 815

Ser Thr Ser Ala Gly Val Gly Val Lys Ser Glu Pro Gln Pro Ile Ile
            820                 825                 830

Ile Gly Arg Arg Asn Glu Val Val Ile Thr Glu Asn Asn Ser Ile
            835                 840                 845

Thr Glu Gln Ile Thr Asp Val Val Lys Gln Pro Ala Phe Ile Ala Gly
850                 855                 860

Ile Gly Gly Ala Cys Trp Val Ile Leu Met Gly Phe Ser Ile Trp Leu
865                 870                 875                 880

Tyr Trp Arg Arg Lys Lys Arg Lys Gly Leu Ser Asn Tyr Ala Val Thr
            885                 890                 895

Phe Gln Arg Gly Asp Gly Gly Leu Met Ser Asn Gly Ser Arg Pro Gly
            900                 905                 910

Leu Leu Asn Ala Gly Asp Pro Ser Tyr Pro Trp Leu Ala Asp Ser Trp
            915                 920                 925

Pro Ala Thr Ser Leu Pro Val Asn Asn Ser Asn Ser Gly Pro Asn Glu
```

-continued

```
            930                 935                 940
Ile Gly Asn Phe Gly Arg Gly Asp Val Leu Pro Pro Val Pro Gly Gln
945                 950                 955                 960

Gly Asp Lys Thr Ala Thr Met Leu Ser Asp Gly Ala Ile Tyr Ser Ser
            965                 970                 975

Ile Asp Phe Thr Thr Lys Thr Ser Tyr Asn Ser Ser Gln Ile Thr
            980                 985                 990

Gln Ala Thr Pro Tyr Ala Thr Thr Gln Ile Leu His Ser Asn Ser Ile
            995                 1000                1005

His Glu Leu Ala Val Asp Leu Pro Asp Pro Gln Trp Lys Ser Ser
        1010                1015                1020

Ile Gln Gln Lys Thr Asp Leu Met Gly Phe Gly Tyr Ser Leu Pro
        1025                1030                1035

Asp Gln Asn Lys Gly Asn Asn Gly Gly Lys Gly Lys Lys Lys
        1040                1045                1050

Lys Asn Lys Asn Ser Ser Lys Pro Gln Lys Asn Asn Gly Ser Thr
        1055                1060                1065

Trp Ala Asn Val Pro Leu Pro Pro Pro Val Gln Pro Leu Pro
        1070                1075                1080

Gly Thr Glu Leu Glu His Tyr Ala Val Glu Gln Gln Glu Asn Gly
        1085                1090                1095

Tyr Asp Ser Asp Ser Trp Cys Pro Pro Leu Pro Val Gln Thr Tyr
        1100                1105                1110

Leu His Gln Gly Leu Glu Asp Glu Leu Glu Glu Asp Asp Asp Arg
        1115                1120                1125

Val Pro Thr Pro Pro Val Arg Gly Val Ala Ser Ser Pro Ala Ile
        1130                1135                1140

Ser Phe Gly Gln Gln Ser Thr Ala Thr Leu Thr Pro Ser Pro Arg
        1145                1150                1155

Glu Glu Met Gln Pro Met Leu Gln Ala His Leu Asp Glu Leu Thr
        1160                1165                1170

Arg Ala Tyr Gln Phe Asp Ile Ala Lys Gln Thr Trp His Ile Gln
        1175                1180                1185

Ser Asn Asn Gln Pro Pro Gln Pro Pro Val Pro Pro Leu Gly Tyr
        1190                1195                1200

Val Ser Gly Ala Leu Ile Ser Asp Leu Glu Thr Asp Val Ala Asp
        1205                1210                1215

Asp Asp Ala Asp Asp Glu Glu Glu Ala Leu Glu Ile Pro Arg Pro
        1220                1225                1230

Leu Arg Ala Leu Asp Gln Thr Pro Gly Ser Ser Met Asp Asn Leu
        1235                1240                1245

Asp Ser Ser Val Thr Gly Lys Ala Phe Thr Ser Ser Gln Arg Pro
        1250                1255                1260

Arg Pro Thr Ser Pro Phe Ser Thr Asp Ser Asn Thr Ser Ala Ala
        1265                1270                1275

Leu Ser Gln Ser Gln Arg Pro Arg Pro Thr Lys Lys His Lys Gly
        1280                1285                1290

Gly Arg Met Asp Gln Gln Pro Ala Leu Pro His Arg Arg Glu Gly
        1295                1300                1305

Met Thr Asp Glu Glu Ala Leu Val Pro Tyr Ser Lys Pro Ser Phe
        1310                1315                1320

Pro Ser Pro Gly Gly His Ser Ser Ser Gly Thr Ala Ser Ser Lys
        1325                1330                1335
```

Gly Ser Thr Gly Pro Arg Lys Thr Glu Val Leu Arg Ala Gly His
    1340                1345                1350

Gln Arg Asn Ala Ser Asp Leu Leu Asp Ile Gly Tyr Met Gly Ser
    1355                1360                1365

Asn Ser Gln Gly Gln Phe Thr Gly Glu Leu
    1370                1375

<210> SEQ ID NO 18
<211> LENGTH: 1651
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Trp Lys His Val Pro Phe Leu Val Met Ile Ser Leu Leu Ser
1               5                   10                  15

Leu Ser Pro Asn His Leu Phe Leu Ala Gln Leu Ile Pro Asp Pro Glu
            20                  25                  30

Asp Val Glu Arg Gly Asn Asp His Gly Thr Pro Ile Pro Thr Ser Asp
        35                  40                  45

Asn Asp Asp Asn Ser Leu Gly Tyr Thr Gly Ser Arg Leu Arg Gln Glu
50                  55                  60

Asp Phe Pro Pro Arg Ile Val Glu His Pro Ser Asp Leu Ile Val Ser
65                  70                  75                  80

Lys Gly Glu Pro Ala Thr Leu Asn Cys Lys Ala Glu Gly Arg Pro Thr
                85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Arg Ser Lys Pro Asp Glu Gly Val
    130                 135                 140

Tyr Val Cys Val Ala Arg Asn Tyr Leu Gly Glu Ala Val Ser His Asn
145                 150                 155                 160

Ala Ser Leu Glu Val Ala Ile Leu Arg Asp Asp Phe Arg Gln Asn Pro
                165                 170                 175

Ser Asp Val Met Val Ala Val Gly Glu Pro Ala Val Met Glu Cys Gln
            180                 185                 190

Pro Pro Arg Gly His Pro Glu Pro Thr Ile Ser Trp Lys Lys Asp Gly
        195                 200                 205

Ser Pro Leu Asp Asp Lys Asp Glu Arg Ile Thr Ile Arg Gly Gly Lys
    210                 215                 220

Leu Met Ile Thr Tyr Thr Arg Lys Ser Asp Ala Gly Lys Tyr Val Cys
225                 230                 235                 240

Val Gly Thr Asn Met Val Gly Arg Glu Ser Glu Val Ala Glu Leu
                245                 250                 255

Thr Val Leu Glu Arg Pro Ser Phe Val Lys Arg Pro Ser Asn Leu Ala
            260                 265                 270

Val Thr Val Asp Asp Ser Ala Glu Phe Lys Cys Glu Ala Arg Gly Asp
        275                 280                 285

Pro Val Pro Thr Val Arg Trp Arg Lys Asp Asp Gly Glu Leu Pro Lys
    290                 295                 300

Ser Arg Tyr Glu Ile Arg Asp Asp His Thr Leu Lys Ile Arg Lys Val

```
            305                 310                 315                 320
        Thr Ala Gly Asp Met Gly Ser Tyr Thr Cys Val Ala Glu Asn Met Val
                        325                 330                 335
        Gly Lys Ala Glu Ala Ser Ala Thr Leu Thr Val Gln Glu Pro Pro His
                        340                 345                 350
        Phe Val Val Lys Pro Arg Asp Gln Val Val Ala Leu Gly Arg Thr Val
                        355                 360                 365
        Thr Phe Gln Cys Glu Ala Thr Gly Asn Pro Gln Pro Ala Ile Phe Trp
            370                 375                 380
        Arg Arg Glu Gly Ser Gln Asn Leu Leu Phe Ser Tyr Gln Pro Pro Gln
        385                 390                 395                 400
        Ser Ser Ser Arg Phe Ser Val Ser Gln Thr Gly Asp Leu Thr Ile Thr
                        405                 410                 415
        Asn Val Gln Arg Ser Asp Val Gly Tyr Tyr Ile Cys Gln Thr Leu Asn
                        420                 425                 430
        Val Ala Gly Ser Ile Ile Thr Lys Ala Tyr Leu Glu Val Thr Asp Val
                        435                 440                 445
        Ile Ala Asp Arg Pro Pro Val Ile Arg Gln Gly Pro Val Asn Gln
            450                 455                 460
        Thr Val Ala Val Asp Gly Thr Phe Val Leu Ser Cys Val Ala Thr Gly
        465                 470                 475                 480
        Ser Pro Val Pro Thr Ile Leu Trp Arg Lys Asp Gly Val Leu Val Ser
                        485                 490                 495
        Thr Gln Asp Ser Arg Ile Lys Gln Leu Glu Asn Gly Val Leu Gln Ile
                        500                 505                 510
        Arg Tyr Ala Lys Leu Gly Asp Thr Gly Arg Tyr Thr Cys Ile Ala Ser
                        515                 520                 525
        Thr Pro Ser Gly Glu Ala Thr Trp Ser Ala Tyr Ile Glu Val Gln Glu
                        530                 535                 540
        Phe Gly Val Pro Val Gln Pro Pro Arg Pro Thr Asp Pro Asn Leu Ile
        545                 550                 555                 560
        Pro Ser Ala Pro Ser Lys Pro Glu Val Thr Asp Val Ser Arg Asn Thr
                        565                 570                 575
        Val Thr Leu Ser Trp Gln Pro Asn Leu Asn Ser Gly Ala Thr Pro Thr
                        580                 585                 590
        Ser Tyr Ile Ile Glu Ala Phe Ser His Ala Ser Gly Ser Ser Trp Gln
                        595                 600                 605
        Thr Val Ala Glu Asn Val Lys Thr Glu Thr Ser Ala Ile Lys Gly Leu
                        610                 615                 620
        Lys Pro Asn Ala Ile Tyr Leu Phe Leu Val Arg Ala Ala Asn Ala Tyr
        625                 630                 635                 640
        Gly Ile Ser Asp Pro Ser Gln Ile Ser Asp Pro Val Lys Thr Gln Asp
                        645                 650                 655
        Val Leu Pro Thr Ser Gln Gly Val Asp His Lys Gln Val Gln Arg Glu
                        660                 665                 670
        Leu Gly Asn Ala Val Leu His Leu His Asn Pro Thr Val Leu Ser Ser
                        675                 680                 685
        Ser Ser Ile Glu Val His Trp Thr Val Asp Gln Gln Ser Gln Tyr Ile
                        690                 695                 700
        Gln Gly Tyr Lys Ile Leu Tyr Arg Pro Ser Gly Ala Asn His Gly Glu
        705                 710                 715                 720
        Ser Asp Trp Leu Val Phe Glu Val Arg Thr Pro Ala Lys Asn Ser Val
                        725                 730                 735
```

```
Val Ile Pro Asp Leu Arg Lys Gly Val Asn Tyr Glu Ile Lys Ala Arg
            740                 745                 750

Pro Phe Phe Asn Glu Phe Gln Gly Ala Asp Ser Glu Ile Lys Phe Ala
            755                 760                 765

Lys Thr Leu Glu Glu Ala Pro Ser Ala Pro Gln Gly Val Thr Val
        770                 775                 780

Ser Lys Asn Asp Gly Asn Gly Thr Ala Ile Leu Val Ser Trp Gln Pro
785                 790                 795                 800

Pro Pro Glu Asp Thr Gln Asn Gly Met Val Gln Glu Tyr Lys Val Trp
            805                 810                 815

Cys Leu Gly Asn Glu Thr Arg Tyr His Ile Asn Lys Thr Val Asp Gly
            820                 825                 830

Ser Thr Phe Ser Val Val Ile Pro Phe Leu Val Pro Gly Ile Arg Tyr
            835                 840                 845

Ser Val Glu Val Ala Ala Ser Thr Gly Ala Gly Ser Gly Val Lys Ser
        850                 855                 860

Glu Pro Gln Phe Ile Gln Leu Asp Ala His Gly Asn Pro Val Ser Pro
865                 870                 875                 880

Glu Asp Gln Val Ser Leu Ala Gln Gln Ile Ser Asp Val Val Lys Gln
            885                 890                 895

Pro Ala Phe Ile Ala Gly Ile Gly Ala Ala Cys Trp Ile Ile Leu Met
            900                 905                 910

Val Phe Ser Ile Trp Leu Tyr Arg His Arg Lys Lys Arg Asn Gly Leu
            915                 920                 925

Thr Ser Thr Tyr Ala Gly Ile Arg Lys Val Pro Ser Phe Thr Phe Thr
            930                 935                 940

Pro Thr Val Thr Tyr Gln Arg Gly Gly Glu Ala Val Ser Ser Gly Gly
945                 950                 955                 960

Arg Pro Gly Leu Leu Asn Ile Ser Glu Pro Ala Ala Gln Pro Trp Leu
            965                 970                 975

Ala Asp Thr Trp Pro Asn Thr Gly Asn Asn His Asn Asp Cys Ser Ile
            980                 985                 990

Ser Cys Cys Thr Ala Gly Asn Gly Asn Ser Asp Ser Asn Leu Thr Thr
        995                 1000                1005

Tyr Ser Arg Pro Ala Asp Cys Ile Ala Asn Tyr Asn Asn Gln Leu
    1010                1015                1020

Asp Asn Lys Gln Thr Asn Leu Met Leu Pro Glu Ser Thr Val Tyr
    1025                1030                1035

Gly Asp Val Asp Leu Ser Asn Lys Ile Asn Glu Met Lys Thr Phe
    1040                1045                1050

Asn Ser Pro Asn Leu Lys Asp Gly Arg Phe Val Asn Pro Ser Gly
    1055                1060                1065

Gln Pro Thr Pro Tyr Ala Thr Thr Gln Leu Ile Gln Ser Asn Leu
    1070                1075                1080

Ser Asn Asn Met Asn Asn Gly Ser Gly Asp Ser Gly Glu Lys His
    1085                1090                1095

Trp Lys Pro Leu Gly Gln Gln Lys Gln Glu Val Ala Pro Val Gln
    1100                1105                1110

Tyr Asn Ile Val Glu Gln Asn Lys Leu Asn Lys Asp Tyr Arg Ala
    1115                1120                1125

Asn Asp Thr Val Pro Pro Thr Ile Pro Tyr Asn Gln Ser Tyr Asp
    1130                1135                1140
```

-continued

| | | | | | | | | | | |
|---|---|---|---|---|---|---|---|---|---|---|
|Gln|Asn|Thr|Gly|Gly|Ser|Tyr|Asn|Ser|Ser|Asp|Arg|Gly|Ser|Ser|
| |1145| | | |1150| | | |1155| |

Thr Ser Gly Ser Gln Gly His Lys Lys Gly Ala Arg Thr Pro Lys
    1160              1165              1170

Val Pro Lys Gln Gly Gly Met Asn Trp Ala Asp Leu Leu Pro Pro
    1175              1180              1185

Pro Pro Ala His Pro Pro His Ser Asn Ser Glu Glu Tyr Asn
    1190              1195              1200

Ile Ser Val Asp Glu Ser Tyr Asp Gln Glu Met Pro Cys Pro Val
    1205              1210              1215

Pro Pro Ala Arg Met Tyr Leu Gln Gln Asp Glu Leu Glu Glu Glu
    1220              1225              1230

Glu Asp Glu Arg Gly Pro Thr Pro Pro Val Arg Gly Ala Ala Ser
    1235              1240              1245

Ser Pro Ala Ala Val Ser Tyr Ser His Gln Ser Thr Ala Thr Leu
    1250              1255              1260

Thr Pro Ser Pro Gln Glu Glu Leu Gln Pro Met Leu Gln Asp Cys
    1265              1270              1275

Pro Glu Glu Thr Gly His Met Gln His Gln Pro Asp Arg Arg Arg
    1280              1285              1290

Gln Pro Val Ser Pro Pro Pro Pro Arg Pro Ile Ser Pro Pro
    1295              1300              1305

His Thr Tyr Gly Tyr Ile Ser Gly Pro Leu Val Ser Asp Met Asp
    1310              1315              1320

Thr Asp Ala Pro Glu Glu Glu Asp Glu Ala Asp Met Glu Val
    1325              1330              1335

Ala Lys Met Gln Thr Arg Arg Leu Leu Leu Arg Gly Leu Glu Gln
    1340              1345              1350

Thr Pro Ala Ser Ser Val Gly Asp Leu Glu Ser Ser Val Thr Gly
    1355              1360              1365

Ser Met Ile Asn Gly Trp Gly Ser Ala Ser Glu Glu Asp Asn Ile
    1370              1375              1380

Ser Ser Gly Arg Ser Ser Val Ser Ser Ser Asp Gly Ser Phe Phe
    1385              1390              1395

Thr Asp Ala Asp Phe Ala Gln Ala Val Ala Ala Ala Glu Tyr
    1400              1405              1410

Ala Gly Leu Lys Val Ala Arg Arg Gln Met Gln Asp Ala Ala Gly
    1415              1420              1425

Arg Arg His Phe His Ala Ser Gln Cys Pro Arg Pro Thr Ser Pro
    1430              1435              1440

Val Ser Thr Asp Ser Asn Met Ser Ala Ala Val Met Gln Lys Thr
    1445              1450              1455

Arg Pro Ala Lys Lys Leu Lys His Gln Pro Gly His Leu Arg Arg
    1460              1465              1470

Glu Thr Tyr Thr Asp Asp Leu Pro Pro Pro Val Pro Pro Pro
    1475              1480              1485

Ala Ile Lys Ser Pro Thr Ala Gln Ser Lys Thr Gln Leu Glu Val
    1490              1495              1500

Arg Pro Val Val Val Pro Lys Leu Pro Ser Met Asp Ala Arg Thr
    1505              1510              1515

Asp Arg Ser Ser Asp Arg Lys Gly Ser Ser Tyr Lys Gly Arg Glu
    1520              1525              1530

Val Leu Asp Gly Arg Gln Val Val Asp Met Arg Thr Asn Pro Gly

```
                    1535                1540                1545

Asp Pro Arg Glu Ala Gln Glu Gln Gln Asn Asp Gly Lys Gly Arg
        1550                1555                1560

Gly Asn Lys Ala Ala Lys Arg Asp Leu Pro Pro Ala Lys Thr His
    1565                1570                1575

Leu Ile Gln Glu Asp Ile Leu Pro Tyr Cys Arg Pro Thr Phe Pro
    1580                1585                1590

Thr Ser Asn Asn Pro Arg Asp Pro Ser Ser Ser Ser Met Ser
    1595                1600                1605

Ser Arg Gly Ser Gly Ser Arg Gln Arg Glu Gln Ala Asn Val Gly
    1610                1615                1620

Arg Arg Asn Ile Ala Glu Met Gln Val Leu Gly Tyr Glu Arg
    1625                1630                1635

Gly Glu Asp Asn Asn Glu Glu Leu Glu Glu Thr Glu Ser
    1640                1645                1650

<210> SEQ ID NO 19
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Lys Ser Arg Pro Asp Glu Gly Ser Tyr Val Cys Val
65                  70                  75                  80

Ala Arg Asn Tyr Leu Gly Glu Ala Val Ser Arg Asn Ala Ser Leu Glu
                85                  90                  95

Val Ala Leu Leu Arg Asp Asp Phe Arg Gln Asn Pro Thr Asp Val Val
            100                 105                 110

Val Ala Ala Gly Glu Pro Ala Ile Leu Glu Cys Gln Pro Pro Arg Gly
        115                 120                 125

His Pro Glu Pro Thr Ile Tyr Trp Lys Lys Asp Lys Val Arg Ile Asp
    130                 135                 140

Asp Lys Glu Glu Arg Ile Ser Ile Arg Gly Gly Lys Leu Met Ile Ser
145                 150                 155                 160

Asn Thr Arg Lys Ser Asp Ala Gly Met Tyr Thr Cys Val Gly Thr Asn
                165                 170                 175

Met Val Gly Glu Arg Asp Ser Asp Pro Ala Glu Leu Thr
            180                 185

<210> SEQ ID NO 20
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 20

Pro Arg Ile Val Glu His Pro Ser Asp Leu Ile Val Ser Lys Gly Glu
1               5                   10                  15

Pro Ala Thr Leu Asn Cys Lys Ala Glu Gly Arg Pro Thr Pro Thr Ile
            20                  25                  30

Glu Trp Tyr Lys Gly Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Arg Ser Lys Pro Asp Glu Gly Val Tyr Val Cys
65                  70                  75                  80

Val Ala Arg Asn Tyr Leu Gly Glu Ala Val Ser His Asn Ala Ser Leu
                85                  90                  95

Glu Val Ala Ile Leu Arg Asp Asp Phe Arg Gln Asn Pro Ser Asp Val
            100                 105                 110

Met Val Ala Val Gly Glu Pro Ala Val Met Glu Cys Gln Pro Pro Arg
        115                 120                 125

Gly His Pro Glu Pro Thr Ile Ser Trp Lys Lys Asp Gly Ser Pro Leu
    130                 135                 140

Asp Asp Lys Asp Glu Arg Ile Thr Ile Arg Gly Lys Leu Met Ile
145                 150                 155                 160

Thr Tyr Thr Arg Lys Ser Asp Ala Gly Lys Tyr Val Cys Val Gly Thr
                165                 170                 175

Asn Met Val Gly Glu Arg Glu Ser Glu Val Ala Glu Leu Thr
            180                 185                 190

<210> SEQ ID NO 21
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgggatgga gctgtatcat cctcttcttg gtagcaacag ctacaggcgt gcactccgag      60
gtccagctgg tgcagtctgg ggctgaggtg aagaagcctg gggcctcagt gaaggtctcc     120
tgcaaggctt ctgggtacac cttcaccggc tactatatgc actgggtgcg acaggcccct     180
ggacaagggc ttgagtggat gggatggatc aatcctaaga atggtgatac agagtttcca     240
cagaagtttc agggcagggt caccatgacc aggacacgt ccatcaccac agcctacatg      300
gacctgagca ggctcagatc tgacgacacg gccgtgtatt actgtgcgag agaaagtggg     360
gatgatgctt ttgatatttg gggccaaggg acaatggtca ccgtctcgag c              411

<210> SEQ ID NO 22
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

```
Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Lys Asn Gly Asp Thr Glu Phe Pro
65                  70                  75                  80

Gln Lys Phe Gln Gly Arg Val Thr Met Thr Arg Asp Thr Ser Ile Thr
                85                  90                  95

Thr Ala Tyr Met Asp Leu Ser Arg Leu Arg Ser Asp Asp Thr Ala Val
            100                 105                 110

Tyr Tyr Cys Ala Arg Glu Ser Gly Asp Asp Ala Phe Asp Ile Trp Gly
        115                 120                 125

Gln Gly Thr Met Val Thr Val Ser Ser
        130                 135

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Gly Trp Ser Cys Ile Ile Leu Phe Leu Val Ala Thr Ala Thr Gly
1               5                   10                  15

Val His Ser

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Tyr Thr Phe Thr Gly Tyr Tyr Met His
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Ile Asn Pro Lys Asn Gly Asp Thr Glu Phe Pro Gln Lys Phe Gln
1               5                   10                  15

Gly

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

<210> SEQ ID NO 27
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atgggatgga gctgtatcat cctcttcttg gtagcaacag ctacaggcgt gcactccgac      60
atcgtgatga cccagtctcc atcctccctg tctgcatctg taggagacag agtcaccatc     120
acttgccggg caagtcagag cattagcagc tatttaaatt ggtatcagca gaaaccaggg     180
aaagccccta agctcctgat ctatgctgca tccagtttgc aaagtggggt cccatcaagg     240
ttcagtggca gtggatctgg gacagatttc actctcacca tcagcagtct gcaacctgaa     300
gattttgcaa cttactactg tcaacagtcg gttggtcttt ttttcggcgg agggaccaag     360
gtggagatca aa                                                         372
```

<210> SEQ ID NO 28
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Ser Ala
            20                  25                  30

Ser Val Gly Asp Arg Val Thr Ile Thr Cys Arg Ala Ser Gln Ser Ile
        35                  40                  45

Ser Ser Tyr Leu Asn Trp Tyr Gln Gln Lys Pro Gly Lys Ala Pro Lys
    50                  55                  60

Leu Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Val Gly
            100                 105                 110

Leu Phe Phe Gly Gly Gly Thr Lys Val Glu Ile Lys
        115                 120

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser Gln Ser Ile Ser Ser Tyr Leu Asn
1               5                   10

<210> SEQ ID NO 30

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ala Ser Ser Leu Gln Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Ser Val Gly Leu Phe
1               5

<210> SEQ ID NO 32
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Gly Gln Gly Thr Met Val Thr Val Ser Ser
1               5                   10

<210> SEQ ID NO 34
<211> LENGTH: 98
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Pro Lys Ser Cys Asp Lys Thr His Thr Cys Pro Pro Cys Pro
1               5                   10                  15

<210> SEQ ID NO 36
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 37
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 37

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 38
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

```
His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 39
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys
            100                 105

<210> SEQ ID NO 40
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 40

Phe Gly Gly Gly Thr Lys Val Glu Ile Lys
1               5                   10

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 42
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140
```

```
Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Ala Thr Asn Phe Pro Gln Lys Phe
        50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Ile Asn Pro Asn Ser Gly Ala Thr Asn Phe Pro Gln Lys Phe Gln
1               5                   10                  15

Gly

<210> SEQ ID NO 45
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Ala Thr Asn Phe Pro Gln Lys Phe
50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
            85                  90                  95

Ala Arg Glu Ser Gly Asp Ala Phe Asp Ile Trp Gly Gln Gly Thr
                100                 105                 110

Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 46
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys
            100                 105

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Ser Tyr Ser Thr Ser
1               5

<210> SEQ ID NO 48
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys Arg Thr Val Ala Ala Pro Ser

```
            100                 105                 110
Val Phe Ile Phe Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asp Met His Trp Val Arg Gln Ala Pro Gly Gln Gly Leu Glu Trp Met
        35                  40                  45

Gly Trp Ile Asn Pro Asn Ser Gly Ala Thr Asn Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Tyr Thr Phe Thr Gly Tyr Asp Met His
1               5                   10

<210> SEQ ID NO 51
<211> LENGTH: 448
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 51

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Asp Met His Trp Val Arg Gln Ala Pro Gly Gln Gly Leu Glu Trp Met
        35                  40                  45
Gly Trp Ile Asn Pro Asn Ser Gly Ala Thr Asn Phe Pro Gln Lys Phe
    50                  55                  60
Gln Gly Arg Val Thr Met Thr Arg Asp Thr Ser Ile Thr Thr Ala Tyr
65                  70                  75                  80
Met Asp Leu Ser Arg Leu Arg Ser Asp Thr Ala Val Tyr Tyr Cys
                85                  90                  95
Ala Arg Glu Ser Gly Asp Asp Ala Phe Asp Ile Trp Gly Gln Gly Thr
            100                 105                 110
Met Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Ala Ala Gly Ala Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445
```

<210> SEQ ID NO 52
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys
            100                 105
```

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Arg Ala Ser Gln Lys Ile Ser Ser Tyr Leu Asn
1               5                   10
```

<210> SEQ ID NO 54
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Thr Ser Phe
                    85                  90                  95

Gly Gly Gly Thr Lys Val Glu Ile Lys Arg Thr Val Ala Ala Pro Ser
                100                 105                 110

Val Phe Ile Phe Pro Pro Ser Asp Glu Gln Leu Lys Ser Gly Thr Ala
                115                 120                 125

Ser Val Val Cys Leu Leu Asn Asn Phe Tyr Pro Arg Glu Ala Lys Val
            130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
                180                 185                 190

Glu Val Thr His Gln Gly Leu Ser Ser Pro Val Thr Lys Ser Phe Asn
                195                 200                 205

Arg Gly Glu Cys
        210

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Lys Ser Gly Ala Thr Asn Phe Pro Gln Lys Phe
        50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
                100                 105                 110

Met Val Thr Val Ser Ser
        115

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Ile Asn Pro Lys Ser Gly Ala Thr Asn Phe Pro Gln Lys Phe Gln
1               5                   10                  15

Gly
```

<210> SEQ ID NO 57
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Ala Thr Asn Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
            85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
```

```
                355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 58
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys
            100                 105

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ala Ser Gln Arg Ile Ser Ser Tyr Leu Asn
1               5                   10

<210> SEQ ID NO 60
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Ser Tyr
            20                  25                  30
```

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
            195                 200                 205

Arg Gly Glu Cys
    210

<210> SEQ ID NO 61
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys
            100                 105

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

```
Ala Ala Ser Ser Leu Gln Asp
1               5

<210> SEQ ID NO 63
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys Arg Thr Val Ala Ala Pro Ser
                100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 64
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Glu Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Ser Phe
                 85                  90                  95

Gly Gly Gly Thr Lys Val Glu Ile Lys
            100                 105

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Ser Ser Leu Gln Glu
1               5

<210> SEQ ID NO 66
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Val Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Glu Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Ser Phe
                 85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
            195                 200                 205

Arg Gly Glu Cys
    210

<210> SEQ ID NO 67
```

<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys
            100                 105

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ala Ser Ser Leu Gln Tyr
1               5

<210> SEQ ID NO 69
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
                180                 185                 190

Glu Val Thr His Gln Gly Leu Ser Ser Pro Val Thr Lys Ser Phe Asn
                195                 200                 205

Arg Gly Glu Cys
    210

<210> SEQ ID NO 70
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Arg Ser Gly Ala Thr Asn Phe Pro Gln Lys Phe
50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Ile Asn Pro Arg Ser Gly Ala Thr Asn Phe Pro Gln Lys Phe Gln
1               5                   10                  15

Gly

<210> SEQ ID NO 72
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Glu Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Arg Ser Gly Ala Thr Asn Phe Pro Gln Lys Phe
50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ala Ile Asp Pro Lys Ser Gly Thr Thr Met Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Ile Asp Pro Lys Ser Gly Thr Thr Met Phe Pro Gln Lys Phe Gln
1               5                   10                  15

Gly

<210> SEQ ID NO 75
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ala Ile Asp Pro Lys Ser Gly Thr Thr Met Phe Pro Gln Lys Phe
    50                  55                  60

Gln Gly Arg Val Thr Met Thr Arg Asp Thr Ser Ile Thr Thr Ala Tyr
 65                  70                  75                  80

Met Asp Leu Ser Arg Leu Arg Ser Asp Asp Thr Ala Val Tyr Tyr Cys
                 85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 76
<211> LENGTH: 118
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 76

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ala Ile Asp Pro Lys Leu Gly Ile Thr Ile Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 77

Ala Ile Asp Pro Lys Leu Gly Ile Thr Ile Phe Pro Gln Lys Phe Gln
1               5                   10                  15

Gly

<210> SEQ ID NO 78
<211> LENGTH: 448
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 78

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ala Ile Asp Pro Lys Leu Gly Ile Thr Ile Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 79
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met

```
                35                  40                  45
Gly Met Ile Asn Pro Lys Ser Gly Phe Thr Ala Phe Pro Gln Lys Phe
         50                  55                  60

Gln Gly Arg Val Thr Met Thr Arg Asp Thr Ser Ile Thr Thr Ala Tyr
 65                  70                  75                  80

Met Asp Leu Ser Arg Leu Arg Ser Asp Thr Ala Val Tyr Tyr Cys
                 85                  90                  95

Ala Arg Glu Ser Gly Asp Asp Ala Phe Asp Ile Trp Gly Gln Gly Thr
                100                 105                 110

Met Val Thr Val Ser Ser
            115

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Met Ile Asn Pro Lys Ser Gly Phe Thr Ala Phe Pro Gln Lys Phe Gln
1               5                   10                  15

Gly

<210> SEQ ID NO 81
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Met Ile Asn Pro Lys Ser Gly Phe Thr Ala Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
                100                 105                 110

Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190
```

Ser Leu Gly Thr Gln Thr Tyr Ile Cys Asn Val Asn His Lys Pro Ser
       195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 82
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ala Ile Asp Pro Lys His Gly Phe Thr Ile Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr

```
                      100                 105                 110

Met Val Thr Val Ser Ser
            115

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ile Asp Pro Lys His Gly Phe Thr Ile Phe Pro Gln Lys Phe Gln
1               5                   10                  15

Gly

<210> SEQ ID NO 84
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ala Ile Asp Pro Lys His Gly Phe Thr Ile Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 85
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asp Gly Asp Thr Glu Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Trp Ile Asn Pro Lys Asp Gly Asp Thr Glu Phe Pro Gln Lys Phe Gln
1               5                   10                  15
Gly

<210> SEQ ID NO 87
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Lys Asp Gly Asp Thr Glu Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Arg Asn Gly Ile Thr Ser Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
            85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Ile Asn Pro Arg Asn Gly Ile Thr Ser Phe Pro Gln Lys Phe Gln
1               5                   10                  15

Gly

<210> SEQ ID NO 90
<211> LENGTH: 448

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Arg Asn Gly Ile Thr Ser Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 91
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Ser Phe
                85                  90                  95

Gly Gly Gly Thr Lys Val Glu Ile Lys
            100                 105

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln Ser Val Gly Leu Ser
1               5

<210> SEQ ID NO 93
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Gly Leu Ser Phe
                 85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
                195                 200                 205

Arg Gly Glu Cys
    210

<210> SEQ ID NO 94
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Leu Glu Leu Gly Phe
                 85                  90                  95

Gly Gly Gly Thr Lys Val Glu Ile Lys
            100                 105

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Ser Leu Glu Leu Gly
 1               5

<210> SEQ ID NO 96
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Glu Leu Gly Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 97
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Leu Glu Leu Gly Phe
                85                  90                  95

Gly Gly Gly Thr Lys Val Glu Ile Lys
            100                 105
```

<210> SEQ ID NO 98
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Glu Leu Gly Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 99
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45
```

Tyr Ala Ala Ser Ser Leu Gln Tyr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Ser Phe
                85                  90                  95

Gly Gly Gly Thr Lys Val Glu Ile Lys
                100                 105

<210> SEQ ID NO 100
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Tyr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Ser Phe
                85                  90                  95

Gly Gly Gly Thr Lys Val Glu Ile Lys Arg Thr Val Ala Ala Pro Ser
                100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
                180                 185                 190

Glu Val Thr His Gln Gly Leu Ser Ser Pro Val Thr Lys Ser Phe Asn
            195                 200                 205

Arg Gly Glu Cys
    210

<210> SEQ ID NO 101
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys
            100                 105

<210> SEQ ID NO 102
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 103
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys
            100                 105

<210> SEQ ID NO 104
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 105

```
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Glu Leu Gly Phe
                85                  90                  95

Gly Gly Gly Thr Lys Val Glu Ile Lys
            100                 105

<210> SEQ ID NO 106
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Glu Leu Gly Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205
```

```
Arg Gly Glu Cys
    210

<210> SEQ ID NO 107
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys
            100                 105

<210> SEQ ID NO 108
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175
```

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 109
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Glu Leu Gly Phe
                85                  90                  95

Gly Gly Gly Thr Lys Val Glu Ile Lys
            100                 105

<210> SEQ ID NO 110
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Glu Leu Gly Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

```
Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
            165                 170                 175

Leu Thr Leu Ser Lys Ala Asp Tyr Glu Lys His Lys Val Tyr Ala Cys
        180                 185                 190

Glu Val Thr His Gln Gly Leu Ser Ser Pro Val Thr Lys Ser Phe Asn
    195                 200                 205

Arg Gly Glu Cys
    210

<210> SEQ ID NO 111
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Ser Phe
                85                  90                  95

Gly Gly Gly Thr Lys Val Glu Ile Lys
            100                 105

<210> SEQ ID NO 112
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Ser Phe
                85                  90                  95

Gly Gly Gly Thr Lys Val Glu Ile Lys Arg Thr Val Ala Ala Pro Ser
            100                 105                 110
```

```
Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
        180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 113
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys
            100                 105

<210> SEQ ID NO 114
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Val Gly Leu Phe Phe
                85                  90                  95
Gly Gly Gly Thr Lys Val Glu Ile Lys Arg Thr Val Ala Ala Pro Ser
            100                 105                 110
Val Phe Ile Phe Pro Pro Ser Asp Glu Gln Leu Lys Ser Gly Thr Ala
        115                 120                 125
Ser Val Val Cys Leu Leu Asn Asn Phe Tyr Pro Arg Glu Ala Lys Val
    130                 135                 140
Gln Trp Lys Val Asp Asn Ala Leu Gln Ser Gly Asn Ser Gln Glu Ser
145                 150                 155                 160
Val Thr Glu Gln Asp Ser Lys Asp Ser Thr Tyr Ser Leu Ser Ser Thr
                165                 170                 175
Leu Thr Leu Ser Lys Ala Asp Tyr Glu Lys His Lys Val Tyr Ala Cys
            180                 185                 190
Glu Val Thr His Gln Gly Leu Ser Ser Pro Val Thr Lys Ser Phe Asn
        195                 200                 205
Arg Gly Glu Cys
    210

<210> SEQ ID NO 115
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Arg Gly Tyr
            20                  25                  30
Ala Met His Trp Val Arg Gln Ala Pro Gly Gln Gly Leu Glu Trp Met
        35                  40                  45
Gly Trp Ile Asn Pro Arg Ser Gly Val Thr Glu Phe Pro Gln Lys Phe
    50                  55                  60
Gln Gly Arg Val Thr Met Thr Arg Asp Thr Ser Ile Thr Thr Ala Tyr
65                  70                  75                  80
Met Asp Leu Ser Arg Leu Arg Ser Asp Asp Thr Ala Val Tyr Tyr Cys
                85                  90                  95
Ala Arg Glu Ser Gly Asp Asp Ala Phe Asp Ile Trp Gly Gln Gly Thr
            100                 105                 110
Met Val Thr Val Ser Ser
        115

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Tyr Thr Phe Arg Gly Tyr Ala Met His
1               5                   10

<210> SEQ ID NO 117
```

<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Trp Ile Asn Pro Arg Ser Gly Val Thr Glu Phe Pro Gln Lys Phe Gln
1               5                   10                  15

Gly

<210> SEQ ID NO 118
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Ala Met His Trp Val Arg Gln Ala Pro Gly Gln Gly Leu Glu Trp Met
        35                  40                  45

Gly Trp Ile Asn Pro Arg Ser Gly Val Thr Glu Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 119
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
                20                  25                  30

Ala Met His Trp Val Arg Gln Ala Pro Gly Gln Gly Leu Glu Trp Met
            35                  40                  45

Gly Trp Ile Asp Pro Arg Thr Gly Leu Thr Lys Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
                100                 105                 110

Met Val Thr Val Ser Ser
            115

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Trp Ile Asp Pro Arg Thr Gly Leu Thr Lys Phe Pro Gln Lys Phe Gln
1               5                   10                  15
```

Gly

<210> SEQ ID NO 121
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Glu Val Gln Leu Val Gln Ser Gly Ala Glu Val Lys Pro Gly Ala
1               5                   10                  15

Ser Val Lys Val Ser Cys Lys Ala Ser Gly Tyr Thr Phe Arg Gly Tyr
            20                  25                  30

Ala Met His Trp Val Arg Gln Ala Pro Gly Gln Gly Leu Glu Trp Met
        35                  40                  45

Gly Trp Ile Asp Pro Arg Thr Gly Leu Thr Lys Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 122
<211> LENGTH: 838
<212> TYPE: PRT
<213> ORGANISM: Homo sapiens

<400> SEQUENCE: 122

Ser Arg Leu Arg Gln Glu Asp Phe Pro Pro Arg Ile Val Glu His Pro
1               5                   10                  15

Ser Asp Val Ile Val Ser Lys Gly Glu Pro Thr Thr Leu Asn Cys Lys
                20                  25                  30

Ala Glu Gly Arg Pro Thr Pro Thr Ile Glu Trp Tyr Lys Asp Gly Glu
            35                  40                  45

Arg Val Glu Thr Asp Lys Asp Asp Pro Arg Ser His Arg Met Leu Leu
        50                  55                  60

Pro Ser Gly Ser Leu Phe Phe Leu Arg Ile Val His Gly Arg Arg Ser
65                  70                  75                  80

Lys Pro Asp Glu Gly Ser Tyr Val Cys Val Ala Arg Asn Tyr Leu Gly
                85                  90                  95

Glu Ala Val Ser Arg Asn Ala Ser Leu Glu Val Ala Leu Leu Arg Asp
            100                 105                 110

Asp Phe Arg Gln Asn Pro Thr Asp Val Val Val Ala Ala Gly Glu Pro
        115                 120                 125

Ala Ile Leu Glu Cys Gln Pro Pro Arg Gly His Pro Glu Pro Thr Ile
130                 135                 140

Tyr Trp Lys Lys Asp Lys Val Arg Ile Asp Asp Lys Glu Glu Arg Ile
145                 150                 155                 160

Ser Ile Arg Gly Gly Lys Leu Met Ile Ser Asn Thr Arg Lys Ser Asp
                165                 170                 175

Ala Gly Met Tyr Thr Cys Val Gly Thr Asn Met Val Gly Glu Arg Asp
            180                 185                 190

Ser Asp Pro Ala Glu Leu Thr Val Phe Glu Arg Pro Thr Phe Leu Arg
        195                 200                 205

Arg Pro Ile Asn Gln Val Val Leu Glu Glu Ala Val Glu Phe Arg
210                 215                 220

Cys Gln Val Gln Gly Asp Pro Gln Pro Thr Val Arg Trp Lys Lys Asp
225                 230                 235                 240

Asp Ala Asp Leu Pro Arg Gly Arg Tyr Asp Ile Lys Asp Asp Tyr Thr
                245                 250                 255

Leu Arg Ile Lys Lys Thr Met Ser Thr Asp Glu Gly Thr Tyr Met Cys
            260                 265                 270

Ile Ala Glu Asn Arg Val Gly Lys Met Glu Ala Ser Ala Thr Leu Thr
        275                 280                 285
```

```
Val Arg Ala Pro Pro Gln Phe Val Arg Pro Arg Asp Gln Ile Val
    290                 295                 300
Ala Gln Gly Arg Thr Val Thr Phe Pro Cys Glu Thr Lys Gly Asn Pro
305                 310                 315                 320
Gln Pro Ala Val Phe Trp Gln Lys Glu Gly Ser Gln Asn Leu Leu Phe
                325                 330                 335
Pro Asn Gln Pro Gln Pro Asn Ser Arg Cys Ser Val Ser Pro Thr
                340                 345                 350
Gly Asp Leu Thr Ile Thr Asn Ile Gln Arg Ser Asp Ala Gly Tyr Tyr
            355                 360                 365
Ile Cys Gln Ala Leu Thr Val Ala Gly Ser Ile Leu Ala Lys Ala Gln
370                 375                 380
Leu Glu Val Thr Asp Val Leu Thr Asp Arg Pro Pro Pro Ile Ile Leu
385                 390                 395                 400
Gln Gly Pro Ala Asn Gln Thr Leu Ala Val Asp Gly Thr Ala Leu Leu
                405                 410                 415
Lys Cys Lys Ala Thr Gly Asp Pro Leu Pro Val Ile Ser Trp Leu Lys
                420                 425                 430
Glu Gly Phe Thr Phe Pro Gly Arg Asp Pro Arg Ala Thr Ile Gln Glu
            435                 440                 445
Gln Gly Thr Leu Gln Ile Lys Asn Leu Arg Ile Ser Asp Thr Gly Thr
    450                 455                 460
Tyr Thr Cys Val Ala Thr Ser Ser Ser Gly Glu Thr Ser Trp Ser Ala
465                 470                 475                 480
Val Leu Asp Val Thr Glu Ser Gly Ala Thr Ile Ser Lys Asn Tyr Asp
                485                 490                 495
Leu Ser Asp Leu Pro Gly Pro Pro Ser Lys Pro Gln Val Thr Asp Val
                500                 505                 510
Thr Lys Asn Ser Val Thr Leu Ser Trp Gln Pro Gly Thr Pro Gly Thr
            515                 520                 525
Leu Pro Ala Ser Ala Tyr Ile Ile Glu Ala Phe Ser Gln Ser Val Ser
    530                 535                 540
Asn Ser Trp Gln Thr Val Ala Asn His Val Lys Thr Thr Leu Tyr Thr
545                 550                 555                 560
Val Arg Gly Leu Arg Pro Asn Thr Ile Tyr Leu Phe Met Val Arg Ala
                565                 570                 575
Ile Asn Pro Gln Gly Leu Ser Asp Pro Ser Pro Met Ser Asp Pro Val
                580                 585                 590
Arg Thr Gln Asp Ile Ser Pro Pro Ala Gln Gly Val Asp His Arg Gln
            595                 600                 605
Val Gln Lys Glu Leu Gly Asp Val Leu Val Arg Leu His Asn Pro Val
    610                 615                 620
Val Leu Thr Pro Thr Thr Val Gln Val Thr Trp Thr Val Asp Arg Gln
625                 630                 635                 640
Pro Gln Phe Ile Gln Gly Tyr Arg Val Met Tyr Arg Gln Thr Ser Gly
                645                 650                 655
Leu Gln Ala Thr Ser Ser Trp Gln Asn Leu Asp Ala Lys Val Pro Thr
                660                 665                 670
Glu Arg Ser Ala Val Leu Val Asn Leu Lys Lys Gly Val Thr Tyr Glu
            675                 680                 685
Ile Lys Val Arg Pro Tyr Phe Asn Glu Phe Gln Gly Met Asp Ser Glu
    690                 695                 700
```

```
Ser Lys Thr Val Arg Thr Thr Glu Glu Ala Pro Ser Ala Pro Pro Gln
705                 710                 715                 720

Ser Val Thr Val Leu Thr Val Gly Ser Tyr Asn Ser Thr Ser Ile Ser
                725                 730                 735

Val Ser Trp Asp Pro Pro Pro Asp His Gln Asn Gly Ile Ile Gln
            740                 745                 750

Glu Tyr Lys Ile Trp Cys Leu Gly Asn Glu Thr Arg Phe His Ile Asn
                755                 760                 765

Lys Thr Val Asp Ala Ala Ile Arg Ser Val Ile Ile Gly Gly Leu Phe
                770                 775                 780

Pro Gly Ile Gln Tyr Arg Val Glu Val Ala Ala Ser Thr Ser Ala Gly
785                 790                 795                 800

Val Gly Val Lys Ser Glu Pro Gln Pro Ile Ile Ile Gly Arg Arg Asn
                805                 810                 815

Glu Val Val Ile Thr Glu Asn Asn Asn Ser Ile Thr Glu Gln Ile Thr
                820                 825                 830

Asp Val Val Lys Gln Pro
            835

<210> SEQ ID NO 123
<211> LENGTH: 872
<212> TYPE: PRT
<213> ORGANISM: Homo sapiens

<400> SEQUENCE: 123

Gln Leu Ile Pro Asp Pro Glu Asp Val Glu Arg Gly Asn Asp His Gly
1               5                   10                  15

Thr Pro Ile Pro Thr Ser Asp Asn Asp Asn Ser Leu Gly Tyr Thr
                20                  25                  30

Gly Ser Arg Leu Arg Gln Glu Asp Phe Pro Pro Arg Ile Val Glu His
            35                  40                  45

Pro Ser Asp Leu Ile Val Ser Lys Gly Glu Pro Ala Thr Leu Asn Cys
    50                  55                  60

Lys Ala Glu Gly Arg Pro Thr Pro Thr Ile Glu Trp Tyr Lys Gly Gly
65                  70                  75                  80

Glu Arg Val Glu Thr Asp Lys Asp Asp Pro Arg Ser His Arg Met Leu
                85                  90                  95

Leu Pro Ser Gly Ser Leu Phe Phe Leu Arg Ile Val His Gly Arg Lys
            100                 105                 110

Ser Arg Pro Asp Glu Gly Val Tyr Val Cys Val Ala Arg Asn Tyr Leu
        115                 120                 125

Gly Glu Ala Val Ser His Asn Ala Ser Leu Glu Val Ala Ile Leu Arg
    130                 135                 140

Asp Asp Phe Arg Gln Asn Pro Ser Asp Val Met Val Ala Val Gly Glu
145                 150                 155                 160

Pro Ala Val Met Glu Cys Gln Pro Pro Arg Gly His Pro Glu Pro Thr
                165                 170                 175

Ile Ser Trp Lys Lys Asp Gly Ser Pro Leu Asp Asp Lys Asp Glu Arg
            180                 185                 190

Ile Thr Ile Arg Gly Gly Lys Leu Met Ile Thr Tyr Thr Arg Lys Ser
        195                 200                 205

Asp Ala Gly Lys Tyr Val Cys Val Gly Thr Asn Met Val Gly Glu Arg
    210                 215                 220

Glu Ser Glu Val Ala Glu Leu Thr Val Leu Glu Arg Pro Ser Phe Val
225                 230                 235                 240
```

-continued

```
Lys Arg Pro Ser Asn Leu Ala Val Thr Val Asp Asp Ser Ala Glu Phe
            245                 250                 255

Lys Cys Glu Ala Arg Gly Asp Pro Val Pro Thr Val Arg Trp Arg Lys
            260                 265                 270

Asp Asp Gly Glu Leu Pro Lys Ser Arg Tyr Glu Ile Arg Asp Asp His
            275                 280                 285

Thr Leu Lys Ile Arg Lys Val Thr Ala Gly Asp Met Gly Ser Tyr Thr
            290                 295                 300

Cys Val Ala Glu Asn Met Val Gly Lys Ala Glu Ala Ser Ala Thr Leu
305                 310                 315                 320

Thr Val Gln Glu Pro Pro His Phe Val Lys Pro Arg Asp Gln Val
            325                 330                 335

Val Ala Leu Gly Arg Thr Val Thr Phe Gln Cys Glu Ala Thr Gly Asn
            340                 345                 350

Pro Gln Pro Ala Ile Phe Trp Arg Arg Glu Gly Ser Gln Asn Leu Leu
            355                 360                 365

Phe Ser Tyr Gln Pro Pro Gln Ser Ser Arg Phe Ser Val Ser Gln
            370                 375                 380

Thr Gly Asp Leu Thr Ile Thr Asn Val Gln Arg Ser Asp Val Gly Tyr
385                 390                 395                 400

Tyr Ile Cys Gln Thr Leu Asn Val Ala Gly Ser Ile Ile Thr Lys Ala
            405                 410                 415

Tyr Leu Glu Val Thr Asp Val Ile Ala Asp Arg Pro Pro Val Ile
            420                 425                 430

Arg Gln Gly Pro Val Asn Gln Thr Val Ala Val Asp Gly Thr Phe Val
            435                 440                 445

Leu Ser Cys Val Ala Thr Gly Ser Pro Val Pro Thr Ile Leu Trp Arg
450                 455                 460

Lys Asp Gly Val Leu Val Ser Thr Gln Asp Ser Arg Ile Lys Gln Leu
465                 470                 475                 480

Glu Asn Gly Val Leu Gln Ile Arg Tyr Ala Lys Leu Gly Asp Thr Gly
            485                 490                 495

Arg Tyr Thr Cys Ile Ala Ser Thr Pro Ser Gly Glu Ala Thr Trp Ser
            500                 505                 510

Ala Tyr Ile Glu Val Gln Glu Phe Gly Val Pro Val Gln Pro Pro Arg
            515                 520                 525

Pro Thr Asp Pro Asn Leu Ile Pro Ser Ala Pro Ser Lys Pro Glu Val
            530                 535                 540

Thr Asp Val Ser Arg Asn Thr Val Thr Leu Ser Trp Gln Pro Asn Leu
545                 550                 555                 560

Asn Ser Gly Ala Thr Pro Thr Ser Tyr Ile Ile Glu Ala Phe Ser His
            565                 570                 575

Ala Ser Gly Ser Ser Trp Gln Thr Val Ala Glu Asn Val Lys Thr Glu
            580                 585                 590

Thr Ser Ala Ile Lys Gly Leu Lys Pro Asn Ala Ile Tyr Leu Phe Leu
            595                 600                 605

Val Arg Ala Ala Asn Ala Tyr Gly Ile Ser Asp Pro Ser Gln Ile Ser
            610                 615                 620

Asp Pro Val Lys Thr Gln Asp Val Leu Pro Thr Ser Gln Gly Val Asp
625                 630                 635                 640

His Lys Gln Val Gln Arg Glu Leu Gly Asn Ala Val Leu His Leu His
            645                 650                 655
```

```
Asn Pro Thr Val Leu Ser Ser Ser Ile Glu Val His Trp Thr Val
            660                 665                 670

Asp Gln Gln Ser Gln Tyr Ile Gln Gly Tyr Lys Ile Leu Tyr Arg Pro
        675                 680                 685

Ser Gly Ala Asn His Gly Glu Ser Asp Trp Leu Val Phe Glu Val Arg
        690                 695                 700

Thr Pro Ala Lys Asn Ser Val Val Ile Pro Asp Leu Arg Lys Gly Val
705                 710                 715                 720

Asn Tyr Glu Ile Lys Ala Arg Pro Phe Phe Asn Glu Phe Gln Gly Ala
                725                 730                 735

Asp Ser Glu Ile Lys Phe Ala Lys Thr Leu Glu Glu Ala Pro Ser Ala
            740                 745                 750

Pro Pro Gln Gly Val Thr Val Ser Lys Asn Asp Gly Asn Gly Thr Ala
        755                 760                 765

Ile Leu Val Ser Trp Gln Pro Pro Glu Asp Thr Gln Asn Gly Met
        770                 775                 780

Val Gln Glu Tyr Lys Val Trp Cys Leu Gly Asn Glu Thr Arg Tyr His
785                 790                 795                 800

Ile Asn Lys Thr Val Asp Gly Ser Thr Phe Ser Val Val Ile Pro Phe
                805                 810                 815

Leu Val Pro Gly Ile Arg Tyr Ser Val Glu Val Ala Ala Ser Thr Gly
            820                 825                 830

Ala Gly Ser Gly Val Lys Ser Glu Pro Gln Phe Ile Gln Leu Asp Ala
        835                 840                 845

His Gly Asn Pro Val Ser Pro Glu Asp Gln Val Ser Leu Ala Gln Gln
        850                 855                 860

Ile Ser Asp Val Val Lys Gln Pro
865                 870

<210> SEQ ID NO 124
<211> LENGTH: 97
<212> TYPE: PRT
<213> ORGANISM: Homo sapiens

<400> SEQUENCE: 124

Pro Arg Ile Val Glu His Pro Ser Asp Val Ile Val Ser Lys Gly Glu
1               5                   10                  15

Pro Thr Thr Leu Asn Cys Lys Ala Glu Gly Arg Pro Thr Pro Thr Ile
            20                  25                  30

Glu Trp Tyr Lys Asp Gly Glu Arg Val Glu Thr Asp Lys Asp Asp Pro
        35                  40                  45

Arg Ser His Arg Met Leu Leu Pro Ser Gly Ser Leu Phe Phe Leu Arg
    50                  55                  60

Ile Val His Gly Arg Arg Ser Lys Pro Asp Glu Gly Ser Tyr Val Cys
65                  70                  75                  80

Val Ala Arg Asn Tyr Leu Gly Glu Ala Val Ser Arg Asn Ala Ser Leu
                85                  90                  95

Glu

<210> SEQ ID NO 125
<211> LENGTH: 97
<212> TYPE: PRT
<213> ORGANISM: Homo sapiens

<400> SEQUENCE: 125

Pro Arg Ile Val Glu His Pro Ser Asp Leu Ile Val Ser Lys Gly Glu
```

-continued

```
1               5                   10                  15
Pro Ala Thr Leu Asn Cys Lys Ala Glu Gly Arg Pro Thr Pro Thr Ile
                20                  25                  30
Glu Trp Tyr Lys Gly Gly Glu Arg Val Glu Thr Asp Lys Asp Asp Pro
                35                  40                  45
Arg Ser His Arg Met Leu Leu Pro Ser Gly Ser Leu Phe Phe Leu Arg
            50                  55                  60
Ile Val His Gly Arg Lys Ser Arg Pro Asp Glu Gly Val Tyr Val Cys
65                  70                  75                  80
Val Ala Arg Asn Tyr Leu Gly Glu Ala Val Ser His Asn Ala Ser Leu
                85                  90                  95
Glu
```

<210> SEQ ID NO 126
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Met
                35                  40                  45
Gly Trp Ile Asn Pro Lys Asn Gly Asp Thr Glu Phe Pro Gln Lys Phe
            50                  55                  60
Gln Gly Arg Val Thr Met Thr Arg Asp Thr Ser Ile Ser Thr Ala Tyr
65                  70                  75                  80
Met Asp Leu Ser Arg Leu Arg Ser Asp Asp Thr Ala Val Tyr Tyr Cys
                85                  90                  95
Ala Arg Glu Ser Gly Asp Asp Ala Phe Asp Ile Trp Gly Gln Gly Thr
                100                 105                 110
Met Val Thr Val Ser Ser
        115
```

<210> SEQ ID NO 127
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Met
                35                  40                  45
Gly Trp Ile Asn Pro Lys Asn Gly Asp Thr Glu Phe Pro Gln Lys Phe
            50                  55                  60
Gln Gly Arg Val Thr Met Thr Arg Asp Thr Ser Ile Thr Thr Ala Tyr
65                  70                  75                  80
```

```
Met Glu Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 128
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 129
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115
```

<210> SEQ ID NO 130
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 131
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Thr Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 132
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser
        115

<210> SEQ ID NO 133
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys
            100                 105

<210> SEQ ID NO 134
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

```
Gly Trp Ile Asn Pro Lys Asn Gly Asp Thr Glu Phe Pro Gln Lys Phe
 50                  55                  60
Gln Gly Arg Val Thr Met Thr Arg Asp Thr Ser Ile Ser Thr Ala Tyr
 65                  70                  75                  80
Met Asp Leu Ser Arg Leu Arg Ser Asp Thr Ala Val Tyr Tyr Cys
                 85                  90                  95
Ala Arg Glu Ser Gly Asp Asp Ala Phe Asp Ile Trp Gly Gln Gly Thr
                100                 105                 110
Met Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Ala Ala Gly Ala Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445

<210> SEQ ID NO 135
<211> LENGTH: 448
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Thr Thr Ala Tyr
65                  70                  75                  80

Met Glu Leu Ser Arg Leu Arg Ser Asp Thr Ala Val Tyr Tyr Cys
                85                  90                  95

Ala Arg Glu Ser Gly Asp Asp Ala Phe Asp Ile Trp Gly Gln Gly Thr
                100                 105                 110

Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 136
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Ser Gly Asp Asp Ala Phe Asp Ile Trp Gly Gln Gly Thr
        100                 105                 110

Met Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 137
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

```
                210                 215                 220
His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 138
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Lys Asn Gly Asp Thr Glu Phe Pro Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Tyr Tyr Cys
                85                  90                  95

Ala Arg Glu Ser Gly Asp Asp Ala Phe Asp Ile Trp Gly Gln Gly Thr
                100                 105                 110

Met Val Thr Val Ser Ser Ala Ser Thr Lys Gly Pro Ser Val Phe Pro
            115                 120                 125
```

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 139
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Asn Gly Asp Thr Glu Phe Pro Gln Lys Phe
            50                  55                  60
Gln Gly Arg Val Thr Met Thr Arg Asp Thr Ser Ile Thr Thr Ala Tyr
 65                  70                  75                  80
Met Glu Leu Ser Arg Leu Arg Ser Asp Asp Thr Ala Val Tyr Tyr Cys
                 85                  90                  95
Ala Arg Glu Ser Gly Asp Asp Ala Phe Asp Ile Trp Gly Gln Gly Thr
                100                 105                 110
Met Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Ala Ala Gly Ala Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
            435                 440                 445

<210> SEQ ID NO 140
<211> LENGTH: 448

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Lys Asn Gly Asp Thr Glu Phe Pro Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Glu Ser Gly Asp Asp Ala Phe Asp Ile Trp Gly Gln Gly Thr
            100                 105                 110
Met Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Ala Ala Gly Ala Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 141
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Gly Leu Phe Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 142
<211> LENGTH: 1529
<212> TYPE: PRT
<213> ORGANISM: Homo sapiens

<400> SEQUENCE: 142

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

```
Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
                100                 105                 110

Asn His Leu Gln Leu Phe Pro Glu Leu Leu Phe Leu Gly Thr Ala Lys
                115                 120                 125

Leu Tyr Arg Leu Asp Leu Ser Glu Asn Gln Ile Gln Ala Ile Pro Arg
        130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
                180                 185                 190

Ala Ser Phe Asn His Met Pro Lys Leu Arg Thr Phe Arg Leu His Ser
                195                 200                 205

Asn Asn Leu Tyr Cys Asp Cys His Leu Ala Trp Leu Ser Asp Trp Leu
        210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
                260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
        290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
                325                 330                 335

Ser Glu Leu Ala Pro Asp Ala Phe Gln Gly Leu Arg Ser Leu Asn Ser
                340                 345                 350

Leu Val Leu Tyr Gly Asn Lys Ile Thr Glu Leu Pro Lys Ser Leu Phe
                355                 360                 365

Glu Gly Leu Phe Ser Leu Gln Leu Leu Leu Leu Asn Ala Asn Lys Ile
        370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Ile Ala Lys Gly Thr Phe
                405                 410                 415

Ser Pro Leu Arg Ala Ile Gln Thr Met His Leu Ala Gln Asn Pro Phe
                420                 425                 430

Ile Cys Asp Cys His Leu Lys Trp Leu Ala Asp Tyr Leu His Thr Asn
                435                 440                 445
```

```
Pro Ile Glu Thr Ser Gly Ala Arg Cys Thr Ser Pro Arg Arg Leu Ala
    450                 455                 460

Asn Lys Arg Ile Gly Gln Ile Lys Ser Lys Lys Phe Arg Cys Ser Ala
465                 470                 475                 480

Lys Glu Gln Tyr Phe Ile Pro Gly Thr Glu Asp Tyr Arg Ser Lys Leu
                485                 490                 495

Ser Gly Asp Cys Phe Ala Asp Leu Ala Cys Pro Glu Lys Cys Arg Cys
            500                 505                 510

Glu Gly Thr Thr Val Asp Cys Ser Asn Gln Lys Leu Asn Lys Ile Pro
            515                 520                 525

Glu His Ile Pro Gln Tyr Thr Ala Glu Leu Arg Leu Asn Asn Asn Glu
    530                 535                 540

Phe Thr Val Leu Glu Ala Thr Gly Ile Phe Lys Lys Leu Pro Gln Leu
545                 550                 555                 560

Arg Lys Ile Asn Phe Ser Asn Asn Lys Ile Thr Asp Ile Glu Glu Gly
                565                 570                 575

Ala Phe Glu Gly Ala Ser Gly Val Asn Glu Ile Leu Leu Thr Ser Asn
            580                 585                 590

Arg Leu Glu Asn Val Gln His Lys Met Phe Lys Gly Leu Glu Ser Leu
    595                 600                 605

Lys Thr Leu Met Leu Arg Ser Asn Arg Ile Thr Cys Val Gly Asn Asp
610                 615                 620

Ser Phe Ile Gly Leu Ser Ser Val Arg Leu Leu Ser Leu Tyr Asp Asn
625                 630                 635                 640

Gln Ile Thr Thr Val Ala Pro Gly Ala Phe Asp Thr Leu His Ser Leu
                645                 650                 655

Ser Thr Leu Asn Leu Leu Ala Asn Pro Phe Asn Cys Asn Cys Tyr Leu
            660                 665                 670

Ala Trp Leu Gly Glu Trp Leu Arg Lys Lys Arg Ile Val Thr Gly Asn
    675                 680                 685

Pro Arg Cys Gln Lys Pro Tyr Phe Leu Lys Glu Ile Pro Ile Gln Asp
    690                 695                 700

Val Ala Ile Gln Asp Phe Thr Cys Asp Asp Gly Asn Asp Asp Asn Ser
705                 710                 715                 720

Cys Ser Pro Leu Ser Arg Cys Pro Thr Glu Cys Thr Cys Leu Asp Thr
                725                 730                 735

Val Val Arg Cys Ser Asn Lys Gly Leu Lys Val Leu Pro Lys Gly Ile
            740                 745                 750

Pro Arg Asp Val Thr Glu Leu Tyr Leu Asp Gly Asn Gln Phe Thr Leu
    755                 760                 765

Val Pro Lys Glu Leu Ser Asn Tyr Lys His Leu Thr Leu Ile Asp Leu
770                 775                 780

Ser Asn Asn Arg Ile Ser Thr Leu Ser Asn Gln Ser Phe Ser Asn Met
785                 790                 795                 800

Thr Gln Leu Leu Thr Leu Ile Leu Ser Tyr Asn Arg Leu Arg Cys Ile
                805                 810                 815

Pro Pro Arg Thr Phe Asp Gly Leu Lys Ser Leu Arg Leu Leu Ser Leu
            820                 825                 830

His Gly Asn Asp Ile Ser Val Val Pro Glu Gly Ala Phe Asn Asp Leu
    835                 840                 845

Ser Ala Leu Ser His Leu Ala Ile Gly Ala Asn Pro Leu Tyr Cys Asp
850                 855                 860

Cys Asn Met Gln Trp Leu Ser Asp Trp Val Lys Ser Glu Tyr Lys Glu
```

-continued

```
                865               870               875               880
           Pro Gly Ile Ala Arg Cys Ala Gly Pro Gly Glu Met Ala Asp Lys Leu
                           885               890               895
           Leu Leu Thr Thr Pro Ser Lys Lys Phe Thr Cys Gln Gly Pro Val Asp
                           900               905               910
           Val Asn Ile Leu Ala Lys Cys Asn Pro Cys Leu Ser Asn Pro Cys Lys
                           915               920               925
           Asn Asp Gly Thr Cys Asn Ser Asp Pro Val Asp Phe Tyr Arg Cys Thr
                           930               935               940
           Cys Pro Tyr Gly Phe Lys Gly Gln Asp Cys Asp Val Pro Ile His Ala
           945               950               955               960
           Cys Ile Ser Asn Pro Cys Lys His Gly Gly Thr Cys His Leu Lys Glu
                           965               970               975
           Gly Glu Glu Asp Gly Phe Trp Cys Ile Cys Ala Asp Gly Phe Glu Gly
                           980               985               990
           Glu Asn Cys Glu Val Asn Val Asp Asp Cys Glu Asp Asn Asp Cys Glu
                           995               1000              1005
           Asn Asn Ser Thr Cys Val Asp Gly Ile Asn Asn Tyr Thr Cys Leu
                           1010              1015              1020
           Cys Pro Pro Glu Tyr Thr Gly Glu Leu Cys Glu Glu Lys Leu Asp
                           1025              1030              1035
           Phe Cys Ala Gln Asp Leu Asn Pro Cys Gln His Asp Ser Lys Cys
                           1040              1045              1050
           Ile Leu Thr Pro Lys Gly Phe Lys Cys Asp Cys Thr Pro Gly Tyr
                           1055              1060              1065
           Val Gly Glu His Cys Asp Ile Asp Phe Asp Asp Cys Gln Asp Asn
                           1070              1075              1080
           Lys Cys Lys Asn Gly Ala His Cys Thr Asp Ala Val Asn Gly Tyr
                           1085              1090              1095
           Thr Cys Ile Cys Pro Glu Gly Tyr Ser Gly Leu Phe Cys Glu Phe
                           1100              1105              1110
           Ser Pro Pro Met Val Leu Pro Arg Thr Ser Pro Cys Asp Asn Phe
                           1115              1120              1125
           Asp Cys Gln Asn Gly Ala Gln Cys Ile Val Arg Ile Asn Glu Pro
                           1130              1135              1140
           Ile Cys Gln Cys Leu Pro Gly Tyr Gln Gly Glu Lys Cys Glu Lys
                           1145              1150              1155
           Leu Val Ser Val Asn Phe Ile Asn Lys Glu Ser Tyr Leu Gln Ile
                           1160              1165              1170
           Pro Ser Ala Lys Val Arg Pro Gln Thr Asn Ile Thr Leu Gln Ile
                           1175              1180              1185
           Ala Thr Asp Glu Asp Ser Gly Ile Leu Leu Tyr Lys Gly Asp Lys
                           1190              1195              1200
           Asp His Ile Ala Val Glu Leu Tyr Arg Gly Arg Val Arg Ala Ser
                           1205              1210              1215
           Tyr Asp Thr Gly Ser His Pro Ala Ser Ala Ile Tyr Ser Val Glu
                           1220              1225              1230
           Thr Ile Asn Asp Gly Asn Phe His Ile Val Glu Leu Leu Ala Leu
                           1235              1240              1245
           Asp Gln Ser Leu Ser Leu Ser Val Asp Gly Gly Asn Pro Lys Ile
                           1250              1255              1260
           Ile Thr Asn Leu Ser Lys Gln Ser Thr Leu Asn Phe Asp Ser Pro
                           1265              1270              1275
```

Leu Tyr Val Gly Gly Met Pro Gly Lys Ser Asn Val Ala Ser Leu
    1280                1285                1290

Arg Gln Ala Pro Gly Gln Asn Gly Thr Ser Phe His Gly Cys Ile
    1295                1300                1305

Arg Asn Leu Tyr Ile Asn Ser Glu Leu Gln Asp Phe Gln Lys Val
    1310                1315                1320

Pro Met Gln Thr Gly Ile Leu Pro Gly Cys Glu Pro Cys His Lys
    1325                1330                1335

Lys Val Cys Ala His Gly Thr Cys Gln Pro Ser Ser Gln Ala Gly
    1340                1345                1350

Phe Thr Cys Glu Cys Gln Glu Gly Trp Met Gly Pro Leu Cys Asp
    1355                1360                1365

Gln Arg Thr Asn Asp Pro Cys Leu Gly Asn Lys Cys Val His Gly
    1370                1375                1380

Thr Cys Leu Pro Ile Asn Ala Phe Ser Tyr Ser Cys Lys Cys Leu
    1385                1390                1395

Glu Gly His Gly Gly Val Leu Cys Asp Glu Glu Asp Leu Phe
    1400                1405                1410

Asn Pro Cys Gln Ala Ile Lys Cys Lys His Gly Lys Cys Arg Leu
    1415                1420                1425

Ser Gly Leu Gly Gln Pro Tyr Cys Glu Cys Ser Ser Gly Tyr Thr
    1430                1435                1440

Gly Asp Ser Cys Asp Arg Glu Ile Ser Cys Arg Gly Glu Arg Ile
    1445                1450                1455

Arg Asp Tyr Tyr Gln Lys Gln Gly Tyr Ala Ala Cys Gln Thr
    1460                1465                1470

Thr Lys Lys Val Ser Arg Leu Glu Cys Arg Gly Gly Cys Ala Gly
    1475                1480                1485

Gly Gln Cys Cys Gly Pro Leu Arg Ser Lys Arg Arg Lys Tyr Ser
    1490                1495                1500

Phe Glu Cys Thr Asp Gly Ser Ser Phe Val Asp Glu Val Glu Lys
    1505                1510                1515

Val Val Lys Cys Gly Cys Thr Arg Cys Val Ser
    1520                1525

<210> SEQ ID NO 143
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
gaggtccagc tggtgcagtc tggggctgag gtgaagaagc tggggcctc agtgaaggtc      60 tcctgcaagg cttctgggta caccttcacc ggctactata tgcactgggt gcgacaggcc    120
cctggacaag ggcttgagtg gatgggatgg atcaatccta gaatggtga tacagagttt     180 ccacagaagt ttcagggcag ggtcaccatg accaggaca cgtccatcac cacagcctac     240
atggagctga gcaggctcag atctgacgac acggccgtgt attactgtgc gagagaaagt    300
ggggatgatg cttttgatat ttggggccaa gggacaatgg tcaccgtctc gagc          354

<210> SEQ ID NO 144
<211> LENGTH: 315
<212> TYPE: DNA

<213> ORGANISM: Artificial Sequence
<220> FEATURE:
<223> OTHER INFORMATION: Description of Artificial Sequence: Synthetic
    polynucleotide

<400> SEQUENCE: 144
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag tcggttggtc tttttttcgg cggagggacc     300
aaggtggaga tcaaa                                                      315

<210> SEQ ID NO 145
<211> LENGTH: 354
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 145
gaggtccagc tggtgcagtc tggggctgag gtgaagaagc ctggggcctc agtgaaggtc      60
tcctgcaagg cttctgggta caccttcacc ggctactata tgcactgggt gcgacaggcc     120
cctggacaag gcttgagtg gatgggatgg atcaatccta gaatggtga tacagagttt      180 ccacagaagt ttcagggcag ggtcaccatg accagggaca cgtccatcac cacagcctac     240
atggacctga gcaggctcag atctgacgac acggccgtgt attactgtgc gagagaaagt     300
ggggatgatg cttttgatat ttggggccaa gggacaatgg tcaccgtctc gagc           354

<210> SEQ ID NO 146
<211> LENGTH: 315
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 146
gacatcgtga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag tcggttggtc tttttttcgg cggagggacc     300
aaggtggaga tcaaa                                                      315